(12) United States Patent
Spiegelman et al.

(10) Patent No.: US 9,181,315 B2
(45) Date of Patent: Nov. 10, 2015

(54) COMPOSITIONS AND METHODS FOR INDUCED BROWN FAT DIFFERENTIATION

(75) Inventors: Bruce M. Spiegelman, Waban, MA (US); Shingo Kajimura, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 143 days.

(21) Appl. No.: 13/143,645

(22) PCT Filed: Jan. 8, 2010

(86) PCT No.: PCT/US2010/020480
§ 371 (c)(1),
(2), (4) Date: Sep. 23, 2011

(87) PCT Pub. No.: WO2010/080985
PCT Pub. Date: Jul. 15, 2010

(65) Prior Publication Data
US 2012/0022500 A1 Jan. 26, 2012

Related U.S. Application Data

(60) Provisional application No. 61/204,607, filed on Jan. 8, 2009.

(51) Int. Cl.
| | |
|---|---|
| *A61K 48/00* | (2006.01) |
| *C12N 15/63* | (2006.01) |
| *C07H 21/04* | (2006.01) |
| *C07K 14/47* | (2006.01) |
| *C12N 5/16* | (2006.01) |
| *A61K 38/00* | (2006.01) |

(52) U.S. Cl.
CPC ............ *C07K 14/4702* (2013.01); *A61K 38/00* (2013.01); *C07H 21/04* (2013.01); *C12N 5/16* (2013.01); *C12N 15/63* (2013.01)

(58) Field of Classification Search
CPC ........... C12N 5/16; C12N 15/63; C07H 21/04
USPC .................. 424/93.21; 435/455; 536/23.5
See application file for complete search history.

(56) References Cited

FOREIGN PATENT DOCUMENTS

| WO | WO-2008/063330 | 5/2008 |
| WO | WO-2009/156413 | 12/2009 |

OTHER PUBLICATIONS

Taha, Masoumeh F., 2010, Current Stem Cell research & therapy, vol. 5, p. 23-36.*
Li et al., 2009, Transplant Immunology, vol. 21, p. 70-74.*
Sprangers et al., 2008, Kidney International, vol. 74, p. 14-21.*
Richard et al., 2010, International Journal of Obesity, vol. 34, p. S59-S66.*
Descombes et al., "A Liver-Enriched Transcriptional Activator Protein, LAP, and a Transcriptional Inhibitory Protein, LIP, Are Translated from the Same mRNA," Cell, 67:569-579 (1991).
Farmer, Stephen R., "Transcriptional control of adipocyte formation," Cell Metabolism, 4:263-273 (2006).
Kajimura et al., "Initiation of myoblast to brown fat switch by a PRDM16-C/EBP-β transcriptional complex," Nature, 460:1154-1158 (2009).
Kajimura et al., "Regulation of the brown and white fat gene programs through a PRDM16/CtBP transcriptional complex," Genes & Development, 22(10):1397-1409 (2008).
Mochizuki et al., "A novel gene, *MEL1*, mapped to 1p36.3 is highly homologous to the *MDS1/EV11* gene and is transcriptionally activated in t(1;3)(p36;q21)-positive leukemia cells," Blood, 96:3209-3214 (2000).
Nishikata et al., "A novel *EV11* gene family, *MEL1*, lacking a PR domain (*MELIS*) is expressed mainly in t(1;3)(p36;q21)-positive AML and blocks G-CSF-induced myeloid differentiation," Blood, 102(9):3323-3332 (2003).
Seale et al., "PRDM16 controls a brown fat/skeletal muscle switch," Nature, 454:961-968 (2008).
Seale et al., "Transcriptional Control of Brown Fat Determination by PRDM16," Cell Metabolism, 6:38-54 (2007).
Wu et al., "Conditional ectopic expression of C/EBPβ in NIH-3T3 cells induces PPARγ and stimulates adipogenesis," Genes & Development, 9:2350-2363 (1995).
International Search Report dated Jun. 22, 2010 from PCT/US2010/020480.

* cited by examiner

*Primary Examiner* — Shin Lin Chen
(74) *Attorney, Agent, or Firm* — Foley Hoag LLP

(57) ABSTRACT

The invention provides methods and compositions for inducing brown fat cell differentiation through modulation of both Prdm1β and C/EBPβ activity and/or expression. Also provided are methods for preventing or treating obesity or an obesity related disorder in a subject through stimulation of both Prdm1β and C/EBPβ expression and/or activity. Further provided are methods for identifying compounds that are capable of modulating both Prdm1β and C/EBPβ expression and/or activity.

5 Claims, 13 Drawing Sheets

SEQUENCE LISTING

<160> NUMBER OF SEQ ID NOS: 136

<210> SEQ ID NO 1
<211> LENGTH: 3828
<212> TYPE: DNA
<213> ORGANISM: Homo sapiens

<400> SEQUENCE: 1

| | | | | | | |
|---|---|---|---|---|---|---|
| atgcgatcca | aggcgagggc | gaggaagcta | gccaaaagtg | acggtgacgt | tgtaaataat | 60 |
| atgtatgagc | ccaaccggga | cctgctggcc | agccacagcg | cggaggacga | ggccgaggac | 120 |
| agtgccatgt | cgcccatccc | cgtggggcca | ccgtccccct | tccccaccag | cgaggacttc | 180 |
| accccccaagg | agggctcgcc | gtacgaggcc | cctgtctaca | ttcctgaaga | cattccgatc | 240 |
| ccagcagact | tcgagctccg | agagtcctcc | atcccagggg | ctggcctggg | ggtctgggcc | 300 |
| aagaggaaga | tggaagccgg | ggagaggctg | ggccctgcg | tggtggtgcc | ccgggcggcg | 360 |
| gcaaaggaga | cagacttcgg | atgggagcaa | atactgacgg | acgtggaagt | gtcgccccag | 420 |
| gaaggctgca | tcacaaagat | ctccgaagac | ctgggcagtg | agaagttctg | cgtggatgca | 480 |
| aatcaggcgg | ggctggcag | ctggctcaag | tacatccgtg | tggcgtgctc | ctgcgatgac | 540 |
| cagaacctca | ccatgtgtca | gatcagtgag | cagatttact | ataaagtcat | taaggacatt | 600 |
| gagccaggtg | aggagctgct | ggtgcacgtg | aaggaaggcg | tctaccccct | gggcacagtg | 660 |
| ccgcccggcc | tggacgagga | gcccacgttc | cgctgtgacg | agtgtgacga | actcttccag | 720 |
| tccaagctgg | acctgcggcg | ccataagaag | tacacgtgtg | gctcagtggg | ggctgcgctc | 780 |
| tacgagggcc | tggctgagga | gctcaagccc | gagggccttg | gcggtggcag | cggccaagcc | 840 |
| cacgagtgca | aggactgcga | gcggatgttc | cccaacaagt | acagcctgga | gcagcacatg | 900 |
| gtcatccaca | cggaggagcg | cgagtacaaa | tgcgaccagt | gtcccaaggc | cttcaactgg | 960 |
| aagtccaacc | tcatccgcca | ccagatgtcc | cacgacagcg | gcaaacgctt | cgaatgtgaa | 1020 |
| aactgcgtga | aggtgttcac | ggaccccagc | aaccttcagc | ggcacatccg | ctcgcagcac | 1080 |
| gtgggcgctc | gggcccacgc | ctgccccgac | tgcgggaaga | ccttcgccac | gtcctccggc | 1140 |
| ctcaagcagc | acaagcatat | ccacagcacg | gtgaagcctt | tcatatgtga | ggtctgccac | 1200 |
| aagtcctaca | cgcagttctc | caacctgtgc | cggcacaagc | ggatgcacgc | cgactgccgc | 1260 |
| acgcagatca | agtgcaagga | ctgtggccag | atgttcagca | ctacctcctc | cctcaacaag | 1320 |
| caccggcgct | tctgcgaggg | caagaaccat | tacacgccgg | cggcatctt | tgccccgggc | 1380 |
| ctgcccttga | cccccagccc | catgatggac | aaggcaaaac | cctcccccag | cctcaatcac | 1440 |
| gccagcctgg | gcttcaacga | gtactttccc | tccaggccgc | accgggggag | cctgcccttc | 1500 |
| tccacggcgc | ctcccacgtt | ccccgcactc | accccggct | tcccgggcat | cttccctcca | 1560 |
| tccttgtacc | cccggccgcc | tctgctacct | cccacatcgc | tgctcaagag | cccctgaac | 1620 |
| cacacccagg | acgccaagct | ccccagtccc | ctggggaacc | cagccctgcc | cctggtctcc | 1680 |
| gccgtcagca | acagcagcca | gggcacgacg | gcagctgcgg | ggcccgagga | gaagttcgag | 1740 |
| agccgcctgg | aggactcctg | tgtggagaag | ctgaagacca | ggagcagcga | catgtcggac | 1800 |
| ggcagtgact | ttgaggacgt | caacaccacc | acgggaccg | acctggacac | gaccacgggg | 1860 |
| acgggctcgg | acctggacag | cgacgtggac | agcgaccctg | acaaggacaa | gggcaagggc | 1920 |
| aagtccgccg | agggccagcc | caagtttggg | gcggcttgg | cgccccggg | ggccccgaac | 1980 |
| agcgtggccg | aggtgcctgt | cttctattcc | cagcactcat | tcttcccgcc | acccgacgag | 2040 |
| cagctgctga | ctgcaacggg | cgccgccggg | gactccatca | aggccatcgc | atccattgcc | 2100 |

-continued

```
gagaagtact ttggccccgg cttcatgggg atgcaggaga agaagctggg ctcgctcccc    2160
taccactcgg cgttcccctt ccagttcctg cccaacttcc cccactccct ttacccct tc   2220
acggaccgag ccctcgccca caacttgctg gtcaaggccg agccaaagtc accccgggac    2280
gccctcaagg tgggcggccc cagtgccgag tgccccttt g atctcaccac caagcccaaa   2340
gacgtgaagc ccatcctgcc catgcccaag ggcccctcgg ccccc gcatc cggcgaggag   2400
cagccgctgg acctgagcat cggcagccgg gcccgtgcca gccaaaacgg cggcgggcgg    2460
gagccccgca agaaccacgt ctatgggaa cgcaagctgg gcgccggcga ggggctgccc     2520
caggtgtgcc cggcgcggat gccccagcag ccccc gctcc actacgccaa gccctcgccc   2580
ttcttcatgg accccatcta cagggtagaa aagcggaagg tcacagaccc cgtgggagcc    2640
ctgaaggaga agtacctgcg gccgtccccg ctgctcttcc accccagat gtcagccata     2700
gagaccatga cagagaagct ggagagcttt gcagccatga aggcggactc gggcagctcc    2760
ctgcagcccc tccccccacca cccccttcaac ttccggtccc cacccccaac gctctccgac  2820
cccatcctca ggaagggcaa ggagcgatac acgtgcaggt actgtgggaa gatcttcccc    2880
agatcagcca atctcaccag acacctgagg acgcacactg gggagcagcc gtacaggtgt    2940
aagtactgcg accgctcctt cagcatctct tcgaacctcc agcggcacgt ccggaacatc    3000
cacaacaagg agaagccttt caagtgccac ctgtgcaacc gctgcttcgg gcagcagacc    3060
aacctggacc ggcacctcaa gaagcacgag cacgagaacg caccagtgag ccagcacccc   3120
ggggtcctca cgaaccacct ggggaccagc gcgtcctctc ccacctcaga gtcggacaac    3180
cacgcacttt tagacgagaa agaagactct tatttctcgg aaatcagaaa ctttattgcc    3240
aatagtgaga tgaaccaagc atcaacgcga acagagaaac gggcggacat gcagatcgtg    3300
gacggcagtg cccagtgtcc aggcctagcc agtgagaagc aggaggacgt ggaggaggag    3360
gacgacgatg acctggagga ggacgatgag gacagcctgg ccgggaagtc gcaggatgac    3420
accgtgtccc ccgcacccga gccccaggcc gcctacgagg atgaggagga tgaggagcca    3480
gccgcctccc tggccgtggg cttt gaccac acccgaaggt gtgctgagga ccacgaaggc    3540
ggtctgttag ctttggagcc gatgccgact tttgggaagg gctggacct ccgcagagca     3600
gctgaggaag catttgaagt taaagatgtg cttaattcca ccttagattc tgaggcttta    3660
aaacatacac tgtgcaggca ggctaagaac caggcatatg caatgatgct gtcccttt cc   3720
gaagacactc ctctccacac ccctcccag ggttctctgg acgcttggtt gaaggtcact    3780
ggagccacgt cggagtctgg agcatttcac cccatcaacc acctctga               3828
```

<210> SEQ ID NO 2
<211> LENGTH: 1275
<212> TYPE: PRT
<213> ORGANISM: Homo sapiens

<400> SEQUENCE: 2

```
Met Arg Ser Lys Ala Arg Ala Arg Lys Leu Ala Lys Ser Asp Gly Asp
1               5                   10                  15

Val Val Asn Asn Met Tyr Glu Pro Asn Arg Asp Leu Leu Ala Ser His
                20                  25                  30

Ser Ala Glu Asp Glu Ala Glu Asp Ser Ala Met Ser Pro Ile Pro Val
            35                  40                  45

Gly Pro Pro Ser Pro Phe Pro Thr Ser Glu Asp Phe Thr Pro Lys Glu
        50                  55                  60
```

```
Gly Ser Pro Tyr Glu Ala Pro Val Tyr Ile Pro Glu Asp Ile Pro Ile
 65                  70                  75                  80

Pro Ala Asp Phe Glu Leu Arg Glu Ser Ser Ile Pro Gly Ala Gly Leu
                 85                  90                  95

Gly Val Trp Ala Lys Arg Lys Met Glu Ala Gly Glu Arg Leu Gly Pro
            100                 105                 110

Cys Val Val Val Pro Arg Ala Ala Lys Glu Thr Asp Phe Gly Trp
        115                 120                 125

Glu Gln Ile Leu Thr Asp Val Glu Val Ser Pro Gln Glu Gly Cys Ile
        130                 135                 140

Thr Lys Ile Ser Glu Asp Leu Gly Ser Glu Lys Phe Cys Val Asp Ala
145                 150                 155                 160

Asn Gln Ala Gly Ala Gly Ser Trp Leu Lys Tyr Ile Arg Val Ala Cys
                165                 170                 175

Ser Cys Asp Asp Gln Asn Leu Thr Met Cys Gln Ile Ser Glu Gln Ile
                180                 185                 190

Tyr Tyr Lys Val Ile Lys Asp Ile Glu Pro Gly Glu Glu Leu Leu Val
            195                 200                 205

His Val Lys Glu Gly Val Tyr Pro Leu Gly Thr Val Pro Pro Gly Leu
        210                 215                 220

Asp Glu Glu Pro Thr Phe Arg Cys Asp Glu Cys Asp Glu Leu Phe Gln
225                 230                 235                 240

Ser Lys Leu Asp Leu Arg Arg His Lys Lys Tyr Thr Cys Gly Ser Val
                245                 250                 255

Gly Ala Ala Leu Tyr Glu Gly Leu Ala Glu Glu Leu Lys Pro Glu Gly
            260                 265                 270

Leu Gly Gly Gly Ser Gly Gln Ala His Glu Cys Lys Asp Cys Glu Arg
        275                 280                 285

Met Phe Pro Asn Lys Tyr Ser Leu Glu Gln His Met Val Ile His Thr
        290                 295                 300

Glu Glu Arg Glu Tyr Lys Cys Asp Gln Cys Pro Lys Ala Phe Asn Trp
305                 310                 315                 320

Lys Ser Asn Leu Ile Arg His Gln Met Ser His Asp Ser Gly Lys Arg
                325                 330                 335

Phe Glu Cys Glu Asn Cys Val Lys Val Phe Thr Asp Pro Ser Asn Leu
            340                 345                 350

Gln Arg His Ile Arg Ser Gln His Val Gly Ala Arg Ala His Ala Cys
        355                 360                 365

Pro Asp Cys Gly Lys Thr Phe Ala Thr Ser Ser Gly Leu Lys Gln His
        370                 375                 380

Lys His Ile His Ser Thr Val Lys Pro Phe Ile Cys Glu Val Cys His
385                 390                 395                 400

Lys Ser Tyr Thr Gln Phe Ser Asn Leu Cys Arg His Lys Arg Met His
                405                 410                 415

Ala Asp Cys Arg Thr Gln Ile Lys Cys Lys Asp Cys Gly Gln Met Phe
            420                 425                 430

Ser Thr Thr Ser Ser Leu Asn Lys His Arg Arg Phe Cys Glu Gly Lys
        435                 440                 445

Asn His Tyr Thr Pro Gly Gly Ile Phe Ala Pro Gly Leu Pro Leu Thr
        450                 455                 460

Pro Ser Pro Met Met Asp Lys Ala Lys Pro Ser Pro Ser Leu Asn His
465                 470                 475                 480

Ala Ser Leu Gly Phe Asn Glu Tyr Phe Pro Ser Arg Pro His Pro Gly
```

-continued

```
                485                 490                 495
Ser Leu Pro Phe Ser Thr Ala Pro Pro Thr Phe Pro Ala Leu Thr Pro
                500                 505                 510
Gly Phe Pro Gly Ile Phe Pro Pro Ser Leu Tyr Pro Arg Pro Pro Leu
                515                 520                 525
Leu Pro Pro Thr Ser Leu Leu Lys Ser Pro Leu Asn His Thr Gln Asp
            530                 535                 540
Ala Lys Leu Pro Ser Pro Leu Gly Asn Pro Ala Leu Pro Leu Val Ser
545                 550                 555                 560
Ala Val Ser Asn Ser Ser Gln Gly Thr Thr Ala Ala Gly Pro Glu
                565                 570                 575
Glu Lys Phe Glu Ser Arg Leu Glu Asp Ser Cys Val Glu Lys Leu Lys
                580                 585                 590
Thr Arg Ser Ser Asp Met Ser Asp Gly Ser Asp Phe Glu Asp Val Asn
            595                 600                 605
Thr Thr Thr Gly Thr Asp Leu Asp Thr Thr Gly Thr Gly Ser Asp
            610                 615                 620
Leu Asp Ser Asp Val Asp Ser Asp Pro Asp Lys Asp Lys Gly Lys
625                 630                 635                 640
Lys Ser Ala Glu Gly Gln Pro Lys Phe Gly Gly Leu Ala Pro Pro
                    645                 650                 655
Gly Ala Pro Asn Ser Val Ala Glu Val Pro Val Phe Tyr Ser Gln His
                660                 665                 670
Ser Phe Phe Pro Pro Asp Glu Gln Leu Leu Thr Ala Thr Gly Ala
                675                 680                 685
Ala Gly Asp Ser Ile Lys Ala Ile Ala Ser Ile Ala Glu Lys Tyr Phe
            690                 695                 700
Gly Pro Gly Phe Met Gly Met Gln Glu Lys Lys Leu Gly Ser Leu Pro
705                 710                 715                 720
Tyr His Ser Ala Phe Pro Phe Gln Phe Leu Pro Asn Phe Pro His Ser
                    725                 730                 735
Leu Tyr Pro Phe Thr Asp Arg Ala Leu Ala His Asn Leu Leu Val Lys
                740                 745                 750
Ala Glu Pro Lys Ser Pro Arg Asp Ala Leu Lys Val Gly Gly Pro Ser
            755                 760                 765
Ala Glu Cys Pro Phe Asp Leu Thr Thr Lys Pro Lys Asp Val Lys Pro
            770                 775                 780
Ile Leu Pro Met Pro Lys Gly Pro Ser Ala Pro Ala Ser Gly Glu Glu
785                 790                 795                 800
Gln Pro Leu Asp Leu Ser Ile Gly Ser Arg Ala Arg Ala Ser Gln Asn
                    805                 810                 815
Gly Gly Gly Arg Glu Pro Arg Lys Asn His Val Tyr Gly Glu Arg Lys
                820                 825                 830
Leu Gly Ala Gly Glu Gly Leu Pro Gln Val Cys Pro Ala Arg Met Pro
            835                 840                 845
Gln Gln Pro Pro Leu His Tyr Ala Lys Pro Ser Pro Phe Phe Met Asp
    850                 855                 860
Pro Ile Tyr Arg Val Glu Lys Arg Lys Val Thr Asp Pro Val Gly Ala
865                 870                 875                 880
Leu Lys Glu Lys Tyr Leu Arg Pro Ser Pro Leu Leu Phe His Pro Gln
                    885                 890                 895
Met Ser Ala Ile Glu Thr Met Thr Glu Lys Leu Glu Ser Phe Ala Ala
                900                 905                 910
```

```
Met Lys Ala Asp Ser Gly Ser Ser Leu Gln Pro Leu His His Pro
        915                 920                 925

Phe Asn Phe Arg Ser Pro Pro Thr Leu Ser Asp Pro Ile Leu Arg
    930                 935                 940

Lys Gly Lys Glu Arg Tyr Thr Cys Arg Tyr Cys Gly Lys Ile Phe Pro
945                 950                 955                 960

Arg Ser Ala Asn Leu Thr Arg His Leu Arg Thr His Thr Gly Glu Gln
                965                 970                 975

Pro Tyr Arg Cys Lys Tyr Cys Asp Arg Ser Phe Ser Ile Ser Ser Asn
            980                 985                 990

Leu Gln Arg His Val Arg Asn Ile His Asn Lys Glu Lys Pro Phe Lys
        995                 1000                1005

Cys His Leu Cys Asn Arg Cys Phe Gly Gln Gln Thr Asn Leu Asp
    1010                1015                1020

Arg His Leu Lys Lys His Glu His Glu Asn Ala Pro Val Ser Gln
    1025                1030                1035

His Pro Gly Val Leu Thr Asn His Leu Gly Thr Ser Ala Ser Ser
    1040                1045                1050

Pro Thr Ser Glu Ser Asp Asn His Ala Leu Leu Asp Glu Lys Glu
    1055                1060                1065

Asp Ser Tyr Phe Ser Glu Ile Arg Asn Phe Ile Ala Asn Ser Glu
    1070                1075                1080

Met Asn Gln Ala Ser Thr Arg Thr Glu Lys Arg Ala Asp Met Gln
    1085                1090                1095

Ile Val Asp Gly Ser Ala Gln Cys Pro Gly Leu Ala Ser Glu Lys
    1100                1105                1110

Gln Glu Asp Val Glu Glu Asp Asp Asp Leu Glu Glu Asp
    1115                1120                1125

Asp Glu Asp Ser Leu Ala Gly Lys Ser Gln Asp Thr Val Ser
    1130                1135                1140

Pro Ala Pro Glu Pro Gln Ala Ala Tyr Glu Asp Glu Glu Asp Glu
    1145                1150                1155

Glu Pro Ala Ala Ser Leu Ala Val Gly Phe Asp His Thr Arg Arg
    1160                1165                1170

Cys Ala Glu Asp His Glu Gly Leu Leu Ala Leu Glu Pro Met
    1175                1180                1185

Pro Thr Phe Gly Lys Gly Leu Asp Leu Arg Arg Ala Ala Glu Glu
    1190                1195                1200

Ala Phe Glu Val Lys Asp Val Leu Asn Ser Thr Leu Asp Ser Glu
    1205                1210                1215

Ala Leu Lys His Thr Leu Cys Arg Gln Ala Lys Asn Gln Ala Tyr
    1220                1225                1230

Ala Met Met Leu Ser Leu Ser Glu Asp Thr Pro Leu His Thr Pro
    1235                1240                1245

Ser Gln Gly Ser Leu Asp Ala Trp Leu Lys Val Thr Gly Ala Thr
    1250                1255                1260

Ser Glu Ser Gly Ala Phe His Pro Ile Asn His Leu
    1265                1270                1275

<210> SEQ ID NO 3
<211> LENGTH: 3771
<212> TYPE: DNA
<213> ORGANISM: Homo sapiens
```

```
<400> SEQUENCE: 3
atgcgatcca aggcgagggc gaggaagcta gccaaaagtg acggtgacgt tgtaaataat      60
atgtatgagc ccaaccggga cctgctggcc agccacagcg cggaggacga ggccgaggac     120
agtgccatgt cgcccatccc cgtggggcca ccgtccccct tccccaccag cgaggacttc     180
acccccaagg agggctcgcc gtacgaggcc cctgtctaca ttcctgaaga cattccgatc     240
ccagcagact cgagctccg agagtcctcc atcccagggg ctggcctggg ggtctgggcc      300
aagaggaaga tggaagccgg ggagaggctg ggccctgcg tggtggtgcc ccgggcggcg      360
gcaaaggaga cagacttcgg atgggagcaa atactgacgg acgtggaagt gtcgccccag     420
gaaggctgca tcacaaagat ctccgaagac ctgggcagtg agaagttctg cgtggatgca     480
aatcaggcgg gggctggcag ctggctcaag tacatccgtg tggcgtgctc ctgcgatgac     540
cagaacctca ccatgtgtca gatcagtgag cagatttact ataaagtcat taggacatt     600 gagccaggtg aggagctgct ggtgcacgtg aaggaaggcg tctaccccct gggcacagtg     660
ccgcccggcc tggacgagga gcccacgttc cgctgtgacg agtgtgacga actcttccag     720
tccaagctgg acctgcggcg ccataagaag tacacgtgtg gctcagtggg ggctgcgctc     780
tacgagggcc tggctgagga gctcaagccc gagggccttg gcggtggcag cggccaagcc     840
cacgagtgca aggactgcga gcggatgttc cccaacaagt acagcctgga gcagcacatg     900
gtcatccaca cggaggagcg cgagtacaaa tgcgaccagt gtcccaaggc cttcaactgg     960
aagtccaacc tcatccgcca ccagatgtcc cacgacagcg gcaaacgctt cgaatgtgaa    1020
aactgcgtga aggtgttcac ggaccccagc aaccttcagc ggcacatccg ctcgcagcac    1080
gtgggcgctc gggccacgcc ctgccccgac tgcgggaaga ccttcgccac gtcctccggc    1140
ctcaagcagc acaagcatat ccacagcacg gtgaagcctt tcatatgtga ggtctgccac    1200
aagtcctaca cgcagttctc caacctgtgc cggcacaagc ggatgcacgc cgactgccgc    1260
acgcagatca agtgcaagga ctgtggccag atgttcagca ctacctcctc cctcaacaag    1320
caccggcgct tctgcgaggg caagaaccat tacacgccgg gcggcatctt tgccccgggc    1380
ctgcccttga ccccccagcc catgatggac aaggcaaaac cctcccccag cctcaatcac    1440
gccagcctgg gcttcaacga gtactttccc tccaggccgc accgggggag cctgcccttc    1500
tccacggcgc ctcccacgtt ccccgcactc accccggct tcccgggcat cttccctcca    1560
tccttgtacc ccggccgcc tctgctacct cccacatcgc tgctcaagag cccctgaac     1620 cacacccagg acgccaagct ccccagtccc ctggggaacc cagccctgcc cctggtctcc    1680
gccgtcagca acagcagcca gggcacgacg gcagctgcgg ggccgaggg aagttcgag     1740 agccgcctgg aggactcctg tgtggagaag ctgaagacca ggagcagcga catgtcggac    1800
ggcagtgact ttgaggacgt caacaccacc acggggaccg acctggacac gaccacgggg    1860
acgggctcgg acctggacag cgacgtggac agcgaccctg acaaggacaa gggcaagggc    1920
aagtccgccg agggccagcc caagtttggg ggcggcttgg cgccccgggg ggccccgaac    1980
agcgtggccg aggtgcctgt cttctattcc cagcactcat tcttcccgcc acccgacgag    2040
cagctgctga ctgcaacggg cgccgccggg gactccatca aggccatcgc atccattgcc    2100
gagaagtact ttggccccgg cttcatgggg atgcaggaga agaagctggg ctcgctcccc    2160
taccactcgg cgttcccctt ccagttcctg cccaacttcc ccactccct ttaccccttc     2220 acggaccgag ccctcgccca aacttgctg gtcaaggccg agccaaagtc accccgggac    2280
gccctcaagg tgggcggccc cagtgccgag tgcccctttg atctcaccac caagcccaaa    2340
```

```
gacgtgaagc ccatcctgcc catgcccaag ggcccctcgg cccccgcatc cggcgaggag      2400
cagccgctgg acctgagcat cggcagccgg cccgtgcca gccaaaacgg cggcgggcgg      2460
gagccccgca agaaccacgt ctatggggaa cgcaagctgg gcgccggcga ggggctgccc      2520
caggtgtgcc cggcgcggat gccccagcag cccccgctcc actacgccaa gccctcgccc      2580
ttcttcatgg accccatcta cagggtagaa aagcggaagg tcacagaccc cgtgggagcc      2640
ctgaaggaga agtacctgcg gccgtccccg ctgctcttcc accccagat gtcagccata      2700 gagaccatga cagagaagct ggagagcttt gcagccatga aggcggactc gggcagctcc      2760
ctgcagcccc tcccccacca cccccttcaac ttccggtccc caccccaac gctctccgac      2820 cccatcctca ggaagggcaa ggagcgatac acgtgcaggt actgtgggaa gatcttcccc      2880
agatcagcca atctcaccag acacctgagg acgcacactg gggagcagcc gtacaggtgt      2940
aagtactgcg accgctcctt cagcatctct tcgaacctcc agcggcacgt ccggaacatc      3000
cacaacaagg agaagccttt caagtgccac ctgtgcaacc gctgcttcgg gcagcagacc      3060
aacctggacc ggcacctcaa gaagcacgag cacgagaacg caccagtgag ccagcacccc      3120
ggggtcctca cgaaccacct ggggaccagc gcgtcctctc ccacctcaga gtcggacaac      3180
cacgcacttt tagacgagaa agaagactct tatttctcgg aaatcagaaa ctttattgcc      3240
aatagtgaga tgaaccaagc atcaacgcga acagagaaac gggcggacat gcagatcgtg      3300
gacggcagtg cccagtgtcc aggcctagcc agtgagaagc aggaggacgt ggaggaggag      3360
gacgacgatg acctggagga ggacgatgag gacagcctgg ccgggaagtc gcaggatgac      3420
accgtgtccc ccgcacccga gccccaggcc gcctacgagg atgaggagga tgaggagcca      3480
gccgcctccc tggccgtggg ctttgaccac acccgaaggt gtgctgagga ccacgaaggc      3540
ggtctgttag ctttggagcc gatgccgact tttgggaagg ggctggacct ccgcagagca      3600
gctgaggaag catttgaagt taaagatgtg cttaattcca ccttagattc tgaggcttta      3660
aaacatacac tgtgcaggca ggctaagaac cagggttctc tggacgcttg gttgaaggtc      3720
actggagcca cgtcggagtc tggagcattt caccccatca accacctctg a              3771
```

<210> SEQ ID NO 4
<211> LENGTH: 1256
<212> TYPE: PRT
<213> ORGANISM: Homo sapiens

<400> SEQUENCE: 4

Met Arg Ser Lys Ala Arg Ala Arg Lys Leu Ala Lys Ser Asp Gly Asp
1               5                   10                  15

Val Val Asn Asn Met Tyr Glu Pro Asn Arg Asp Leu Leu Ala Ser His
            20                  25                  30

Ser Ala Glu Asp Glu Ala Glu Asp Ser Ala Met Ser Pro Ile Pro Val
        35                  40                  45

Gly Pro Pro Ser Pro Phe Pro Thr Ser Glu Asp Phe Thr Pro Lys Glu
    50                  55                  60

Gly Ser Pro Tyr Glu Ala Pro Val Tyr Ile Pro Glu Asp Ile Pro Ile
65                  70                  75                  80

Pro Ala Asp Phe Glu Leu Arg Glu Ser Ser Ile Pro Gly Ala Gly Leu
                85                  90                  95

Gly Val Trp Ala Lys Arg Lys Met Glu Ala Gly Glu Arg Leu Gly Pro
            100                 105                 110

Cys Val Val Val Pro Arg Ala Ala Ala Lys Glu Thr Asp Phe Gly Trp

```
                115                 120                 125
Glu Gln Ile Leu Thr Asp Val Glu Val Ser Pro Gln Glu Gly Cys Ile
            130                 135                 140
Thr Lys Ile Ser Glu Asp Leu Gly Ser Glu Lys Phe Cys Val Asp Ala
145                 150                 155                 160
Asn Gln Ala Gly Ala Gly Ser Trp Leu Lys Tyr Ile Arg Val Ala Cys
                165                 170                 175
Ser Cys Asp Asp Gln Asn Leu Thr Met Cys Gln Ile Ser Glu Gln Ile
            180                 185                 190
Tyr Tyr Lys Val Ile Lys Asp Ile Glu Pro Gly Glu Glu Leu Leu Val
                195                 200                 205
His Val Lys Glu Gly Val Tyr Pro Leu Gly Thr Val Pro Pro Gly Leu
            210                 215                 220
Asp Glu Glu Pro Thr Phe Arg Cys Asp Glu Cys Asp Glu Leu Phe Gln
225                 230                 235                 240
Ser Lys Leu Asp Leu Arg Arg His Lys Lys Tyr Thr Cys Gly Ser Val
                245                 250                 255
Gly Ala Ala Leu Tyr Glu Gly Leu Ala Glu Glu Leu Lys Pro Glu Gly
            260                 265                 270
Leu Gly Gly Gly Ser Gly Gln Ala His Glu Cys Lys Asp Cys Glu Arg
                275                 280                 285
Met Phe Pro Asn Lys Tyr Ser Leu Glu Gln His Met Val Ile His Thr
            290                 295                 300
Glu Glu Arg Glu Tyr Lys Cys Asp Gln Cys Pro Lys Ala Phe Asn Trp
305                 310                 315                 320
Lys Ser Asn Leu Ile Arg His Gln Met Ser His Asp Ser Gly Lys Arg
                325                 330                 335
Phe Glu Cys Glu Asn Cys Val Lys Val Phe Thr Asp Pro Ser Asn Leu
            340                 345                 350
Gln Arg His Ile Arg Ser Gln His Val Gly Ala Arg Ala His Ala Cys
                355                 360                 365
Pro Asp Cys Gly Lys Thr Phe Ala Thr Ser Ser Gly Leu Lys Gln His
            370                 375                 380
Lys His Ile His Ser Thr Val Lys Pro Phe Ile Cys Glu Val Cys His
385                 390                 395                 400
Lys Ser Tyr Thr Gln Phe Ser Asn Leu Cys Arg His Lys Arg Met His
                405                 410                 415
Ala Asp Cys Arg Thr Gln Ile Lys Cys Lys Asp Cys Gly Gln Met Phe
            420                 425                 430
Ser Thr Thr Ser Ser Leu Asn Lys His Arg Arg Phe Cys Glu Gly Lys
            435                 440                 445
Asn His Tyr Thr Pro Gly Gly Ile Phe Ala Pro Gly Leu Pro Leu Thr
            450                 455                 460
Pro Ser Pro Met Met Asp Lys Ala Lys Pro Ser Pro Ser Leu Asn His
465                 470                 475                 480
Ala Ser Leu Gly Phe Asn Glu Tyr Phe Pro Ser Arg Pro His Pro Gly
                485                 490                 495
Ser Leu Pro Phe Ser Thr Ala Pro Pro Thr Phe Pro Ala Leu Thr Pro
            500                 505                 510
Gly Phe Pro Gly Ile Phe Pro Pro Ser Leu Tyr Pro Arg Pro Pro Leu
            515                 520                 525
Leu Pro Pro Thr Ser Leu Leu Lys Ser Pro Leu Asn His Thr Gln Asp
530                 535                 540
```

```
Ala Lys Leu Pro Ser Pro Leu Gly Asn Pro Ala Leu Pro Leu Val Ser
545                 550                 555                 560

Ala Val Ser Asn Ser Ser Gln Gly Thr Thr Ala Ala Gly Pro Glu
            565                 570                 575

Glu Lys Phe Glu Ser Arg Leu Glu Asp Ser Cys Val Glu Lys Leu Lys
        580                 585                 590

Thr Arg Ser Ser Asp Met Ser Asp Gly Ser Asp Phe Glu Asp Val Asn
            595                 600                 605

Thr Thr Thr Gly Thr Asp Leu Asp Thr Thr Thr Gly Thr Gly Ser Asp
        610                 615                 620

Leu Asp Ser Asp Val Asp Ser Asp Pro Asp Lys Asp Lys Gly Lys Gly
625                 630                 635                 640

Lys Ser Ala Glu Gly Gln Pro Lys Phe Gly Gly Leu Ala Pro Pro
            645                 650                 655

Gly Ala Pro Asn Ser Val Ala Glu Val Pro Val Phe Tyr Ser Gln His
            660                 665                 670

Ser Phe Phe Pro Pro Asp Glu Gln Leu Leu Thr Ala Thr Gly Ala
        675                 680                 685

Ala Gly Asp Ser Ile Lys Ala Ile Ala Ser Ile Ala Glu Lys Tyr Phe
690                 695                 700

Gly Pro Gly Phe Met Gly Met Gln Glu Lys Lys Leu Gly Ser Leu Pro
705                 710                 715                 720

Tyr His Ser Ala Phe Pro Phe Gln Phe Leu Pro Asn Phe Pro His Ser
            725                 730                 735

Leu Tyr Pro Phe Thr Asp Arg Ala Leu Ala His Asn Leu Leu Val Lys
            740                 745                 750

Ala Glu Pro Lys Ser Pro Arg Asp Ala Leu Lys Val Gly Gly Pro Ser
            755                 760                 765

Ala Glu Cys Pro Phe Asp Leu Thr Thr Lys Pro Lys Asp Val Lys Pro
            770                 775                 780

Ile Leu Pro Met Pro Lys Gly Pro Ser Ala Pro Ala Ser Gly Glu Glu
785                 790                 795                 800

Gln Pro Leu Asp Leu Ser Ile Gly Ser Arg Ala Arg Ala Ser Gln Asn
            805                 810                 815

Gly Gly Gly Arg Glu Pro Arg Lys Asn His Val Tyr Gly Glu Arg Lys
            820                 825                 830

Leu Gly Ala Gly Glu Gly Leu Pro Gln Val Cys Pro Ala Arg Met Pro
            835                 840                 845

Gln Gln Pro Pro Leu His Tyr Ala Lys Pro Ser Pro Phe Phe Met Asp
            850                 855                 860

Pro Ile Tyr Arg Val Glu Lys Arg Lys Val Thr Asp Pro Val Gly Ala
865                 870                 875                 880

Leu Lys Glu Lys Tyr Leu Arg Pro Ser Pro Leu Leu Phe His Pro Gln
            885                 890                 895

Met Ser Ala Ile Glu Thr Met Thr Glu Lys Leu Glu Ser Phe Ala Ala
            900                 905                 910

Met Lys Ala Asp Ser Gly Ser Ser Leu Gln Pro Leu Pro His His Pro
            915                 920                 925

Phe Asn Phe Arg Ser Pro Pro Thr Leu Ser Asp Pro Ile Leu Arg
            930                 935                 940

Lys Gly Lys Glu Arg Tyr Thr Cys Arg Tyr Cys Gly Lys Ile Phe Pro
945                 950                 955                 960
```

Arg Ser Ala Asn Leu Thr Arg His Leu Arg Thr His Thr Gly Glu Gln
                965                 970                 975

Pro Tyr Arg Cys Lys Tyr Cys Asp Arg Ser Phe Ser Ile Ser Ser Asn
            980                 985                 990

Leu Gln Arg His Val Arg Asn Ile His Asn Lys Glu Lys Pro Phe Lys
        995                 1000                1005

Cys His Leu Cys Asn Arg Cys Phe Gly Gln Gln Thr Asn Leu Asp
    1010                1015                1020

Arg His Leu Lys Lys His Glu His Glu Asn Ala Pro Val Ser Gln
    1025                1030                1035

His Pro Gly Val Leu Thr Asn His Leu Gly Thr Ser Ala Ser Ser
    1040                1045                1050

Pro Thr Ser Glu Ser Asp Asn His Ala Leu Leu Asp Glu Lys Glu
    1055                1060                1065

Asp Ser Tyr Phe Ser Glu Ile Arg Asn Phe Ile Ala Asn Ser Glu
    1070                1075                1080

Met Asn Gln Ala Ser Thr Arg Thr Glu Lys Arg Ala Asp Met Gln
    1085                1090                1095

Ile Val Asp Gly Ser Ala Gln Cys Pro Gly Leu Ala Ser Glu Lys
    1100                1105                1110

Gln Glu Asp Val Glu Glu Glu Asp Asp Asp Leu Glu Glu Asp
    1115                1120                1125

Asp Glu Asp Ser Leu Ala Gly Lys Ser Gln Asp Asp Thr Val Ser
    1130                1135                1140

Pro Ala Pro Glu Pro Gln Ala Ala Tyr Glu Asp Glu Asp Glu
    1145                1150                1155

Glu Pro Ala Ala Ser Leu Ala Val Gly Phe Asp His Thr Arg Arg
    1160                1165                1170

Cys Ala Glu Asp His Glu Gly Gly Leu Leu Ala Leu Glu Pro Met
    1175                1180                1185

Pro Thr Phe Gly Lys Gly Leu Asp Leu Arg Arg Ala Ala Glu Glu
    1190                1195                1200

Ala Phe Glu Val Lys Asp Val Leu Asn Ser Thr Leu Asp Ser Glu
    1205                1210                1215

Ala Leu Lys His Thr Leu Cys Arg Gln Ala Lys Asn Gln Gly Ser
    1220                1225                1230

Leu Asp Ala Trp Leu Lys Val Thr Gly Ala Thr Ser Glu Ser Gly
    1235                1240                1245

Ala Phe His Pro Ile Asn His Leu
    1250                1255

<210> SEQ ID NO 5
<211> LENGTH: 3828
<212> TYPE: DNA
<213> ORGANISM: Mus musculus

<400> SEQUENCE: 5
atgcgatcca aggcgagggc gaggaagcta gccaaaagtg acggtgacgt tgtaaataat     60
atgtatgaac ctgaccccga cctgctggcc ggccagagtg ccgaggagga gaccgaagac    120
ggcatcctgt cccccatccc catggggcca ccgtccccct tccccaccag cgaggacttc    180
actcccaagg agggctcgcc ctatgaggct cctgtctaca ttcctgaaga cattccaatc    240
ccaccagact tcgagctacg agagtcctcc ataccaggag ctggcctggg gatctgggcc    300
aagcggaaga tggaaatcgg ggagaggttt ggcccctacg tggtgacgcc ccgggccgca    360

```
ctgaaggagg ccgactttgg atgggagatg ctgacggata cagaggtgtc atcccaggag    420
agctgcatca aaaagcagat ctctgaagac ttgggtagcg agaagttctg cgtggatgcc    480
aatcaggcgg ggtctggcag ctggctcaag tacatccgtg tagcgtgttc ctgtgatgac    540
caaaacctcg ccatgtgtca gatcaacgaa cagatttact ataaagtcat taaggacatc    600
gagcctggag aggaactgtt ggtgcatgtg aaagaaggtg cctactcctt gggtgtcatg    660 gccccccagct tggatgagga ccccacattc cgctgtgatg agtgtgatga gctcttccag    720
tgcaggctgg acctgaggcg ccacaagaag tacgcgtgca gctctgcagg agcccagctc    780
tacgagggcc taggggagga actcaagccc gagggccttg gcgtgggcag cgacgggcaa    840
gcgcatgagt gcaaggattg cgagcggatg ttccccaaca agtacagctt ggagcaacac    900
atgatcgtcc acacgaaga gcgtgagtac aaatgtgacc agtgtcccaa ggccttcaac    960
tggaagtcca acctcatccg ccaccagatg tctcacgaca gtggcaagcg cttcgaatgt   1020
gaaaactgtg tcaaggtgtt cacggacccc agcaacctcc agcgtcacat ccgctcacag   1080
catgtcggtg cccgggccca tgcctgccct gactgtggca agaccttcgc cacatcctct   1140
ggcctcaaac agcacaagca tatccacagc acggtgaagc cattcatatg cgaggtctgc   1200
cacaagtcct acacgcagtt ctccaacctg tgccggcaca agcggatgca cgccgactgc   1260
aggacgcaga tcaagtgcaa ggactgtggg cagatgttca gcactacctc ctccctcaac   1320
aagcatcgga gattctgcga gggcaagaac cattacacgc tggcagcat cttcaccca   1380 ggcctgccct tgaccccag ccccatgatg gacaagacaa accctcccc gaccctcaac   1440 cacgggggcc taggcttcag cgagtacttc ccctccagac ctcatcctgg gagcctgccc   1500
ttctcggctg ctcctccggc cttccccgca ctcactccgg gcttcccggg catctttcct   1560
ccatccctgt acccacgacc acctctgcta cctcccacgc cgctgctcaa gagccccctg   1620
aaccacgcgc aggacgccaa gctacccagc ccgctgggaa acccagccct gccccttgtc   1680
tccgcggtca gcaatagcag ccagggtgcc acagcggcca ccgggtcaga ggagaaattt   1740
gatggccgct tggaagacgc atatgcggag aaggtcaaaa ataggagccc tgacatgtcg   1800
gatggcagtg actttgagga tatcaacacc acgaccggga cagacttgga cactaccacg   1860
ggcacggggt cagacctgga cagcgacctg gacagtgaca gagacaaagg caaggacaag   1920
gggaagccag tggagagcaa acctgagttt gggggtgcat ctgtgccccc tggggccatg   1980
aacagtgtgg ccgaggtacc ggccttctac tcacagcatt ccttcttccc gccacccgag   2040
gaacagctgc tgacgcctc gggagctgcc ggcgactcca tcaaggccat cgcgtccatc   2100
gcggagaaat acttcggtcc tggcttcatg agcatgcagg agaagaagct gggctcacta   2160
ccctaccact ccgtgttccc cttccagttc ctgcctaact ttcccacact cctctacccc   2220
tttacggacc gagccctcgc ccacaacttg ctggtcaagg ctgagccaaa gtcaccccgg   2280
gatgccctca aggtgggcgg ccccagtgcg gagtgcccct cgacctcac caccaaacca   2340 aaagaggcca acccgcccct gctcgcaccc aaggtccccc tcatccctc atctggcgag   2400 gaacagccac tggacctgag catcggcagc agggccaggg caagccagaa cggaggtggc   2460
cgtgagccgg gaagaaccaa cgtctacggt gaacggaagc cggggtcag cgaggggctg   2520 cctaaggtgt gcccagcaca gctgccccag cagccctcct tgcattatgc taagccttca   2580
ccgttcttca tggatcccat ctacagggta gaaaagcgga aggtggcaga ccctgtggga   2640
gtcctgaaag agaagtacct gcggccgtcc ccacttctgt tccaccccca gatgtcagcc   2700
```

```
atagaaacca tgacggagaa gctggagagc tttgcagcca tgaaggccga ctcaggcagc    2760
tccctgcagc ccctgcctca ccacccgttc aacttccgct ccccaccccc aacgctctcg    2820
gatcccatcc tcaggaaggg gaaggagaga tacacgtgca ggtactgtgg caagatcttc    2880
cccagatctg caaatctcac aagacatctg aggacacaca caggggagca gccatacagg    2940
tgcaagtact gtgaccggtc attcagcatc tcctccaacc tccagcggca cgtgaggaac    3000
atccacaaca aagagaagcc gttcaagtgc catctgtgca accgctgctt cgggcagcag    3060
accaacctag accggcacct gaagaagcac gaacacgagg gcgcaccagt gagccagcac    3120 tccgggtgc tcacgaacca cctgggcacc agcgcctcct cccccacctc cgagtcggac    3180
aaccatgcac ttttagatga aggaagat tcttacttct ccgagatccg aaacttcatc    3240
gccaacagcg agatgaacca ggcatccact cgaatggaca aacggcctga gatccaagac    3300
ctggacagca acccaccgtg tccaggctca gccagtgcaa agccagagga cgtagaggag    3360
gaggaagagg aggagctgga ggaagaggat gatgacagct tagccgggaa gtcacaggag    3420
gacacggtgt cccccacacc tgagcccaa ggagtctatg aagatgaaga ggatgaggaa    3480
ccacccagcc tgaccatggg cttttgaccat acccggaggt gtgttgagga gcgaggaggc    3540
ggcctgttag cttttggagcc gacgccgacc tttgggaagg ggctggatct ccgcagagca    3600
gctgaggaag catttgaagt taaagatgtg cttaattcca ccttagattc tgaggtttta    3660
aaacaaaccc tgtacaggca ggctaagaac caggcatatg caatgatgct gtccctctct    3720
gaagacactc ctctccacgc cccctcccag agctcactgg atgcttggtt gaacatcaca    3780
ggaccctcgt cagagtccgg agcctttaac cccatcaacc acctctga                 3828

<210> SEQ ID NO 6
<211> LENGTH: 1275
<212> TYPE: PRT
<213> ORGANISM: Mus musculus

<400> SEQUENCE: 6

Met Arg Ser Lys Ala Arg Ala Arg Lys Leu Ala Lys Ser Asp Gly Asp
1               5                   10                  15

Val Val Asn Asn Met Tyr Glu Pro Asp Pro Asp Leu Leu Ala Gly Gln
            20                  25                  30

Ser Ala Glu Glu Glu Thr Glu Asp Gly Ile Leu Ser Pro Ile Pro Met
        35                  40                  45

Gly Pro Pro Ser Pro Phe Pro Thr Ser Glu Asp Phe Thr Pro Lys Glu
    50                  55                  60

Gly Ser Pro Tyr Glu Ala Pro Val Tyr Ile Pro Glu Asp Ile Pro Ile
65                  70                  75                  80

Pro Pro Asp Phe Glu Leu Arg Glu Ser Ser Ile Pro Gly Ala Gly Leu
                85                  90                  95

Gly Ile Trp Ala Lys Arg Lys Met Glu Ile Gly Glu Arg Phe Gly Pro
            100                 105                 110

Tyr Val Val Thr Pro Arg Ala Ala Leu Lys Glu Ala Asp Phe Gly Trp
        115                 120                 125

Glu Met Leu Thr Asp Thr Glu Val Ser Ser Gln Glu Ser Cys Ile Lys
    130                 135                 140

Lys Gln Ile Ser Glu Asp Leu Gly Ser Glu Lys Phe Cys Val Asp Ala
145                 150                 155                 160

Asn Gln Ala Gly Ser Gly Ser Trp Leu Lys Tyr Ile Arg Val Ala Cys
                165                 170                 175
```

```
Ser Cys Asp Asp Gln Asn Leu Ala Met Cys Gln Ile Asn Glu Gln Ile
            180                 185                 190

Tyr Tyr Lys Val Ile Lys Asp Ile Glu Pro Gly Glu Glu Leu Leu Val
        195                 200                 205

His Val Lys Glu Gly Ala Tyr Ser Leu Gly Val Met Ala Pro Ser Leu
    210                 215                 220

Asp Glu Asp Pro Thr Phe Arg Cys Asp Glu Cys Asp Glu Leu Phe Gln
225                 230                 235                 240

Cys Arg Leu Asp Leu Arg Arg His Lys Lys Tyr Ala Cys Ser Ser Ala
                245                 250                 255

Gly Ala Gln Leu Tyr Glu Gly Leu Gly Glu Glu Leu Lys Pro Glu Gly
            260                 265                 270

Leu Gly Val Gly Ser Asp Gly Gln Ala His Glu Cys Lys Asp Cys Glu
        275                 280                 285

Arg Met Phe Pro Asn Lys Tyr Ser Leu Glu Gln His Met Ile Val His
    290                 295                 300

Thr Glu Glu Arg Glu Tyr Lys Cys Asp Gln Cys Pro Lys Ala Phe Asn
305                 310                 315                 320

Trp Lys Ser Asn Leu Ile Arg His Gln Met Ser His Asp Ser Gly Lys
                325                 330                 335

Arg Phe Glu Cys Glu Asn Cys Val Lys Val Phe Thr Asp Pro Ser Asn
            340                 345                 350

Leu Gln Arg His Ile Arg Ser Gln His Val Gly Ala Arg Ala His Ala
        355                 360                 365

Cys Pro Asp Cys Gly Lys Thr Phe Ala Thr Ser Ser Gly Leu Lys Gln
370                 375                 380

His Lys His Ile His Ser Thr Val Lys Pro Phe Ile Cys Glu Val Cys
385                 390                 395                 400

His Lys Ser Tyr Thr Gln Phe Ser Asn Leu Cys Arg His Lys Arg Met
                405                 410                 415

His Ala Asp Cys Arg Thr Gln Ile Lys Cys Lys Asp Cys Gly Gln Met
            420                 425                 430

Phe Ser Thr Thr Ser Ser Leu Asn Lys His Arg Arg Phe Cys Glu Gly
        435                 440                 445

Lys Asn His Tyr Thr Pro Gly Ser Ile Phe Thr Pro Gly Leu Pro Leu
450                 455                 460

Thr Pro Ser Pro Met Met Asp Lys Thr Lys Pro Ser Pro Thr Leu Asn
465                 470                 475                 480

His Gly Gly Leu Gly Phe Ser Glu Tyr Phe Pro Ser Arg Pro His Pro
                485                 490                 495

Gly Ser Leu Pro Phe Ser Ala Ala Pro Pro Ala Phe Pro Ala Leu Thr
            500                 505                 510

Pro Gly Phe Pro Gly Ile Phe Pro Pro Ser Leu Tyr Pro Arg Pro Pro
        515                 520                 525

Leu Leu Pro Pro Thr Pro Leu Leu Lys Ser Pro Leu Asn His Ala Gln
530                 535                 540

Asp Ala Lys Leu Pro Ser Pro Leu Gly Asn Pro Ala Leu Pro Leu Val
545                 550                 555                 560

Ser Ala Val Ser Asn Ser Ser Gln Gly Ala Thr Ala Thr Gly Ser
                565                 570                 575

Glu Glu Lys Phe Asp Gly Arg Leu Glu Asp Ala Tyr Ala Glu Lys Val
            580                 585                 590

Lys Asn Arg Ser Pro Asp Met Ser Asp Gly Ser Asp Phe Glu Asp Ile
```

```
                    595                 600                 605
Asn Thr Thr Thr Gly Thr Asp Leu Asp Thr Thr Thr Gly Thr Gly Ser
610                 615                 620

Asp Leu Asp Ser Asp Leu Asp Ser Asp Arg Asp Lys Gly Lys Asp Lys
625                 630                 635                 640

Gly Lys Pro Val Glu Ser Lys Pro Glu Phe Gly Gly Ala Ser Val Pro
                645                 650                 655

Pro Gly Ala Met Asn Ser Val Ala Glu Val Pro Ala Phe Tyr Ser Gln
                660                 665                 670

His Ser Phe Phe Pro Pro Glu Glu Gln Leu Leu Thr Ala Ser Gly
                675                 680                 685

Ala Ala Gly Asp Ser Ile Lys Ala Ile Ala Ser Ile Ala Glu Lys Tyr
690                 695                 700

Phe Gly Pro Gly Phe Met Ser Met Gln Glu Lys Lys Leu Gly Ser Leu
705                 710                 715                 720

Pro Tyr His Ser Val Phe Pro Phe Gln Phe Leu Pro Asn Phe Pro His
                725                 730                 735

Ser Leu Tyr Pro Phe Thr Asp Arg Ala Leu Ala His Asn Leu Leu Val
                740                 745                 750

Lys Ala Glu Pro Lys Ser Pro Arg Asp Ala Leu Lys Val Gly Gly Pro
                755                 760                 765

Ser Ala Glu Cys Pro Phe Asp Leu Thr Thr Lys Pro Lys Glu Ala Lys
770                 775                 780

Pro Ala Leu Leu Ala Pro Lys Val Pro Leu Ile Pro Ser Ser Gly Glu
785                 790                 795                 800

Glu Gln Pro Leu Asp Leu Ser Ile Gly Ser Arg Ala Arg Ala Ser Gln
                805                 810                 815

Asn Gly Gly Gly Arg Glu Pro Arg Lys Asn His Val Tyr Gly Glu Arg
                820                 825                 830

Lys Pro Gly Val Ser Glu Gly Leu Pro Lys Val Cys Pro Ala Gln Leu
                835                 840                 845

Pro Gln Gln Pro Ser Leu His Tyr Ala Lys Pro Ser Pro Phe Phe Met
850                 855                 860

Asp Pro Ile Tyr Arg Val Glu Lys Arg Lys Val Ala Asp Pro Val Gly
865                 870                 875                 880

Val Leu Lys Glu Lys Tyr Leu Arg Pro Ser Pro Leu Leu Phe His Pro
                885                 890                 895

Gln Met Ser Ala Ile Glu Thr Met Thr Glu Lys Leu Glu Ser Phe Ala
                900                 905                 910

Ala Met Lys Ala Asp Ser Gly Ser Ser Leu Gln Pro Leu Pro His His
                915                 920                 925

Pro Phe Asn Phe Arg Ser Pro Pro Thr Leu Ser Asp Pro Ile Leu
                935                 940

Arg Lys Gly Lys Glu Arg Tyr Thr Cys Arg Tyr Cys Gly Lys Ile Phe
945                 950                 955                 960

Pro Arg Ser Ala Asn Leu Thr Arg His Leu Arg Thr His Thr Gly Glu
                965                 970                 975

Gln Pro Tyr Arg Cys Lys Tyr Cys Asp Arg Ser Phe Ser Ile Ser Ser
                980                 985                 990

Asn Leu Gln Arg His Val Arg Asn Ile His Asn Lys Glu Lys Pro Phe
                995                 1000                1005

Lys Cys His Leu Cys Asn Arg Cys Phe Gly Gln Gln Thr Asn Leu
    1010                1015                1020
```

| Asp | Arg | His | Leu | Lys | Lys | His | Glu | His | Glu | Gly | Ala | Pro | Val | Ser |
|---|---|---|---|---|---|---|---|---|---|---|---|---|---|---|
| 1025 | | | | | 1030 | | | | | 1035 | | | | |

| Gln | His | Ser | Gly | Val | Leu | Thr | Asn | His | Leu | Gly | Thr | Ser | Ala | Ser |
|---|---|---|---|---|---|---|---|---|---|---|---|---|---|---|
| 1040 | | | | | 1045 | | | | | 1050 | | | | |

| Ser | Pro | Thr | Ser | Glu | Ser | Asp | Asn | His | Ala | Leu | Leu | Asp | Glu | Lys |
|---|---|---|---|---|---|---|---|---|---|---|---|---|---|---|
| 1055 | | | | | 1060 | | | | | 1065 | | | | |

| Glu | Asp | Ser | Tyr | Phe | Ser | Glu | Ile | Arg | Asn | Phe | Ile | Ala | Asn | Ser |
|---|---|---|---|---|---|---|---|---|---|---|---|---|---|---|
| 1070 | | | | | 1075 | | | | | 1080 | | | | |

| Glu | Met | Asn | Gln | Ala | Ser | Thr | Arg | Met | Asp | Lys | Arg | Pro | Glu | Ile |
|---|---|---|---|---|---|---|---|---|---|---|---|---|---|---|
| 1085 | | | | | 1090 | | | | | 1095 | | | | |

| Gln | Asp | Leu | Asp | Ser | Asn | Pro | Pro | Cys | Pro | Gly | Ser | Ala | Ser | Ala |
|---|---|---|---|---|---|---|---|---|---|---|---|---|---|---|
| 1100 | | | | | 1105 | | | | | 1110 | | | | |

| Lys | Pro | Glu | Asp | Val | Glu | Glu | Glu | Glu | Glu | Glu | Leu | Glu | Glu | |
|---|---|---|---|---|---|---|---|---|---|---|---|---|---|---|
| 1115 | | | | | 1120 | | | | | 1125 | | | | |

| Glu | Asp | Asp | Asp | Ser | Leu | Ala | Gly | Lys | Ser | Gln | Glu | Asp | Thr | Val |
|---|---|---|---|---|---|---|---|---|---|---|---|---|---|---|
| 1130 | | | | | 1135 | | | | | 1140 | | | | |

| Ser | Pro | Thr | Pro | Glu | Pro | Gln | Gly | Val | Tyr | Glu | Asp | Glu | Glu | Asp |
|---|---|---|---|---|---|---|---|---|---|---|---|---|---|---|
| 1145 | | | | | 1150 | | | | | 1155 | | | | |

| Glu | Glu | Pro | Pro | Ser | Leu | Thr | Met | Gly | Phe | Asp | His | Thr | Arg | Arg |
|---|---|---|---|---|---|---|---|---|---|---|---|---|---|---|
| 1160 | | | | | 1165 | | | | | 1170 | | | | |

| Cys | Val | Glu | Glu | Arg | Gly | Gly | Gly | Leu | Leu | Ala | Leu | Glu | Pro | Thr |
|---|---|---|---|---|---|---|---|---|---|---|---|---|---|---|
| 1175 | | | | | 1180 | | | | | 1185 | | | | |

| Pro | Thr | Phe | Gly | Lys | Gly | Leu | Asp | Leu | Arg | Arg | Ala | Ala | Glu | Glu |
|---|---|---|---|---|---|---|---|---|---|---|---|---|---|---|
| 1190 | | | | | 1195 | | | | | 1200 | | | | |

| Ala | Phe | Glu | Val | Lys | Asp | Val | Leu | Asn | Ser | Thr | Leu | Asp | Ser | Glu |
|---|---|---|---|---|---|---|---|---|---|---|---|---|---|---|
| 1205 | | | | | 1210 | | | | | 1215 | | | | |

| Val | Leu | Lys | Gln | Thr | Leu | Tyr | Arg | Gln | Ala | Lys | Asn | Gln | Ala | Tyr |
|---|---|---|---|---|---|---|---|---|---|---|---|---|---|---|
| 1220 | | | | | 1225 | | | | | 1230 | | | | |

| Ala | Met | Met | Leu | Ser | Leu | Ser | Glu | Asp | Thr | Pro | Leu | His | Ala | Pro |
|---|---|---|---|---|---|---|---|---|---|---|---|---|---|---|
| 1235 | | | | | 1240 | | | | | 1245 | | | | |

| Ser | Gln | Ser | Ser | Leu | Asp | Ala | Trp | Leu | Asn | Ile | Thr | Gly | Pro | Ser |
|---|---|---|---|---|---|---|---|---|---|---|---|---|---|---|
| 1250 | | | | | 1255 | | | | | 1260 | | | | |

| Ser | Glu | Ser | Gly | Ala | Phe | Asn | Pro | Ile | Asn | His | Leu | | | |
|---|---|---|---|---|---|---|---|---|---|---|---|---|---|---|
| 1265 | | | | | 1270 | | | | | 1275 | | | | |

<210> SEQ ID NO 7
<211> LENGTH: 1038
<212> TYPE: DNA
<213> ORGANISM: Homo sapiens

<400> SEQUENCE: 7

```
atgcaacgcc tggtggcctg ggacccagca tgtctccccc tgccgccgcc gccgcctgcc      60
tttaaatcca tggaagtggc caacttctac tacgaggcgg actgcttggc tgctgcgtac     120
ggcggcaagg cggccccgc ggcgcccccc gcggccagac ccgggccgcg ccccccccgcc     180
ggcgagctgg cagcatcgg cgaccacgag cgcgccatcg acttcagccc gtacctggag     240
ccgctgggcg cgccgcaggc cccggcgccc gccacggcca cggacacctt cgaggcggct     300
ccgcccgcgc cgccccccgc gccgcctcc tccgggcagc accacgactt cctctccgac     360
ctcttctccg acgactacgg gggcaagaac tgcaagaagc cggccgagta cggctacgtg     420
agcctggggc gctgggggc cgccaagggc gcgctgcacc ccggctgctt cgcgcccctg     480
cacccaccgc cccgcgcgcc gccgccgccc gccgagctca ggcggagcc gggcttcgag     540
cccgcggact gcaagcggaa ggaggaggcc ggggcgccgg cggcggcgc aggcatggcg     600
```

-continued

```
gcgggcttcc cgtacgcgct gcgcgcttac ctcggctacc aggcggtgcc gagcggcagc    660
agcgggagcc tctccacgtc ctcctcgtcc agcccgcccg gcacgccgag ccccgctgac    720
gccaaggcgc cccgaccgc ctgctacgcg ggggccgcgc cggcgccctc gcaggtcaag     780
agcaaggcca agaagaccgt ggacaagcac agcgacgagt acaagatccg cgcgagcgc    840 aacaacatcg ccgtgcgcaa gagccgcgac aaggccaaga tgcgcaacct ggagacgcag   900
cacaaggtcc tggagctcac ggccgagaac gagcggctgc agaagaaggt ggagcagctg   960
tcgcgcgagc tcagcaccct gcggaacttg ttcaagcagc tgcccgagcc cctgctcgcc  1020
tcctccggcc actgctag                                                1038
```

<210> SEQ ID NO 8
<211> LENGTH: 345
<212> TYPE: PRT
<213> ORGANISM: Homo sapiens

<400> SEQUENCE: 8

```
Met Gln Arg Leu Val Ala Trp Asp Pro Ala Cys Leu Pro Leu Pro Pro
 1               5                  10                  15

Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
            35                  40                  45

Pro Pro Ala Ala Arg Pro Gly Pro Arg Pro Pro Ala Gly Glu Leu Gly
        50                  55                  60

Ser Ile Gly Asp His Glu Arg Ala Ile Asp Phe Ser Pro Tyr Leu Glu
 65                  70                  75                  80

Pro Leu Gly Ala Pro Gln Ala Pro Ala Pro Ala Thr Ala Thr Asp Thr
                85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
        115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
    210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Ala Pro Ala Pro
                245                 250                 255

Ser Gln Val Lys Ser Lys Ala Lys Lys Thr Val Asp Lys His Ser Asp
            260                 265                 270

Glu Tyr Lys Ile Arg Arg Glu Arg Asn Asn Ile Ala Val Arg Lys Ser
        275                 280                 285
```

Arg Asp Lys Ala Lys Met Arg Asn Leu Glu Thr Gln His Lys Val Leu
290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
            325                 330                 335

Pro Leu Leu Ala Ser Ser Gly His Cys
            340                 345

<210> SEQ ID NO 9
<211> LENGTH: 891
<212> TYPE: DNA
<213> ORGANISM: Mus musculus

<400> SEQUENCE: 9
atgcaccgcc tgctggcctg ggacgcagca tgcctcccgc cgccgcccgc cgcctttaga     60
cccatggaag tggccaactt ctactacgag cccgactgcc tggcctacgg ggccaaggcg    120
gcccgcgccc gccgcgcgc ccccgccgcc gagccggcca ttggcgagca cgagcgcgcc    180
atcgacttca gcccctacct ggagccgctc gcgcccgccg cggacttcgc cgcgcccgcg    240
cccgcgcacc acgacttcct ctccgacctc ttcgccgacg actacggcgc caagccgagc    300
aagaagccgg ccgactacgg ttacgtgagc ctcggccgcg cgggcgccaa ggccgcgccg    360
cccgcctgct cccgccgcc gcctcccgcc gcgctcaagg cggagccggg cttcgaaccc    420
gcggactgca agcgcgcgga cgacgcgccc gccatggcgg ccggtttccc gttcgccctg    480
cgcgcctacc tgggctacca gcgacgcgcg agcggcagca cggcagcct gtccacgtcg    540 tcgtcgtcca gcccgcccgg cacgccgagc ccgccgacg ccaaggccgc gccgccgcc    600 tgcttcgcgg gccgccggc cgcgcccgcc aaggccaagg ccaagaagac ggtggacaag    660
ctgagcgacg agtacaagat gcggcgcgag cgcaacaaca tcgcggtgcg caagagccgc    720
gacaaggcca agatgcgcaa cctggagacg cagcacaagg tgctggagct gacggcggag    780
aacgagcggc tgcagaagaa ggtggagcag ctgtcgcgag agctcagcac cctgcggaac    840
ttgttcaagc agctgcccga ccgctgctg gcctcggcgg ccactgcta g              891

<210> SEQ ID NO 10
<211> LENGTH: 296
<212> TYPE: PRT
<213> ORGANISM: Mus musculus

<400> SEQUENCE: 10

Met His Arg Leu Leu Ala Trp Asp Ala Ala Cys Leu Pro Pro Pro Pro
1               5                   10                  15

Ala Ala Phe Arg Pro Met Glu Val Ala Asn Phe Tyr Tyr Glu Pro Asp
            20                  25                  30

Cys Leu Ala Tyr Gly Ala Lys Ala Ala Arg Ala Ala Pro Arg Ala Pro
        35                  40                  45

Ala Ala Glu Pro Ala Ile Gly Glu His Glu Arg Ala Ile Asp Phe Ser
    50                  55                  60

Pro Tyr Leu Glu Pro Leu Ala Pro Ala Ala Asp Phe Ala Ala Pro Ala
65                  70                  75                  80

Pro Ala His His Asp Phe Leu Ser Asp Leu Phe Ala Asp Asp Tyr Gly
                85                  90                  95

Ala Lys Pro Ser Lys Lys Pro Ala Asp Tyr Gly Tyr Val Ser Leu Gly
            100                 105                 110

```
Arg Ala Gly Ala Lys Ala Ala Pro Ala Cys Phe Pro Pro Pro
        115                 120                 125

Pro Ala Ala Leu Lys Ala Glu Pro Gly Phe Glu Pro Ala Asp Cys Lys
    130                 135                 140

Arg Ala Asp Asp Ala Pro Ala Met Ala Ala Gly Phe Pro Phe Ala Leu
145                 150                 155                 160

Arg Ala Tyr Leu Gly Tyr Gln Ala Thr Pro Ser Gly Ser Ser Gly Ser
                165                 170                 175

Leu Ser Thr Ser Ser Ser Ser Pro Pro Gly Thr Pro Ser Pro Ala
            180                 185                 190

Asp Ala Lys Ala Ala Pro Ala Ala Cys Phe Ala Gly Pro Pro Ala Ala
                195                 200                 205

Pro Ala Lys Ala Lys Ala Lys Lys Thr Val Asp Lys Leu Ser Asp Glu
    210                 215                 220

Tyr Lys Met Arg Arg Glu Arg Asn Asn Ile Ala Val Arg Lys Ser Arg
225                 230                 235                 240

Asp Lys Ala Lys Met Arg Asn Leu Glu Thr Gln His Lys Val Leu Glu
                245                 250                 255

Leu Thr Ala Glu Asn Glu Arg Leu Gln Lys Lys Val Glu Gln Leu Ser
            260                 265                 270

Arg Glu Leu Ser Thr Leu Arg Asn Leu Phe Lys Gln Leu Pro Glu Pro
        275                 280                 285

Leu Leu Ala Ser Ala Gly His Cys
    290                 295

<210> SEQ ID NO 11
<211> LENGTH: 1190
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Asp Tyr Lys Asp Asp Asp Lys Gly Ser Leu Glu Arg Ser Lys
1               5                   10                  15

Ala Arg Ala Arg Lys Leu Ala Lys Ser Asp Gly Asp Val Val Asn Asn
                20                  25                  30

Met Tyr Glu Pro Asp Pro Asp Leu Leu Ala Gly Gln Ser Ala Glu Glu
            35                  40                  45

Glu Thr Glu Asp Gly Ile Leu Ser Pro Ile Pro Met Gly Pro Pro Ser
    50                  55                  60

Pro Phe Pro Thr Ser Glu Asp Phe Thr Pro Lys Glu Gly Ser Pro Tyr
65                  70                  75                  80

Glu Ala Pro Val Tyr Ile Pro Glu Asp Ile Pro Ile Pro Pro Asp Phe
                85                  90                  95

Glu Leu Arg Glu Ser Ser Ile Pro Gly Ala Gly Leu Gly Ile Trp Ala
            100                 105                 110

Lys Arg Lys Met Glu Ile Gly Glu Arg Phe Gly Pro Tyr Val Val Thr
        115                 120                 125

Pro Arg Ala Ala Leu Lys Glu Ala Asp Phe Gly Trp Glu Gln Met Leu
    130                 135                 140

Thr Asp Thr Glu Val Ser Ser Gln Glu Ser Cys Ile Lys Lys Gln Ile
145                 150                 155                 160

Ser Glu Asp Leu Gly Ser Glu Lys Phe Cys Val Asp Ala Asn Gln Ala
```

165                 170                 175
Gly Ser Gly Ser Trp Leu Lys Tyr Ile Arg Val Ala Cys Ser Cys Asp
            180                 185                 190

Asp Gln Asn Leu Ala Met Cys Gln Ile Asn Glu Gln Ile Tyr Tyr Lys
            195                 200                 205

Val Ile Lys Asp Ile Glu Pro Gly Glu Glu Leu Leu Val His Val Lys
            210                 215                 220

Glu Gly Ala Tyr Ser Leu Gly Val Met Ala Pro Ser Leu Asp Glu Asp
225                 230                 235                 240

Pro Thr Phe Arg Cys Asp Glu Cys Asp Glu Leu Phe Gln Cys Arg Leu
            245                 250                 255

Asp Leu Arg Arg His Lys Lys Tyr Ala Cys Ser Ser Ala Gly Ala Gln
            260                 265                 270

Leu Tyr Glu Gly Leu Gly Glu Glu Leu Lys Pro Glu Gly Leu Gly Val
            275                 280                 285

Gly Ser Asp Gly Gln Ala His Glu Cys Lys Asp Cys Glu Arg Met Phe
            290                 295                 300

Pro Asn Lys Tyr Ser Leu Glu Gln His Met Ile Val His Thr Glu Glu
305                 310                 315                 320

Arg Glu Tyr Lys Cys Asp Gln Cys Pro Lys Ala Phe Asn Trp Lys Ser
            325                 330                 335

Asn Leu Ile Arg His Gln Met Ser His Asp Ser Gly Lys Arg Phe Glu
            340                 345                 350

Cys Glu Asn Cys Val Lys Val Phe Thr Asp Pro Ser Asn Leu Gln Arg
            355                 360                 365

His Ile Arg Ser Gln His Val Gly Ala Arg Ala His Ala Cys Pro Asp
            370                 375                 380

Cys Gly Lys Thr Phe Ala Thr Ser Ser Gly Leu Lys Gln His Lys His
385                 390                 395                 400

Ile His Ser Thr Val Lys Pro Phe Ile Cys Glu Val Cys His Lys Ser
            405                 410                 415

Tyr Thr Gln Phe Ser Asn Leu Cys Arg His Lys Arg Met His Ala Asp
            420                 425                 430

Cys Arg Thr Gln Ile Lys Cys Lys Asp Cys Gly Gln Met Phe Ser Thr
            435                 440                 445

Thr Ser Ser Leu Asn Lys His Arg Arg Phe Cys Glu Gly Lys Asn His
            450                 455                 460

Tyr Thr Pro Gly Ser Ile Phe Thr Pro Gly Leu Pro Leu Thr Pro Ser
465                 470                 475                 480

Pro Met Met Asp Lys Thr Lys Pro Ser Pro Thr Leu Asn His Gly Gly
            485                 490                 495

Leu Gly Phe Ser Glu Tyr Phe Pro Ser Arg Pro His Pro Gly Ser Leu
            500                 505                 510

Pro Phe Ser Ala Ala Pro Pro Ala Phe Pro Ala Leu Thr Pro Gly Phe
            515                 520                 525

Pro Gly Ile Phe Pro Pro Ser Leu Tyr Pro Arg Pro Pro Leu Leu Pro
            530                 535                 540

Pro Thr Pro Leu Leu Lys Ser Pro Leu Asn His Ala Gln Asp Ala Lys
545                 550                 555                 560

Leu Pro Ser Pro Leu Gly Asn Pro Ala Leu Pro Leu Val Ser Ala Val
            565                 570                 575

Ser Asn Ser Ser Gln Gly Ala Thr Ala Ala Thr Gly Ser Glu Glu Lys
            580                 585                 590

```
Phe Asp Gly Arg Leu Glu Asp Ala Tyr Ala Glu Lys Val Lys Asn Arg
        595                 600                 605

Ser Pro Asp Met Ser Asp Gly Ser Asp Phe Glu Asp Ile Asn Thr Thr
    610                 615                 620

Thr Gly Thr Asp Leu Asp Thr Thr Thr Gly Thr Gly Ser Asp Leu Asp
625                 630                 635                 640

Ser Asp Leu Asp Ser Asp Arg Asp Lys Gly Lys Asp Lys Gly Lys Pro
                645                 650                 655

Val Glu Ser Lys Pro Glu Phe Gly Gly Ala Ser Val Pro Pro Gly Ala
            660                 665                 670

Met Asn Ser Val Ala Glu Val Pro Ala Phe Tyr Ser Gln His Ser Phe
        675                 680                 685

Phe Pro Pro Pro Glu Glu Gln Leu Leu Thr Ala Ser Gly Ala Ala Gly
    690                 695                 700

Asp Ser Ile Lys Ala Ile Ala Ser Ile Ala Glu Lys Tyr Phe Gly Pro
705                 710                 715                 720

Gly Phe Met Ser Met Gln Glu Lys Lys Leu Gly Ser Leu Pro Tyr His
                725                 730                 735

Ser Val Phe Pro Phe Gln Phe Leu Pro Asn Phe Pro His Ser Leu Tyr
            740                 745                 750

Pro Phe Thr Asp Arg Ala Leu Ala His Asn Leu Leu Val Lys Ala Glu
        755                 760                 765

Pro Lys Ser Pro Arg Asp Ala Leu Lys Val Gly Gly Pro Ser Ala Glu
    770                 775                 780

Cys Pro Phe Asp Leu Thr Thr Lys Pro Lys Glu Ala Lys Pro Ala Leu
785                 790                 795                 800

Leu Ala Pro Lys Val Pro Leu Ile Pro Ser Ser Gly Glu Gln Pro
                805                 810                 815

Leu Asp Leu Ser Ile Gly Ser Arg Ala Arg Ala Ser Gln Asn Gly Gly
            820                 825                 830

Gly Arg Glu Pro Arg Lys Asn His Val Tyr Gly Glu Arg Lys Pro Gly
        835                 840                 845

Val Ser Glu Gly Leu Pro Lys Val Cys Pro Ala Gln Leu Pro Gln Gln
    850                 855                 860

Pro Ser Leu His Tyr Ala Lys Pro Ser Pro Phe Phe Met Asp Pro Ile
865                 870                 875                 880

Tyr Ser Arg Val Glu Lys Arg Lys Val Ala Asp Pro Val Gly Val Leu
                885                 890                 895

Lys Glu Lys Tyr Leu Arg Pro Ser Pro Leu Leu Phe His Pro Gln Met
            900                 905                 910

Ser Ala Ile Glu Thr Met Thr Glu Lys Leu Glu Ser Phe Ala Ala Met
        915                 920                 925

Lys Ala Asp Ser Gly Ser Ser Leu Gln Pro Leu Pro His His Pro Phe
    930                 935                 940

Asn Phe Arg Ser Pro Pro Pro Thr Leu Ser Asp Pro Ile Leu Arg Lys
945                 950                 955                 960

Gly Lys Glu Arg Tyr Thr Cys Arg Tyr Cys Gly Lys Ile Phe Pro Arg
                965                 970                 975

Ser Ala Asn Leu Thr Arg His Leu Arg Thr His Thr Gly Glu Gln Pro
            980                 985                 990

Tyr Arg Cys Lys Tyr Cys Asp Arg  Ser Phe Ser Ile Ser  Ser Asn Leu
        995                 1000                1005
```

Gln Arg His Val Arg Asn Ile His Asn Lys Glu Lys Pro Phe Lys
    1010                1015                1020

Cys His Leu Cys Asn Arg Cys Phe Gly Gln Gln Thr Asn Leu Asp
    1025                1030                1035

Arg His Leu Lys Lys His Glu His Glu Gly Ala Pro Val Ser Gln
    1040                1045                1050

His Ser Gly Val Leu Thr Asn His Leu Gly Thr Ser Ala Ser Ser
    1055                1060                1065

Pro Thr Ser Glu Ser Asp Asn His Ala Leu Leu Asp Glu Lys Glu
    1070                1075                1080

Asp Ser Tyr Phe Ser Glu Ile Arg Asn Phe Ile Ala Asn Ser Glu
    1085                1090                1095

Met Asn Gln Ala Ser Thr Arg Met Asp Lys Arg Pro Glu Ile Gln
    1100                1105                1110

Asp Leu Asp Ser Asn Pro Pro Cys Pro Gly Ser Ala Ser Ala Lys
    1115                1120                1125

Pro Glu Asp Val Glu Glu Glu Glu Glu Glu Leu Glu Glu Glu
    1130                1135                1140

Asp Asp Asp Ser Leu Ala Gly Lys Ser Gln Glu Asp Thr Val Ser
    1145                1150                1155

Pro Thr Pro Glu Pro Gln Gly Val Tyr Glu Asp Glu Glu Asp Glu
    1160                1165                1170

Glu Pro Pro Ser Leu Thr Met Gly Phe Asp His Thr Arg Arg His
    1175                1180                1185

Met Gln
    1190

<210> SEQ ID NO 12
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Arg Ser Lys Ala Arg Ala Arg Lys Leu Ala Lys Ser Asp Gly Asp
1               5                   10                  15

Val Val Asn Asn Met Tyr Glu Pro Asp Pro Asp Leu Leu Ala Gly Gln
                20                  25                  30

Ser Ala Glu Glu Glu Thr Glu Asp Gly Ile Leu Ser Pro Ile Pro Met
            35                  40                  45

Gly Pro Pro Ser Pro Phe Pro Thr Ser Glu Asp Phe Thr Pro Lys Glu
        50                  55                  60

Gly Ser Pro Tyr Glu Ala Pro Val Tyr Ile Pro Glu Asp Ile Pro Ile
65                  70                  75                  80

Pro Pro Asp Phe Glu Leu Arg Glu Ser Ser Ile Pro Gly Ala Gly Leu
                85                  90                  95

Gly Ile Trp Ala Lys Arg Lys Met Glu Ile Gly Glu Arg Phe Gly Pro
            100                 105                 110

Tyr Val Val Thr Pro Arg Ala Ala Leu Lys Glu Ala Asp Phe Gly Trp
        115                 120                 125

Glu Gln Met Leu Thr Asp Thr Glu Val Ser Ser Gln Glu Ser Cys Ile
    130                 135                 140

Lys Lys Gln Ile Ser Glu Asp Leu Gly Ser Glu Lys Phe Cys Val Asp

```
                145                 150                 155                 160
Ala Asn Gln Ala Gly Ser Gly Ser Trp Leu Lys Tyr Ile Arg Val Ala
                    165                 170                 175

Cys Ser Cys Asp Asp Gln Asn Leu Ala Met Cys Gln Ile Asn Glu Gln
                    180                 185                 190

Ile Tyr Tyr Lys Val Ile Lys Asp Ile Glu Pro Gly Glu Glu Leu Leu
                    195                 200                 205

Val His Val Lys Glu Gly Ala Tyr Ser Leu Gly Val Met Ala Pro
                    210                 215                 220

<210> SEQ ID NO 13
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Ser Leu Asp Glu Asp Pro Thr Phe Arg Cys Asp Glu Cys Asp Glu
1               5                   10                  15

Leu Phe Gln Cys Arg Leu Asp Leu Arg Arg His Lys Lys Tyr Ala Cys
                20                  25                  30

Ser Ser Ala Gly Ala Gln Leu Tyr Glu Gly Leu Gly Glu Glu Leu Lys
            35                  40                  45

Pro Glu Gly Leu Gly Val Gly Ser Asp Gly Gln Ala His Glu Cys Lys
        50                  55                  60

Asp Cys Glu Arg Met Phe Pro Asn Lys Tyr Ser Leu Glu Gln His Met
65                  70                  75                  80

Ile Val His Thr Glu Glu Arg Glu Tyr Lys Cys Asp Gln Cys Pro Lys
                85                  90                  95

Ala Phe Asn Trp Lys Ser Asn Leu Ile Arg His Gln Met Ser His Asp
                100                 105                 110

Ser Gly Lys Arg Phe Glu Cys Glu Asn Cys Val Lys Val Phe Thr Asp
            115                 120                 125

Pro Ser Asn Leu Gln Arg His Ile Arg Ser Gln His Val Gly Ala Arg
        130                 135                 140

Ala His Ala Cys Pro Asp Cys Gly Lys Thr Phe Ala Thr Ser Ser Gly
145                 150                 155                 160

Leu Lys Gln His Lys His Ile His Ser Thr Val Lys Pro Phe Ile Cys
                165                 170                 175

Glu Val Cys His Lys Ser Tyr Thr Gln Phe Ser Asn Leu Cys Arg His
                180                 185                 190

Lys Arg Met His Ala Asp Cys Arg Thr Gln Ile Lys Cys Lys Asp Cys
            195                 200                 205

Gly Gln Met Phe Ser Thr Thr Ser Ser Leu Asn Lys His Arg Arg Phe
        210                 215                 220

Cys Glu Gly Lys Asn His Tyr Thr
225                 230

<210> SEQ ID NO 14
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 14

Met Pro Gly Ser Ile Phe Thr Pro Gly Leu Pro Leu Thr Pro Ser Pro
1               5                   10                  15

Met Met Asp Lys Thr Lys Pro Ser Pro Thr Leu Asn His Gly Gly Leu
            20                  25                  30

Gly Phe Ser Glu Tyr Phe Pro Ser Arg Pro His Pro Gly Ser Leu Pro
        35                  40                  45

Phe Ser Ala Ala Pro Pro Ala Phe Pro Ala Leu Thr Pro Gly Phe Pro
    50                  55                  60

Gly Ile Phe Pro Pro Ser Leu Tyr Pro Arg Pro Leu Leu Pro Pro
65                  70                  75                  80

Thr Pro Leu Leu Lys Ser Pro Leu Asn His Ala Gln Asp Ala Lys Leu
                85                  90                  95

Pro Ser Pro Leu Gly Asn Pro Ala Leu Pro Leu Val Ser Ala Val Ser
            100                 105                 110

Asn Ser Ser Gln Gly Ala Thr Ala Ala Thr Gly Ser Glu Glu Lys Phe
        115                 120                 125

Asp Gly Arg Leu Glu Asp Ala Tyr Ala Glu Lys Val Lys Asn Arg Ser
    130                 135                 140

Pro Asp Met Ser Asp Gly Ser Asp Phe Glu Asp Ile Asn Thr Thr Thr
145                 150                 155                 160

Gly Thr Asp Leu Asp Thr Thr Thr Gly Thr Gly Ser Asp Leu Asp Ser
                165                 170                 175

Asp Leu Asp Ser Asp Arg Asp Lys Gly Lys Asp Lys Gly Lys Pro Val
            180                 185                 190

Glu Ser Lys Pro Glu Phe Gly Gly Ala Ser Val Pro Pro Gly Ala Met
        195                 200                 205

Asn Ser Val Ala Glu Val Pro Ala Phe Tyr Ser Gln His Ser Phe Phe
    210                 215                 220

Pro Pro Pro
225

<210> SEQ ID NO 15
<211> LENGTH: 202
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Met Pro Glu Glu Gln Leu Leu Thr Ala Ser Gly Ala Ala Gly Asp Ser
1               5                   10                  15

Ile Lys Ala Ile Ala Ser Ile Ala Glu Lys Tyr Phe Gly Pro Gly Phe
            20                  25                  30

Met Ser Met Gln Glu Lys Lys Leu Gly Ser Leu Pro Tyr His Ser Val
        35                  40                  45

Phe Pro Phe Gln Phe Leu Pro Asn Phe Pro His Ser Leu Tyr Pro Phe
    50                  55                  60

Thr Asp Arg Ala Leu Ala His Asn Leu Leu Val Lys Ala Glu Pro Lys
65                  70                  75                  80

Ser Pro Arg Asp Ala Leu Lys Val Gly Gly Pro Ser Ala Glu Cys Pro
                85                  90                  95

```
Phe Asp Leu Thr Thr Lys Pro Lys Glu Ala Lys Pro Ala Leu Leu Ala
            100                 105                 110

Pro Lys Val Pro Leu Ile Pro Ser Ser Gly Glu Glu Gln Pro Leu Asp
        115                 120                 125

Leu Ser Ile Gly Ser Arg Ala Arg Ala Ser Gln Asn Gly Gly Gly Arg
    130                 135                 140

Glu Pro Arg Lys Asn His Val Tyr Gly Glu Arg Lys Pro Gly Val Ser
145                 150                 155                 160

Glu Gly Leu Pro Lys Val Cys Pro Ala Gln Leu Pro Gln Gln Pro Ser
                165                 170                 175

Leu His Tyr Ala Lys Pro Ser Pro Phe Phe Met Asp Pro Ile Tyr Ser
            180                 185                 190

Arg Val Glu Lys Arg Lys Val Ala Asp Pro
        195                 200

<210> SEQ ID NO 16
<211> LENGTH: 159
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Val Gly Val Leu Lys Glu Lys Tyr Leu Arg Pro Ser Pro Leu Leu
1               5                   10                  15

Phe His Pro Gln Met Ser Ala Ile Glu Thr Met Thr Glu Lys Leu Glu
            20                  25                  30

Ser Phe Ala Ala Met Lys Ala Asp Ser Gly Ser Ser Leu Gln Pro Leu
        35                  40                  45

Pro His His Pro Phe Asn Phe Arg Ser Pro Pro Thr Leu Ser Asp
    50                  55                  60

Pro Ile Leu Arg Lys Gly Lys Glu Arg Tyr Thr Cys Arg Tyr Cys Gly
65                  70                  75                  80

Lys Ile Phe Pro Arg Ser Ala Asn Leu Thr Arg His His Leu Arg Thr His
            85                  90                  95

Thr Gly Glu Gln Pro Tyr Arg Cys Lys Tyr Cys Asp Arg Ser Phe Ser
            100                 105                 110

Ile Ser Ser Asn Leu Gln Arg His Val Arg Asn Ile His Asn Lys Glu
        115                 120                 125

Lys Pro Phe Lys Cys His Leu Cys Asn Arg Cys Phe Gly Gln Gln Thr
    130                 135                 140

Asn Leu Asp Arg His Leu Lys Lys His Glu His Glu Gly Ala Pro
145                 150                 155

<210> SEQ ID NO 17
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Val Ser Gln His Ser Gly Val Leu Thr Asn His Leu Gly Thr Ser
1               5                   10                  15

Ala Ser Ser Pro Thr Ser Glu Ser Asp Asn His Ala Leu Leu Asp Glu
```

```
            20                  25                  30
Lys Glu Asp Ser Tyr Phe Ser Glu Ile Arg Asn Phe Ile Ala Asn Ser
            35                  40                  45

Glu Met Asn Gln Ala Ser Thr Arg Met Asp Lys Arg Pro Glu Ile Gln
 50                  55                  60

Asp Leu Asp Ser Asn Pro Pro Cys Pro Gly Ser Ala Ser Ala Lys Pro
 65                  70                  75                  80

Glu Asp Val Glu Glu Glu Glu Glu Leu Glu Glu Asp Asp
                     85                  90                  95

Asp Ser Leu Ala Gly Lys Ser Gln Glu Asp Thr Val Ser Pro Thr Pro
            100                 105                 110

Glu Pro Gln Gly Val Tyr Glu Asp Glu Glu Asp Glu Glu Pro Pro Ser
            115                 120                 125

Leu Thr Met Gly Phe Asp His Thr Arg Arg His Met Gln
            130                 135                 140
```

<210> SEQ ID NO 18
<211> LENGTH: 435
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
atggcggccg gtttcccgtt cgccctgcgc gcctacctgg ctaccaggc gacgccgagc      60 ggcagcagcg gcagcctgtc cacgtcgtcg tcgtccagcc cgcccggcac gccgagcccc     120
gccgacgcca aggccgcgcc cgccgcctgc ttcgcggggc cgccggccgc gcccgccaag     180
gctaaggcca agaagacggt ggacaagctg agcgacgagt acaagatgcg gcgcgagcgc     240
aacaacatcg cggtgcgcaa gagccgcgac aaggccaaga tgcgcaacct ggagacgcag     300
cacaaggtgc tggagctgac ggcggagaac gagcggctgc agaagaaggt ggagcagctg     360
tcgcgagagc tcagcaccct gcggaacttg ttcaagcagc tgcccaagcc gctgctggcc     420
tcggccggtc actgc                                                     435
```

<210> SEQ ID NO 19
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Met Ala Ala Gly Phe Pro Phe Ala Leu Arg Ala Tyr Leu Gly Tyr Gln
 1               5                  10                  15

Ala Thr Pro Ser Gly Ser Ser Gly Ser Leu Ser Thr Ser Ser Ser Ser
            20                  25                  30

Ser Pro Pro Gly Thr Pro Ser Pro Ala Asp Ala Lys Ala Ala Pro Ala
            35                  40                  45

Ala Cys Phe Ala Gly Pro Pro Ala Pro Ala Lys Ala Lys Ala Lys
            50                  55                  60

Lys Thr Val Asp Lys Leu Ser Asp Glu Tyr Lys Met Arg Arg Glu Arg
 65                  70                  75                  80

Asn Asn Ile Ala Val Arg Lys Ser Arg Asp Lys Ala Lys Met Arg Asn
```

```
                    85                  90                  95
Leu Glu Thr Gln His Lys Val Leu Glu Leu Thr Ala Glu Asn Glu Arg
                100                 105                 110

Leu Gln Lys Lys Val Glu Gln Leu Ser Arg Glu Leu Ser Thr Leu Arg
        115                 120                 125

Asn Leu Phe Lys Gln Leu Pro Lys Pro Leu Leu Ala Ser Ala Gly His
    130                 135                 140

Cys
145

<210> SEQ ID NO 20
<211> LENGTH: 64
<212> TYPE: DNA
<213> ORGANISM: Unknown
<220> FEATURE:
<221> NAME/KEY: source
<223> OTHER INFORMATION: /note="Description of Unknown: sh-Beta-1 shRNA
      sequence"

<400> SEQUENCE: 20
gatccccgcc ctgagtaatc acttaaagtt caagagactt taagtgatta ctcagggctt      60
ttta                                                                  64

<210> SEQ ID NO 21
<211> LENGTH: 64
<212> TYPE: DNA
<213> ORGANISM: Unknown
<220> FEATURE:
<221> NAME/KEY: source
<223> OTHER INFORMATION: /note="Description of Unknown: sh-Beta-1 shRNA
      sequence"

<400> SEQUENCE: 21
agcttaaaaa gccctgagta atcacttaaa gtctcttgaa ctttaagtga ttactcaggg      60
cggg                                                                  64

<210> SEQ ID NO 22
<211> LENGTH: 60
<212> TYPE: DNA
<213> ORGANISM: Unknown
<220> FEATURE:
<221> NAME/KEY: source
<223> OTHER INFORMATION: /note="Description of Unknown: sh-Beta-2 shRNA
      sequence"

<400> SEQUENCE: 22 gatcccccccg ggccctgagt aatcacttca agagagtgat tactcagggc ccggtttta     60

<210> SEQ ID NO 23
<211> LENGTH: 60
<212> TYPE: DNA
<213> ORGANISM: Unknown
<220> FEATURE:
<221> NAME/KEY: source
<223> OTHER INFORMATION: /note="Description of Unknown: sh-Beta-2 shRNA
      sequence"

<400> SEQUENCE: 23
agcttaaaaa ccgggccctg agtaatcact ctcttgaagt gattactcag ggcccggggg     60

<210> SEQ ID NO 24
<211> LENGTH: 2910
<212> TYPE: DNA
<213> ORGANISM: Unknown
```

-continued

```
<220> FEATURE:
<221> NAME/KEY: source
<223> OTHER INFORMATION: /note="Description of Unknown: DeltaZF-1
      sequence"
<220> FEATURE:
<221> NAME/KEY: CDS
<222> LOCATION: (1)..(2907)

<400> SEQUENCE: 24
```

| | | | | | | | | | | | | | | | | |
|---|---|---|---|---|---|---|---|---|---|---|---|---|---|---|---|---|
| atg | cga | tcc | aag | gcg | agg | gcg | agg | aag | cta | gcc | aaa | agt | gac | ggt | gac | 48 |
| Met | Arg | Ser | Lys | Ala | Arg | Ala | Arg | Lys | Leu | Ala | Lys | Ser | Asp | Gly | Asp | |
| 1 | | | 5 | | | | | 10 | | | | | 15 | | | |
| gtt | gta | aat | aat | atg | tat | gaa | cct | gac | ccg | gac | ctg | ctg | gcc | ggc | cag | 96 |
| Val | Val | Asn | Asn | Met | Tyr | Glu | Pro | Asp | Pro | Asp | Leu | Leu | Ala | Gly | Gln | |
| | | | 20 | | | | | 25 | | | | | 30 | | | |
| agt | gcc | gag | gag | gag | acc | gaa | gac | ggc | atc | ctg | tcc | ccc | atc | ccc | atg | 144 |
| Ser | Ala | Glu | Glu | Glu | Thr | Glu | Asp | Gly | Ile | Leu | Ser | Pro | Ile | Pro | Met | |
| | 35 | | | | | 40 | | | | | 45 | | | | | |
| ggg | cca | ccg | tcc | ccc | ttc | ccc | acc | agc | gag | gac | ttc | act | ccc | aag | gag | 192 |
| Gly | Pro | Pro | Ser | Pro | Phe | Pro | Thr | Ser | Glu | Asp | Phe | Thr | Pro | Lys | Glu | |
| 50 | | | | | 55 | | | | | 60 | | | | | | |
| ggc | tcg | ccc | tat | gag | gct | cct | gtc | tac | att | cct | gaa | gac | att | cca | atc | 240 |
| Gly | Ser | Pro | Tyr | Glu | Ala | Pro | Val | Tyr | Ile | Pro | Glu | Asp | Ile | Pro | Ile | |
| 65 | | | | 70 | | | | | 75 | | | | | 80 | | |
| cca | cca | gac | ttc | gag | cta | cga | gag | tcc | tcc | ata | cca | gga | gct | ggc | ctg | 288 |
| Pro | Pro | Asp | Phe | Glu | Leu | Arg | Glu | Ser | Ser | Ile | Pro | Gly | Ala | Gly | Leu | |
| | | | | 85 | | | | | 90 | | | | | 95 | | |
| ggg | atc | tgg | gcc | aag | cgg | aag | atg | gaa | atc | ggg | gag | agg | ttt | ggc | ccc | 336 |
| Gly | Ile | Trp | Ala | Lys | Arg | Lys | Met | Glu | Ile | Gly | Glu | Arg | Phe | Gly | Pro | |
| | | | 100 | | | | | 105 | | | | | 110 | | | |
| tac | gtg | gtg | acg | ccc | cgg | gcc | gca | ctg | aag | gag | gcc | gac | ttt | gga | tgg | 384 |
| Tyr | Val | Val | Thr | Pro | Arg | Ala | Ala | Leu | Lys | Glu | Ala | Asp | Phe | Gly | Trp | |
| | 115 | | | | | 120 | | | | | 125 | | | | | |
| gag | cag | atg | ctg | acg | gat | aca | gag | gtg | tca | tcc | cag | gag | agc | tgc | atc | 432 |
| Glu | Gln | Met | Leu | Thr | Asp | Thr | Glu | Val | Ser | Ser | Gln | Glu | Ser | Cys | Ile | |
| 130 | | | | | 135 | | | | | 140 | | | | | | |
| aaa | aag | cag | atc | tct | gaa | gac | ttg | ggt | agc | gag | aag | ttc | tgc | gtg | gat | 480 |
| Lys | Lys | Gln | Ile | Ser | Glu | Asp | Leu | Gly | Ser | Glu | Lys | Phe | Cys | Val | Asp | |
| 145 | | | | | 150 | | | | | 155 | | | | | 160 | |
| gcc | aat | cag | gcg | ggg | tct | ggc | agc | tgg | ctc | aag | tac | atc | cgt | gta | gcg | 528 |
| Ala | Asn | Gln | Ala | Gly | Ser | Gly | Ser | Trp | Leu | Lys | Tyr | Ile | Arg | Val | Ala | |
| | | | | 165 | | | | | 170 | | | | | 175 | | |
| tgt | tcc | tgt | gat | gac | caa | aac | ctc | gcc | atg | tgt | cag | atc | aac | gaa | cag | 576 |
| Cys | Ser | Cys | Asp | Asp | Gln | Asn | Leu | Ala | Met | Cys | Gln | Ile | Asn | Glu | Gln | |
| | | | 180 | | | | | 185 | | | | | 190 | | | |
| att | tac | tat | aaa | gtc | att | aag | gac | atc | gag | cct | gga | gag | gaa | ctg | ttg | 624 |
| Ile | Tyr | Tyr | Lys | Val | Ile | Lys | Asp | Ile | Glu | Pro | Gly | Glu | Glu | Leu | Leu | |
| | 195 | | | | | 200 | | | | | 205 | | | | | |
| gtg | cat | gtg | aaa | gaa | ggt | gcc | tac | tcc | ttg | ggt | gtc | atg | gcc | ccc | agc | 672 |
| Val | His | Val | Lys | Glu | Gly | Ala | Tyr | Ser | Leu | Gly | Val | Met | Ala | Pro | Ser | |
| 210 | | | | | 215 | | | | | 220 | | | | | | |
| ttg | gat | gag | gac | ccc | aca | ttc | cgc | tgt | gat | cgg | aga | ttc | tgc | gag | ggc | 720 |
| Leu | Asp | Glu | Asp | Pro | Thr | Phe | Arg | Cys | Asp | Arg | Arg | Phe | Cys | Glu | Gly | |
| 225 | | | | | 230 | | | | | 235 | | | | | 240 | |
| aag | aac | cat | tac | acg | cct | ggc | agc | atc | ttc | acc | cca | ggc | ctg | ccc | ttg | 768 |
| Lys | Asn | His | Tyr | Thr | Pro | Gly | Ser | Ile | Phe | Thr | Pro | Gly | Leu | Pro | Leu | |
| | | | | 245 | | | | | 250 | | | | | 255 | | |
| acc | ccc | agc | ccc | atg | atg | gac | aag | aca | aaa | ccc | tcc | ccg | acc | ctc | aac | 816 |
| Thr | Pro | Ser | Pro | Met | Met | Asp | Lys | Thr | Lys | Pro | Ser | Pro | Thr | Leu | Asn | |
| | | | 260 | | | | | 265 | | | | | 270 | | | |
| cac | ggg | ggc | cta | ggc | ttc | agc | gag | tac | ttc | ccc | tcc | aga | cct | cat | cct | 864 |

```
                    His Gly Gly Leu Gly Phe Ser Glu Tyr Phe Pro Ser Arg Pro His Pro
                                275                 280                 285 ggg agc ctg ccc ttc tcg gct gct cct ccg gcc ttc ccc gca ctc act        912
Gly Ser Leu Pro Phe Ser Ala Ala Pro Pro Ala Phe Pro Ala Leu Thr
        290                 295                 300 ccg ggc ttc ccg ggc atc ttt cct cca tcc ctg tac cca cga cca cct        960
Pro Gly Phe Pro Gly Ile Phe Pro Pro Ser Leu Tyr Pro Arg Pro Pro
305                 310                 315                 320 ctg cta cct ccc acg ccg ctg ctc aag agc ccc ctg aac cac gcg cag       1008
Leu Leu Pro Pro Thr Pro Leu Leu Lys Ser Pro Leu Asn His Ala Gln
                325                 330                 335 gac gcc aag cta ccc agc ccg ctg gga aac cca gcc ctg ccc ctt gtc       1056
Asp Ala Lys Leu Pro Ser Pro Leu Gly Asn Pro Ala Leu Pro Leu Val
        340                 345                 350 tcc gcg gtc agc aat agc agc cag ggt gcc aca gcg gcc acc ggg tca       1104
Ser Ala Val Ser Asn Ser Ser Gln Gly Ala Thr Ala Ala Thr Gly Ser
                355                 360                 365 gag gag aaa ttt gat ggc cgc ttg gaa gac gca tat gcg gag aag gtc       1152
Glu Glu Lys Phe Asp Gly Arg Leu Glu Asp Ala Tyr Ala Glu Lys Val
        370                 375                 380 aaa aat agg agc cct gac atg tcg gat ggc agt gac ttt gag gat atc       1200
Lys Asn Arg Ser Pro Asp Met Ser Asp Gly Ser Asp Phe Glu Asp Ile
385                 390                 395                 400 aac acc acg acc ggg aca gac ttg gac act acc acg ggc acg ggg tca       1248
Asn Thr Thr Thr Gly Thr Asp Leu Asp Thr Thr Thr Gly Thr Gly Ser
                405                 410                 415 gac ctg gac agc gac ctg gac agt gac aga gac aaa ggc aag gac aag       1296
Asp Leu Asp Ser Asp Leu Asp Ser Asp Arg Asp Lys Gly Lys Asp Lys
        420                 425                 430 ggg aag cca gtg gag agc aaa cct gag ttt ggg ggt gca tct gtg ccc       1344
Gly Lys Pro Val Glu Ser Lys Pro Glu Phe Gly Gly Ala Ser Val Pro
                435                 440                 445 cct ggg gcc atg aac agt gtg gcc gag gta ccg gcc ttc tac tca cag       1392
Pro Gly Ala Met Asn Ser Val Ala Glu Val Pro Ala Phe Tyr Ser Gln
        450                 455                 460 cat tcc ttc ttc ccg cca ccc gag gaa cag ctg ctg acg gcc tcg gga       1440
His Ser Phe Phe Pro Pro Pro Glu Glu Gln Leu Leu Thr Ala Ser Gly
465                 470                 475                 480 gct gcc ggc gac tcc atc aag gcc atc gcg tcc atc gcg gag aaa tac       1488
Ala Ala Gly Asp Ser Ile Lys Ala Ile Ala Ser Ile Ala Glu Lys Tyr
                485                 490                 495 ttc ggt cct ggc ttc atg agc atg cag gag aag aag ctg ggc tca cta       1536
Phe Gly Pro Gly Phe Met Ser Met Gln Glu Lys Lys Leu Gly Ser Leu
        500                 505                 510 ccc tac cac tcc gtg ttc ccc ttc cag ttc ctg cct aac ttt ccc cac       1584
Pro Tyr His Ser Val Phe Pro Phe Gln Phe Leu Pro Asn Phe Pro His
                515                 520                 525 tcc ctc tac ccc ttt acg gac cga gcc ctc gcc cac aac ttg ctg gtc       1632
Ser Leu Tyr Pro Phe Thr Asp Arg Ala Leu Ala His Asn Leu Leu Val
        530                 535                 540 aag gct gag cca aag tca ccc cgg gat gcc ctc aag gtg ggc ggc ccc       1680
Lys Ala Glu Pro Lys Ser Pro Arg Asp Ala Leu Lys Val Gly Gly Pro
545                 550                 555                 560 agt gcg gag tgc ccc ttc gac ctc acc acc aaa cca aaa gag gcc aaa       1728
Ser Ala Glu Cys Pro Phe Asp Leu Thr Thr Lys Pro Lys Glu Ala Lys
                565                 570                 575 ccc gcc ctg ctc gca ccc aag gtc ccc ctc atc ccc tca tct ggc gag       1776
Pro Ala Leu Leu Ala Pro Lys Val Pro Leu Ile Pro Ser Ser Gly Glu
        580                 585                 590
```

```
gaa cag cca ctg gac ctg agc atc ggc agc agg gcc agg gca agc cag    1824
Glu Gln Pro Leu Asp Leu Ser Ile Gly Ser Arg Ala Arg Ala Ser Gln
            595                 600                 605 aac gga ggt ggc cgt gag ccg cgg aag aac cac gtc tac ggt gaa cgg    1872
Asn Gly Gly Gly Arg Glu Pro Arg Lys Asn His Val Tyr Gly Glu Arg
610                 615                 620 aag ccg ggg gtc agc gag ggg ctg cct aag gtg tgc cca gca cag ctg    1920
Lys Pro Gly Val Ser Glu Gly Leu Pro Lys Val Cys Pro Ala Gln Leu
625                 630                 635                 640 ccc cag cag ccc tcc ttg cat tat gct aag cct tca ccg ttc ttc atg    1968
Pro Gln Gln Pro Ser Leu His Tyr Ala Lys Pro Ser Pro Phe Phe Met
                645                 650                 655 gat ccc atc tac agc agg gta gaa aag cgg aag gtg gca gac cct gtg    2016
Asp Pro Ile Tyr Ser Arg Val Glu Lys Arg Lys Val Ala Asp Pro Val
            660                 665                 670 gga gtc ctg aaa gag aag tac ctg cgg ccg tcc cca ctt ctg ttc cac    2064
Gly Val Leu Lys Glu Lys Tyr Leu Arg Pro Ser Pro Leu Leu Phe His
        675                 680                 685 ccc cag atg tca gcc ata gaa acc atg acg gag aag ctg gag agc ttt    2112
Pro Gln Met Ser Ala Ile Glu Thr Met Thr Glu Lys Leu Glu Ser Phe
690                 695                 700 gca gcc atg aag gcc gac tca ggc agc tcc ctg cag ccc ctg cct cac    2160
Ala Ala Met Lys Ala Asp Ser Gly Ser Ser Leu Gln Pro Leu Pro His
705                 710                 715                 720 cac ccg ttc aac ttc cgc tcc cca ccc cca acg ctc tcg gat ccc atc    2208
His Pro Phe Asn Phe Arg Ser Pro Pro Pro Thr Leu Ser Asp Pro Ile
                725                 730                 735 ctc agg aag ggg aag gag aga tac acg tgc agg tac tgt ggc aag atc    2256
Leu Arg Lys Gly Lys Glu Arg Tyr Thr Cys Arg Tyr Cys Gly Lys Ile
            740                 745                 750 ttc ccc aga tct gca aat ctc aca aga cat ctg agg aca cac aca ggg    2304
Phe Pro Arg Ser Ala Asn Leu Thr Arg His Leu Arg Thr His Thr Gly
        755                 760                 765 gag cag cca tac agg tgc aag tac tgt gac cgg tca ttc agc atc tcc    2352
Glu Gln Pro Tyr Arg Cys Lys Tyr Cys Asp Arg Ser Phe Ser Ile Ser
770                 775                 780 tcc aac ctc cag cgg cac gtg agg aac atc cac aac aaa gag aag ccg    2400
Ser Asn Leu Gln Arg His Val Arg Asn Ile His Asn Lys Glu Lys Pro
785                 790                 795                 800 ttc aag tgc cat ctg tgc aac cgc tgc ttc ggg cag cag acc aac cta    2448
Phe Lys Cys His Leu Cys Asn Arg Cys Phe Gly Gln Gln Thr Asn Leu
                805                 810                 815 gac cgg cac ctg aag aag cac gaa cac gag ggc gca cca gtg agc cag    2496
Asp Arg His Leu Lys Lys His Glu His Glu Gly Ala Pro Val Ser Gln
            820                 825                 830 cac tcc ggg gtg ctc acg aac cac ctg ggc acc agc gcc tcc tcc ccc    2544
His Ser Gly Val Leu Thr Asn His Leu Gly Thr Ser Ala Ser Ser Pro
        835                 840                 845 acc tcc gag tcg gac aac cat gca ctt tta gat gag aag gaa gat tct    2592
Thr Ser Glu Ser Asp Asn His Ala Leu Leu Asp Glu Lys Glu Asp Ser
850                 855                 860 tac ttc tcc gag atc cga aac ttc atc gcc aac agc gag atg aac cag    2640
Tyr Phe Ser Glu Ile Arg Asn Phe Ile Ala Asn Ser Glu Met Asn Gln
865                 870                 875                 880 gca tcc act cga atg gac aaa cgg cct gag atc caa gac ctg gac agc    2688
Ala Ser Thr Arg Met Asp Lys Arg Pro Glu Ile Gln Asp Leu Asp Ser
                885                 890                 895 aac cca ccg tgt cca ggc tca gcc agt gca aag cca gag gac gta gag    2736
Asn Pro Pro Cys Pro Gly Ser Ala Ser Ala Lys Pro Glu Asp Val Glu
            900                 905                 910
```

| | | | | | | | | | | | | | | | | |
|---|---|---|---|---|---|---|---|---|---|---|---|---|---|---|---|---|
|gag|gag|gaa|gag|gag|gag|ctg|gag|gaa|gag|gat|gat|gac|agc|tta|gcc|2784|
|Glu|Glu|Glu|Glu|Glu|Glu|Leu|Glu|Glu|Glu|Asp|Asp|Asp|Ser|Leu|Ala| |
| | | | |915| | | |920| | | | |925| | | |

| | | | | | | | | | | | | | | | | |
|---|---|---|---|---|---|---|---|---|---|---|---|---|---|---|---|---|
|ggg|aag|tca|cag|gag|gac|acg|gtg|tcc|ccc|aca|cct|gag|ccc|caa|gga|2832|
|Gly|Lys|Ser|Gln|Glu|Asp|Thr|Val|Ser|Pro|Thr|Pro|Glu|Pro|Gln|Gly| |
| |930| | | | |935| | | | |940| | | | | |

| | | | | | | | | | | | | | | | | |
|---|---|---|---|---|---|---|---|---|---|---|---|---|---|---|---|---|
|gtc|tat|gaa|gat|gaa|gag|gat|gag|gaa|cca|ccc|agc|ctg|acc|atg|ggc|2880|
|Val|Tyr|Glu|Asp|Glu|Glu|Asp|Glu|Glu|Pro|Pro|Ser|Leu|Thr|Met|Gly| |
|945| | | |950| | | | |955| | | | |960| | |

| | | | | | | | | |
|---|---|---|---|---|---|---|---|---|
|ttt|gac|cat|acc|cgg|agg|cat|atg|caa|tga|2910|
|Phe|Asp|His|Thr|Arg|Arg|His|Met|Gln| |
| | | | |965| | | | | |

<210> SEQ ID NO 25
<211> LENGTH: 969
<212> TYPE: PRT
<213> ORGANISM: Unknown
<220> FEATURE:
<221> NAME/KEY: source
<223> OTHER INFORMATION: /note="Description of Unknown: DeltaZF-1 sequence"

<400> SEQUENCE: 25

Met Arg Ser Lys Ala Arg Ala Arg Lys Leu Ala Lys Ser Asp Gly Asp
1               5                   10                  15

Val Val Asn Asn Met Tyr Glu Pro Asp Pro Asp Leu Leu Ala Gly Gln
            20                  25                  30

Ser Ala Glu Glu Glu Thr Glu Asp Gly Ile Leu Ser Pro Ile Pro Met
        35                  40                  45

Gly Pro Pro Ser Pro Phe Pro Thr Ser Glu Asp Phe Thr Pro Lys Glu
    50                  55                  60

Gly Ser Pro Tyr Glu Ala Pro Val Tyr Ile Pro Glu Asp Ile Pro Ile
65                  70                  75                  80

Pro Pro Asp Phe Glu Leu Arg Glu Ser Ile Pro Gly Ala Gly Leu
                85                  90                  95

Gly Ile Trp Ala Lys Arg Lys Met Glu Ile Gly Glu Arg Phe Gly Pro
            100                 105                 110

Tyr Val Val Thr Pro Arg Ala Ala Leu Lys Glu Ala Asp Phe Gly Trp
        115                 120                 125

Glu Gln Met Leu Thr Asp Thr Glu Val Ser Ser Gln Glu Ser Cys Ile
    130                 135                 140

Lys Lys Gln Ile Ser Glu Asp Leu Gly Ser Glu Lys Phe Cys Val Asp
145                 150                 155                 160

Ala Asn Gln Ala Gly Ser Gly Ser Trp Leu Lys Tyr Ile Arg Val Ala
                165                 170                 175

Cys Ser Cys Asp Asp Gln Asn Leu Ala Met Cys Gln Ile Asn Glu Gln
            180                 185                 190

Ile Tyr Tyr Lys Val Ile Lys Asp Ile Glu Pro Gly Glu Glu Leu Leu
        195                 200                 205

Val His Val Lys Glu Gly Ala Tyr Ser Leu Gly Val Met Ala Pro Ser
    210                 215                 220

Leu Asp Glu Asp Pro Thr Phe Arg Cys Asp Arg Arg Phe Cys Glu Gly
225                 230                 235                 240

Lys Asn His Tyr Thr Pro Gly Ser Ile Phe Thr Pro Gly Leu Pro Leu
                245                 250                 255

Thr Pro Ser Pro Met Met Asp Lys Thr Lys Pro Ser Pro Thr Leu Asn
            260                 265                 270

```
His Gly Gly Leu Gly Phe Ser Glu Tyr Phe Pro Ser Arg Pro His Pro
            275                 280                 285

Gly Ser Leu Pro Phe Ser Ala Ala Pro Pro Ala Phe Pro Ala Leu Thr
        290                 295                 300

Pro Gly Phe Pro Gly Ile Phe Pro Pro Ser Leu Tyr Pro Arg Pro Pro
305                 310                 315                 320

Leu Leu Pro Pro Thr Pro Leu Leu Lys Ser Pro Leu Asn His Ala Gln
                325                 330                 335

Asp Ala Lys Leu Pro Ser Pro Leu Gly Asn Pro Ala Leu Pro Leu Val
            340                 345                 350

Ser Ala Val Ser Asn Ser Ser Gln Gly Ala Thr Ala Ala Thr Gly Ser
        355                 360                 365

Glu Glu Lys Phe Asp Gly Arg Leu Glu Asp Ala Tyr Ala Glu Lys Val
    370                 375                 380

Lys Asn Arg Ser Pro Asp Met Ser Asp Gly Ser Asp Phe Glu Asp Ile
385                 390                 395                 400

Asn Thr Thr Thr Gly Thr Asp Leu Asp Thr Thr Thr Gly Thr Gly Ser
                405                 410                 415

Asp Leu Asp Ser Asp Leu Asp Ser Asp Arg Asp Lys Gly Lys Asp Lys
            420                 425                 430

Gly Lys Pro Val Glu Ser Lys Pro Glu Phe Gly Gly Ala Ser Val Pro
        435                 440                 445

Pro Gly Ala Met Asn Ser Val Ala Glu Val Pro Ala Phe Tyr Ser Gln
    450                 455                 460

His Ser Phe Phe Pro Pro Glu Glu Gln Leu Leu Thr Ala Ser Gly
465                 470                 475                 480

Ala Ala Gly Asp Ser Ile Lys Ala Ile Ala Ser Ile Ala Glu Lys Tyr
            485                 490                 495

Phe Gly Pro Gly Phe Met Ser Met Gln Glu Lys Lys Leu Gly Ser Leu
        500                 505                 510

Pro Tyr His Ser Val Phe Pro Phe Gln Phe Leu Pro Asn Phe Pro His
    515                 520                 525

Ser Leu Tyr Pro Phe Thr Asp Arg Ala Leu Ala His Asn Leu Leu Val
        530                 535                 540

Lys Ala Glu Pro Lys Ser Pro Arg Asp Ala Leu Lys Val Gly Gly Pro
545                 550                 555                 560

Ser Ala Glu Cys Pro Phe Asp Leu Thr Thr Lys Pro Lys Glu Ala Lys
                565                 570                 575

Pro Ala Leu Leu Ala Pro Lys Val Pro Leu Ile Pro Ser Ser Gly Glu
            580                 585                 590

Glu Gln Pro Leu Asp Leu Ser Ile Gly Ser Arg Ala Arg Ala Ser Gln
        595                 600                 605

Asn Gly Gly Gly Arg Glu Pro Arg Lys Asn His Val Tyr Gly Glu Arg
    610                 615                 620

Lys Pro Gly Val Ser Glu Gly Leu Pro Lys Val Cys Pro Ala Gln Leu
625                 630                 635                 640

Pro Gln Gln Pro Ser Leu His Tyr Ala Lys Pro Ser Pro Phe Phe Met
                645                 650                 655

Asp Pro Ile Tyr Ser Arg Val Glu Lys Arg Lys Val Ala Asp Pro Val
            660                 665                 670

Gly Val Leu Lys Glu Lys Tyr Leu Arg Pro Ser Pro Leu Leu Phe His
        675                 680                 685
```

```
Pro Gln Met Ser Ala Ile Glu Thr Met Thr Glu Lys Leu Glu Ser Phe
    690                 695                 700

Ala Ala Met Lys Ala Asp Ser Gly Ser Ser Leu Gln Pro Leu Pro His
705                 710                 715                 720

His Pro Phe Asn Phe Arg Ser Pro Pro Thr Leu Ser Asp Pro Ile
            725                 730                 735

Leu Arg Lys Gly Lys Glu Arg Tyr Thr Cys Arg Tyr Cys Gly Lys Ile
            740                 745                 750

Phe Pro Arg Ser Ala Asn Leu Thr Arg His Leu Arg Thr His Thr Gly
            755                 760                 765

Glu Gln Pro Tyr Arg Cys Lys Tyr Cys Asp Arg Ser Phe Ser Ile Ser
770                 775                 780

Ser Asn Leu Gln Arg His Val Arg Asn Ile His Asn Lys Glu Lys Pro
785                 790                 795                 800

Phe Lys Cys His Leu Cys Asn Arg Cys Phe Gly Gln Gln Thr Asn Leu
            805                 810                 815

Asp Arg His Leu Lys Lys His Glu His Glu Gly Ala Pro Val Ser Gln
            820                 825                 830

His Ser Gly Val Leu Thr Asn His Leu Gly Thr Ser Ala Ser Ser Pro
            835                 840                 845

Thr Ser Glu Ser Asp Asn His Ala Leu Leu Asp Glu Lys Glu Asp Ser
850                 855                 860

Tyr Phe Ser Glu Ile Arg Asn Phe Ile Ala Asn Ser Glu Met Asn Gln
865                 870                 875                 880

Ala Ser Thr Arg Met Asp Lys Arg Pro Glu Ile Gln Asp Leu Asp Ser
            885                 890                 895

Asn Pro Pro Cys Pro Gly Ser Ala Ser Ala Lys Pro Glu Asp Val Glu
            900                 905                 910

Glu Glu Glu Glu Glu Glu Leu Glu Glu Asp Asp Asp Ser Leu Ala
            915                 920                 925

Gly Lys Ser Gln Glu Asp Thr Val Ser Pro Thr Pro Gly Pro Gln Gly
            930                 935                 940

Val Tyr Glu Asp Glu Glu Asp Glu Glu Pro Pro Ser Leu Thr Met Gly
945                 950                 955                 960

Phe Asp His Thr Arg Arg His Met Gln
                965
```

<210> SEQ ID NO 26
<211> LENGTH: 3138
<212> TYPE: DNA
<213> ORGANISM: Unknown
<220> FEATURE:
<221> NAME/KEY: source
<223> OTHER INFORMATION: /note="Description of Unknown: DeltaPR sequence"
<220> FEATURE:
<221> NAME/KEY: CDS
<222> LOCATION: (1)..(3135)

<400> SEQUENCE: 26

```
atg cga tcc aag gcg agg gcg agg aag cta gcc aaa agt gac ggt gac     48
Met Arg Ser Lys Ala Arg Ala Arg Lys Leu Ala Lys Ser Asp Gly Asp
1               5                   10                  15 gtt gta aat aat atg tat gaa cct gac ccg gac ctg ctg gcc ggc cag     96
Val Val Asn Asn Met Tyr Glu Pro Asp Pro Asp Leu Leu Ala Gly Gln
                20                  25                  30 agt gcc gag gag gag acc gaa gac ggc atc ctg tcc ccc atc ccc atg    144
Ser Ala Glu Glu Glu Thr Glu Asp Gly Ile Leu Ser Pro Ile Pro Met
```

-continued

```
              35                  40                  45
ggg cca ccg tcc ccc ttc ccc acc agc gag gac ttc act ccc aag gag      192
Gly Pro Pro Ser Pro Phe Pro Thr Ser Glu Asp Phe Thr Pro Lys Glu
 50                  55                  60 ggc tcg ccc tat gag gct cct gtc tac att cct gaa gac att cca atc      240
Gly Ser Pro Tyr Glu Ala Pro Val Tyr Ile Pro Glu Asp Ile Pro Ile
 65                  70                  75                  80 cca cca gac ttc gag cta cga gag tcc tcc agc ttg gat gag gac ccc      288
Pro Pro Asp Phe Glu Leu Arg Glu Ser Ser Ser Leu Asp Glu Asp Pro
                 85                  90                  95 aca ttc cgc tgt gat gag tgt gat gag ctc ttc cag tgc agg ctg gac      336
Thr Phe Arg Cys Asp Glu Cys Asp Glu Leu Phe Gln Cys Arg Leu Asp
                100                 105                 110 ctg agg cgc cac aag aag tac gcg tgc agc tct gca gga gcc cag ctc      384
Leu Arg Arg His Lys Lys Tyr Ala Cys Ser Ser Ala Gly Ala Gln Leu
            115                 120                 125 tac gag ggc cta ggg gag gaa ctc aag ccc gag ggc ctt ggc gtg ggc      432
Tyr Glu Gly Leu Gly Glu Glu Leu Lys Pro Glu Gly Leu Gly Val Gly
130                 135                 140 agc gac ggg caa gcg cat gag tgc aag gat tgc gag cgg atg ttc ccc      480
Ser Asp Gly Gln Ala His Glu Cys Lys Asp Cys Glu Arg Met Phe Pro
145                 150                 155                 160 aac aag tac agc ttg gag caa cac atg atc gtc cac acg gaa gag cgt      528
Asn Lys Tyr Ser Leu Glu Gln His Met Ile Val His Thr Glu Glu Arg
                165                 170                 175 gag tac aaa tgt gac cag tgt ccc aag gcc ttc aac tgg aag tcc aac      576
Glu Tyr Lys Cys Asp Gln Cys Pro Lys Ala Phe Asn Trp Lys Ser Asn
                180                 185                 190 ctc atc cgc cac cag atg tct cac gac agt ggc aag cgc ttc gaa tgt      624
Leu Ile Arg His Gln Met Ser His Asp Ser Gly Lys Arg Phe Glu Cys
            195                 200                 205 gaa aac tgt gtc aag gtg ttc acg gac ccc agc aac ctc cag cgt cac      672
Glu Asn Cys Val Lys Val Phe Thr Asp Pro Ser Asn Leu Gln Arg His
210                 215                 220 atc cgc tca cag cat gtc ggt gcc cgg gcc cat gcc tgc cct gac tgt      720
Ile Arg Ser Gln His Val Gly Ala Arg Ala His Ala Cys Pro Asp Cys
225                 230                 235                 240 ggc aag acc ttc gcc aca tcc tct ggc ctc aaa cag cac aag cat atc      768
Gly Lys Thr Phe Ala Thr Ser Ser Gly Leu Lys Gln His Lys His Ile
                245                 250                 255 cac agc acg gtg aag cca ttc ata tgc gag gtc tgc cac aag tcc tac      816
His Ser Thr Val Lys Pro Phe Ile Cys Glu Val Cys His Lys Ser Tyr
                260                 265                 270 acg cag ttc tcc aac ctg tgc cgg cac aag cgg atg cac gcc gac tgc      864
Thr Gln Phe Ser Asn Leu Cys Arg His Lys Arg Met His Ala Asp Cys
            275                 280                 285 agg acg cag atc aag tgc aag gac tgt ggg cag atg ttc agc act acc      912
Arg Thr Gln Ile Lys Cys Lys Asp Cys Gly Gln Met Phe Ser Thr Thr
290                 295                 300 tcc tcc ctc aac aag cat cgg aga ttc tgc gag ggc aag aac cat tac      960
Ser Ser Leu Asn Lys His Arg Arg Phe Cys Glu Gly Lys Asn His Tyr
305                 310                 315                 320 acg cct ggc agc atc ttc acc cca ggc ctg ccc ttg acc ccc agc ccc     1008
Thr Pro Gly Ser Ile Phe Thr Pro Gly Leu Pro Leu Thr Pro Ser Pro
                325                 330                 335 atg atg gac aag aca aaa ccc tcc ccg acc ctc aac cac ggg ggc cta     1056
Met Met Asp Lys Thr Lys Pro Ser Pro Thr Leu Asn His Gly Gly Leu
                340                 345                 350 ggc ttc agc gag tac ttc ccc tcc aga cct cat cct ggg agc ctg ccc     1104
Gly Phe Ser Glu Tyr Phe Pro Ser Arg Pro His Pro Gly Ser Leu Pro
```

```
                                            -continued

Gly Phe Ser Glu Tyr Phe Pro Ser Arg Pro His Pro Gly Ser Leu Pro
        355                 360                 365 ttc tcg gct gct cct ccg gcc ttc ccc gca ctc act ccg ggc ttc ccg    1152
Phe Ser Ala Ala Pro Pro Ala Phe Pro Ala Leu Thr Pro Gly Phe Pro
370                 375                 380 ggc atc ttt cct cca tcc ctg tac cca cga cca cct ctg cta cct ccc    1200
Gly Ile Phe Pro Pro Ser Leu Tyr Pro Arg Pro Pro Leu Leu Pro Pro
385                 390                 395                 400 acg ccg ctg ctc aag agc ccc ctg aac cac gcg cag gac gcc aag cta    1248
Thr Pro Leu Leu Lys Ser Pro Leu Asn His Ala Gln Asp Ala Lys Leu
                405                 410                 415 ccc agc ccg ctg gga aac cca gcc ctg ccc ctt gtc tcc gcg gtc agc    1296
Pro Ser Pro Leu Gly Asn Pro Ala Leu Pro Leu Val Ser Ala Val Ser
            420                 425                 430 aat agc agc cag ggt gcc aca gcg gcc acc ggg tca gag gag aaa ttt    1344
Asn Ser Ser Gln Gly Ala Thr Ala Ala Thr Gly Ser Glu Glu Lys Phe
        435                 440                 445 gat ggc cgc ttg gaa gac gca tat gcg gag aag gtc aaa aat agg agc    1392
Asp Gly Arg Leu Glu Asp Ala Tyr Ala Glu Lys Val Lys Asn Arg Ser
450                 455                 460 cct gac atg tcg gat ggc agt gac ttt gag gat atc aac acc acg acc    1440
Pro Asp Met Ser Asp Gly Ser Asp Phe Glu Asp Ile Asn Thr Thr Thr
465                 470                 475                 480 ggg aca gac ttg gac act acc acg ggc acg ggg tca gac ctg gac agc    1488
Gly Thr Asp Leu Asp Thr Thr Thr Gly Thr Gly Ser Asp Leu Asp Ser
                485                 490                 495 gac ctg gac agt gac aga gac aaa ggc aag gac aag ggg aag cca gtg    1536
Asp Leu Asp Ser Asp Arg Asp Lys Gly Lys Asp Lys Gly Lys Pro Val
            500                 505                 510 gag agc aaa cct gag ttt ggg ggt gca tct gtg ccc cct ggg gcc atg    1584
Glu Ser Lys Pro Glu Phe Gly Gly Ala Ser Val Pro Pro Gly Ala Met
        515                 520                 525 aac agt gtg gcc gag gta ccg gcc ttc tac tca cag cat tcc ttc ttc    1632
Asn Ser Val Ala Glu Val Pro Ala Phe Tyr Ser Gln His Ser Phe Phe
530                 535                 540 ccg cca ccc gag gaa cag ctg ctg acg gcc tcg gga gct gcc ggc gac    1680
Pro Pro Pro Glu Glu Gln Leu Leu Thr Ala Ser Gly Ala Ala Gly Asp
545                 550                 555                 560 tcc atc aag gcc atc gcg tcc atc gcg gag aaa tac ttc ggt cct ggc    1728
Ser Ile Lys Ala Ile Ala Ser Ile Ala Glu Lys Tyr Phe Gly Pro Gly
                565                 570                 575 ttc atg agc atg cag gag aag aag ctg ggc tca cta ccc tac cac tcc    1776
Phe Met Ser Met Gln Glu Lys Lys Leu Gly Ser Leu Pro Tyr His Ser
            580                 585                 590 gtg ttc ccc ttc cag ttc ctg cct aac ttt ccc cac tcc ctc tac ccc    1824
Val Phe Pro Phe Gln Phe Leu Pro Asn Phe Pro His Ser Leu Tyr Pro
        595                 600                 605 ttt acg gac cga gcc ctc gcc cac aac ttg ctg gtc aag gct gag cca    1872
Phe Thr Asp Arg Ala Leu Ala His Asn Leu Leu Val Lys Ala Glu Pro
610                 615                 620 aag tca ccc cgg gat gcc ctc aag gtg ggc ggc ccc agt gcg gag tgc    1920
Lys Ser Pro Arg Asp Ala Leu Lys Val Gly Gly Pro Ser Ala Glu Cys
625                 630                 635                 640 ccc ttc gac ctc acc acc aaa cca aag gag gcc aaa ccc gcc ctg ctc    1968
Pro Phe Asp Leu Thr Thr Lys Pro Lys Glu Ala Lys Pro Ala Leu Leu
                645                 650                 655 gca ccc aag gtc ccc ctc atc ccc tca tct ggc gag gaa cag cca ctg    2016
Ala Pro Lys Val Pro Leu Ile Pro Ser Ser Gly Glu Glu Gln Pro Leu
            660                 665                 670
```

```
gac ctg agc atc ggc agc agg gcc agg gca agc cag aac gga ggt ggc     2064
Asp Leu Ser Ile Gly Ser Arg Ala Arg Ala Ser Gln Asn Gly Gly Gly
            675                 680                 685 cgt gag ccg cgg aag aac cac gtc tac ggt gaa cgg aag ccg ggg gtc     2112
Arg Glu Pro Arg Lys Asn His Val Tyr Gly Glu Arg Lys Pro Gly Val
690                 695                 700 agc gag ggg ctg cct aag gtg tgc cca gca cag ctg ccc cag cag ccc     2160
Ser Glu Gly Leu Pro Lys Val Cys Pro Ala Gln Leu Pro Gln Gln Pro
705                 710                 715                 720 tcc ttg cat tat gct aag cct tca ccg ttc ttc atg gat ccc atc tac     2208
Ser Leu His Tyr Ala Lys Pro Ser Pro Phe Phe Met Asp Pro Ile Tyr
                725                 730                 735 agc agg gta gaa aag cgg aag gtg gca gac cct gtg gga gtc ctg aaa     2256
Ser Arg Val Glu Lys Arg Lys Val Ala Asp Pro Val Gly Val Leu Lys
            740                 745                 750 gag aag tac ctg cgg ccg tcc cca ctt ctg ttc cac ccc cag atg tca     2304
Glu Lys Tyr Leu Arg Pro Ser Pro Leu Leu Phe His Pro Gln Met Ser
        755                 760                 765 gcc ata gaa acc atg acg gag aag ctg gag agc ttt gca gcc atg aag     2352
Ala Ile Glu Thr Met Thr Glu Lys Leu Glu Ser Phe Ala Ala Met Lys
770                 775                 780 gcc gac tca ggc agc tcc ctg cag ccc ctg cct cac cac ccg ttc aac     2400
Ala Asp Ser Gly Ser Ser Leu Gln Pro Leu Pro His His Pro Phe Asn
785                 790                 795                 800 ttc cgc tcc cca ccc cca acg ctc tcg gat ccc atc ctc agg aag ggg     2448
Phe Arg Ser Pro Pro Pro Thr Leu Ser Asp Pro Ile Leu Arg Lys Gly
                805                 810                 815 aag gag aga tac acg tgc agg tac tgt ggc aag atc ttc ccc aga tct     2496
Lys Glu Arg Tyr Thr Cys Arg Tyr Cys Gly Lys Ile Phe Pro Arg Ser
            820                 825                 830 gca aat ctc aca aga cat ctg agg aca cac aca ggg gag cag cca tac     2544
Ala Asn Leu Thr Arg His Leu Arg Thr His Thr Gly Glu Gln Pro Tyr
        835                 840                 845 agg tgc aag tac tgt gac cgg tca ttc agc atc tcc tcc aac ctc cag     2592
Arg Cys Lys Tyr Cys Asp Arg Ser Phe Ser Ile Ser Ser Asn Leu Gln
850                 855                 860 cgg cac gtg agg aac atc cac aac aaa gag aag ccg ttc aag tgc cat     2640
Arg His Val Arg Asn Ile His Asn Lys Glu Lys Pro Phe Lys Cys His
865                 870                 875                 880 ctg tgc aac cgc tgc ttc ggg cag cag acc aac cta gac cgg cac ctg     2688
Leu Cys Asn Arg Cys Phe Gly Gln Gln Thr Asn Leu Asp Arg His Leu
                885                 890                 895 aag aag cac gaa cac gag ggc gca cca gtg agc cag cac tcc ggg gtg     2736
Lys Lys His Glu His Glu Gly Ala Pro Val Ser Gln His Ser Gly Val
            900                 905                 910 ctc acg aac cac ctg ggc acc agc gcc tcc tcc ccc acc tcc gag tcg     2784
Leu Thr Asn His Leu Gly Thr Ser Ala Ser Ser Pro Thr Ser Glu Ser
        915                 920                 925 gac aac cat gca ctt tta gat gag aag gaa gat tct tac ttc tcc gag     2832
Asp Asn His Ala Leu Leu Asp Glu Lys Glu Asp Ser Tyr Phe Ser Glu
930                 935                 940 atc cga aac ttc atc gcc aac agc gag atg aac cag gca tcc act cga     2880
Ile Arg Asn Phe Ile Ala Asn Ser Glu Met Asn Gln Ala Ser Thr Arg
945                 950                 955                 960 atg gac aaa cgg cct gag atc caa gac ctg gac agc aac cca ccg tgt     2928
Met Asp Lys Arg Pro Glu Ile Gln Asp Leu Asp Ser Asn Pro Pro Cys
                965                 970                 975 cca ggc tca gcc agt gca aag cca gag gac gta gag gag gag gaa gag     2976
Pro Gly Ser Ala Ser Ala Lys Pro Glu Asp Val Glu Glu Glu Glu Glu
            980                 985                 990
```

```
gag gag ctg gag gaa gag gat gat gac agc tta gcc ggg aag tca cag    3024
Glu Glu Leu Glu Glu Glu Asp Asp Asp Ser Leu Ala Gly Lys Ser Gln
        995                 1000                1005 gag gac acg gtg tcc ccc aca cct gag ccc caa gga gtc tat gaa        3069
Glu Asp Thr Val Ser Pro Thr Pro Glu Pro Gln Gly Val Tyr Glu
    1010                1015                1020 gat gaa gag gat gag gaa cca ccc agc ctg acc atg ggc ttt gac        3114
Asp Glu Glu Asp Glu Glu Pro Pro Ser Leu Thr Met Gly Phe Asp
    1025                1030                1035 cat acc cgg agg cat atg caa tga                                    3138
His Thr Arg Arg His Met Gln
    1040            1045

<210> SEQ ID NO 27
<211> LENGTH: 1045
<212> TYPE: PRT
<213> ORGANISM: Unknown
<220> FEATURE:
<221> NAME/KEY: source
<223> OTHER INFORMATION: /note="Description of Unknown: DeltaPR
      sequence"

<400> SEQUENCE: 27

Met Arg Ser Lys Ala Arg Ala Arg Lys Leu Ala Lys Ser Asp Gly Asp
1               5                   10                  15

Val Val Asn Asn Met Tyr Glu Pro Asp Pro Asp Leu Leu Ala Gly Gln
            20                  25                  30

Ser Ala Glu Glu Glu Thr Glu Asp Gly Ile Leu Ser Pro Ile Pro Met
        35                  40                  45

Gly Pro Pro Ser Pro Phe Pro Thr Ser Glu Asp Phe Thr Pro Lys Glu
    50                  55                  60

Gly Ser Pro Tyr Glu Ala Pro Val Tyr Ile Pro Glu Asp Ile Pro Ile
65                  70                  75                  80

Pro Pro Asp Phe Glu Leu Arg Glu Ser Ser Leu Asp Glu Asp Pro
            85                  90                  95

Thr Phe Arg Cys Asp Glu Cys Asp Glu Leu Phe Gln Cys Arg Leu Asp
            100                 105                 110

Leu Arg Arg His Lys Lys Tyr Ala Cys Ser Ser Ala Gly Ala Gln Leu
            115                 120                 125

Tyr Glu Gly Leu Gly Glu Leu Lys Pro Glu Gly Leu Gly Val Gly
            130                 135                 140

Ser Asp Gly Gln Ala His Glu Cys Lys Asp Cys Glu Arg Met Phe Pro
145                 150                 155                 160

Asn Lys Tyr Ser Leu Glu Gln His Met Ile Val His Thr Glu Glu Arg
            165                 170                 175

Glu Tyr Lys Cys Asp Gln Cys Pro Lys Ala Phe Asn Trp Lys Ser Asn
            180                 185                 190

Leu Ile Arg His Gln Met Ser His Asp Ser Gly Lys Arg Phe Glu Cys
            195                 200                 205

Glu Asn Cys Val Lys Val Phe Thr Asp Pro Ser Asn Leu Gln Arg His
            210                 215                 220

Ile Arg Ser Gln His Val Gly Ala Arg Ala His Ala Cys Pro Asp Cys
225                 230                 235                 240

Gly Lys Thr Phe Ala Thr Ser Ser Gly Leu Lys Gln His Lys His Ile
            245                 250                 255

His Ser Thr Val Lys Pro Phe Ile Cys Glu Val Cys His Lys Ser Tyr
            260                 265                 270
```

-continued

```
Thr Gln Phe Ser Asn Leu Cys Arg His Lys Met His Ala Asp Cys
        275                 280                 285
Arg Thr Gln Ile Lys Cys Lys Asp Cys Gly Gln Met Phe Ser Thr Thr
290                 295                 300
Ser Ser Leu Asn Lys His Arg Arg Phe Cys Glu Gly Lys Asn His Tyr
305                 310                 315                 320
Thr Pro Gly Ser Ile Phe Thr Pro Gly Leu Pro Leu Thr Pro Ser Pro
                    325                 330                 335
Met Met Asp Lys Thr Lys Pro Ser Pro Thr Leu Asn His Gly Gly Leu
                340                 345                 350
Gly Phe Ser Glu Tyr Phe Pro Ser Arg Pro His Pro Gly Ser Leu Pro
            355                 360                 365
Phe Ser Ala Ala Pro Pro Ala Phe Pro Ala Leu Thr Pro Gly Phe Pro
370                 375                 380
Gly Ile Phe Pro Pro Ser Leu Tyr Pro Arg Pro Pro Leu Leu Pro Pro
385                 390                 395                 400
Thr Pro Leu Leu Lys Ser Pro Leu Asn His Ala Gln Asp Ala Lys Leu
                    405                 410                 415
Pro Ser Pro Leu Gly Asn Pro Ala Leu Pro Leu Val Ser Ala Val Ser
                420                 425                 430
Asn Ser Ser Gln Gly Ala Thr Ala Ala Thr Gly Ser Glu Glu Lys Phe
            435                 440                 445
Asp Gly Arg Leu Glu Asp Ala Tyr Ala Glu Lys Val Lys Asn Arg Ser
450                 455                 460
Pro Asp Met Ser Asp Gly Ser Asp Phe Glu Asp Ile Asn Thr Thr Thr
465                 470                 475                 480
Gly Thr Asp Leu Asp Thr Thr Thr Gly Thr Gly Ser Asp Leu Asp Ser
                    485                 490                 495
Asp Leu Asp Ser Asp Arg Asp Lys Gly Lys Asp Lys Gly Lys Pro Val
                500                 505                 510
Glu Ser Lys Pro Glu Phe Gly Gly Ala Ser Val Pro Pro Gly Ala Met
            515                 520                 525
Asn Ser Val Ala Glu Val Pro Ala Phe Tyr Ser Gln His Ser Phe Phe
530                 535                 540
Pro Pro Pro Glu Glu Gln Leu Leu Thr Ala Ser Gly Ala Ala Gly Asp
545                 550                 555                 560
Ser Ile Lys Ala Ile Ala Ser Ile Ala Glu Lys Tyr Phe Gly Pro Gly
                    565                 570                 575
Phe Met Ser Met Gln Glu Lys Lys Leu Gly Ser Leu Pro Tyr His Ser
                580                 585                 590
Val Phe Pro Phe Gln Phe Leu Pro Asn Phe Pro His Ser Leu Tyr Pro
            595                 600                 605
Phe Thr Asp Arg Ala Leu Ala His Asn Leu Leu Val Lys Ala Glu Pro
610                 615                 620
Lys Ser Pro Arg Asp Ala Leu Lys Val Gly Pro Ser Ala Glu Cys
625                 630                 635                 640
Pro Phe Asp Leu Thr Thr Lys Pro Lys Glu Ala Lys Pro Ala Leu Leu
                    645                 650                 655
Ala Pro Lys Val Pro Leu Ile Pro Ser Ser Gly Glu Glu Gln Pro Leu
                660                 665                 670
Asp Leu Ser Ile Gly Ser Arg Ala Arg Ala Ser Gln Asn Gly Gly Gly
            675                 680                 685
```

```
Arg Glu Pro Arg Lys Asn His Val Tyr Gly Glu Arg Lys Pro Gly Val
    690                 695                 700

Ser Glu Gly Leu Pro Lys Val Cys Pro Ala Gln Leu Pro Gln Gln Pro
705                 710                 715                 720

Ser Leu His Tyr Ala Lys Pro Ser Pro Phe Phe Met Asp Pro Ile Tyr
                725                 730                 735

Ser Arg Val Glu Lys Arg Lys Val Ala Asp Pro Val Gly Val Leu Lys
            740                 745                 750

Glu Lys Tyr Leu Arg Pro Ser Pro Leu Leu Phe His Pro Gln Met Ser
        755                 760                 765

Ala Ile Glu Thr Met Thr Glu Lys Leu Glu Ser Phe Ala Ala Met Lys
770                 775                 780

Ala Asp Ser Gly Ser Ser Leu Gln Pro Leu Pro His His Pro Phe Asn
785                 790                 795                 800

Phe Arg Ser Pro Pro Thr Leu Ser Asp Pro Ile Leu Arg Lys Gly
                805                 810                 815

Lys Glu Arg Tyr Thr Cys Arg Tyr Cys Gly Lys Ile Phe Pro Arg Ser
            820                 825                 830

Ala Asn Leu Thr Arg His Leu Arg Thr His Thr Gly Glu Gln Pro Tyr
        835                 840                 845

Arg Cys Lys Tyr Cys Asp Arg Ser Phe Ser Ile Ser Ser Asn Leu Gln
850                 855                 860

Arg His Val Arg Asn Ile His Asn Lys Glu Lys Pro Phe Lys Cys His
865                 870                 875                 880

Leu Cys Asn Arg Cys Phe Gly Gln Gln Thr Asn Leu Asp Arg His Leu
                885                 890                 895

Lys Lys His Glu His Glu Gly Ala Pro Val Ser Gln His Ser Gly Val
            900                 905                 910

Leu Thr Asn His Leu Gly Thr Ser Ala Ser Ser Pro Thr Ser Glu Ser
        915                 920                 925

Asp Asn His Ala Leu Leu Asp Glu Lys Glu Asp Ser Tyr Phe Ser Glu
930                 935                 940

Ile Arg Asn Phe Ile Ala Asn Ser Glu Met Asn Gln Ala Ser Thr Arg
945                 950                 955                 960

Met Asp Lys Arg Pro Glu Ile Gln Asp Leu Asp Ser Asn Pro Cys
                965                 970                 975

Pro Gly Ser Ala Ser Ala Lys Pro Glu Asp Val Glu Glu Glu Glu
            980                 985                 990

Glu Glu Leu Glu Glu Glu Asp  Asp Ser Leu Ala Gly  Lys Ser Gln
        995                 1000                1005

Glu Asp  Thr Val Ser Pro Thr  Pro Glu Pro Gln Gly  Val Tyr Glu
    1010                1015                    1020

Asp Glu  Glu Asp Glu Glu Pro  Pro Ser Leu Thr Met  Gly Phe Asp
    1025                1030                    1035

His Thr  Arg Arg His Met Gln
    1040                1045

<210> SEQ ID NO 28
<211> LENGTH: 2651
<212> TYPE: DNA
<213> ORGANISM: Mus musculus

<400> SEQUENCE: 28
attcgcgacc cgaagctgcg cgggcgcgag ccagttgggg cactgggtgg gcggcggcga    60
```

```
cagcggcgcc acgcgcaggc tggaggccgc cgaggctcgc catgccggga gaactctaac      120
tcccccatgg agtcggccga cttctacgag gtggagccgc ggcccccgat gagcagtcac      180
ctccagagcc cccgcacgc gcccagcaac gccgcctttg gctttccccg gggcgcgggc       240
cccgcgccgc ccccagcccc acctgccgcc ccggagccgc tgggcggcat ctgcgagcac      300
gagacgtcta tagacatcag cgcctacatc gacccggccg ccttcaacga cgagttcctg     360
gccgacctct tccagcacag ccgacagcag gagaaggcca aggcggcggc gggccccgcg      420
ggtggcggcg gtgactttga ctacccggga gccccggcgg gccccggcgg cgcggtcatg      480
tccgcggggg cgcacgggcc ccctcccggc tacggctgtg cggcggccgg ctacctggac      540
ggcaggctgg agccctgta cgagcgcgtc ggggcgcccg cgctacggcc gctggtgatc       600
aaacaagagc cccgcgagga ggacgaggcg aagcagctgg cgctggccgg cctcttcccc      660
taccagccac cgccgccacc gccaccgccg cacccgcacg cgtctcccgc gcacctggcc      720
gccccccact tgcagttcca gatcgcgcac tgcggccaga ccaccatgca cctgcagcct      780
ggccacccca caccgccgcc cacgcccgtg cccagcccgc acgctgcgcc cgccttgggt      840
gctgcgggcc tgcctggccc cgggagcgcg ctcaagggct tggccggtgc gcaccccgac     900
ctccgcacgg gaggcggcgg cggtggcagc ggtgccggtg cgggcaaagc caagaagtcg     960
gtggacaaga acagcaacga gtaccgggta cggcgggaac gcaacaacat cgcggtgcgc    1020
aagagccgag ataaagccaa acaacgcaac gtggagacgc aacagaaggt gctggagttg    1080
accagtgaca atgaccgcct gcgcaagcgg gtggaacagc tgagccgtga actggacacg    1140
ctgcggggca tcttccgcca gctgcctgag agctccttgg tcaaggccat gggcaactgc    1200
gcgtgaggcg cgcggctgcg ggaccgcctt gggccggccc cctggctgga cccagagg     1260 atggtttcgg gtcgctggat ctctaggctg cccgggccgc gcaagccagg actaggagat    1320
tccggtgtgg cctgaaagcc tggcctgctc cgcgtgtccc ctcccttcct ctgagccgga    1380
ctcggtgcgt ctaagatgag ggagtcaggc cgtggtggtt tctccttgag accgagagac    1440
tttccgcgga gctgagctgg gggcccggca gtactagtat taaggaagta accttgtgcc    1500
ttggatactc aaaactcgct ccttttccta ccgagtaggg ggagcaaaaa tgtgccttga    1560
tattttattt ggaggattcc tgcttcctct cgggcctcag ctggccccgt gagaaaaatg    1620
aagggtgcag gccagggca ggaggaagat acaggaagct gagatcccgg cagtgccctg     1680
agctgcccct cagtccctgt ctttagaggg gagggactta ggtgttgggg atttgagtct    1740
gtgtcctcac cccagctac agggaggtgg agggctccta atcccttgct ttttgcacct     1800
ccacctacat cccccccccc ccactcagct tacaacaggc caggtttcct gggtgagttc    1860
atggagaatg ggggcaccac ccccagtcag accagaaagc tgagttgtga gttagccatg    1920
tggtaggaga cagagaccta ggtttctggg ctttgtgggg tggggatag gaggacacgg     1980 ggaccattag ccttgtgtgt actgtatgtc gccagccgct gttgctgaag gaacttgaag    2040
cacaatcgat ccatcccaga gggactggag ttatgacaag cttcccaaat attttgcttt    2100
atcatccgat atcaacactt gtatctggtc tctgtgtccc agcggtgcct tgtgcaatgg    2160
cagtgtgcac gtctatgcta aaccaccatt ttatttggtc ttttgttttg ttttggtttt    2220
gctctgattc ttgccaaact gagactcttc actaacggct gggggaagga gctgagtgag    2280
gctctcattc tttttggttt agggatgttt gggtttttc gtctgcctcc cagaggacca    2340
atgaaatgaa gtgggcttcc ccctctcccc tagttgtcca agggtgtatg tagtagtggg    2400
tcttagcttc ctccggctaa gacttaggct tccccaccca cccaacccca tccccaacgg    2460
```

```
ccctggctct gggtctggaa agaaggccac ctccagccag ttcatacaca caccctgtg  2520 gctgggagca gggctggacc gcttccttct cttcttttt ttggggggg gggacacaaa  2580 gtttcatgct agatgtcgta tgtattatat ctataatata aacatatcaa actcaaaaaa  2640
aaaaaaaaaa a                                                     2651

<210> SEQ ID NO 29
<211> LENGTH: 359
<212> TYPE: PRT
<213> ORGANISM: Mus musculus

<400> SEQUENCE: 29

Met Glu Ser Ala Asp Phe Tyr Glu Val Glu Pro Arg Pro Pro Met Ser
1               5                   10                  15

Ser His Leu Gln Ser Pro His Ala Pro Ser Asn Ala Ala Phe Gly
            20                  25                  30

Phe Pro Arg Gly Ala Gly Pro Ala Pro Pro Ala Pro Pro Ala Ala
        35                  40                  45

Pro Glu Pro Leu Gly Gly Ile Cys Glu His Glu Thr Ser Ile Asp Ile
50                  55                  60

Ser Ala Tyr Ile Asp Pro Ala Ala Phe Asn Asp Glu Phe Leu Ala Asp
65                  70                  75                  80

Leu Phe Gln His Ser Arg Gln Gln Glu Lys Ala Lys Ala Ala Ala Gly
                85                  90                  95

Pro Ala Gly Gly Gly Gly Asp Phe Asp Tyr Pro Gly Ala Pro Ala Gly
            100                 105                 110

Pro Gly Gly Ala Val Met Ser Ala Gly Ala His Gly Pro Pro Pro Gly
            115                 120                 125

Tyr Gly Cys Ala Ala Ala Gly Tyr Leu Asp Gly Arg Leu Glu Pro Leu
        130                 135                 140

Tyr Glu Arg Val Gly Ala Pro Ala Leu Arg Pro Leu Val Ile Lys Gln
145                 150                 155                 160

Glu Pro Arg Glu Glu Asp Glu Ala Lys Gln Leu Ala Leu Ala Gly Leu
                165                 170                 175

Phe Pro Tyr Gln Pro Pro Pro Pro Pro Pro Pro His Pro His Ala
            180                 185                 190

Ser Pro Ala His Leu Ala Ala Pro His Leu Gln Phe Gln Ile Ala His
        195                 200                 205

Cys Gly Gln Thr Thr Met His Leu Gln Pro Gly His Pro Thr Pro Pro
210                 215                 220

Pro Thr Pro Val Pro Ser Pro His Ala Ala Pro Ala Leu Gly Ala Ala
225                 230                 235                 240

Gly Leu Pro Gly Pro Gly Ser Ala Leu Lys Gly Leu Ala Gly Ala His
                245                 250                 255

Pro Asp Leu Arg Thr Gly Gly Gly Gly Gly Ser Gly Ala Gly Ala
            260                 265                 270

Gly Lys Ala Lys Lys Ser Val Asp Lys Asn Ser Asn Glu Tyr Arg Val
275                 280                 285

Arg Arg Glu Arg Asn Asn Ile Ala Val Arg Lys Ser Arg Asp Lys Ala
        290                 295                 300

Lys Gln Arg Asn Val Glu Thr Gln Gln Lys Val Leu Glu Leu Thr Ser
305                 310                 315                 320

Asp Asn Asp Arg Leu Arg Lys Arg Val Glu Gln Leu Ser Arg Glu Leu
                325                 330                 335
```

Asp Thr Leu Arg Gly Ile Phe Arg Gln Leu Pro Glu Ser Ser Leu Val
                340                 345                 350

Lys Ala Met Gly Asn Cys Ala
        355

<210> SEQ ID NO 30
<211> LENGTH: 2260
<212> TYPE: DNA
<213> ORGANISM: Mus musculus

<400> SEQUENCE: 30

| | | | | | |
|---|---|---|---|---|---|
| gacagcccaa | cttggacgcc | aggtccggcc | gacgccgcca | tgagcgccgc | gcttttcagc | 60 |
| ctggacagcc | cggtgcgcgg | cacaccctgg | cccacagaac | ccgcggcctt | ctacgagcca | 120 |
| ggcagggtgg | acaagcccgg | ccgagggccc | gagccagggg | atctggggga | gctgggctcc | 180 |
| acgactcctg | ccatgtacga | cgacgagagc | gccatcgact | tcagcgccta | cattgactcc | 240 |
| atggccgccg | tgcccaccct | agagctgtgc | acgacgaac | tcttcgccga | cctcttcaac | 300 |
| agcaaccaca | aagcggccgg | cgcgggcggc | ctggagctgc | tgcagggcgg | ccctacgcga | 360 |
| cccccgggtg | tggggtctgt | cgctaggggg | ccgctcaagc | gcgaacccga | ctggggcgac | 420 |
| ggcgacgcgc | cgggctccct | gctgccggcg | caagtggcgg | tgtgcgcgca | gacagtggtg | 480 |
| agcttggcgg | ccgcggctca | gcccactcca | cccacttcgc | cggagcctcc | tcgaggcagc | 540 |
| ccggggccga | gcctcgcgcc | cggcacagtc | cgagaaaagg | gcgcgggcaa | gagggtccg | 600 |
| gaccgcggca | gccggagta | ccggcagcgg | cgcgagcgca | acaacatcgc | tgtgcgcaag | 660 |
| agccgcgaca | aggccaagcg | ccgcaaccag | gagatgcagc | agaagctggt | ggagttgtcg | 720 |
| gccgagaacg | agaagctgca | tcagcgcgtg | gagcagctca | cccgggacct | ggctggcctc | 780 |
| cggcagttct | tcaaaaaact | gcccagcccg | cctttcctgc | cgcccaccgg | cgccgactgc | 840 |
| cggtaacgcg | cggcgtgggc | ctttgagact | ctgaacgacc | tatacctcag | accccgacag | 900 |
| cggggagcag | acgccgcccg | aatcgctagt | ttctttggga | cctgcgagcg | acaggaagct | 960 |
| gcagcttggg | cactggactg | cgagagaagc | tatattaatc | tttcccctta | aattattttt | 1020 |
| tataatggta | gcattttcta | cgtcttatta | ccattgcagc | taaggtacat | ttgtagaaaa | 1080 |
| gacatttccg | acagactttt | gtagataaga | ggaagagact | gcgcatgctt | tttatattca | 1140 |
| tttttacagt | atttgtaaga | ataaagaagc | atttaaatcg | ctgcagcttc | ctatgttcat | 1200 |
| tctctcccgc | acacaacata | ctgagacttc | accagggaaa | agcaagcacc | tgggagccac | 1260 |
| ccgaccaggt | gcgttgccca | cacggggtaa | ggagatggac | gcgtttcctc | gcggtctcta | 1320 |
| ttgcccgcgg | aaggaacacg | ggaaagcatg | actaattcat | gtgtgtgatc | ccagagtagg | 1380 |
| ctgacctggg | gcgagaaca | gttggcctaa | cttttaggtg | gttgccgaag | ggtgaggggg | 1440 |
| tggaagagag | ctgggagtct | gaaacttgat | tcctcgttgc | ctctactttc | ctcaatctag | 1500 |
| ggacaacgtg | tagatttaaa | aatgtgtacc | agtacaaatt | aatatcctag | tatataaaaa | 1560 |
| gggcagcccc | aaaagccagt | aattgtaatg | tttgcgggct | taacccccc | cccccccaaa | 1620 |
| gctatgtgcc | tttctactaa | gatactggtt | gttccaaccc | cttccctgat | ctgcacggcc | 1680 |
| tgttgtacag | aaaacacaaa | ccctccaggg | tctaaataca | tagcttttgtt | tgtaattcaa | 1740 |
| atccctgccc | aaagtgcagg | cttgtggact | gctgtgagtc | tgtgatcttt | gccctctgca | 1800 |
| gttcttcagg | gtctctgaca | ggtgggcagt | ggagtaaggt | acagaaattt | ctcttttata | 1860 |
| cagctctcct | cacacccaac | attgtatggg | tgacagtgcc | acctctggca | gctcccagaa | 1920 |

```
cactaaaacc acaaagtgtt taggttggac atttatttat tgtaacagaa cagtaatatt   1980
tcaatatgag atactggctg aagctttaca gaacaatcta gcagagaata ttagatactg   2040
caaagaaaaa acatatataa tattgataaa ttgtaactac tttaaagcta caacaaagca   2100
catttcctaa gcccaagtag ctgcaaaatg aagacacaga agacatgaga aacactcaaa   2160
gaaacatgtt atcaaacttg taggaaggta aagtttaaaa aatgtgtat tagaggtatc    2220 ttgattttta atttaaaact atcctattaa tctctttacc                          2260
```

```
<210> SEQ ID NO 31
<211> LENGTH: 268
<212> TYPE: PRT
<213> ORGANISM: Mus musculus

<400> SEQUENCE: 31
```

| | | | | | | | | | | | | | | |
|---|---|---|---|---|---|---|---|---|---|---|---|---|---|---|
| Met | Ser | Ala | Ala | Leu | Phe | Ser | Leu | Asp | Ser | Pro | Val | Arg | Gly | Thr | Pro |
| 1 | | | | 5 | | | | | 10 | | | | | 15 | |
| Trp | Pro | Thr | Glu | Pro | Ala | Ala | Phe | Tyr | Glu | Pro | Gly | Arg | Val | Asp | Lys |
| | | | 20 | | | | | 25 | | | | | 30 | | |
| Pro | Gly | Arg | Gly | Pro | Glu | Pro | Gly | Asp | Leu | Gly | Glu | Leu | Gly | Ser | Thr |
| | | 35 | | | | | 40 | | | | | 45 | | | |
| Thr | Pro | Ala | Met | Tyr | Asp | Asp | Glu | Ser | Ala | Ile | Asp | Phe | Ser | Ala | Tyr |
| | 50 | | | | | 55 | | | | | 60 | | | | |
| Ile | Asp | Ser | Met | Ala | Ala | Val | Pro | Thr | Leu | Glu | Leu | Cys | His | Asp | Glu |
| 65 | | | | | 70 | | | | | 75 | | | | | 80 |
| Leu | Phe | Ala | Asp | Leu | Phe | Asn | Ser | Asn | His | Lys | Ala | Ala | Gly | Ala | Gly |
| | | | | 85 | | | | | 90 | | | | | 95 | |
| Gly | Leu | Glu | Leu | Leu | Gln | Gly | Gly | Pro | Thr | Arg | Pro | Pro | Gly | Val | Gly |
| | | | 100 | | | | | 105 | | | | | 110 | | |
| Ser | Val | Ala | Arg | Gly | Pro | Leu | Lys | Arg | Glu | Pro | Asp | Trp | Gly | Asp | Gly |
| | | 115 | | | | | 120 | | | | | 125 | | | |
| Asp | Ala | Pro | Gly | Ser | Leu | Leu | Pro | Ala | Gln | Val | Ala | Val | Cys | Ala | Gln |
| | 130 | | | | | 135 | | | | | 140 | | | | |
| Thr | Val | Val | Ser | Leu | Ala | Ala | Ala | Ala | Gln | Pro | Thr | Pro | Pro | Thr | Ser |
| 145 | | | | | 150 | | | | | 155 | | | | | 160 |
| Pro | Glu | Pro | Pro | Arg | Gly | Ser | Pro | Gly | Pro | Ser | Leu | Ala | Pro | Gly | Thr |
| | | | | 165 | | | | | 170 | | | | | 175 | |
| Val | Arg | Glu | Lys | Gly | Ala | Gly | Lys | Arg | Gly | Pro | Asp | Arg | Gly | Ser | Pro |
| | | | 180 | | | | | 185 | | | | | 190 | | |
| Glu | Tyr | Arg | Gln | Arg | Arg | Glu | Arg | Asn | Asn | Ile | Ala | Val | Arg | Lys | Ser |
| | | 195 | | | | | 200 | | | | | 205 | | | |
| Arg | Asp | Lys | Ala | Lys | Arg | Arg | Asn | Gln | Glu | Met | Gln | Gln | Lys | Leu | Val |
| | 210 | | | | | 215 | | | | | 220 | | | | |
| Glu | Leu | Ser | Ala | Glu | Asn | Glu | Lys | Leu | His | Gln | Arg | Val | Glu | Gln | Leu |
| 225 | | | | | 230 | | | | | 235 | | | | | 240 |
| Thr | Arg | Asp | Leu | Ala | Gly | Leu | Arg | Gln | Phe | Phe | Lys | Lys | Leu | Pro | Ser |
| | | | | 245 | | | | | 250 | | | | | 255 | |
| Pro | Pro | Phe | Leu | Pro | Pro | Thr | Gly | Ala | Asp | Cys | Arg | | | | |
| | | | 260 | | | | | 265 | | | | | | | |

```
<210> SEQ ID NO 32
<211> LENGTH: 6464
<212> TYPE: DNA
<213> ORGANISM: Mus musculus

<400> SEQUENCE: 32
```

-continued

```
gtcatgtgac tggggactgt agtaagacag gtgccttcag ttcactctca gtaagggct      60 ggttgcctgc atgagtgtgt gctgtgtgtc agagtggatt ggagttgaaa aagcttgact    120
ggcgtcattc gggagctgga tggcttggga catgtgcagc caagactctg tatggagtga    180
catagagtgt gctgctctgg ttggtgagga ccagcctctt tgcccagatc ttcctgaact    240
tgacctttct gaacttgatg tgaatgactt ggatacagac agctttctgg gtggattgaa    300
gtggtgtagc gaccaatcgg aaatcatatc caaccagtac aacaatgagc ctgcgaacat    360
atttgagaag atagatgaag agaatgaggc aaacttgcta gcggttctca cagagacact    420
ggacagtctc cccgtggatg aagacggatt gccctcattt gatgcactga cagatggagc    480
cgtgaccact gacaacgagg ccagtccttc ctccatgcct gacggcaccc ctccccctca    540
ggaggcagaa gagccgtctc tacttaagaa gctcttactg gcaccagcca acactcagct    600
cagctacaat gaatgcagcg tcttagcac tcagaaccat gcagcaaacc acacccacag    660
gatcagaaca aaccctgcca ttgttaagac cgagaattca tggagcaata aagcgaagag    720
catttgtcaa cagcaaaagc cacaaagacg tccctgctca gagcttctca gtatctgac     780 cacaaacgat gaccctcctc acaccaaacc cacagaaaac aggaacagca gcagagacaa    840
atgtgcttcg aaaaagaagt cccatacaca accgcagtcg caacatgctc aagccaaacc    900
aacaacttta tctcttcctc tgaccccaga gtcaccaaat gaccccaagg gttccccatt    960
tgagaacaag actattgagc gaaccttaag tgtggaactc tctggaactg caggcctaac   1020
tcctcccaca actcctcctc ataaagccaa ccaagataac cctttcaagg cttcgccaaa   1080
gctgaagccc tcttgcaaga ccgtggtgcc accgccaacc aagagggccc ggtacagtga   1140
gtgttctggt acccaaggca gccactccac caagaaaggg cccgagcaat ctgagttgta   1200
cgcacaactc agcaagtcct cagggctcag ccgaggacac gaggaaagga agactaaacg   1260
gcccagtctc cggctgtttg gtgaccatga ctactgtcag tcactcaatt ccaaaacgga   1320
tatactcatt aacatatcac aggagctcca agactctaga caactagact tcaaagatgc   1380
ctcctgtgac tggcaggggc acatctgttc ttccacagat tcaggccagt gctacctgag   1440
agagactttg gaggccagca agcaggtctc tccttgcagc accagaaaac agctccaaga   1500
ccaggaaatc cgagcggagc tgaacaagca cttcggtcat ccctgtcaag ctgtgtttga   1560
cgacaaatca gacaagacca gtgaactaag ggatggcgac ttcagtaatg aacaattctc   1620
caaactacct gtgttttataa attcaggact agccatggat ggcctatttg atgacagtga   1680
agatgaaagt gataaactga gctacccttg ggatggcacg cagccctatt cattgttcga   1740
tgtgtcgcct tcttgctctt cctttaactc tccgtgtcga gactcagtgt caccaccgaa   1800 atccttatt tctcaaagac cccaaaggat gcgctctcgt tcaagatcct tttctcgaca   1860
caggtcgtgt tcccgatcac catattccag gtcaagatca aggtccccag gcagtagatc   1920
ctcttcaaga tcctgttact actatgaatc aagccactac agacaccgca cacaccgcaa   1980
ttctcccttg tatgtgagat cacgttcaag gtcaccctac agccgtaggc ccaggtacga   2040
cagctatgaa gcctatgagc acgaaaggct caagagggat gaataccgca aagagcacga   2100
gaagcgggag tctgaaaggg ccaaacagag agagaggcag aagcagaaag caattgaaga   2160
gcgccgtgtg atttacgttg gtaaaatcag acctgacaca acgcggacag aattgagaga   2220
ccgctttgaa gtttttggtg aaattgagga atgcaccgta atctgcgggg atgatggaga   2280
cagctatggt ttcatcacct accgttacac ctgtgacgct ttcgctgctc ttgagaatgg   2340
atatacttta cgcaggtcga acgaaactga cttcgagctg tactttgtg acggaagca    2400
```

```
atttttcaag tctaactatg cagacctaga taccaactca gacgattttg accctgcttc    2460
caccaagagc aagtatgact ctctggattt tgatagttta ctgaaggaag ctcagagaag    2520
cttgcgcagg taacgtgttc ccaggctgag gaatgacaga gagatggtca atacctcatg    2580
ggacagcgtg tcctttccca agactcttgc aagtcatact taggaatttc tcctacttta    2640
cactctctgt acaaaaataa aacaaaacaa aacaacaata acaacaacaa caacaacaat    2700
aacaacaaca accataccag aacaagaaca acggtttaca tgaacacagc tgctgaagag    2760
gcaagagaca gaatgataat ccagtaagca cacgtttatt cacgggtgtc agctttgctt    2820
tccctggagg ctcttggtga cagtgtgtgt gcgtgtgtgt gtgtgggtgt gcgtgtgtgt    2880
atgtgtgtgt gtgtacttgt ttggaaagta catatgtaca catgtgagga cttggggggca   2940 cctgaacaga acgaacaagg gcgacccctt caaatggcag catttccatg aagcacact    3000 taaaacctac aacttcaaaa tgttcgtatt ctatacaaaa ggaaaataaa taaatataaa    3060
ttaaaaggaa agaaaactca caaaccaccc taaaatgaca ctgctgatgc ctgttgtcag    3120
cctccggtac cgtctttttca gaaagtgcaa aacccagaaa gtgcaaaacc aacctgcagc    3180
aagctctctc tctctcttaa tgtaatcatt acgtgacaat cccgaagaca ctacaggttc    3240
catagaactc atatccacct ctctctctct ctctctctct ctctctctct ctctctctct    3300
cctctctcct ctctcctctc tccctccctt ctttgccatt gaatctgggt gggagaggat    3360
actgcaggca ccagatgcta aactttccta acattttgaa gtttctgtag tttgtccttt    3420
gtcctgacac ctatgtatat gttcaaaatg ttgatcttcc actgcagatt ttgaaaagcc    3480
ttgttattgg tcaagcgggg agtgtgttca gtggctcctt ctgaggagca gacgcggtgt    3540
tacatgagta ctgagagttg agtagaactc tctggatgtg ttcagatagt gtaattgcta    3600
cattctctga tgtagttaag tatttacaga tgttaaatgg agtattttta ttttatgtac    3660
atactctaca actatgttct tttttgttac agctatgcac tgtaaatgca gccttctttt    3720
caaaactgct aaattttttct taatcaagaa tattcaaatg taattatgag gtgaaacaat    3780
tattgtacac taacatattt agaagctaaa cttactgctt atatatattt gattgtaaaa    3840
aaaaaaaaaa acaaaaccaa caaaacaaaa gacagtgtgt gtgtgtgtgt ccgttgagtg    3900
caagtccaac aaaatggcgc ttcacgcaca tccatccctt cttaggtgag cttcaatcta    3960
agcatcttgt caacaacaac aaaaatccta ggcccctcaa ggtattaacc acttctgcaa    4020
tatttttcca catttctttg ttgcttgttt ttctttgaag ttttatacac tggatttgtt    4080
aggggaatga aattttctca tctaaaattt ttctagacaa tatcatgatt ttatgtaaag    4140
tctctcaatg gggaaccatt aagaaatgtt tttattttct ctatcaacag tagatttgaa    4200
actagaggtc aaaaaaaatc ttttaaaat gctgttttgt tttaattttt gtgatttttaa    4260 tttgatacaa aatgctgagg taataattac agtatgattt ttacaatagt caatgtgtgt    4320
ctgaagacta tctttgaagc cagtatctct ttcccttggc agagtatgat gatggtattt    4380
aatctgtatt ttttacagtt atacatcctg taaaatactg atatttcatt cctttgttta    4440
ctaaagagac atatttatca gttgcagata gcctatttat tataaattaa gagatgatga    4500
aaataataag gtcagtggag actttctacc cagggtgcat ggcagttgtc aggctggagt    4560
gtaccttctt cgtttgggaa actcagctct cgcagaagca gtgttccatc tttcactagc    4620
atggcctctg atacgaccat ggtgttgttc ttggtgacat tgcttctgct aaatttaata    4680
ttaataataa taaatgtcag aaaaaaaacc ctccatttg agcatcagga tttcatctga    4740
```

-continued

```
gtatggagtc gctgccatgg gagtcactaa actttggagt atgtatttca tttccaaatt    4800
gagatgcatt tactgtttgg ctgacatgaa ttttctggaa gatatgatag acctactact    4860
taaccgtttt tgtttgtttt ttttctcttg ttgttgttgt tttgttttttt gttttttttgt   4920
ttttctctct cacccaacac tatcttacaa aatgggtttc accccaggc caatgcagct    4980
aattttgaca gctgcattca tttatcacca gcatattgtg ttctgagtga atccactgtc    5040
tgtcctgtcg aatgcttgct caagtgtttg gcttattatt tctaagtaga tagaaagcaa    5100
taaataacta tgaaataaaa aagaattgtg ttcacaggtt ctgcgttaca acagtaacac    5160
atctttaatc cgcctaattc ttgttctgta ggataaatgc aggtatttta actctttgtg    5220
aacgccaaac taaagtttac agtctttctt tctgaatttt gagtatcttc tgttgtagaa    5280
taataataaa aagactatta agagcaataa attattttta agaaatcaat atttagtaaa    5340
tcctgttatg tgtttaagga ccagatgcgt tctctatttt gcctttaaat ttttgtgatc    5400
caactttaaa aacatacgtt gtcttgtttg ccctggatca tggacatgac taaaattttg    5460
tggtttcttt tcttacttat caaaagacaa cactacagat ttcatgttga ggattcattg    5520
agctctcacc ctctggcctg acaaatcttg ttaccatgaa gatagttttc ctccgtggac    5580
ttcaaattgc atctaaaatt agtgaagctt gtgtatctta tgcagacact gtgggtagcc    5640
catcaaaata taagctgtaa gctttgttcc tttcatttttt tttttttttac ttcttttggg    5700
agagaatatt ccaacaaac acatgcaccc caccaacagg ggaggcaaat ttcagcatag    5760
atctataaga ctttcagatg accatgggcc attgccttca tgctgtggta agtactacat    5820
ctacaatttt ggtacccgaa ctggtgcttt agaaatgcgg ggttttttatt aaaaaaaaaa    5880
aaaagaaatg tagcagaata attcttttag tgcagcaact cagttttttgt aaaggactct    5940
gagaacactt gggctgtgaa cattcaaagc agcagagagg gaacctggca ctattggggt    6000
aaagtgtttg ggtcagttga aaaaaaggaa acctttttcat gcctttagat gtgagctaac    6060
agtaggtaat gatcatgtgt ccctttttga tggctgtacg aagaacttca atcactgtag    6120
tctaagatct gatctataga tgacctagaa tagccatgta atataatgtg atgattctaa    6180
atttgtacct atgtgacaga catttttcaat aatgtgaaaa ctgcagattt gatggagcta    6240
ctttaagatt tgtaggtgaa agtgtgctac tgttggttga actatgctga agagggaaag    6300
tgagtgatta gtttgagccc ttgctggctc ttttccacct gccaattcta catgtattgt    6360
tgtggtttta ttcattgtat gaaaattcct gtgattttttt tttaaatgtg cagtacacat    6420
cagcctcact gagctaataa agggaaaaga atgtttcaaa tcta                      6464
```

<210> SEQ ID NO 33
<211> LENGTH: 797
<212> TYPE: PRT
<213> ORGANISM: Mus musculus

<400> SEQUENCE: 33

Met Ala Trp Asp Met Cys Ser Gln Asp Ser Val Trp Ser Asp Ile Glu
1               5                   10                  15

Cys Ala Ala Leu Val Gly Glu Asp Gln Pro Leu Cys Pro Asp Leu Pro
            20                  25                  30

Glu Leu Asp Leu Ser Glu Leu Asp Val Asn Asp Leu Thr Asp Ser
        35                  40                  45

Phe Leu Gly Gly Leu Lys Trp Cys Ser Asp Gln Ser Glu Ile Ile Ser
    50                  55                  60

Asn Gln Tyr Asn Asn Glu Pro Ala Asn Ile Phe Glu Lys Ile Asp Glu

```
             65                  70                  75                  80
Glu Asn Glu Ala Asn Leu Leu Ala Val Leu Thr Glu Thr Leu Asp Ser
                    85                  90                  95
Leu Pro Val Asp Glu Asp Gly Leu Pro Ser Phe Asp Ala Leu Thr Asp
                100                 105                 110
Gly Ala Val Thr Thr Asp Asn Glu Ala Ser Pro Ser Met Pro Asp
                115                 120                 125
Gly Thr Pro Pro Gln Glu Ala Glu Pro Ser Leu Leu Lys Lys
        130                 135                 140
Leu Leu Leu Ala Pro Ala Asn Thr Gln Leu Ser Tyr Asn Glu Cys Ser
145                 150                 155                 160
Gly Leu Ser Thr Gln Asn His Ala Ala Asn His Thr His Arg Ile Arg
                165                 170                 175
Thr Asn Pro Ala Ile Val Lys Thr Glu Asn Ser Trp Ser Asn Lys Ala
                180                 185                 190
Lys Ser Ile Cys Gln Gln Gln Lys Pro Gln Arg Arg Pro Cys Ser Glu
                195                 200                 205
Leu Leu Lys Tyr Leu Thr Thr Asn Asp Asp Pro Pro His Thr Lys Pro
                210                 215                 220
Thr Glu Asn Arg Asn Ser Ser Arg Asp Lys Cys Ala Ser Lys Lys Lys
225                 230                 235                 240
Ser His Thr Gln Pro Gln Ser Gln His Ala Gln Ala Lys Pro Thr Thr
                245                 250                 255
Leu Ser Leu Pro Leu Thr Pro Glu Ser Pro Asn Asp Pro Lys Gly Ser
                260                 265                 270
Pro Phe Glu Asn Lys Thr Ile Glu Arg Thr Leu Ser Val Glu Leu Ser
                275                 280                 285
Gly Thr Ala Gly Leu Thr Pro Pro Thr Thr Pro Pro His Lys Ala Asn
                290                 295                 300
Gln Asp Asn Pro Phe Lys Ala Ser Pro Lys Leu Lys Pro Ser Cys Lys
305                 310                 315                 320
Thr Val Val Pro Pro Pro Thr Lys Arg Ala Arg Tyr Ser Glu Cys Ser
                325                 330                 335
Gly Thr Gln Gly Ser His Ser Thr Lys Lys Gly Pro Glu Gln Ser Glu
                340                 345                 350
Leu Tyr Ala Gln Leu Ser Lys Ser Ser Gly Leu Ser Arg Gly His Glu
                355                 360                 365
Glu Arg Lys Thr Lys Arg Pro Ser Leu Arg Leu Phe Gly Asp His Asp
                370                 375                 380
Tyr Cys Gln Ser Leu Asn Ser Lys Thr Asp Ile Leu Ile Asn Ile Ser
385                 390                 395                 400
Gln Glu Leu Gln Asp Ser Arg Gln Leu Asp Phe Lys Asp Ala Ser Cys
                405                 410                 415
Asp Trp Gln Gly His Ile Cys Ser Ser Thr Asp Ser Gly Gln Cys Tyr
                420                 425                 430
Leu Arg Glu Thr Leu Glu Ala Ser Lys Gln Val Ser Pro Cys Ser Thr
                435                 440                 445
Arg Lys Gln Leu Gln Asp Gln Glu Ile Arg Ala Glu Leu Asn Lys His
                450                 455                 460
Phe Gly His Pro Cys Gln Ala Val Phe Asp Lys Ser Asp Lys Thr
465                 470                 475                 480
Ser Glu Leu Arg Asp Gly Asp Phe Ser Asn Glu Gln Phe Ser Lys Leu
                485                 490                 495
```

```
Pro Val Phe Ile Asn Ser Gly Leu Ala Met Asp Gly Leu Phe Asp Asp
            500                 505                 510
Ser Glu Asp Glu Ser Asp Lys Leu Ser Tyr Pro Trp Asp Gly Thr Gln
            515                 520                 525
Pro Tyr Ser Leu Phe Asp Val Ser Pro Ser Cys Ser Ser Phe Asn Ser
            530                 535                 540
Pro Cys Arg Asp Ser Val Ser Pro Pro Lys Ser Leu Phe Ser Gln Arg
545                 550                 555                 560
Pro Gln Arg Met Arg Ser Arg Ser Arg Ser Phe Ser Arg His Arg Ser
                565                 570                 575
Cys Ser Arg Ser Pro Tyr Ser Arg Ser Arg Ser Arg Ser Pro Gly Ser
            580                 585                 590
Arg Ser Ser Ser Arg Ser Cys Tyr Tyr Tyr Glu Ser Ser His Tyr Arg
            595                 600                 605
His Arg Thr His Arg Asn Ser Pro Leu Tyr Val Arg Ser Arg Ser Arg
            610                 615                 620
Ser Pro Tyr Ser Arg Arg Pro Arg Tyr Asp Ser Tyr Glu Ala Tyr Glu
625                 630                 635                 640
His Glu Arg Leu Lys Arg Asp Glu Tyr Arg Lys Glu His Glu Lys Arg
                645                 650                 655
Glu Ser Glu Arg Ala Lys Gln Arg Glu Arg Gln Lys Gln Lys Ala Ile
            660                 665                 670
Glu Glu Arg Arg Val Ile Tyr Val Gly Lys Ile Arg Pro Asp Thr Thr
            675                 680                 685
Arg Thr Glu Leu Arg Asp Arg Phe Glu Val Phe Gly Glu Ile Glu Glu
            690                 695                 700
Cys Thr Val Asn Leu Arg Asp Asp Gly Asp Ser Tyr Gly Phe Ile Thr
705                 710                 715                 720
Tyr Arg Tyr Thr Cys Asp Ala Phe Ala Ala Leu Glu Asn Gly Tyr Thr
                725                 730                 735
Leu Arg Arg Ser Asn Glu Thr Asp Phe Glu Leu Tyr Phe Cys Gly Arg
            740                 745                 750
Lys Gln Phe Phe Lys Ser Asn Tyr Ala Asp Leu Asp Thr Asn Ser Asp
            755                 760                 765
Asp Phe Asp Pro Ala Ser Thr Lys Ser Lys Tyr Asp Ser Leu Asp Phe
770                 775                 780
Asp Ser Leu Leu Lys Glu Ala Gln Arg Ser Leu Arg Arg
785                 790                 795

<210> SEQ ID NO 34
<211> LENGTH: 7404
<212> TYPE: DNA
<213> ORGANISM: Unknown
<220> FEATURE:
<221> NAME/KEY: source
<223> OTHER INFORMATION: /note="Description of Unknown: PGC-1 alpha
      promoter 2kb luciferase plasmid sequence"

<400> SEQUENCE: 34 ggtaccctg tgctctctct agcttcacat acccctttt atgaaggtag aggacagagt     60
ggctgtttta agcagatcat tagcttcatg gatgtgctgg gttagtttct tttcttttct    120
tttcttttct ttttttaaag tagaattagg tggcaaaaaa agaaagaaag aaagaaagaa    180
agaaagaaat tatcttttca aagcaaagaa aaagaaaatc ctgccacaat tcagtgtgag    240
caagttaaga tatcaaaaca ataatgcaga gttatctagt gcaagcaacc atctgtaaga    300
```

```
agaggtgtgc atgaggtttg aaaaagtatg gtggatgcct aatggatgac aaagagaaac    360
caaagtatca gttaccatca ggatgccagg attgcttgat aatgatgaat aaacatcgac    420
tctttatagc taagtggcca gcattatttc acagttgact gtgtggaaag tagagcccat    480
gacctttgtc ctgaatttta atagtttact gaagttttac attaagtaaa aatctaattg    540
gcaagaaaaa ttagtgtttc tttgtgggag tacagagtaa ggctactaat tgcatgtaga    600
aaatgatccc agggttgtct ctctctctct ctgaattaga aaattaaatg aataatacct    660
ttctgatgtt tggaagagga cagttgtagc agtgaagtat attcacctaa tttagaatgt    720
caaagctgtt ggccatcttg ttctgttcac ttattgacaa actgtcgatt tcattaccat    780
attccctgtc tactagttgt ggacatccaa gcaaacagac cccttatacg gggtctgaag    840
caaacagcaa gcttgtgggc tttgtgtgtg tgtgtgtgtg tgtgtgtgtg tgtgtgtgtg    900
tgtgtgtgtg tgcacgctcg ctgcatttct ttctttcact ttactgtatt agtaactgac    960
tatataaagt cagactgaga gaagtcacca atgttttcct tctaagggga gagaaaataa   1020
agagcacatt aaattaacct cagtggaata ggagtttaaa tgaatggtgc tttataaatt   1080
atatttagat gcatagggac ttttttcttc ttctaaatta ctgtcaagta aaggaaatga   1140
gctggttttt gagtctgtgg ggtttgaggt attgtgaaaa tatgttttca aggtcccct    1200 gtgcatttct cactgggcct ggaagggtta agtctgagca cccaagtgtt atggaaagtg   1260
ctgagagttg gttatgtcct ctgtctgtaa tgtcacagga aaaacagtgg cacctgcatt   1320 accccctcatt gactcaggaa cgacaaaaaa gtattagtaa gcaaagctca agaaatgagt   1380
atctctgctg ataccatttc agtgttttc cttcattccc tggacattct tgatttcaaa    1440
aacaaactgt acagcccaag gcactagggt tggagtccaa tgtttattca aaaaggcacc   1500
ctgaagccat gaggaagact gtgctacata tgagaaaaga aataagggggt gggggcaggt  1560 gagtagctaa gctgtttcag ggatggcagc agcaattgta ttttctagca tttgttttct   1620
gggagcctat gagatccacg gaaagaatca tgaggggaa cccaagagtc tagggtgttg    1680
tggcttgctt gctttacaag gagcaaggca aactgcagta acagtttagg agactgcatt   1740
ctctactgcc aaggagacag ctgatttggg gtagagaaat ttgtttagac ctaaacaaat   1800
gtggcggttt tgttgactaa acatggaaag aaagaaagaa agaaagaaag aaagaaagaa   1860
agaaagaaag aaagaaagaa agaaacaaag aaagaaagaa agaaaggaag gaaggaagga   1920
agaaaggaag aaaggaagga aggaaggaag gaaagaaagg agagagagaa agaaaatcgg   1980
gggtgttgcc ttcaaacact cctctaatag ggagggaaaa aaaagaatct catgaaaatg   2040
tatcacatga ggagcgcttg cttcagttcc aagctgagtc tggggctact tggaaaccat   2100
ttcttaaagc acacacattt taggcaaggg tgtagttact gtgtcagtaa caggggatct   2160
ttgctatttg cctgttttgg atggaaaata aatttaaaaa aaaagattg caggagattt    2220 gagttattat gtgagcaggg ctccggttta gagttggtgg cattcaaagc tggcttcagt   2280
cacagtgtga tgcttgaagc ctcccaaagg ccaagtgttt ccttttcttt cttctatttt   2340
ttttttcctc tctctctaag cgttacttca ctgaggcaga gggctgcctt ggagtgacgt   2400
caggagtttg tgcagcaagc ttgcacagga aagggaggc tgggtgagtg acagcccagc    2460 ctactttta atagctttgt catgtgactg gggactgtag taagacaggt gccttcagtt    2520
cactctcagt aagggggctgg ttgcctgcat gagtgtgtgc tgtgtgtcag agtggattgg  2580
agttgaaaaa gcttgactgg cgtcattcgg gagctggctc gagatctgcg atctaagtaa   2640
```

```
gcttggcatt ccggtactgt tggtaaagcc accatggaag acgccaaaaa cataaagaaa    2700
ggcccggcgc cattctatcc gctggaagat ggaaccgctg gagagcaact gcataaggct    2760
atgaagagat acgccctggt tcctggaaca attgctttta cagatgcaca tatcgaggtg    2820
gacatcactt acgctgagta cttcgaaatg tccgttcggt tggcagaagc tatgaaacga    2880
tatgggctga atacaaatca cagaatcgtc gtatgcagtg aaaactctct tcaattcttt    2940
atgccggtgt tgggcgcgtt atttatcgga gttgcagttg cgcccgcgaa cgacatttat    3000
aatgaacgtg aattgctcaa cagtatgggc atttcgcagc ctaccgtggt gttcgtttcc    3060
aaaaaggggg tgcaaaaaat tttgaacgtg caaaaaaagc tcccaatcat ccaaaaaatt    3120
attatcatgg attctaaaac ggattaccag ggatttcagt cgatgtacac gttcgtcaca    3180
tctcatctac ctcccggttt taatgaatac gattttgtgc cagagtcctt cgatagggac    3240
aagacaattg cactgatcat gaactcctct ggatctactg gtctgcctaa aggtgtcgct    3300
ctgcctcata gaactgcctg cgtgagattc tcgcatgcca gagatcctat ttttggcaat    3360
caaatcattc cggatactgc gattttaagt gttgttccat tccatcacgg ttttggaatg    3420
tttactacac tcggatattt gatatgtgga tttcgagtcg tcttaatgta tagatttgaa    3480
gaagagctgt ttctgaggag ccttcaggat tacaagattc aaagtgcgct gctggtgcca    3540
accctattct ccttcttcgc caaaagcact ctgattgaca atacgattta tctaatttta    3600
cacgaaattg cttctggtgg cgctcccctc tctaaggaag tcggggaagc ggttgccaag    3660
aggttccatc tgccaggtat caggcaagga tatgggctca ctgagactac atcagctatt    3720
ctgattacac ccgagggggat gataaaccg gcgcggtcg gtaaagttgt tccattttt     3780
```

```
ccctgccgct taccggatac ctgtccgcct ttctcccttc gggaagcgtg gcgctttctc   5100
aatgctcacg ctgtaggtat ctcagttcgg tgtaggtcgt tcgctccaag ctgggctgtg   5160
tgcacgaacc ccccgttcag cccgaccgct gcgccttatc cggtaactat cgtcttgagt   5220
ccaacccggt aagacacgac ttatcgccac tggcagcagc cactggtaac aggattagca   5280
gagcgaggta tgtaggcggt gctacagagt tcttgaagtg gtggcctaac tacggctaca   5340
ctagaaggac agtatttggt atctcgctc tgctgaagcc agttaccttc ggaaaaagag   5400
ttggtagctc ttgatccggc aaacaaacca ccgctggtag cggtggtttt tttgtttgca   5460
agcagcagat tacgcgcaga aaaaaaggat ctcaagaaga tcctttgatc ttttctacgg   5520
ggtctgacgc tcagtggaac gaaaactcac gttaagggat tttggtcatg agattatcaa   5580
aaaggatctt cacctagatc cttttaaatt aaaaatgaag ttttaaatca atctaaagta   5640
tatatgagta aacttggtct gacagttacc aatgcttaat cagtgaggca cctatctcag   5700
cgatctgtct atttcgttca tccatagttg cctgactccc cgtcgtgtag ataactacga   5760
tacgggaggg cttaccatct ggccccagtg ctgcaatgat accgcgagac ccacgctcac   5820
cggctccaga tttatcagca ataaaccagc cagccggaag ggccgagcgc agaagtggtc   5880
ctgcaacttt atccgcctcc atccagtcta ttaattgttg ccgggaagct agagtaagta   5940
gttcgccagt taatagtttg cgcaacgttg ttgccattgc tacaggcatc gtggtgtcac   6000
gctcgtcgtt tggtatggct tcattcagct ccggttccca acgatcaagg cgagttacat   6060 gatccccat gttgtgcaaa aaagcggtta gctccttcgg tcctccgatc gttgtcagaa   6120
gtaagttggc cgcagtgtta tcactcatgg ttatggcagc actgcataat tctcttactg   6180
tcatgccatc cgtaagatgc ttttctgtga ctggtgagta ctcaaccaag tcattctgag   6240
aatagtgtat gcggcgaccg agttgctctt gcccggcgtc aatacgggat aataccgcgc   6300
cacatagcag aactttaaaa gtgctcatca ttggaaaacg ttcttcgggg cgaaaactct   6360
caaggatctt accgctgttg agatccagtt cgatgtaacc cactcgtgca cccaactgat   6420
cttcagcatc ttttactttc accagcgttt ctgggtgagc aaaaacagga aggcaaaatg   6480
ccgcaaaaaa gggaataagg gcgacacgga aatgttgaat actcatactc ttccttttc   6540 aatattattg aagcatttat cagggttatt gtctcatgag cggatacata tttgaatgta   6600
tttagaaaaa taaacaaata ggggttccgc gcacatttcc ccgaaaagtg ccacctgacg   6660
cgccctgtag cggcgcatta agcgcggcgg gtgtggtggt tacgcgcagc gtgaccgcta   6720
cacttgccag cgccctagcg cccgctcctt tcgctttctt cccttccttt ctcgccacgt   6780
tcgccggctt tccccgtcaa gctctaaatc ggggctccc tttagggttc cgatttagtg   6840
ctttacggca cctcgacccc aaaaaacttg attagggtga tggttcacgt agtgggccat   6900
cgccctgata gacggttttt cgccctttga cgttggagtc cacgttcttt aatagtggac   6960
tcttgttcca aactggaaca cactcaacc ctatctcggt ctattctttt gatttataag   7020
ggattttgcc gatttcggcc tattggttaa aaaatgagct gatttaacaa aaatttaacg   7080
cgaattttaa caaatatta acgtttacaa tttcccattc gccattcagg ctgcgcaact   7140
gttgggaagg gcgatcggtg cgggcctctt cgctattacg ccagcccaag ctaccatgat   7200
aagtaagtaa tattaaggta cgggaggtac ttggagcggc cgcaataaaa tatctttatt   7260
ttcattacat ctgtgtgttg gttttttgtg tgaatcgata gtactaacat acgctctcca   7320
tcaaaacaaa acgaaacaaa acaaactagc aaaataggct gtcccagtg caagtgcagg   7380
```

```
tgccagaaca tttctctatc gata                                         7404
```

<210> SEQ ID NO 35
<211> LENGTH: 1857
<212> TYPE: DNA
<213> ORGANISM: Mus musculus

<400> SEQUENCE: 35

```
gtgtgacgac aaggtgaccg ggctgagggg acgggctgag gagaagtcac actctgacag     60
gagcctgtga gaccaacagc ctgacggggt ctcggttgag gggacgcggg ctgagaagtc    120
acgttctgac aggactgtgt gacagacaag atttgaaaga agcggtgaac cactgatatt    180
caggacattt ttaaaaacaa gactaccctt tactgaaatt accatggttg acacagagat    240
gccattctgg cccaccaact tcggaatcag ctctgtggac ctctccgtga tggaagacca    300
ctcgcattcc tttgacatca gcccttttac cacagttgat ttctccagca tttctgctcc    360
acactatgaa gacattccat tcacaagagc tgacccaatg gttgctgatt acaaatatga    420
cctgaagctc caagaatacc aaagtgcgat caaagtagaa cctgcatctc caccttatta    480
ttctgaaaag acccagctct acaacaggcc tcatgaagaa ccttctaact ccctcatggc    540
cattgagtgc cgagtctgtg gggataaagc atcaggcttc cactatggag ttcatgcttg    600
tgaaggatgc aagggttttt tccgaagaac catccgattg aagcttattt atgataggtg    660
tgatcttaac tgccggatcc acaaaaaaag tagaaataaa tgtcagtact gtcggtttca    720
gaagtgcctt gctgtgggga tgtctcacaa tgccatcagg tttgggcgga tgccacaggc    780
cgagaaggag aagctgttgg cggagatctc cagtgatatc gaccagctga acccagagtc    840
tgctgatctg cgagccctgg caaagcattt gtatgactca tacataaagt ccttcccgct    900
gaccaaagcc aaggcgaggg cgatcttgac aggaaagaca acggacaaat caccatttgt    960
catctacgac atgaattcct taatgatggg agaagataaa atcaagttca acatatcac   1020
cccctgcag gagcagagca aagaggtggc catccgaatt tttcaagggt gccagtttcg   1080
atccgtagaa gccgtgcaag agatcacaga gtatgccaaa aatatccctg gtttcattaa   1140
ccttgatttg aatgaccaag tgactctgct caagtatggt gtccatgaga tcatctacac   1200
gatgctggcc tccctgatga ataaagatgg agtcctcatc tcagagggcc aaggattcat   1260
gaccagggag ttcctcaaaa gcctgcggaa gccctttggt gactttatgg agcctaagtt   1320
tgagtttgct gtgaagttca atgcactgga attagatgac agtgacttgg ctatatttat   1380
agctgtcatt attctcagtg gagaccgccc aggcttgctg aacgtgaagc ccatcgagga   1440
catccaagac aacctgctgc aggccctgga actgcagctc aagctgaatc acccagagtc   1500
ctctcagctg ttcgccaagg tgctccagaa gatgacagac ctcaggcaga tcgtcacaga   1560
gcacgtgcag ctactgcatg tgatcaagaa gacagagaca gacatgagcc ttcacccct   1620
gctccaggag atctacaagg acttgtatta gcaggaaagt cccacccgct gacaacgtgt   1680
tccttctatt gattgcacta ttattttgag ggaaaaaaat ctgacaccta agaaatttac   1740
tgtgaaaaag catttaaaaa caaaaagttt tagaacatga tctattttat gcatattgtt   1800
tataaagata catttacaat ttacttttaa tattaaaaat taccacatta taaaatt      1857
```

<210> SEQ ID NO 36
<211> LENGTH: 475
<212> TYPE: PRT
<213> ORGANISM: Mus musculus

<400> SEQUENCE: 36

-continued

```
Met Val Asp Thr Glu Met Pro Phe Trp Pro Thr Asn Phe Gly Ile Ser
 1               5                  10                  15

Ser Val Asp Leu Ser Val Met Glu Asp His Ser His Ser Phe Asp Ile
             20                  25                  30

Lys Pro Phe Thr Thr Val Asp Phe Ser Ser Ile Ser Ala Pro His Tyr
             35                  40                  45

Glu Asp Ile Pro Phe Thr Arg Ala Asp Pro Met Val Ala Asp Tyr Lys
 50                  55                  60

Tyr Asp Leu Lys Leu Gln Glu Tyr Gln Ser Ala Ile Lys Val Glu Pro
 65                  70                  75                  80

Ala Ser Pro Pro Tyr Tyr Ser Glu Lys Thr Gln Leu Tyr Asn Arg Pro
                 85                  90                  95

His Glu Glu Pro Ser Asn Ser Leu Met Ala Ile Glu Cys Arg Val Cys
                 100                 105                 110

Gly Asp Lys Ala Ser Gly Phe His Tyr Gly Val His Ala Cys Glu Gly
             115                 120                 125

Cys Lys Gly Phe Phe Arg Arg Thr Ile Arg Leu Lys Leu Ile Tyr Asp
 130                 135                 140

Arg Cys Asp Leu Asn Cys Arg Ile His Lys Lys Ser Arg Asn Lys Cys
145                 150                 155                 160

Gln Tyr Cys Arg Phe Gln Lys Cys Leu Ala Val Gly Met Ser His Asn
                 165                 170                 175

Ala Ile Arg Phe Gly Arg Met Pro Gln Ala Glu Lys Glu Lys Leu Leu
             180                 185                 190

Ala Glu Ile Ser Ser Asp Ile Asp Gln Leu Asn Pro Glu Ser Ala Asp
             195                 200                 205

Leu Arg Ala Leu Ala Lys His Leu Tyr Asp Ser Tyr Ile Lys Ser Phe
210                 215                 220

Pro Leu Thr Lys Ala Lys Ala Arg Ala Ile Leu Thr Gly Lys Thr Thr
225                 230                 235                 240

Asp Lys Ser Pro Phe Val Ile Tyr Asp Met Asn Ser Leu Met Met Gly
                 245                 250                 255

Glu Asp Lys Ile Lys Phe Lys His Ile Thr Pro Leu Gln Glu Gln Ser
             260                 265                 270

Lys Glu Val Ala Ile Arg Ile Phe Gln Gly Cys Gln Phe Arg Ser Val
             275                 280                 285

Glu Ala Val Gln Glu Ile Thr Glu Tyr Ala Lys Asn Ile Pro Gly Phe
 290                 295                 300

Ile Asn Leu Asp Leu Asn Asp Gln Val Thr Leu Leu Lys Tyr Gly Val
305                 310                 315                 320

His Glu Ile Ile Tyr Thr Met Leu Ala Ser Leu Met Asn Lys Asp Gly
                 325                 330                 335

Val Leu Ile Ser Glu Gly Gln Gly Phe Met Thr Arg Glu Phe Leu Lys
             340                 345                 350

Ser Leu Arg Lys Pro Phe Gly Asp Phe Met Glu Pro Lys Phe Glu Phe
             355                 360                 365

Ala Val Lys Phe Asn Ala Leu Glu Leu Asp Asp Ser Asp Leu Ala Ile
 370                 375                 380

Phe Ile Ala Val Ile Ile Leu Ser Gly Asp Arg Pro Gly Leu Leu Asn
385                 390                 395                 400

Val Lys Pro Ile Glu Asp Ile Gln Asp Asn Leu Leu Gln Ala Leu Glu
                 405                 410                 415
```

```
Leu Gln Leu Lys Leu Asn His Pro Glu Ser Ser Gln Leu Phe Ala Lys
            420                 425                 430

Val Leu Gln Lys Met Thr Asp Leu Arg Gln Ile Val Thr Glu His Val
        435                 440                 445

Gln Leu Leu His Val Ile Lys Lys Thr Glu Thr Asp Met Ser Leu His
    450                 455                 460

Pro Leu Leu Gln Glu Ile Tyr Lys Asp Leu Tyr
465                 470                 475

<210> SEQ ID NO 37
<211> LENGTH: 1769
<212> TYPE: DNA
<213> ORGANISM: Mus musculus

<400> SEQUENCE: 37
caaaacacca gtgtgaatta cagcaaatct ctgttttatg ctgttatggg tgaaactctg      60
ggagattctc ctgttgaccc agagcatggt gccttcgctg atgcactgcc tatgagcact     120
tcacaagaaa ttaccatggt tgacacagag atgccattct ggcccaccaa cttcggaatc     180
agctctgtgg acctctccgt gatggaagac cactcgcatt cctttgacat caagcccttt     240
accacagttg atttctccag catttctgct ccacactatg aagacattcc attcacaaga     300
gctgacccaa tggttgctga ttacaaatat gacctgaagc tccaagaata ccaaagtgcg     360
atcaaagtag aacctgcatc tccaccttat tattctgaaa agacccagct ctacaacagg     420
cctcatgaag aaccttctaa ctccctcatg gccattgagt gccgagtctg tggggataaa     480
gcatcaggct ccactatgg agttcatgct tgtgaaggat gcaagggttt tttccgaaga     540
accatccgat tgaagcttat ttatgatagg tgtgatctta actgccggat ccacaaaaaa     600
agtagaaata atgtcagta ctgtcggttt cagaagtgcc ttgctgtggg gatgtctcac     660
aatgccatca ggtttgggcg gatgccacag gccgagaagg agaagctgtt ggcggagatc     720
tccagtgata tcgaccagct gaacccgag tctgctgatc tgcgagcccct ggcaaagcat     780 ttgtatgact catacataaa gtccttcccg ctgaccaaag ccaaggcgag ggcgatcttg     840
acaggaaaga caacggacaa atcaccattt gtcatctacg acatgaattc cttaatgatg     900
ggagaagata aaatcaagtt caaacatatc accccctgc aggagcagag caaagaggtg     960
gccatccgaa tttttcaagg gtgccagttt cgatccgtag aagccgtgca agagatcaca    1020
gagtatgcca aaaatatccc tggtttcatt aaccttgatt tgaatgacca agtgactctg    1080
ctcaagtatg gtgtccatga gatcatctac acgatgctgg cctccctgat gaataaagat    1140
ggagtcctca tctcagaggg ccaaggattc atgaccaggg agttcctcaa aagcctgcgg    1200
aagccctttg gtgactttat ggagcctaag tttgagtttg ctgtgaagtt caatgcactg    1260
gaattagatg acagtgactt ggctatattt atagctgtca ttattctcag tggagaccgc    1320
ccaggcttgc tgaacgtgaa gcccatcgag gacatccaag acaacctgct gcaggccctg    1380
gaactgcagc tcaagctgaa tcacccagag tcctctcagc tgttcgccaa ggtgctccag    1440
aagatgacag acctcaggca gatcgtcaca gagcacgtgc agctactgca tgtgatcaag    1500
aagacagaga cagacatgag ccttcacccc ctgctccagg agatctacaa ggacttgtat    1560
tagcaggaaa gtcccacccg ctgacaacgt gttccttcta ttgattgcac tattatttg     1620 agggaaaaaa atctgacacc taagaaattt actgtgaaaa agcatttaaa aacaaaaagt    1680
tttagaacat gatctatttt atgcatattg tttataaaga tacatttaca atttactttt    1740
aatattaaaa attaccacat tataaaatt                                      1769
```

<210> SEQ ID NO 38
<211> LENGTH: 505
<212> TYPE: PRT
<213> ORGANISM: Mus musculus

<400> SEQUENCE: 38

Met Gly Glu Thr Leu Gly Asp Ser Pro Val Asp Pro Glu His Gly Ala
1               5                   10                  15

Phe Ala Asp Ala Leu Pro Met Ser Ser Gln Glu Ile Thr Met Val
            20                  25                  30

Asp Thr Glu Met Pro Phe Trp Pro Thr Asn Phe Gly Ile Ser Ser Val
        35                  40                  45

Asp Leu Ser Val Met Glu Asp His Ser His Ser Phe Asp Ile Lys Pro
    50                  55                  60

Phe Thr Thr Val Asp Phe Ser Ser Ile Ser Ala Pro His Tyr Glu Asp
65                  70                  75                  80

Ile Pro Phe Thr Arg Ala Asp Pro Met Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Arg Pro His Glu
        115                 120                 125

Glu Pro Ser Asn Ser Leu Met Ala Ile Glu Cys Arg Val Cys Gly Asp
    130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Met Pro Gln Ala Glu Lys Glu Lys Leu Leu Ala Glu
    210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
    290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Asn Ile Pro Gly Phe Ile Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
        355                 360                 365

Ile Ser Glu Gly Gln Gly Phe Met Thr Arg Glu Phe Leu Lys Ser Leu

|  | 370 |  |  |  | 375 |  |  |  | 380 |  |  |
|---|---|---|---|---|---|---|---|---|---|---|---|
| Arg | Lys | Pro | Phe | Gly | Asp | Phe | Met | Glu | Pro | Lys | Phe | Glu | Phe | Ala | Val |
| 385 |  |  |  |  | 390 |  |  |  |  | 395 |  |  |  |  | 400 |

Lys Phe Asn Ala Leu Glu Leu Asp Asp Ser Asp Leu Ala Ile Phe Ile
                  405                  410                415

Ala Val Ile Ile Leu Ser Gly Asp Arg Pro Gly Leu Leu Asn Val Lys
              420                425              430

Pro Ile Glu Asp Ile Gln Asp Asn Leu Leu Gln Ala Leu Glu Leu Gln
          435              440              445

Leu Lys Leu Asn His Pro Glu Ser Ser Gln Leu Phe Ala Lys Val Leu
450                  455                460

Gln Lys Met Thr Asp Leu Arg Gln Ile Val Thr Glu His Val Gln Leu
465                  470              475              480

Leu His Val Ile Lys Lys Thr Glu Thr Asp Met Ser Leu His Pro Leu
              485                490              495

Leu Gln Glu Ile Tyr Lys Asp Leu Tyr
          500              505

<210> SEQ ID NO 39
<211> LENGTH: 1644
<212> TYPE: DNA
<213> ORGANISM: Mus musculus

<400> SEQUENCE: 39

```
aagtgccggg caatctgggc ttaacgggtc ctccctgccc gagcaagagg aagggacgct      60
cacctttgag ctgctccaca cgccgcctc tgcactggca ctacctagcc caggtggctc     120
tgcaggagtc cgaagtcgcg ggtttcgtgc ccgcatcagg caacagtgcc actgttgtct     180
tcagggctga gtcctttgt tcttgcactc acgcctctct gccctccaag ccaggatggt     240
gaacccgaca acttccgaag tgcaacccac catgggggtc aagatcttct cagccggagt     300
ttcagcttgc ctggcagata tcatcacctt cccgctggac actgccaaag tccgccttca     360
gatccaaggt gaaggccagg cttccagtac cattaggtat aaaggtgtcc tagggaccat     420
caccaccctg gcaaaaacag aaggattgcc gaaactgtac agcggtctgc tgcgggcat     480
tcagaggcaa atcagctttg cctcactcag gattggcctc tacgactcag tccaagagta     540
cttctcttca gggagagaaa cacctgcctc tctcggaaac aagatctcag ccggcttaat     600
gactggaggt gtggcagtgt tcattgggca gcctacagag gtcgtgaagg tcagaatgca     660
agcccagagc catctgcatg ggatcaaacc ccgctacacg ggacctaca atgcttacag     720
agttatagcc accacagaaa gcttgtcaac actttggaaa gggacgaccc ctaatctaat     780
gagaaatgtc atcatcaatt gtacagagct ggtaacatat gacctcatga agggggccct     840
tgtaaacaac aaaatactgg cagatgacgt cccctgccat ttactgtcag ctcttgttgc     900
cgggttttgc accacactcc tggcctctcc agtggatgtg gtaaaaacaa gattcatcaa     960
ctctctgcca ggacagtacc caagcgtacc aagctgtgcg atgtccatgt acaccaagga    1020
aggaccgacg gccttttca aagggtttgt ggcttctttt ctgcgactcg ggtcctggaa    1080
cgtcatcatg tttgtgtgct ttgaacagct gaaaaagag ctgatgaagt ccagacagac    1140
agtggattgt accacataag caacttggag gaagagatac tgaacatcat tgggcttcta    1200
tgctgggaga ccacgaataa aaccaaccaa agaaatcaaa tgaacagctc cgttgacttt    1260
atttacatta caagatcatt tccagtagag agttttgaaa cctctttaa ttttttttaa    1320
agggaaaact aacacataca catagttttt attcttactg tcttaaagac agaagagcat    1380
```

```
agcattcact aatattttga gaaaataata cctatataaa gtcctgtatt taactggtct    1440
ttggggagag gtgggagtgt atgactgggt ataaagaatt ctgattacag ctcaaactag    1500
tgggaaggaa aaattagtcc aaaacccttt acatcgataa acactttaaa aaagaaagct    1560
atcaaaaaaa tattgccatt tcatcttatt tattgaccac agttcacagc taatatactc    1620
aataaagtat tgctaattcc atct                                            1644
```

<210> SEQ ID NO 40
<211> LENGTH: 307
<212> TYPE: PRT
<213> ORGANISM: Mus musculus

<400> SEQUENCE: 40

```
Met Val Asn Pro Thr Ser Glu Val Gln Pro Thr Met Gly Val Lys
1               5                   10                  15

Ile Phe Ser Ala Gly Val Ser Ala Cys Leu Ala Asp Ile Ile Thr Phe
            20                  25                  30

Pro Leu Asp Thr Ala Lys Val Arg Leu Gln Ile Gln Gly Glu Gly Gln
        35                  40                  45

Ala Ser Ser Thr Ile Arg Tyr Lys Gly Val Leu Gly Thr Ile Thr Thr
50                  55                  60

Leu Ala Lys Thr Glu Gly Leu Pro Lys Leu Tyr Ser Gly Leu Pro Ala
65                  70                  75                  80

Gly Ile Gln Arg Gln Ile Ser Phe Ala Ser Leu Arg Ile Gly Leu Tyr
                85                  90                  95

Asp Ser Val Gln Glu Tyr Phe Ser Ser Gly Arg Glu Thr Pro Ala Ser
            100                 105                 110

Leu Gly Asn Lys Ile Ser Ala Gly Leu Met Thr Gly Gly Val Ala Val
        115                 120                 125

Phe Ile Gly Gln Pro Thr Glu Val Val Lys Val Arg Met Gln Ala Gln
130                 135                 140

Ser His Leu His Gly Ile Lys Pro Arg Tyr Thr Gly Thr Tyr Asn Ala
145                 150                 155                 160

Tyr Arg Val Ile Ala Thr Thr Glu Ser Leu Ser Thr Leu Trp Lys Gly
                165                 170                 175

Thr Thr Pro Asn Leu Met Arg Asn Val Ile Ile Asn Cys Thr Glu Leu
            180                 185                 190

Val Thr Tyr Asp Leu Met Lys Gly Ala Leu Val Asn Asn Lys Ile Leu
        195                 200                 205

Ala Asp Asp Val Pro Cys His Leu Leu Ser Ala Leu Val Ala Gly Phe
210                 215                 220

Cys Thr Thr Leu Leu Ala Ser Pro Val Asp Val Val Lys Thr Arg Phe
225                 230                 235                 240

Ile Asn Ser Leu Pro Gly Gln Tyr Pro Ser Val Pro Ser Cys Ala Met
                245                 250                 255

Ser Met Tyr Thr Lys Glu Gly Pro Thr Ala Phe Phe Lys Gly Phe Val
            260                 265                 270

Ala Ser Phe Leu Arg Leu Gly Ser Trp Asn Val Ile Met Phe Val Cys
        275                 280                 285

Phe Glu Gln Leu Lys Lys Glu Leu Met Lys Ser Arg Gln Thr Val Asp
290                 295                 300

Cys Thr Thr
305
```

<210> SEQ ID NO 41
<211> LENGTH: 1879
<212> TYPE: DNA
<213> ORGANISM: Mus musculus

<400> SEQUENCE: 41

| | | | | | | |
|---|---|---|---|---|---|---|
| gagcgggctg | gttagcagcg | cacgtgccag | gctccggggc | ccttctgctt | atacacaatt | 60 |
| tctttctgtc | ctgggtttct | tcgtccctga | gacccactcc | atcttctact | tctttggctc | 120 |
| tcgcccagct | ccctacccca | agctctgtaa | ctcgtcgtct | gcaaaatcga | aatggacaca | 180 |
| tccatgaatt | tctcacgcgg | gttaaaaatg | gacctgatgc | aaccctatga | cttcgagacg | 240 |
| tttcaggact | taaggcccct | tttggaggag | tactgggtaa | gctcatttct | catagtggtc | 300 |
| gtctatctgt | tgctcatcgt | tgttggccag | acctacatga | aacgcggaa | gagcttcagc | 360 |
| ttgcagaggc | ctctcatcct | ctggtccttc | ttcctggcaa | tattcagtat | cctgggtact | 420 |
| ctgaggatgt | ggaagtttat | ggcaacagtg | atgtttacag | tgggcctcaa | gcaaaccgtg | 480 |
| tgctttgcca | tctacacgga | tgacgccgta | gtcagattct | ggtcctttct | ctttcttctc | 540 |
| agcaaggttg | ttgaactggg | agacacggcc | ttcatcatcc | tgcgtaagcg | tccactcatc | 600 |
| tttgtccact | ggtaccacca | cagcacagtg | ctactgttca | caagctttgg | atacaagaac | 660 |
| aaagtgcctt | cgggtggctg | gttcatgacc | atgaactttg | gcgtccattc | tgtcatgtac | 720 |
| acttactaca | ctatgaaggc | tgccaaactg | aagcatccta | atcttctccc | catggtcatc | 780 |
| accagcctgc | agattctgca | gatggttctg | ggcaccatct | ttggcatact | gaattacatc | 840 |
| tggaggcagg | agaaaggatg | ccacacaaca | acggaacact | tcttctggtc | ttttatgcta | 900 |
| tatgggacct | atttcatcct | attcgctcac | ttcttccacc | gagcctacct | caggcccaag | 960 |
| ggcaaagttg | catccaagag | ccaatgagag | taggaaagaa | agatggagcc | tcagccgttc | 1020 |
| ctccgtggca | ctaagggtat | gggagaatga | ttagggtacc | tccctgtatg | gtttcccca | 1080 |
| tgggatatgt | accctcaaag | ttgcaggaag | ctatgacaac | caagaaatgt | cacccttggg | 1140 |
| gatagggggt | gtgtggtttg | gtactttgat | gtttctgtct | ttaatgtgaa | ggaaaaccaa | 1200 |
| gccctaggaa | ggagatagga | ctgaggtcct | taaaatggag | ttatttatat | ttatatttag | 1260 |
| aaatctttct | cttcttgctc | tattttaaa | agaggtcaac | atgatcttga | ggatttgtgg | 1320 |
| acttggaggg | gaggggagag | tggactgact | ctgtggtagg | aggaggctga | ctctggggag | 1380 |
| tgagtgatct | gcagggggg | agcctgaggg | tgtgtggaag | gacagaggca | cacacaaaca | 1440 |
| ctcaataaga | attctaggcc | tggtaggcgc | ttaataaatg | tcttttacag | actagaagtt | 1500 |
| tattgctgtt | agagacccaa | gcctctgaaa | ggaacagtga | gaaacaagtc | ctaaaatcat | 1560 |
| aggctaaact | gcagaagaga | tcgctgcgtg | gaagcacggg | tgaccagacc | taccggctgt | 1620 |
| cctcccagag | accaccaggt | ggcgtcgcag | caccagcaga | gaacgatccc | tgtcagctag | 1680 |
| ctggtcacac | caagcttcat | actccttta | ctccaggaga | ccctgcttcc | ctatcctgga | 1740 |
| ggaaaggagt | gagacggcaa | ccttagaagc | ctggacgctc | actcggttcc | tgtacatcca | 1800 |
| gctgtccttt | tggacaatgg | gaaggatgaa | gggaaggagg | gctcaaccgc | aagtctgaat | 1860 |
| catcaggcct | ttgacagtc | | | | | 1879 |

<210> SEQ ID NO 42
<211> LENGTH: 271
<212> TYPE: PRT
<213> ORGANISM: Mus musculus

<400> SEQUENCE: 42

```
Met Asp Thr Ser Met Asn Phe Ser Arg Gly Leu Lys Met Asp Leu Met
1               5                   10                  15

Gln Pro Tyr Asp Phe Glu Thr Phe Gln Asp Leu Arg Pro Phe Leu Glu
            20                  25                  30

Glu Tyr Trp Val Ser Ser Phe Leu Ile Val Val Tyr Leu Leu Leu
        35                  40                  45

Ile Val Val Gly Gln Thr Tyr Met Arg Thr Arg Lys Ser Phe Ser Leu
50                      55                  60

Gln Arg Pro Leu Ile Leu Trp Ser Phe Phe Leu Ala Ile Phe Ser Ile
65                  70                  75                  80

Leu Gly Thr Leu Arg Met Trp Lys Phe Met Ala Thr Val Met Phe Thr
                85                  90                  95

Val Gly Leu Lys Gln Thr Val Cys Phe Ala Ile Tyr Thr Asp Asp Ala
            100                 105                 110

Val Val Arg Phe Trp Ser Phe Leu Phe Leu Ser Lys Val Val Glu
            115                 120                 125

Leu Gly Asp Thr Ala Phe Ile Ile Leu Arg Lys Arg Pro Leu Ile Phe
130                 135                 140

Val His Trp Tyr His His Ser Thr Val Leu Leu Phe Thr Ser Phe Gly
145                 150                 155                 160

Tyr Lys Asn Lys Val Pro Ser Gly Gly Trp Phe Met Thr Met Asn Phe
                165                 170                 175

Gly Val His Ser Val Met Tyr Thr Tyr Tyr Thr Met Lys Ala Ala Lys
            180                 185                 190

Leu Lys His Pro Asn Leu Leu Pro Met Val Ile Thr Ser Leu Gln Ile
            195                 200                 205

Leu Gln Met Val Leu Gly Thr Ile Phe Gly Ile Leu Asn Tyr Ile Trp
210                 215                 220

Arg Gln Glu Lys Gly Cys His Thr Thr Thr Glu His Phe Phe Trp Ser
225                 230                 235                 240

Phe Met Leu Tyr Gly Thr Tyr Phe Ile Leu Phe Ala His Phe Phe His
                245                 250                 255

Arg Ala Tyr Leu Arg Pro Lys Gly Lys Val Ala Ser Lys Ser Gln
            260                 265                 270

<210> SEQ ID NO 43
<211> LENGTH: 393
<212> TYPE: DNA
<213> ORGANISM: Mus musculus

<400> SEQUENCE: 43
aaagtgctgc acgtccttgg gcgaagaggg gaggtgactc ggagctgctg aggacgcaaa      60
atgagggccc tacgggtctc ccaggctctg gtccggtctt ttagctcatc taccagaagc     120
cacttagaaa accgtgtggc agagaagcag aagctcttcc aggccgacaa tgacctccca     180
gtacacttga aaggcggggg aatggacaac gtcctgtaca gactgaccat gacgctgact     240 ctgggggggca ctgcctactg cttatactgc ttgggctggg cctccttccc ccacaagaag     300
tgacaccaag aagcttggag gacttggaca aacatcaata aatatgctaa tctcttgaga     360
acccaaaaaa aaaaaaaaaa aaaaaaaaaa aaa                                  393

<210> SEQ ID NO 44
<211> LENGTH: 80
<212> TYPE: PRT
<213> ORGANISM: Mus musculus
```

<400> SEQUENCE: 44

Met Arg Ala Leu Arg Val Ser Gln Ala Leu Val Arg Ser Phe Ser Ser
1               5                   10                  15

Ser Thr Arg Ser His Leu Glu Asn Arg Val Ala Glu Lys Gln Lys Leu
            20                  25                  30

Phe Gln Ala Asp Asn Asp Leu Pro Val His Leu Lys Gly Gly Gly Met
        35                  40                  45

Asp Asn Val Leu Tyr Arg Leu Thr Met Thr Leu Thr Leu Gly Gly Thr
50                  55                  60

Ala Tyr Cys Leu Tyr Cys Leu Gly Trp Ala Ser Phe Pro His Lys Lys
65                  70                  75                  80

<210> SEQ ID NO 45
<211> LENGTH: 383
<212> TYPE: DNA
<213> ORGANISM: Mus musculus

<400> SEQUENCE: 45
cagctataaa aagccccagc tggctaccta agtggtcaga ggacgtgcag cggacattca      60
gggtgcctct ttggggccaa ggaaggagtg cgaccccgag aatcatgcca aggctccccc    120
ctatcctgcg gctgctccaa gcgcctgcga agttcacagt ggttcccaaa gcccatgtct    180
ctgccaagcc agccaaaact cccacttccg ccgtggagca ggctgtgggg atctcagcca    240
tagtcgttgg cttcatggtt ccagcaggat gggtcttagc ccacttggag agctataaaa    300
agagctccgc agcatgaagt tgcacatccc tgagagattt cattaaacat gtccatctgc    360
ctaaaaaaaa aaaaaaaaaa aaa                                             383

<210> SEQ ID NO 46
<211> LENGTH: 70
<212> TYPE: PRT
<213> ORGANISM: Mus musculus

<400> SEQUENCE: 46

Met Pro Arg Leu Pro Pro Ile Leu Arg Leu Leu Gln Ala Pro Ala Lys
1               5                   10                  15

Phe Thr Val Val Pro Lys Ala His Val Ser Ala Lys Pro Ala Lys Thr
            20                  25                  30

Pro Thr Ser Ala Val Glu Gln Ala Val Gly Ile Ser Ala Ile Val Val
        35                  40                  45

Gly Phe Met Val Pro Ala Gly Trp Val Leu Ala His Leu Glu Ser Tyr
50                  55                  60

Lys Lys Ser Ser Ala Ala
65                  70

<210> SEQ ID NO 47
<211> LENGTH: 1164
<212> TYPE: DNA
<213> ORGANISM: Mus musculus

<400> SEQUENCE: 47
ccagaagaga aaacaaaact gacaagagcc accaacatca ccaaatcctg ggttttggg       60 ccctcggtac cgtttgcgca cgaaggggcg tggccccggg acccaggcca gggagccaga    120
actattcgct gctcgcagga gcgcagcctg tcgccaaggt cgggtcaagt cgtcgcgggg    180
cgtggctgat agggcagtga tttaagagac gcggctttgg gacaggagga cccgcaccaa    240

```
tggagaccgc cagggactac gcgggagccc tcatcaggcc cctgacattc atgggattgc    300
agactaagaa ggtcctactg accccctca tacatccagc tcgcccttt cgagtttcaa     360
accatgaccg aagtagccgg cgtggggtga tggccagcag cctgcaggaa cttatcagca   420
agactctgga tgtcttagtc atcacaactg gcctggttac gctggtgctg gaggaggacg   480
gcaccgtggt ggacacagag gagttctttc agaccttaag ggacaacacg catttcatga   540
tcttggaaaa gggacagaaa tggacaccgg gtagtaagta tgtcccagtc tgcaagcaac   600
caaagaaatc gggaatagcc agagtcacct tcgacctata caggctgaac cccaaggact   660
tcctcggctg tctcaatgtc aaagccacga tgtacgagat gtactcggtg tcctacgaca   720
tccgatgcac aagcttcaag gccgtgttaa ggaatctgct gaggtttatg tcctatgctg   780
cacagatgac gggacagttc ctggtctatg cgggcacata catgctccga gtactgggcg   840
atacagaaga gcagccatcc cccaagccta gcaccaaagg ctggttcatg taaccagggc   900
acagctacag aggcccaggg accctgctct ctgttatagg ctgtgggatg ccaggggaag   960
gaatgggggc ttggggtgg tacccagtgc agggctgagt agcaggattc ctgcaaagga   1020
aaggcggcag aggggccttt caagcgcttt aggaagggat caacagcgga gtgtgtggga   1080
actgcgtgga tacgaatcag tttctttgga tccttacata ctgtaataaa ccagtcacat   1140
gagtcgtctt tgatacttcc ttgc                                          1164

<210> SEQ ID NO 48
<211> LENGTH: 217
<212> TYPE: PRT
<213> ORGANISM: Mus musculus

<400> SEQUENCE: 48

Met Glu Thr Ala Arg Asp Tyr Ala Gly Ala Leu Ile Arg Pro Leu Thr
1               5                   10                  15

Phe Met Gly Leu Gln Thr Lys Lys Val Leu Leu Thr Pro Leu Ile His
                20                  25                  30

Pro Ala Arg Pro Phe Arg Val Ser Asn His Asp Arg Ser Ser Arg Arg
            35                  40                  45

Gly Val Met Ala Ser Ser Leu Gln Glu Leu Ile Ser Lys Thr Leu Asp
        50                  55                  60

Val Leu Val Ile Thr Thr Gly Leu Val Thr Leu Val Leu Glu Glu Asp
65                  70                  75                  80

Gly Thr Val Val Asp Thr Glu Glu Phe Phe Gln Thr Leu Arg Asp Asn
                85                  90                  95

Thr His Phe Met Ile Leu Glu Lys Gly Gln Lys Trp Thr Pro Gly Ser
                100                 105                 110

Lys Tyr Val Pro Val Cys Lys Gln Pro Lys Lys Ser Gly Ile Ala Arg
            115                 120                 125

Val Thr Phe Asp Leu Tyr Arg Leu Asn Pro Lys Asp Phe Leu Gly Cys
        130                 135                 140

Leu Asn Val Lys Ala Thr Met Tyr Glu Met Tyr Ser Val Ser Tyr Asp
145                 150                 155                 160

Ile Arg Cys Thr Ser Phe Lys Ala Val Leu Arg Asn Leu Leu Arg Phe
                165                 170                 175

Met Ser Tyr Ala Ala Gln Met Thr Gly Gln Phe Leu Val Tyr Ala Gly
                180                 185                 190

Thr Tyr Met Leu Arg Val Leu Gly Asp Thr Glu Glu Gln Pro Ser Pro
            195                 200                 205
```

Lys Pro Ser Thr Lys Gly Trp Phe Met
    210                 215

<210> SEQ ID NO 49
<211> LENGTH: 2083
<212> TYPE: DNA
<213> ORGANISM: Mus musculus

<400> SEQUENCE: 49

| | | | | | |
|---|---|---|---|---|---|
| cttcccatcc | cccaggaata | tataaagagc | cccaacctca | gccactgacc | gaccctggcc | 60 |
| aacaggcatc | tgtccttgtt | aattacagag | agacagtccc | aaactccggg | agctccgcct | 120 |
| ggatttgctg | gcctgcagca | gccagggact | ggcgtgtctc | cctctctgct | gaatccaggt | 180 |
| attcccacct | gcttctctga | aggatggaca | tgacggacgg | ctgccagttc | tccccttctg | 240 |
| agtacttcta | tgaaggctcc | tgtatcccct | caccagagga | tgagtttggg | gaccagtttg | 300 |
| agccaagagt | agcagccttc | ggagcacaca | agctgagct | gcagggctca | gacgatgagg | 360 |
| agcacgtgcg | tgcacctacc | ggccaccacc | aggctgccca | ctgcctcatg | tgggcctgca | 420 |
| aagcttgcaa | gaggaagtcc | actaccatgg | atcggcgcaa | ggccgccacc | atgcgcgagc | 480 |
| gtagacgcct | gaagaaggtc | aaccaagctt | cgagacgct | caagaggtgc | accaccacca | 540 |
| accctaacca | gagactcccc | aaggtggaga | tcctcaggaa | tgccatccgc | tacattgaga | 600 |
| gcctccagga | gctgctgagg | gaacaggtgg | agaactatta | cagcctgccg | ggacagagct | 660 |
| gctctgagcc | caccagcccc | acctccaact | gctctgacgg | catgcctgaa | tgtaacagcc | 720 |
| ctgtctggtc | ccgaaagaac | agcagctttg | acagcatcta | ctgtcctgat | gtatcaaatg | 780 |
| catgtgctgc | agataaaagc | tccgtgtcca | gcttggattg | cttgtccagc | attgtggatc | 840 |
| ggatcacgtc | tacagagcca | tccgagctgg | ctcttcagga | cacagcttcc | ctctctccag | 900 |
| cgaccagcgc | caactcacag | cctgctaccc | cgggaccctc | cagctccaga | cttatctatc | 960 |
| acgtattatg | aactctctcc | cgatgatcac | tcctgctagg | agggcgtcct | tcatggagga | 1020 |
| aaagaagccc | tgaagctgaa | ggaaagacaa | gctgggcaga | atacgtgctt | tcggttgta | 1080 |
| aatactgtct | tgccactttta | tgagaaaata | gatttaactg | aaagtcacat | ttgcaataat | 1140 |
| ggattctcct | ctgcctgttc | tttttgcttt | cggttttttt | tttttttttt | ttttagctt | 1200 |
| ccaattgctt | tagatacatg | attccagaaa | tatttttctg | ttggaggcaa | ttaattgaca | 1260 |
| gttacttaga | gtaattctta | acttatacat | atatattgta | aatattgcac | atcaaaataa | 1320 |
| ctttggtatt | tagagctcta | tattttttctt | caaaataaca | ttttaacagc | ttggaatcca | 1380 |
| ttacagggaa | ttaaaatat | atttaacttt | tgcttttctc | tttaatcttt | tgttaatagt | 1440 |
| gtatcatcaa | atgaaaatat | aacagttgtg | cctaatggta | tatactttct | taaaatcttt | 1500 |
| taatcgtata | atcttacatc | ttttcttata | agaaatactt | ctttcaatgt | aagctataaa | 1560 |
| taatacattg | agggcaattt | caaactatta | aaatgtaaa | tttccccata | aataacattg | 1620 |
| aaataactaa | tttgtttctt | ggcctttaaa | aataacatcc | ccaatgaaat | tagcaaacca | 1680 |
| tgaacacgaa | acatttaaga | atgggttaaa | tatgatcaca | cagttagcct | tgtagatatg | 1740 |
| tattgaaata | atttatgaat | ttcttttaga | tttgttgatg | tcacttgtaa | aaatattaca | 1800 |
| tttccattgt | aagcacattt | caagaatgcc | tggtaaatga | agcccccttt | tctttgttgt | 1860 |
| tatttcatac | aatgtccagt | tgtatataaa | aaaaaggat | tgtaaaattt | tataggataa | 1920 |
| tatcatttgt | ttaagcaaaa | aagcttaaaa | agtattatgt | catttactta | tatacagtac | 1980 |
| tttgccaatc | atgagccagg | ttttattaac | tatttgtata | tgccttaaaa | taacttgata | 2040 | aataaatgta ctattattat caataaaata tttaaaggag gtg                2083

<210> SEQ ID NO 50
<211> LENGTH: 255
<212> TYPE: PRT
<213> ORGANISM: Mus musculus

<400> SEQUENCE: 50

Met Asp Met Thr Asp Gly Cys Gln Phe Ser Pro Ser Glu Tyr Phe Tyr
1               5                   10                  15

Glu Gly Ser Cys Ile Pro Ser Pro Glu Asp Glu Phe Gly Asp Gln Phe
            20                  25                  30

Glu Pro Arg Val Ala Ala Phe Gly Ala His Lys Ala Glu Leu Gln Gly
        35                  40                  45

Ser Asp Asp Glu Glu His Val Arg Ala Pro Thr Gly His His Gln Ala
    50                  55                  60

Gly His Cys Leu Met Trp Ala Cys Lys Ala Cys Lys Arg Lys Ser Thr
65                  70                  75                  80

Thr Met Asp Arg Arg Lys Ala Ala Thr Met Arg Glu Arg Arg Arg Leu
                85                  90                  95

Lys Lys Val Asn Gln Ala Phe Glu Thr Leu Lys Arg Cys Thr Thr Thr
            100                 105                 110

Asn Pro Asn Gln Arg Leu Pro Lys Val Glu Ile Leu Arg Asn Ala Ile
        115                 120                 125

Arg Tyr Ile Glu Ser Leu Gln Glu Leu Leu Arg Glu Gln Val Glu Asn
    130                 135                 140

Tyr Tyr Ser Leu Pro Gly Gln Ser Cys Ser Glu Pro Thr Ser Pro Thr
145                 150                 155                 160

Ser Asn Cys Ser Asp Gly Met Pro Glu Cys Asn Ser Pro Val Trp Ser
                165                 170                 175

Arg Lys Asn Ser Ser Phe Asp Ser Ile Tyr Cys Pro Asp Val Ser Asn
            180                 185                 190

Ala Cys Ala Ala Asp Lys Ser Ser Val Ser Ser Leu Asp Cys Leu Ser
        195                 200                 205

Ser Ile Val Asp Arg Ile Thr Ser Thr Glu Pro Ser Glu Leu Ala Leu
    210                 215                 220

Gln Asp Thr Ala Ser Leu Ser Pro Ala Thr Ser Ala Asn Ser Gln Pro
225                 230                 235                 240

Ala Thr Pro Gly Pro Ser Ser Ser Arg Leu Ile Tyr His Val Leu
                245                 250                 255

<210> SEQ ID NO 51
<211> LENGTH: 1854
<212> TYPE: DNA
<213> ORGANISM: Mus musculus

<400> SEQUENCE: 51
aggggccagg acgccccagg acacgactgc tttcttcacc actcctctga caggacagga        60
cagggaggag gggtagagga cagccggtgt gcattccaac ccacagaacc tttgtcattg       120
tactgttggg gttccggagt ggcagaaagt taagacgact ctcacggctt gggttgaggc       180
tggacccagg aactgggata tggagcttct atcgccgcca ctccgggaca tagacttgac       240
aggccccgac ggctctctct gctcctttga gacagcagac gacttctatg atgacccgtg       300
tttcgactca ccagacctgc gcttttttga ggacctggac ccgcgcctgg tgcacatggg       360
agccctcctg aaaccggagg agcacgcaca cttccctact gcggtgcacc caggcccagg       420

-continued

```
cgctcgtgag gatgagcatg tgcgcgcgcc cagcgggcac caccaggcgg gtcgctgctt     480
gctgtgggcc tgcaaggcgt gcaagcgcaa gaccaccaac gctgatcgcc gcaaggccgc     540
caccatgcgc gagcgccgcc gcctgagcaa agtgaatgag gccttcgaga cgctcaagcg     600
ctgcacgtcc agcaacccga accagcggct acccaaggtg gagatcctgc gcaacgccat     660
ccgctacatc gaaggtctgc aggctctgct gcgcgaccag gacgccgcgc ccctggcgc      720
cgctgccttc tacgcacctg gaccgctgcc cccaggccgt ggcagcgagc actacagtgg     780
cgactcagat gcatccagcc cgcgctccaa ctgctctgat ggcatgatgg attacagcgg     840
cccccccaagc ggccccgc ggcagaatgg ctacgacacc gcctactaca gtgaggcggc      900
gcgcgagtcc aggccaggga gagtgcggc tgtgtcgagc ctcgactgcc tgtccagcat      960
agtggagcgc atctccacag acagcccgc tgcgcctgcg ctgcttttgg cagatgcacc     1020
accagagtcg cctccgggtc cgccagaggg ggcatcccta agcgacacag aacagggaac    1080
ccagaccccg tctcccgacg ccgcccctca gtgtcctgca ggctcaaacc ccaatgcgat    1140
ttatcaggtg ctttgagaga tcgactgcag cagcagaggg cgcaccaccg taggcactcc    1200
tggggatggt gtccctggtt cttcacgccc aaaagatgaa gcttaaatga cactcttccc    1260
aactgtcctt tcgaagccgt tcttccagag ggaagggaag agcagaagtc tgtcctagat    1320
ccagccccaa agaaaggaca tagtcctttt tgttgttgtt gttgtagtcc ttcagttgtt    1380
tgtttgtttt ttcatgcggc tcacagcgaa ggccacttgc actctggctg cacctcactg    1440
ggccagagct gatccttgag tggccaggcg ctcttccttt cctcatagca caggggtgag    1500
ccttgcacac ctaagccctg ccctccacat ccttttgttt gtcactttct ggagccctcc    1560
tggcacccac ttttccccac agcttgcgga ggccactcag gtctcaggtg taacaggtgt    1620
aaccataccc cactctcccc cttcccgcgg ttcaggacca cttatttttt tatataagac    1680
ttttgtaatc tattcgtgta aataagagtt gcttggccag agcgggagcc ccttgggcta    1740
tatttatctc ccaggcatgc tgtgtagtgc aacaaaaact ttgtatgttt attcctcaag    1800
cgggcgagcc tcgaggctcg ctcgctcagg tgttggaaat aaagacgcta attt          1854
```

<210> SEQ ID NO 52
<211> LENGTH: 318
<212> TYPE: PRT
<213> ORGANISM: Mus musculus

<400> SEQUENCE: 52

```
Met Glu Leu Leu Ser Pro Leu Arg Asp Ile Asp Leu Thr Gly Pro
1               5                   10                  15

Asp Gly Ser Leu Cys Ser Phe Glu Thr Ala Asp Asp Phe Tyr Asp Asp
                20                  25                  30

Pro Cys Phe Asp Ser Pro Asp Leu Arg Phe Phe Glu Asp Leu Asp Pro
            35                  40                  45

Arg Leu Val His Met Gly Ala Leu Leu Lys Pro Glu Glu His Ala His
        50                  55                  60

Phe Pro Thr Ala Val His Pro Gly Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
```

```
            115                 120                 125
Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Phe Tyr Ala Pro Gly Pro Leu Pro Pro Gly Arg Gly Ser Glu His Tyr
            180                 185                 190

Ser Gly Asp Ser Asp Ala Ser Ser Pro Arg Ser Asn Cys Ser Asp Gly
            195                 200                 205

Met Met Asp Tyr Ser Gly Pro Pro Ser Gly Pro Arg Arg Gln Asn Gly
    210                 215                 220

Tyr Asp Thr Ala Tyr Tyr Ser Glu Ala Ala Arg Glu Ser Arg Pro Gly
225                 230                 235                 240

Lys Ser Ala Ala Val Ser Ser Leu Asp Cys Leu Ser Ser Ile Val Glu
                245                 250                 255

Arg Ile Ser Thr Asp Ser Pro Ala Ala Pro Ala Leu Leu Leu Ala Asp
            260                 265                 270

Ala Pro Pro Glu Ser Pro Pro Gly Pro Pro Glu Gly Ala Ser Leu Ser
            275                 280                 285

Asp Thr Glu Gln Gly Thr Gln Thr Pro Ser Pro Asp Ala Ala Pro Gln
    290                 295                 300

Cys Pro Ala Gly Ser Asn Pro Asn Ala Ile Tyr Gln Val Leu
305                 310                 315

<210> SEQ ID NO 53
<211> LENGTH: 1518
<212> TYPE: DNA
<213> ORGANISM: Mus musculus

<400> SEQUENCE: 53
ggggctgcgg gagcttgggg gccagtggca ggaacaagcc ttttccgacc tgatggagct      60
gtatgagaca tccccctatt tctaccagga gccccacttc tatgatgggg aaaactacct     120
tcctgtccac cttcagggct cgagcccccc gggctatgag cggactgagc tcagcttaag     180
cccggaagcc cgagggcccc tggaagaaaa gggactgggg acccctgagc attgtccagg     240
ccagtgcctg ccgtgggcat gtaaggtgtg taagaggaag tctgtgtcgg tggaccggag     300
gagggcagcc acactgaggg agaagcgcag gctcaagaaa gtgatgagg  ccttcgaggc     360 cctgaagagg agcaccctgc tcaaccccaa ccagcggctg cctaaagtgg agatcctgcg     420
cagcgccatc cagtacattg agcgcctaca ggccttgctc agctccctca accaggagga     480
gcgcgatctc cgctacagag gcggggcgg gccccagccc atggtgccca gtgaatgcaa     540
ctcccacagc gcctcctgca gtccggagtg gggcaatgca ctggagttcg gtcccaaccc     600
aggagatcat ttgctcgcgg ctgaccctac agacgcccac aatctgcact cccttacgtc     660
catcgtggac agcatcacgg tggaggatat gtctgttgcc ttcccagacg aaaccatgcc     720
caactgagat tgtctgtcag gctgggtgtg catgtgagcc cccaagttgg tgtcaaaagc     780
catcacttct gtagcagggg gctttttaagt ggggctgtcc tgatgtccag aaaacagccc     840
tgggctgcca caagccagac tcccactcc ccattcacat aaggctaaca cccagcccag     900
cgagggaatt tagctgactc cttaaagcag agagcatcct cttctgagga gagaaagatg     960
gagtccagag agccccttg ttaatgtccc tcagtgggc aaactcagga gcttcttttt    1020
```

-continued

```
tgtttatcat aatatgcctc gaattccacc ccccaccccc aaaatgaaac cgtttgagag    1080
acatgagtgc cctgacctgg acaagtgtgc acatctgttc tagtctcttc ctgaagccag    1140
tggctgggct gggcctgccc tgagttgaga gagaaggggg aggagctatc cggttccaaa    1200
gcctctgggg gccaagcatt tgcagtggat cttgggaacc ttccagtgct ttgtgtattg    1260
tttattgttt tgtgtgttgt ttgtaaagct gccgtctgac caaggtctcc tgtgctgatg    1320
ataccgggaa caggcaggga aggggtgggg ggctcttggg gtgacttctt ttgttaacta    1380
agcattgtgt ggttttgcca attttttttc ttttgtaatt cttttgctaa cttatttgga    1440
tttccttttt taaaaaatga ataaagactg gttgctatca aaaaaaaaaa aaaaaaaaa    1500 aaaaaaaaaa aaaaaaaa                                                   1518
```

<210> SEQ ID NO 54
<211> LENGTH: 224
<212> TYPE: PRT
<213> ORGANISM: Mus musculus

<400> SEQUENCE: 54

```
Met Glu Leu Tyr Glu Thr Ser Pro Tyr Phe Tyr Gln Glu Pro His Phe
1               5                   10                  15

Tyr Asp Gly Glu Asn Tyr Leu Pro Val His Leu Gln Gly Phe Glu Pro
            20                  25                  30

Pro Gly Tyr Glu Arg Thr Glu Leu Ser Leu Ser Pro Glu Ala Arg Gly
        35                  40                  45

Pro Leu Glu Glu Lys Gly Leu Gly Thr Pro His Cys Pro Gly Gln
    50                  55                  60

Cys Leu Pro Trp Ala Cys Lys Val Cys Lys Arg Lys Ser Val Ser Val
65                  70                  75                  80

Asp Arg Arg Arg Ala Ala Thr Leu Arg Glu Lys Arg Arg Leu Lys Lys
                85                  90                  95

Val Asn Glu Ala Phe Glu Ala Leu Lys Arg Ser Thr Leu Leu Asn Pro
            100                 105                 110

Asn Gln Arg Leu Pro Lys Val Glu Ile Leu Arg Ser Ala Ile Gln Tyr
        115                 120                 125

Ile Glu Arg Leu Gln Ala Leu Leu Ser Ser Leu Asn Gln Glu Glu Arg
    130                 135                 140

Asp Leu Arg Tyr Arg Gly Gly Gly Pro Gln Pro Met Val Pro Ser
145                 150                 155                 160

Glu Cys Asn Ser His Ser Ala Ser Cys Ser Pro Glu Trp Gly Asn Ala
                165                 170                 175

Leu Glu Phe Gly Pro Asn Pro Gly Asp His Leu Leu Ala Ala Asp Pro
            180                 185                 190

Thr Asp Ala His Asn Leu His Ser Leu Thr Ser Ile Val Asp Ser Ile
        195                 200                 205

Thr Val Glu Asp Met Ser Val Ala Phe Pro Asp Glu Thr Met Pro Asn
    210                 215                 220
```

<210> SEQ ID NO 55
<211> LENGTH: 1233
<212> TYPE: DNA
<213> ORGANISM: Mus musculus

<400> SEQUENCE: 55

```
taagctgggg tctgcctgtc cccatgagta ccagactaat gagacctggc cactttctcc    60
```

-continued

```
tcatttctgt ctgtacgatt gtcagtggat ctgacgacac caaaagggct caggatgcta      120
ctgttgcaag ctctcctgtt cctcttaatc ctgcccagtc atgccgaaga tgacgttact      180
acaactgaag agctagctcc tgctttggtc cctccaccca agggaacttg tgcaggttgg      240
atggcaggca tcccaggaca tcctggccac aatggcacac caggccgtga tggcagagat      300
ggcactcctg gagagaaggg agagaaagga gatgcaggtc ttcttggtcc taagggtgag      360
acaggagatg ttggaatgac aggagctgaa gggccacggg gcttccccgg aacccctggc      420
aggaaaggag agcctggaga agccgcttat gtgtatcgct cagcgttcag tgtgggctg      480
gagacccgcg tcactgttcc caatgtaccc attcgcttta ctaagatctt ctacaaccaa      540
cagaatcatt atgacggcag cactggcaag ttctactgca cattccggg actctactac       600
ttctcttacc acatcacggt gtacatgaaa gatgtgaagg tgagcctctt caagaaggac      660
aaggccgttc tcttcaccta cgaccagtat caggaaaaga atgtggacca ggcctctggc      720
tctgtgctcc tccatctgga ggtgggagac caagtctggc tccaggtgta tggggatggg      780
gaccacaatg gactctatgc agataacgtc aacgactcta catttactgg ctttcttctc      840
taccatgata ccaactgact gcaactaccc atagcccata caccaggaga atcatggaac      900
agtcgacaca ctttcagctt agtttgagag attgatttta ttgcttagtt tgagagtcct      960
gagtattatc cacacgtgta ctcacttgtt cattaaacga ctttataaaa aataatttgt     1020
gttcctagtc cagaaaaaaa ggcactccct ggtctccacg actcttacat ggtagcaata     1080
acagaatgaa aatcacattt ggtatggggg cttcacaata ttcgcatgac tgtctggaag     1140
tagaccatgc tattttttctg ctcactgtac acaaatattg ttcacataaa ccctataatg   1200
taaatatgaa atacagtgat tactcttctc act                                   1233
```

<210> SEQ ID NO 56
<211> LENGTH: 247
<212> TYPE: PRT
<213> ORGANISM: Mus musculus

<400> SEQUENCE: 56

```
Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
                20                  25                  30

Pro Pro Pro Lys Gly Thr Cys Ala Gly Trp Met Ala Gly Ile Pro Gly
            35                  40                  45

His Pro Gly His Asn Gly Thr Pro Gly Arg Asp Gly Arg Asp Gly Thr
        50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Val Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
    130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
```

```
                165                 170                 175
Ser Leu Phe Lys Lys Asp Lys Ala Val Leu Phe Thr Tyr Asp Gln Tyr
            180                 185                 190

Gln Glu Lys Asn Val Asp Gln Ala Ser Gly Ser Val Leu Leu His Leu
            195                 200                 205

Glu Val Gly Asp Gln Val Trp Leu Gln Val Tyr Gly Asp Gly Asp His
            210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245

<210> SEQ ID NO 57
<211> LENGTH: 926
<212> TYPE: DNA
<213> ORGANISM: Mus musculus

<400> SEQUENCE: 57 agggggcagga ggtaagaggc aggagtccat aaaacagccc tgagagcctg ctgggtcagt      60
gcctgctgtc agaatgcaca gctccgtgta cttcgtggct ctggtgatcc tgggagcggc     120
tgtatgtgca gcacagcccc gaggccggat tctgggtggc caggaggccg cagcccatgc     180
tcggccctac atggcttccg tgcaagtgaa cggcacacac gtgtgcggtg caccctgct     240 ggacgagcag tgggtgctca gtgctgcaca ctgcatggat ggagtgacgg atgacgactc     300
tgtgcaggtg ctcctggtg cccactccct gtccgcccct gaaccctaca gcgatggta     360 tgatgtgcag agtgtagtgc ctcacccggg cagccgacct gacagccttg aggacgacct     420
cattcttttt aagctatccc agaatgcctc gttgggtccc cacgtgagac ccctacccctt    480 gcaatacgag gacaaagaag tggaacccgg cacgctctgc gacgtggctg gttgggtgtg     540
ggtcacccat gcaggacgca ggcctgatgt cctgcatcaa ctcagagtgt caatcatgaa     600
ccggacaacc tgcaatctgc gcacgtacca tgacggggta gtcaccatta acatgatgtg     660
tgcagagagc aaccgcaggg acacttgcag gggagactcc ggcagccctc tagtgtgcgg     720
ggatgcagtc gaaggtgtgg ttacgtgggg ctctcgcgtc tgtggcaatg gcaaaaagcc     780
gggcgtctat acccgagtgt catcctaccg gatgtggatc gaaaacatca caaatggtaa     840
catgacatcc tgaggggaca ccagagacac gtggctcagg gaaacaagag acacgtggct     900
cacaataaat gcatgcatct gagaaa                                          926

<210> SEQ ID NO 58
<211> LENGTH: 259
<212> TYPE: PRT
<213> ORGANISM: Mus musculus

<400> SEQUENCE: 58

Met His Ser Ser Val Tyr Phe Val Ala Leu Val Ile Leu Gly Ala Ala
1               5                   10                  15

Val Cys Ala Ala Gln Pro Arg Gly Arg Ile Leu Gly Gly Gln Glu Ala
            20                  25                  30

Ala Ala His Ala Arg Pro Tyr Met Ala Ser Val Gln Val Asn Gly Thr
            35                  40                  45

His Val Cys Gly Gly Thr Leu Leu Asp Glu Gln Trp Val Leu Ser Ala
        50                  55                  60

Ala His Cys Met Asp Gly Val Thr Asp Asp Ser Val Gln Val Leu
65                  70                  75                  80
```

```
Leu Gly Ala His Ser Leu Ser Ala Pro Glu Pro Tyr Lys Arg Trp Tyr
                85                  90                  95
Asp Val Gln Ser Val Val Pro His Pro Gly Ser Arg Pro Asp Ser Leu
            100                 105                 110
Glu Asp Asp Leu Ile Leu Phe Lys Leu Ser Gln Asn Ala Ser Leu Gly
        115                 120                 125
Pro His Val Arg Pro Leu Pro Leu Gln Tyr Glu Asp Lys Glu Val Glu
    130                 135                 140
Pro Gly Thr Leu Cys Asp Val Ala Gly Trp Gly Val Val Thr His Ala
145                 150                 155                 160
Gly Arg Arg Pro Asp Val Leu His Gln Leu Arg Val Ser Ile Met Asn
                165                 170                 175
Arg Thr Thr Cys Asn Leu Arg Thr Tyr His Asp Gly Val Thr Ile
                180                 185                 190
Asn Met Met Cys Ala Glu Ser Asn Arg Arg Asp Thr Cys Arg Gly Asp
            195                 200                 205
Ser Gly Ser Pro Leu Val Cys Gly Asp Ala Val Glu Gly Val Val Thr
    210                 215                 220
Trp Gly Ser Arg Val Cys Gly Asn Gly Lys Lys Pro Gly Val Tyr Thr
225                 230                 235                 240
Arg Val Ser Ser Tyr Arg Met Trp Ile Glu Asn Ile Thr Asn Gly Asn
                245                 250                 255
Met Thr Ser

<210> SEQ ID NO 59
<211> LENGTH: 3171
<212> TYPE: DNA
<213> ORGANISM: Mus musculus

<400> SEQUENCE: 59
gccgcccggg gaccagactg gaagatgcct gggggcccgg gcgcgccctc ttctcccgca      60
gcatcctcag gctcctcgcg tgccgcgccg tcggggatcg cggcatgccc tctgtcccca     120
cctcccctag cccgagggtc tccacaagct tccggtcccc ggcgcggcgc cagcgtcccg     180
cagaagctgg cggagactct gagcagccag tatggactga acgtgttcgt ggcggggctg     240
ctgttcctgc tggcctgggc ggtgcacgcg acgggtgtgg caagagcga cctgctgtgc     300
gttctaaccg cgcttatgct gctgcagctg ctctggatgc tgtggtacgt gggtcgcagc     360
tacatgcagc gccgcctcat ccgcccaag acacgcacg cgggtgcgcg ctggcttcgc      420
ggaagcatca cgttgttcgc gtttatcact gtcgtcctgg gatgcttgaa agtcgcatac     480
ttcattggat tctcggagtg cttgtcagcc accgagggag ttttcccagt cacccatgca     540
gtgcataccc tattgcaggt gtatttcctc tggggccatg ctaaggatat catcatgtct     600
ttcaaaacac tggaaaggtt tggggtgatc cattcagtgt tcacgaacct cctactgtgg     660
gccaacagcg tcctgaatga atcaaagcac cagctgaatg agcacaagga acggctgatc     720
actctgggct ttggcaacat caccatcgtt ttggatgacc acacaccaca gtgtaactgc     780
acaccacccg ccctctgctc tgccctctcc catgggattt actatctgta ccccttcaac     840
attgagtacc agatcctggc ctcgaccatg ctctacgtgc tgtggaagaa catcgggcgc     900
agagtggaca gctcccagca ccagaagatg cagtgcagat cgacggggt cctagtgggc     960
tccgtgctgg gcttgacagt gctggctgcc accatcgccg tggttgtggt gtacatgatc    1020
cacatcgggc gctccaaatc caagagcgag tcggctctca tcatgttcta tttgtacgct    1080
```

```
atcacggtgc tgctgcttat gggggccgca gggctagtcg gaagctggat ttacagggtg    1140
gatgagaagt ctctggatga gtcaaagaac ccagcgcgca agctggatgt tgacctgttg    1200
gtggccaccg gctccggctc ctggctcctc tcctggggct ccattctggc catcgcctgt    1260
gctgagactc gcccaccgta cacctggtac aacctgccct actcggtcct ggtgatcgtg    1320
gagaagtatg tccaaaacat tttcatcatc gagtccgtgc acctcgagcc tgagggggtc    1380
ccggaggatg tgcgcactct gcgtgtggtc accgtctgca gcagcgaggc tgccgcactg    1440
gctgcatcca ctctcgggag ccaggggatg gcccaggatg ggtcacctgc tgtcaatgga    1500
aatctgtgtc tgcagcagag gtgtgggaaa gaggaccagg agtctggctg gaaggagct    1560
acggggacaa cccgatgtct ggacttcctt cagggcggca tgaagaggag gcttctcaga    1620
aacatcacgg cctttctgtt tctttgcaac atctcgcttt ggattccccc tgcctttggc    1680
tgccgtcccg agtatgacaa cggattggag gaaattgtct ttggctttga accctggata    1740
attgtggtca acctggccat gccctttccc attttctacc ggatgcacgc agctgctgcc    1800
ctctttgagg tctattgtaa gatctagcct gagtcctcat gaaaggagaa gggacggggg    1860
agcaaggggg ttctgcagcc acctgcgaag ggcgggatg agcaaacact gtctgacaaa    1920
ggcgggaagg atgccttttg ttctgactgt ctggagttgc cctcgacctg ggggagagcg    1980
agcagttaaa tcaactgcac aagatagctg gagcctgtcc ttagccaatt ccaatcagat    2040
ccaaaatgag ttgagcattt tctggctgag accctgtgtt ttagaagaag gtgatccagg    2100
tttggatgaa aatgatggag ttttttcataa caagcatttc ctgtctgtaa tttgtatgac    2160
tgtgtacaac tttttttctgg ccatctgtgt atcaatccat ttacatttt ttttttttcct    2220
gctcagggtt actgggtttg gaaacaaatg catttttagtt tgtagtttaa tatttgagct    2280
ggtttaattt tggataaaaa ttagttttga tcaactgcat gagagtctga ttctagactt    2340
gttctacaaa cacaagacct tccctaaatt ttttggtccat tttttatttgt gttcattatg    2400
aaatattaaa agaaaataaa cattgatgtt ctctttttttg ctacatctat atccagttcc    2460
tgacgtagaa aatctgaata ttttttgggag gagagacagg aaaaatggtc catgttgcac    2520
tgctaacagt tactctgaac accatggtgt agctttcagc tgtggtgccg tgcagacttt    2580
tctatattgt tgtacttgct agtgataacc tgacatttct aatgttctcc tcatgctttc    2640
ctatttgaca gtctgatgac accttttctct acactgtcat aaattcctgg caaacatcat    2700
tttactgctg tcagaatctc aaactaatgt accacaatta acctcctttg ccttttttttg    2760
attttagaag gctcacaatg ttgctttcct aagtggctct gcgaaagcca agcgtgtttc    2820
taaaacattt ctcttattta aaaattgcat tttaaaagag acgattggcc ctacatatcc    2880
attgatccca catctacatt cagccaattt tgcatagaaa atgttttgta agagttgggt    2940
cttggggttg gagagatggc ctgctgctct caaaaaggac cagagtttgg tttttagtat    3000
ggcatcagtt ggtttacaac tgcctgcaat tctagctcca gaagatctga tattcttctc    3060
aggtttccag ggacaccagc actcacatgc aagagtgtgc tacccccatg aataataaaa    3120
aataataata ataaagcttt caaaaaggaa aaaaaaaaa aaaaaaaaa a              3171
```

<210> SEQ ID NO 60
<211> LENGTH: 600
<212> TYPE: PRT
<213> ORGANISM: Mus musculus

<400> SEQUENCE: 60

```
Met Pro Gly Gly Pro Gly Ala Pro Ser Ser Pro Ala Ala Ser Ser Gly
1               5                   10                  15

Ser Ser Arg Ala Ala Pro Ser Gly Ile Ala Ala Cys Pro Leu Ser Pro
            20                  25                  30

Pro Pro Leu Ala Arg Gly Ser Pro Gln Ala Ser Gly Pro Arg Arg Gly
            35                  40                  45

Ala Ser Val Pro Gln Lys Leu Ala Glu Thr Leu Ser Ser Gln Tyr Gly
50                  55                  60

Leu Asn Val Phe Val Ala Gly Leu Leu Phe Leu Ala Trp Ala Val
65                  70                  75                  80

His Ala Thr Gly Val Gly Lys Ser Asp Leu Leu Cys Val Leu Thr Ala
            85                  90                  95

Leu Met Leu Leu Gln Leu Leu Trp Met Leu Trp Tyr Val Gly Arg Ser
            100                 105                 110

Tyr Met Gln Arg Arg Leu Ile Arg Pro Lys Asp Thr His Ala Gly Ala
            115                 120                 125

Arg Trp Leu Arg Gly Ser Ile Thr Leu Phe Ala Phe Ile Thr Val Val
    130                 135                 140

Leu Gly Cys Leu Lys Val Ala Tyr Phe Ile Gly Phe Ser Glu Cys Leu
145                 150                 155                 160

Ser Ala Thr Glu Gly Val Phe Pro Val Thr His Ala Val His Thr Leu
            165                 170                 175

Leu Gln Val Tyr Phe Leu Trp Gly His Ala Lys Asp Ile Ile Met Ser
            180                 185                 190

Phe Lys Thr Leu Glu Arg Phe Gly Val Ile His Ser Val Phe Thr Asn
    195                 200                 205

Leu Leu Leu Trp Ala Asn Ser Val Leu Asn Glu Ser Lys His Gln Leu
210                 215                 220

Asn Glu His Lys Glu Arg Leu Ile Thr Leu Gly Phe Gly Asn Ile Thr
225                 230                 235                 240

Ile Val Leu Asp Asp His Thr Pro Gln Cys Asn Cys Thr Pro Pro Ala
            245                 250                 255

Leu Cys Ser Ala Leu Ser His Gly Ile Tyr Tyr Leu Tyr Pro Phe Asn
            260                 265                 270

Ile Glu Tyr Gln Ile Leu Ala Ser Thr Met Leu Tyr Val Leu Trp Lys
            275                 280                 285

Asn Ile Gly Arg Arg Val Asp Ser Ser Gln His Gln Lys Met Gln Cys
            290                 295                 300

Arg Phe Asp Gly Val Leu Val Gly Ser Val Leu Gly Leu Thr Val Leu
305                 310                 315                 320

Ala Ala Thr Ile Ala Val Val Val Tyr Met Ile His Ile Gly Arg
            325                 330                 335

Ser Lys Ser Lys Ser Glu Ser Ala Leu Ile Met Phe Tyr Leu Tyr Ala
            340                 345                 350

Ile Thr Val Leu Leu Leu Met Gly Ala Ala Gly Leu Val Gly Ser Trp
            355                 360                 365

Ile Tyr Arg Val Asp Glu Lys Ser Leu Asp Glu Ser Lys Asn Pro Ala
            370                 375                 380

Arg Lys Leu Asp Val Asp Leu Leu Val Ala Thr Gly Ser Gly Ser Trp
385                 390                 395                 400

Leu Leu Ser Trp Gly Ser Ile Leu Ala Ile Ala Cys Ala Glu Thr Arg
            405                 410                 415

Pro Pro Tyr Thr Trp Tyr Asn Leu Pro Tyr Ser Val Leu Val Ile Val
```

```
                420              425               430
Glu Lys Tyr Val Gln Asn Ile Phe Ile Ile Glu Ser Val His Leu Glu
            435                 440                 445

Pro Glu Gly Val Pro Glu Asp Val Arg Thr Leu Arg Val Thr Val
        450                 455                 460

Cys Ser Ser Glu Ala Ala Ala Leu Ala Ala Ser Thr Leu Gly Ser Gln
465                 470                 475                 480

Gly Met Ala Gln Asp Gly Ser Pro Ala Val Asn Gly Asn Leu Cys Leu
                485                 490                 495

Gln Gln Arg Cys Gly Lys Glu Asp Gln Glu Ser Gly Trp Glu Gly Ala
            500                 505                 510

Thr Gly Thr Thr Arg Cys Leu Asp Phe Leu Gln Gly Met Lys Arg
        515                 520                 525

Arg Leu Leu Arg Asn Ile Thr Ala Phe Leu Phe Leu Cys Asn Ile Ser
            530                 535                 540

Leu Trp Ile Pro Pro Ala Phe Gly Cys Arg Pro Glu Tyr Asp Asn Gly
545                 550                 555                 560

Leu Glu Glu Ile Val Phe Gly Phe Glu Pro Trp Ile Ile Val Val Asn
                565                 570                 575

Leu Ala Met Pro Phe Ser Ile Phe Tyr Arg Met His Ala Ala Ala Ala
                580                 585                 590

Leu Phe Glu Val Tyr Cys Lys Ile
            595                 600

<210> SEQ ID NO 61
<211> LENGTH: 2822
<212> TYPE: DNA
<213> ORGANISM: Mus musculus

<400> SEQUENCE: 61
gcatctttcc ccctcaagcg ggtctcacta gatcccggag agccttggtg ctctccggtt    60
ccgtgggttg tggcagtgag tcccaccaga cccgcccttt gcacacggct tccgaacgcc   120
ggggtctcgt gccggccagg cccggaccct atacccctatt cattttttttc ttattgcagc   180 gcctgagtct tttcttcttt taaaacaaga tgccgtcggg tttccagcag atcggctctg   240
acgatgggga accccctcgg cagcgagtga ctggaacact ggtcctagct gtattctcag   300
ctgtgccttg ctccccttcag tttggctata acattggggt tatcaatgcc ccacagaagg   360
tgattgaaca gagctacaat gcaacgtggc tgggtaggca aggtcctggg ggaccggatt   420
ccatcccaca aggcacccctc actacgctct gggctctctc cgtggccatc ttctctgtgg   480
gtggcatgat ctcttccttt ctcattggca tcatttctca atggttggga aggaaaaggg   540
ctatgctggc caacaatgtc ttggccgtgt tgggggcgc cctcatgggc ctagccaatg   600
ccgcggcctc ctatgagata tcattcttg gacggttcct cattggcgcc tactcagggc   660
taacatcagg gctggtgccc atgtatgtgg gagaaatcgc ccccactcat cttcggggtg   720
ccttgggaac actcaaccaa ctggccatcg tcattggcat tctggttgcc caggtgctgg   780
gcttggagtc tatgctgggc acagctaccc tgtggccact gcttctggct ctcacagtac   840
tccctgctct cctgcagctg attctgctgc ccttctgtcc tgagagcccc agatacctct   900
acatcatccg gaacctggag gggcctgccc gaaagagtct aaagcgcctg accggctggg   960
ctgatgtgtc tgacgcacta gctgagctga aggatgagaa acggaagttg gagagagagc  1020
gtccaatgtc cttgctccag ctcctgggca gccgcaccca ccggcagcct ctgatcatcg  1080
```

```
cagtggtgct gcagctgagc caacagctct caggcatcaa tgctgttttc tactattcaa      1140
ccagcatctt cgagtcggct ggggtgggac agccagccta cgccaccata ggagctggtg      1200
tggtcaatac ggtcttcacg ttggtctcgg tgctcttagt agaacgagct ggacgacgga      1260
cactccatct gttgggcctg gccggcatgt gtggctgtgc catcttgatg accgtggctc      1320
tgctgctgct ggaacgggtt ccagccatga gctatgtctc catcgtggcc atatttggct      1380
ttgtggcctt ctttgagatt ggccctggcc ccattccctg gttcattgtg gcagagctct      1440
tcagccaggg cccccgccca gccgccatgg ctgtcgctgg tttctccaac tggacctgta      1500
acttcattgt cggcatgggt ttccagtatg ttgcggatgc tatgggtcct tacgtcttcc      1560
ttctatttgc cgtcctcctg cttggcttct tcatcttcac cttcctaaaa gtgcctgaaa      1620
ccagaggccg gacgtttgac cagatctcag ctgccttccg acggacacct tcccttttag      1680
agcaggaggt gaaacccagt acagaacttg aatacttagg gccagatgag aatgactgag      1740
gggcaaaaca gggtgggaga gccaccctct ccacccagac tccctccttt cctctacagc      1800
actttagccc tctcttccct gttacctcca ggttgaagga acagcagcct ggggaactgg      1860
gaagctgaag ggaggggtgg tccatgtacc cctcattccc cctgtgtgat tctttggat      1920 tatttatgtg tgtggctagg ctgtggccac ctagatgggc tttctccgtc ctgccttcct      1980
cctgccccta cccagactca gctctagact actttcctcc cctttcgaga aggggtctgc      2040
aggagggtgg ggtggccctg aattcatcag gataaacagc aggggtgggt gtgtgagcga      2100
gtgctttcct cccacaaact ggcacttcca ctgaactctt gccacacagg ctctgggtga      2160 aggggttgt cttgacccct ccagggcaaa ggatacaccc tcccaaaatc tagccctgcc      2220
tccccacagg ctccaccctc ccgggcaaag gaacacaata gtacatacct gacagggcaa      2280
ggacggttag agcgcatcag tctccatttg gggccctagg ttgttcccag gctgcaaag      2340 cgtaggtacc aacactttct tgttcccctc caggaagggt gctaaacccg aaagcttctg      2400
accaactaag gcgggaggg gatttgaaag gctgcctata acactggtt gggagggagc      2460 ctttggtatt tttgtatgtt ttgaagaacg gatagggagc agaaacccaa gggctgctgt      2520
attaaatgtg tatatagaga ttcgtccata aagtcactgt ttgaagatga gtgtcctgtg      2580
ctggaggaac tggagggtgt gcaaaaagaa aatgcctcac tcaccctttg cacttcatcc      2640
ttcctgggct cagggcaccg aggcctctag attctgtcac ctttttttta gggggggcg      2700 ggtttcgaga cagggtttct ctgtcctgga actcactttg tagaccaggc tggccttgaa      2760
ctcaagaaat ccgcctgcct ctgcctcccg attgctggga ttaaaggtgt gcgtgtgcca      2820
cc                                                                     2822
```

<210> SEQ ID NO 62
<211> LENGTH: 509
<212> TYPE: PRT
<213> ORGANISM: Mus musculus

<400> SEQUENCE: 62

```
Met Pro Ser Gly Phe Gln Gln Ile Gly Ser Asp Asp Gly Glu Pro Pro
1               5                   10                  15

Arg Gln Arg Val Thr Gly Thr Leu Val Leu Ala Val Phe Ser Ala Val
                20                  25                  30

Leu Gly Ser Leu Gln Phe Gly Tyr Asn Ile Gly Val Ile Asn Ala Pro
            35                  40                  45

Gln Lys Val Ile Glu Gln Ser Tyr Asn Ala Thr Trp Leu Gly Arg Gln
        50                  55                  60
```

```
Gly Pro Gly Gly Pro Asp Ser Ile Pro Gln Gly Thr Leu Thr Thr Leu
 65                  70                  75                  80

Trp Ala Leu Ser Val Ala Ile Phe Ser Val Gly Met Ile Ser Ser
             85                  90                  95

Phe Leu Ile Gly Ile Ile Ser Gln Trp Leu Gly Arg Lys Arg Ala Met
            100                 105                 110

Leu Ala Asn Asn Val Leu Ala Val Leu Gly Ala Leu Met Gly Leu
            115                 120                 125

Ala Asn Ala Ala Ala Ser Tyr Glu Ile Leu Ile Leu Gly Arg Phe Leu
            130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Val Ala Gln Val Leu Gly Leu
            180                 185                 190

Glu Ser Met Leu Gly Thr Ala Thr Leu Trp Pro Leu Leu Leu Ala Leu
        195                 200                 205

Thr Val Leu Pro Ala Leu Leu Gln Leu Ile Leu Leu Pro Phe Cys Pro
        210                 215                 220

Glu Ser Pro Arg Tyr Leu Tyr Ile Ile Arg Asn Leu Glu Gly Pro Ala
225                 230                 235                 240

Arg Lys Ser Leu Lys Arg Leu Thr Gly Trp Ala Asp Val Ser Asp Ala
                245                 250                 255

Leu Ala Glu Leu Lys Asp Glu Lys Arg Lys Leu Glu Arg Glu Arg Pro
                260                 265                 270

Met Ser Leu Leu Gln Leu Leu Gly Ser Arg Thr His Arg Gln Pro Leu
        275                 280                 285

Ile Ile Ala Val Val Leu Gln Leu Ser Gln Gln Leu Ser Gly Ile Asn
        290                 295                 300

Ala Val Phe Tyr Tyr Ser Thr Ser Ile Phe Glu Ser Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Leu Val Glu Arg Ala Gly Arg Arg Thr Leu
                340                 345                 350

His Leu Leu Gly Leu Ala Gly Met Cys Gly Cys Ala Ile Leu Met Thr
            355                 360                 365

Val Ala Leu Leu Leu Leu Glu Arg Val Pro Ala Met Ser Tyr Val Ser
        370                 375                 380

Ile Val Ala Ile Phe Gly Phe Val Ala Phe Glu Ile Gly Pro Gly
385                 390                 395                 400

Pro Ile Pro Trp Phe Ile Val Ala Glu Leu Phe Ser Gln Gly Pro Arg
                405                 410                 415

Pro Ala Ala Met Ala Val Ala Gly Phe Ser Asn Trp Thr Cys Asn Phe
                420                 425                 430

Ile Val Gly Met Gly Phe Gln Tyr Val Ala Asp Ala Met Gly Pro Tyr
            435                 440                 445

Val Phe Leu Leu Phe Ala Val Leu Leu Gly Phe Phe Ile Phe Thr
        450                 455                 460

Phe Leu Lys Val Pro Glu Thr Arg Gly Arg Thr Phe Asp Gln Ile Ser
465                 470                 475                 480
```

-continued

Ala Ala Phe Arg Arg Thr Pro Ser Leu Leu Glu Gln Glu Val Lys Pro
            485                 490                 495

Ser Thr Glu Leu Glu Tyr Leu Gly Pro Asp Glu Asn Asp
        500                 505

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 63
gccctgagta atcacttaaa g                                         21

<210> SEQ ID NO 64
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 64
ccgggccctg agtaatcac                                            19

<210> SEQ ID NO 65
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 65
ccttgcaata cgaggacaaa ga                                        22

<210> SEQ ID NO 66
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 66
cacaccccaa ccagccac                                             18

<210> SEQ ID NO 67
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 67
gcactggcaa gttctactgc aa                                        22

<210> SEQ ID NO 68
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
gtaggtgaag agaacggcct tgt                                           23

<210> SEQ ID NO 69
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
caccctgatg ttattgggtt ca                                            22

<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
ttagcgccca cttattccac t                                             21

<210> SEQ ID NO 71
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
catcctggga cgagatgaac t                                             21

<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
tgacaagcgt taccacaggc                                               20

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
```
ctgaccttcg gcacgacatt                                               20

<210> SEQ ID NO 74
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
ccaccataag ccgtgtaaaa gac                                           23

<210> SEQ ID NO 75
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
caagaacagc aacgagtacc g                                             21

<210> SEQ ID NO 76
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76
gtcactggtc aactccagca c                                             21

<210> SEQ ID NO 77
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
acgacttcct ctccgacctc t                                             21

<210> SEQ ID NO 78
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
cgaggctcac gtaaccgtag t                                             21

<210> SEQ ID NO 79
<211> LENGTH: 21
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic primer"

<400> SEQUENCE: 79
cgacttcagc gcctacattg a                                              21

<210> SEQ ID NO 80
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
ctagcgacag accccacac                                                 19

<210> SEQ ID NO 81
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
atcacaactg gcctggttac g                                              21

<210> SEQ ID NO 82
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
tactacccgg tgtccatttc t                                              21

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
cagcgtcatg gtcagtctgt                                                20

<210> SEQ ID NO 84
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
agaaaaccgt gtggcagaga                                                20

<210> SEQ ID NO 85
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
gaaccatgaa gccaacgact                                               20

<210> SEQ ID NO 86
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
gcgaagttca cagtggttcc                                               20

<210> SEQ ID NO 87
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
gagtgggaac tggtagtgtt g                                             21

<210> SEQ ID NO 88
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
cgcacagagc gatgaaggt                                                19

<210> SEQ ID NO 89
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
gtaggactcc cggcttcttt ct                                            22

<210> SEQ ID NO 90
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
```

```
agtctggtcc aagaatccga ag                                          22

<210> SEQ ID NO 91
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
gatggttctg ggcaccatct t                                           21

<210> SEQ ID NO 92
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
cgttgttgtg tggcatcctt                                             20

<210> SEQ ID NO 93
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
ccaggaaaca tcagtgagtc c                                           21

<210> SEQ ID NO 94
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
ggatggaact tggaatcggt ca                                          22

<210> SEQ ID NO 95
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
ccctgcgacg agaaagctc                                              19

<210> SEQ ID NO 96
<211> LENGTH: 22
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 96
gctcttttcg ttgaggcaaa cc                                              22

<210> SEQ ID NO 97
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
ctgctgactt taacacaggg ag                                              22

<210> SEQ ID NO 98
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
ggttgccact ttttacccca g                                               21

<210> SEQ ID NO 99
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
actaggaccc cgtcgaatct                                                 20

<210> SEQ ID NO 100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
accatgctct acgtgctgtg                                                 20

<210> SEQ ID NO 101
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
ccctgccatt gttaagacc                                                  19
```

```
<210> SEQ ID NO 102
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
tgctgctgtt cctgttttc                                                19

<210> SEQ ID NO 103
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
tgaaagaagc ggtgaaccac tg                                            22

<210> SEQ ID NO 104
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
tggcatctct gtgtcaacca tg                                            22

<210> SEQ ID NO 105
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
gcatggtgcc ttcgctga                                                 18

<210> SEQ ID NO 106
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
tggcatctct gtgtcaacca tg                                            22

<210> SEQ ID NO 107
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 107
cagcacggtg aagccattc                                                    19

<210> SEQ ID NO 108
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
gcgtgcatcc gcttgtg                                                      17

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
gtcacagcac atgacggagg                                                   20

<210> SEQ ID NO 110
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
tcttccagat gctcgggata c                                                 21

<210> SEQ ID NO 111
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
cccttgcagt tctaagttca aca                                               23

<210> SEQ ID NO 112
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
acctttgaca agcggactct c                                                 21

<210> SEQ ID NO 113
<211> LENGTH: 22
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 113
cagacctgcc ttacgactat gg                                              22

<210> SEQ ID NO 114
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
ctcggtggcg ttgagattgt t                                               21

<210> SEQ ID NO 115
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
actgccacac ctccagtcat t                                               21

<210> SEQ ID NO 116
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 116
ctttgcctca ctcaggattg g                                               21

<210> SEQ ID NO 117
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 117
cagccgtcca gtgttatgtt g                                               21

<210> SEQ ID NO 118
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
tgccccaatt tatcaaggca aa                                              22
```

<210> SEQ ID NO 119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
ggcaagcagt gcagctagaa                                                  20

<210> SEQ ID NO 120
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
cataactgtc tttcgaggtg tgg                                              23

<210> SEQ ID NO 121
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
cagcctttgg agaaccagtc t                                                21

<210> SEQ ID NO 122
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
tcccgctcag agattccatc a                                                21

<210> SEQ ID NO 123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
agaaagtagc cagatggagc c                                                21

<210> SEQ ID NO 124
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 124
atgtgagcct agtagctgtc a                                              21

<210> SEQ ID NO 125
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 125
gataggccgt gtggtgaaat c                                              21

<210> SEQ ID NO 126
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 126
accaggaggg aaaccatact c                                              21

<210> SEQ ID NO 127
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 127
ccctgacatt tatgggatca cag                                            23

<210> SEQ ID NO 128
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 128
catccagagt cttgctgatg ag                                             22

<210> SEQ ID NO 129
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 129
cttcgcgggg tagtgttgg                                                 19

<210> SEQ ID NO 130
<211> LENGTH: 19
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 130
ggccagactt cgacgacaa                                                    19

<210> SEQ ID NO 131
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 131
gtattgggca acctcattcc c                                                 21

<210> SEQ ID NO 132
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 132
gcccccagga tactgaagat t                                                 21

<210> SEQ ID NO 133
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 133
gccaaaccaa caactttatc tcttc                                             25

<210> SEQ ID NO 134
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 134
cacacttaag gtgcgttcaa tagtc                                             25

<210> SEQ ID NO 135
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 135
ctggaatagc ggcgtgctt                                                    19
```

```
<210> SEQ ID NO 136
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 136
aataacactg gacgtcgggc                                               20
```

COMPOSITIONS AND METHODS FOR INDUCED BROWN FAT DIFFERENTIATION

STATEMENT OF RIGHTS

This invention was made with government support under Grant DK31405 awarded by the National Institutes of Health. The U.S. government may have certain rights in the invention.

CROSS-REFERENCE TO RELATED APPLICATIONS

This application is the U.S. National Stage Application of International Application No. PCT/US10/20480, filed on Jan. 8, 2010, which claims the benefit of priority to U.S. Provisional Application No. 61/204,607, filed on Jan. 8, 2009, the entire contents of which are expressly incorporated in their entirety.

BACKGROUND OF THE INVENTION

Obesity represents the most prevalent of body weight disorders, affecting an estimated 30 to 50% of the middle-aged population in the Western world. Obesity, defined as a body mass index (BMI) of 30 kg/$^2$m or more, contributes to diseases such as coronary artery disease, hypertension, stroke, diabetes, hyperlipidemia and some cancers. (See, e.g., Nishina, P. M. et al. (1994), *Metab.* 43:554-558; Grundy, S. M. & Barnett, J. P. (1990), Dis. Mon. 36:641-731). Obesity is a complex multifactorial chronic disease that develops from an interaction of genotype and the environment and involves social, behavioral, cultural, physiological, metabolic and genetic factors.

Generally, obesity results when energy intake exceeds energy expenditure, resulting in the growth and/or formation of adipose tissue via hypertrophic and hyperplastic growth. Hypertrophic growth is an increase in size of adipocytes stimulated by lipid accumulation. Hyperplastic growth is defined as an increase in the number of adipocytes in adipose tissue. It is thought to occur primarily by mitosis of pre-existing adipocytes caused when adipocytes fill with lipid and reach a critical size. An increase in the number of adipocytes has far-reaching consequences for the treatment and prevention of obesity.

Adipose tissue consists primarily of adipocytes. Vertebrates possess two distinct types of adipose tissue: white adipose tissue (WAT) and brown adipose tissue (BAT). WAT stores and releases fat according to the nutritional needs of the animal. This stored fat is used by the body for (1) heat insulation (e.g., subcutaneous fat), (2) mechanical cushion (e.g., surrounding internal organs), and (3) as a source of energy. BAT burns fat, releasing the energy as heat through thermogenesis. BAT thermogenesis is used both (1) to maintain homeothermy by increasing thermogenesis in response to lower temperatures and (2) to maintain energy balance by increasing energy expenditure in response to increases in caloric intake (Sears, I. B. et al. (1996) *Mol. Cell. Biol.* 16(7): 3410-3419). BAT is also the major site of thermogenesis in rodents and plays an important role in thermogenesis in human infants. In humans, and to a lesser extent rodents, brown fat diminishes with age, but can be re-activated under certain conditions, such as prolonged exposure to cold, maintenance on a high fat diet and in the presence of noradrenaline producing tumors.

Fat metabolism is regulated by two pathways, lipogenesis and lipolysis. Lipogenesis is the deposition of fat which occurs in the liver and in adipose tissue at cytoplasmic and mitochondrial sites. This process allows the storage of energy that is ingested which is not needed for current energy demands. Lipolysis is the chemical decomposition and release of fat from adipose and/or other tissues. This process predominates over lipogenesis when additional energy is required by the body.

Any treatment for obesity has to reduce energy intake, increase energy expenditure or combine both effects. Current therapies for obesity predominantly lead to decreased energy intake by acting at satiety centers in the brain or by reducing the efficiency of intestinal absorption. To date, no safe and reliable molecular mechanism for treating and/or preventing obesity by increasing energy expenditure or metabolic activity has been identified. Given the severity and prevalence of obesity related disorders, there exists a great need for the identification of an anti-obesity therapeutic.

SUMMARY OF THE INVENTION

The present invention is based in part on the discovery that Prdm16 and CCAAT/enhancer binding protein beta (C/EBPβ) can cooperatively induce brown fat differentiation in non-adipocyte mammalian cells (e.g., myoblasts and fibroblasts) including activating a distinct set of target genes (including, for example, cidea, adiponectin, type II deiodinase, cig30, pgc1α, elov3, and ucp1) characteristic of brown fat cells. In particular, functional brown fat cells can be differentiated from fibroblastic cells (e.g., embryonic and skin fibroblasts) upon expression and/or activity of both Prdm16 and C/EBPβ. Increased brown fat differentiation in mammals induces the expression of mitochondrial genes (including, for example, cytochrome c, cox 4i1, cox III, cox 5b, cox8b, atpase b2, cox II, atp5o and ndufb5) and cellular respiration (i.e., total and uncoupled respiration). Densely packed mitochondria are a characteristic of brown fat cells. Increased respiration (both total and uncoupled respiration) results in increased heat dissipation and increased energy expenditure by the mammal. The increases in heat dissipation and increased energy expenditure stimulate the metabolic rate of the mammal. Through the stimulation of the metabolic rate, expression and/or activity of both Prdm16 and C/EBPβ may be used to treat and/or prevent obesity or an obesity related disorder. Moreover, the induced brown fat cells of the present invention exhibit heightened expression of biochemical characteristics, metabolic rate, and thermogenesis relative to authentic brown fat cells. In addition, the novel compositions and methods of the present invention can be used to differentiate cells (e.g., autologous cells) that can be easily obtained from subjects (e.g., skin fibroblasts) into functional brown fat cells for use in transplantation. Such methods allow for "custom made" brown fat cells from any individual for use in autologous transplantation.

Accordingly, the present invention provides methods for preventing or treating obesity or an obesity-related disorder in a subject comprising inducing both Prdm16 and C/EBPβ expression and/or activity sufficient to activate brown fat cell differentiation, wherein the differentiated brown fat cells increase energy expenditure to thereby prevent or treat obesity or an obesity-related disorder in the subject. In one embodiment, the obesity-related disorder is selected from the group consisting of: insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia. In another embodiment, the subject is a human.

In another aspect, methods are provided for increasing energy expenditure in a mammal comprising inducing both Prdm16 and C/EBPβ expression and/or activity sufficient to activate brown fat cell differentiation in the mammal, wherein the differentiated brown fat cells promote energy expenditure thereby increasing energy expenditure in the mammal. In one embodiment, the mammal is a human.

In still another aspect, methods are provided for treating obesity or an obesity-related disorder in a subject comprising administering to the subject an agent that induces expression and/or activity of both Prdm16 and C/EBPβ, wherein Prdm16 and C/EBPβ expression and/or activity increases respiration and energy expenditure to thereby treat obesity or an obesity-related disorder in the subject. In one embodiment, respiration is total respiration and/or uncoupled respiration. In another embodiment, the obesity-related disorder is selected from the group consisting of: insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia. In still another embodiment, the subject is a human.

In yet another aspect, methods are provided for inducing brown fat cell differentiation in a mammal comprising expressing both Prdm16 and C/EBPβ in cells; delivering the cells expressing both Prdm16 and C/EBPβ into the mammal; and monitoring the differentiation of brown fat cells in the mammal. In one embodiment, the cells are selected from the group consisting of fibroblasts and myoblasts (e.g., skin fibroblasts, dermal fibroblasts, primary embryonic fibroblasts, immortalized embryonic fibroblasts, and human foreskin fibroblasts). In another embodiment, the cells are autologous, allogeneic, syngeneic, xenogeneic, or HLA compatible with the mammal. In still another embodiment, the cells are delivered by a subcutaneous injection or an intravenous injection. In yet another embodiment, the differentiation of brown fat cells is monitored by measuring the expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, Table 1, Table 2, and Table 3. In another embodiment, the differentiation of brown fat cells is monitored by measuring the degree of cellular locularity. In still another embodiment, the differentiation of brown fat cells is monitored by measuring respiration within the cell expressing Prdm16 and C/EBPβ (e.g., total respiration or uncoupled respiration, as measured by oxygen consumption or positron emission tomography, for example). In another embodiment, the mammal is a human.

In another aspect, methods are provided for inducing brown fat cell differentiation in a mammal comprising: obtaining cells from the mammal; expressing both Prdm16 and C/EBPβ in the cells; delivering the cells expressing both Prdm16 and C/EBPβ into the mammal; and monitoring the differentiation of brown fat cells in the mammal. In still another embodiment, the cells are delivered by a subcutaneous injection or an intravenous injection. In another embodiment, the differentiation of brown fat cells is monitored by measuring the expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, Table 1, Table 2, and Table 3. In still another embodiment, the differentiation of brown fat cells is monitored by measuring the degree of cellular locularity. In yet another embodiment, the differentiation of brown fat cells is monitored by measuring respiration within the cell expressing Prdm16 and C/EBPβ (e.g., total respiration or uncoupled respiration, as measured by oxygen consumption or positron emission tomography, for example). In another embodiment, the cells are selected from the group consisting of fibroblasts and myoblasts (e.g., skin fibroblasts, dermal fibroblasts, primary embryonic fibroblasts, immortalized embryonic fibroblasts, and human foreskin fibroblasts).

In still another aspect, a non-human transgenic animal model of PRDM16 and C/EBPβ expression in cells of the animal model is provided comprising PRDM16 operably linked to a promoter specifically expressed in the cells and C/EBPβ operably linked to a promoter specifically expressed in the cells. In one embodiment, the cells are selected from the group consisting of fibroblasts, myoblasts, preadipocytes, white adipose tissue cells, epithelial, neural cells, epidermal cells, keratinocytes, hematopoietic cells, melanocytes, chondrocytes, B lymphocytes, T lymphocytes, macrophages, monocytes, mononuclear cells, cardiac muscle cells, and skeletal muscle cells. In another embodiment, the non-human transgenic animal is a mouse.

In yet another aspect, the present invention provides for an isolated complex comprising (a) a PRDM16 polypeptide and a C/EBPβ polypeptide; (b) a PRDM16 polypeptide and a fragment of a C/EBPβ polypeptide; (c) a fragment of a PRDM16 polypeptide and a C/EBPβ polypeptide; (d) a fragment of an PRDM16 polypeptide and a fragment of a C/EBPβ polypeptide; or (e) a PRDM16 polypeptide and a polypeptide from Table 1 or Table 3. In one embodiment, the PRDM16 polypeptide comprises an amino acid sequence having at least about 60% identity to the amino acid sequence set forth in SEQ ID NO: 2, 4, or 6. In another embodiment, the C/EBPβ polypeptide fragment comprises an amino acid sequence having at least about 60% identity to the amino acid sequence set forth in SEQ ID NO: 8 or 10. In still another embodiment, the complex is at least about 75% pure by weight as compared to the weight of the total protein in the sample. In yet another embodiment, at least one polypeptide or fragment is a fusion protein or labeled. In another embodiment, the complex is generated within a host cell. In still another embodiment, the PRDM16 polypeptide or polypeptide fragment and said C/EBPβ polypeptide or polypeptide fragment are covalently linked.

It will be appreciated that specific sequence identifiers (SEQ ID NOs) have been referenced throughout the specification for purposes of illustration and should therefore not be construed to be limiting. Any marker of the invention, including, but not limited to, the markers described in the specification and markers presented in Tables 1, 2, and 3, or fragments thereof, can be used in the embodiments of the invention.

In another aspect, a host cell or composition comprising a recombinant amino acid encoding at least one of the polypeptides or polypeptide fragments of the complex is provided.

In still another aspect, an isolated antibody that has a higher binding affinity for the complex than for the uncomplexed PRDM16 or C/EBPβ polypeptides or polypeptide fragments is provided. In one embodiment, the isolated antibody has the ability to stabilize the complex.

In yet another aspect, methods are provided for identifying a compound that modulates a PRDM16/C/EBPβ complex comprising: contacting a complex comprising (a) a PRDM16 polypeptide and a C/EBPβ polypeptide; (b) a PRDM16 polypeptide and a fragment of a C/EBPβ polypeptide; (c) a fragment of a PRDM16 polypeptide and a C/EBPβ polypeptide; or (d) a fragment of an PRDM16 polypeptide and a fragment of a C/EBPβ polypeptide, with a test compound; and assaying the amount or activity of the complex, wherein a change in the amount or activity of the complex in the presence of the test compound as compared to the amount or activity of the complex in the absence of the test compound is indicative of a compound that modulates an PRDM16-C/EBPβ complex.

Other features and advantages of the invention will be apparent from the following detailed description and claims.

BRIEF DESCRIPTION OF TABLES

Figure 1:
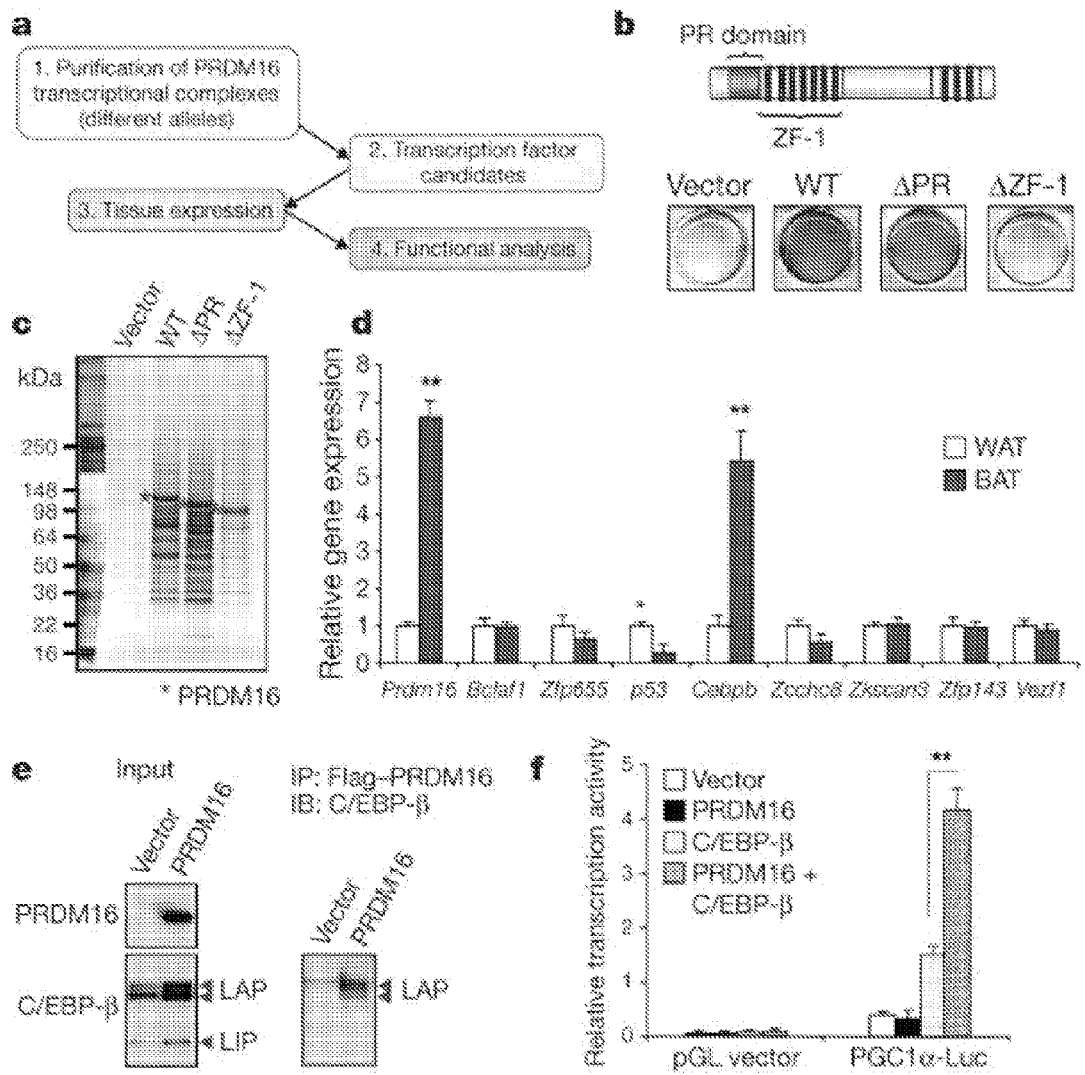
FIGS. 1A-1F show that C/EBP-β is a critical binding partner in the PRDM16 transcriptional complex. (A) shows the strategy for identifying key PRDM16 binding partners. (B) shows the results of C2C12 myoblasts expressing indicated viral vectors stained with Oil Red O 6 days after inducing adipocyte differentiation. (C) shows PRDM16 transcriptional complexes immunopurified from brown fat cells expressing full-length or deletion mutants of PRDM16. (D) shows gene expression of known or predicted transcription factors identified in the PRDM16 complex in BAT and WAT. n=6. (E) shows endogenous C/EBP-β was detected in the PRDM16 complex by Western blotting. Input is shown to the left. IB, immunoblot; IP, immunoprecipitate. (F) shows transcriptional activity of the Pgc1a promoter in response to PRDM16 and/or C/EBP-β. n=3; all error bars are s.e.m.; * P<0.05, ** P<0.01.

Table 1 shows proteins identified in the LC-MS/MS analyses described herein.

Table 2 shows the primer sequences used in the RT-PCR analyses described herein.

Table 3 shows nucleic acid and amino acid sequences referenced herein.

DETAILED DESCRIPTION OF THE INVENTION

The present invention is based in part on the discovery that Prdm16 and CCAAT/enhancer binding protein beta (C/EBPβ) can form an isolated complex and cooperatively induce brown fat differentiation in non-adipocyte mammalian cells (e.g., myoblasts and fibroblasts). The compositions of the present invention are capable of activating a distinct set of target genes (including, for example, cidea, adiponectin, type II deiodinase, cig30, pgc1α, elov3, and ucp1) characteristic of brown fat cells. For example, functional brown fat cells can be differentiated from fibroblastic cells (e.g., embryonic and skin fibroblasts) upon expression and/or activity of both Prdm16 and C/EBPβ. Increased brown fat differentiation in mammals induces the expression of mitochondrial genes (including, for example, cytochrome c, cox 4i1, cox III, cox 5b, cox8b, atpase b2, cox II, atp5o and ndufb5) and cellular respiration (i.e., total and uncoupled respiration).

In order that the present invention may be more readily understood, certain terms are first defined. Additional definitions are set forth throughout the detailed description.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

The term "complex" refers to an association between at least two moieties (e.g. chemical or biochemical) that have an affinity for one another. "Protein complex" or "polypeptide complex" refers to a complex comprising at least one polypeptide. In one embodiment, a complex comprises PRDM16 and C/EBPβ, PRDM16 and C/EBPδ, or PRDM16 and CtBP1. In another embodiment, a complex comprises a fragment of PRDM16 and C/EBPβ, a fragment of PRDM16 and C/EBPδ, or a fragment of PRDM16 and CtBP1. In an exemplary embodiment, a complex comprises a fragment of PRDM16 having amino acid residues from about 224-454 and/or a fragment of PRDM16 having amino acid residues from about 881-1038 and C/EBPβ. In another exemplary embodiment, a complex comprises a fragment of PRDM16 having amino acid residues from about 224-454 and/or a fragment of PRDM16 having amino acid residues from about 881-1038 and C/EBPδ. In yet another exemplary embodiment, a complex comprises a fragment of PRDM16 having amino acid residues from about 680-880 and CtBP1. These embodiments may encompass other molecules (e.g., polypeptides) that can bind to the complex, such as an antibody.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The term "PRDM16 binding domain" or "PRDM16-BD" refers to a region on a PRDM16 polypeptide that is capable of interacting with a C/EBPβ polypeptide, or fragment thereof. In an exemplary embodiment, the term PRDM16-BD refers to a region comprising amino acids 224-454 and/or 881-1038.

The term "PRDM16-C/EBPβ complex polypeptide" refers to a polypeptide that may be found in a complex comprising PRDM16 and C/EBPβ. In one embodiment, the term PRDM16-C/EBPβ complex polypeptide includes PRDM16 polypeptides, and fragments thereof, and/or C/EBPβ polypeptides, and fragments thereof, as described further herein. In another embodiment, the term PRDM16-C/EBPβ complex polypeptide may encompass other polypeptides that can bind to a PRDM16-C/EBPβ complex, such as, for example, an antibody.

The terms "metabolic disorder" and "obesity related disorders" are used interchangeably herein and include a disorder, disease or condition which is caused or characterized by an abnormal metabolism (i.e., the chemical changes in living cells by which energy is provided for vital processes and activities) in a subject. Metabolic disorders include diseases, disorders, or conditions associated with aberrant thermogenesis or aberrant adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response). Examples of metabolic disorders include obesity, insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia.

As used herein, "obesity" refers to a body mass index (BMI) of 30 kg/$^2$m or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/$^2$m or more, 26 kg/$^2$m or more, 27 kg/$^2$m or more, 28 kg/$^2$m or more, 29 kg/$^2$m or more, 29.5 kg/$^2$m or more, or 29.9 kg/$^2$m or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

"Treatment" refers to reducing the BMI of the mammal to less than about 25.9, and maintaining that weight for a period of time, e.g., for at least about 6 months. The treatment suitably results in an increase in metabolic activity.

"Prevention" refers to preventing obesity or an obesity related disorder from occurring if the treatment is administered prior to the onset of the obese condition. Moreover, if treatment is commenced in subjects already suffering from or having symptoms of obesity or an obesity related disorder, such treatment is expected to prevent, or to prevent the progression of obesity or the obesity related disorder, and the medical sequel of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the term "prdm16" refers to a PR-domain containing protein-16 and is intended to include fragments, variants (e.g., allelic variants) and derivatives thereof. Two spliced variants encoding distinct isoforms of Prdm16 have been previously described (Nishikata, et al. (2003) Blood 102(9):3323-32; Mochizuki, N. et al., (2000) Blood 96(9):3209-14). The nucleic acid sequence of human Prdm16 corresponding to spliced transcript variant 1 (Genbank Accession number NM_022114) is provided herein as SEQ ID NOs: 1 (see Table 3). The nucleic acid sequence of human Prdm16 corresponding to spliced transcript variant 2 (Genbank Accession number NM_199454) is provided herein as SEQ ID NOs: 3 (see Table 3). Variant 1 encodes a longer isoform of Prdm16. Variant 2 uses an alternative splice site for the 3' exon compared to variant 1, and thus, lacks an internal region compared to variant 1. The amino acid sequences of human Prdm16 corresponding to spliced transcript variants 1 and 2 are provided herein as SEQ ID NOs: 2 and 4, respectively (Genbank Accession numbers NP_071397 and NP_955533, respectively).

The nucleotide and amino acid sequences of mouse Prdm16, which correspond to Genbank Accession number NM_027504 and NP_081780 respectively, are set forth in SEQ ID NO: 5 and 6 (see Table 3).

The nucleotide and amino acid sequences of human C/EBPβ, which correspond to Genbank Accession number NM_005194 and NP_005185 respectively, are set forth in SEQ ID NO: 7 and 8 (see Table 3). In addition, the nucleotide and amino acid sequences of mouse C/EBPβ, which correspond to Genbank Accession number NM_009883 and NP_034013 respectively, are set forth in SEQ ID NO: 9 and 10 (see Table 3). LAP is full-length C/EBPβ.

As used herein, the term "PGC-1" refers to a PPARγ Coactivator 1 protein and is intended to include any of its' derivatives, including PGC-1α and PGC-1β. PGC-1 has been described previously (Puigserver, P. et al. (1998) *Cell* 92(6): 829-39; U.S. Pat. No. 6,166,192; and PCT International Publication Nos. WO 98/54220; the contents of all of which are incorporated herein by reference). The term PPARγ1 is well known in the art and a representative sequence corresponds to Genbank Accession number NM_001127330. The term PPARγ2 is well known in the art and a representative sequence corresponds to Genbank Accession number NM_011146.

It will be appreciated that specific sequence identifiers (SEQ ID NOs) have been referenced throughout the specification for purposes of illustration and should therefore not be construed to be limiting. Any marker of the invention, including, but not limited to, the markers described in the specification and markers presented in Tables 1, 2, and 3, or fragments thereof, can be used in the embodiments of the invention.

I. Nucleic Acids of the Invention

One aspect of the invention pertains to methods utilizing isolated nucleic acid molecules that encode prdm16 or biologically active portions thereof and/or C/EBPβ or biologically active portions thereof, as well as nucleic acid fragments sufficient for use as hybridization probes to identify prdm16-encoding or C/EBPβ-encoding nucleic acid (i.e., prdm16 or C/EBPβ mRNA). As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated prdm16 or C/EBPβ nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, i.e., a nucleic acid molecule having the nucleotide sequence of SEQ ID NOs: 1, 3, 5, 7, and 9 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in SEQ ID NOs: 1, 3, 5, 7, and 9 or a portion thereof (i.e., 400, 450, 500, or more nucleotides), can be isolated using standard molecular biology techniques and the sequence information provided herein. For example, a human prdm16 and/or C/EBPβ cDNA can be isolated from a human liver, heart, kidney, or brain cell line (from Stratagene, LaJolla, Calif., or Clontech, Palo Alto, Calif.) using all or portion of SEQ ID NOs: 1, 3, 5, 7, and 9 as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of SEQ ID NOs: 1, 3, 5, 7, or 9 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs: 1, 3, 5, 7, or 9 can be isolated by the polymerase chain reaction using oligonucleotide primers designed based upon the sequence of SEQ ID NOs: 1, 3, 5, 7, or 9 or the homologous nucleotide sequence. For example, mRNA can be isolated from liver cells, heart cells, kidney cells, brain cells, or brown adipocytes (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NOs: 1, 3, 5, 7, or 9 or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a prdm16 and/or C/EBPβ nucleotide sequence can be prepared by standard synthetic techniques, i.e., using an automated DNA synthesizer.

Probes based on the prdm16 and/or C/EBPβ nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a prdm16 and/or C/EBPβ protein, such as by measuring a level of a prdm16-encoding and/or C/EBPβ-encoding nucleic acid in a sample of cells from a subject, i.e., detecting prdm16 and/or C/EBPβ mRNA levels.

Nucleic acid molecules encoding other prdm16 family and/or C/EBPβ members and thus which have a nucleotide sequence which differs from the prdm16 and/or C/EBPβ sequences of SEQ ID NOs: 1, 3, 5, 7, or 9 are intended to be of the invention. Moreover, nucleic acid molecules encoding Prdm16 and/or C/EBPβ proteins from different species, and thus which have a nucleotide sequence which differs from the prdm16 and/or C/EBPβ sequences of SEQ ID NOs:1, 3 5, 7, or 9 are intended to be within the scope of the invention. For example, rat or monkey Prdm16 and/or C/EBPβ cDNA can be identified based on the nucleotide sequence of a human and/or mouse Prdm16 and/or C/EBPβ.

In one embodiment, the nucleic acid molecule(s) of the invention encodes a protein or portion thereof which includes an amino acid sequence which is sufficiently homologous to an amino acid sequence of SEQ ID NO: 2, 4, 6, 8, or 10 such that the protein or portion thereof maintains or, in complex, modulates (e.g., enhance), one or more of the following biological activities: 1) it can modulate the expression of cidea, adiponectin, adipsin, type II deiodinase, cig30, pgc-1α, elov3, and ucp1; 2) it can modulate the expression of mitochondrial genes including, cytochrome c, cox 4i1, cox III, cox 5b, cox8b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO: 2, 4, 6, 8, or 10) amino acid residues to an amino acid sequence of SEQ ID NO: 2, 4, 6, 8, or 10 such that the protein or portion thereof maintains or, in complex, modulates (e.g., enhance) one or more of the following biological activities: 1) it can modulate the expression of cidea, adiponectin, adipsin, type II deiodinase, cig30, pgc-1α, elov3, and ucp1; 2) it can modulate the expression of mitochondrial genes including, cytochrome c, cox 4i1, cox III, cox 5b, cox8b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

In another embodiment, the protein is at least about 50%, preferably at least about 60%, more preferably at least about 70%, yet more preferably at least about 80%, still more preferably at least about 90%, and most preferably at least about 95% or more homologous to the entire amino acid sequence of SEQ ID NO: 2, 4, 6, 8, or 10.

Portions of proteins encoded by the Prdm16 and/or C/EBPβ nucleic acid molecule of the invention are preferably biologically active portions of the Prdm16 and/or C/EBPβ protein. As used herein, the term "biologically active portion of Prdm16 and/or C/EBPβ" is intended to include a portion, e.g., a domain/motif, of Prdm16 and/or C/EBPβ or, in complex, modulates (e.g., enhance) that has one or more of the following activities: 1) it can modulate the expression of cidea, adiponectin, adipsin, type II deiodinase, cig30, pgc-1α, elov3, and ucp1; 2) it can modulate the expression of mitochondrial genes including, cytochrome c, cox 4i1, cox III, cox 5b, cox8b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

Standard binding assays, e.g., immunoprecipitations and yeast two-hybrid assays, as described herein, can be performed to determine the ability of a Prdm16 protein and/or C/EBPβ or a biologically active portion thereof or complex thereof to interact with a target of interest. To determine whether a Prdm16 and/or C/EBPβ family member of the present invention modulates cidea, adiponectin, adipsin, type II deiodinase, cig30, pgc-1α, elov3, and ucp1 expression, in vitro transcriptional assays can be performed. To perform such an assay, the full length promoter/enhancer region of the gene of interest (e.g., cidea, type II deiodinase, cig30, pgc-1α, elov3, and ucp1) can be linked to a reporter gene such as chloramphenicol acetyltransferase (CAT) or luciferase and introduced into host cells (e.g., liver cells such as Fao hepatoma cells, or COS cells). The same host cells can then be transfected a nucleic acid molecule encoding the Prdm16 molecule and/or C/EBPβ molecule. In some embodiments, nucleic acid molecules encoding PPARγ can also be transfected. The effect of the Prdm16 and/or C/EBPβ molecule can be measured by testing CAT or luciferase activity and comparing it to CAT or luciferase activity in cells which do not contain nucleic acid encoding the Prdm16 molecule and/or C/EBPβ molecule. An increase or decrease in CAT or luciferase activity indicates a modulation of expression of the gene of interest. In another embodiment, because cidea, adiponectin, adipsin type II deiodinase, cig30, pgc-1α, elov3, and ucp1 expression is known to be a critical component in the cascade of events leading to elevated thermogenesis, this assay can also measure the ability of the Prdm16 and/or C/EBPβ molecule or complex thereof to modulate thermogenesis in adipocytes.

The invention further encompasses nucleic acid molecules that differ from the nucleotide sequence shown in SEQ ID NO: 1, 3, 5, 7, or 9 (and portions thereof) due to degeneracy of the genetic code and thus encode the same Prdm16 and/or C/EBPβ protein as that encoded by the nucleotide sequence shown in SEQ ID NO: 1, 3, 5, 7, or 9. In another embodiment, an isolated nucleic acid molecule of the invention has a nucleotide sequence encoding a protein having an amino acid sequence shown in SEQ ID NO: 2, 4, 6, 8, or 10 or a protein having an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO: 2, 4, 6, 8, or 10.

It will be appreciated by those skilled in the art that DNA sequence polymorphisms that lead to changes in the amino acid sequences of Prdm16 and/or C/EBPβ may exist within a population (e.g., a mammalian population, e.g., a human population). Such genetic polymorphism in the Prdm16 and/or C/EBPβ gene may exist among individuals within a population due to natural allelic variation. As used herein, the terms "gene" and "recombinant gene" refer to nucleic acid molecules comprising an open reading frame encoding a Prdm16 and/or C/EBPβ protein, preferably a mammalian, e.g., human, Prdm16 and/or C/EBPβ protein. Such natural allelic variations can typically result in 1-5% variance in the nucleotide sequence of the Prdm16 and/or C/EBPβ gene. Any and all such nucleotide variations and resulting amino acid polymorphisms in Prdm16 and/or C/EBPβ that are the result of natural allelic variation and that do not alter the functional activity of Prdm16 and/or C/EBPβ are intended to be within the scope of the invention. Moreover, nucleic acid molecules encoding Prdm16 and/or C/EBPβ proteins from other species, and thus which have a nucleotide sequence which differs from the human or mouse sequences of SEQ ID NO: 1, 3, 5, 7, or 9, are intended to be within the scope of the invention. Nucleic acid molecules corresponding to natural allelic variants and homologues of the human or mouse Prdm16 and/or C/EBPβ cDNAs of the invention can be isolated based on their homology to the human or mouse Prdm16 and/or C/EBPβ nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the Prdm16 and/or C/EBPβ sequence that may exist in the population, the skilled artisan will further appreciate that changes can be introduced by mutation into the nucleotide sequence of SEQ ID NO: 1, 3, 5, 7, or 9 thereby leading to changes in the amino acid sequence of the encoded Prdm16 and/or C/EBPβ protein, without altering the functional ability of the Prdm16 and/or C/EBPβ protein. For example, nucleotide substitutions leading to amino acid substitutions at "non-essential" amino acid residues can be made in the sequence of SEQ ID NO: 1, 3, 5, 7, or 9. A "non-essential" amino acid residue is a residue that can be altered from the wild-type sequence of Prdm16 and/or C/EBPβ (e.g., the sequence of SEQ ID NO: 2, 4, 6, 8, or 10) without altering the activity of Prdm16 and/or C/EBPβ, whereas an "essential" amino acid residue is required for Prdm16 and/or C/EBPβ activity. Other amino acid residues, however, (e.g., those that are not conserved or only semi-conserved between mouse and human) may not be essential for activity and thus are likely to be amenable to alteration without altering Prdm16 and/or C/EBPβ activity. Furthermore, amino acid residues that are essential for Prdm16 and/or C/EBPβ functions related to thermogenesis and/or adipogenesis, but not essential for Prdm16 and/or C/EBPβ functions related to gluconeogenesis, are likely to be amenable to alteration.

Accordingly, another aspect of the invention pertains to nucleic acid molecules encoding Prdm16 and/or C/EBPβ proteins that contain changes in amino acid residues that are not essential for Prdm16 and/or C/EBPβ activity. Such Prdm16 and/or C/EBPβ proteins differ in amino acid sequence from SEQ ID NO: 2, 4, 6, 8, or 10 yet retain at least one of the Prdm16 and/or C/EBPβ activities described herein. In one embodiment, the isolated nucleic acid molecule comprises a nucleotide sequence encoding a protein, wherein the protein comprises an amino acid sequence at least about 60% homologous to the amino acid sequence of SEQ ID NO: 2, 4, 6, 8, or 10 and is capable of inducing brown fat differentiation. Preferably, the protein encoded by the nucleic acid molecule is at least about 70% homologous, preferably at least about 80-85% homologous, still more preferably at least about 90%, and most preferably at least about 95% homologous to the amino acid sequence of SEQ ID NO: 2, 4, 6, 8, or 10.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (J. Mol. Biol. (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a Prdm16 and/or C/EBPβ protein homologous to the protein of SEQ ID NO: 2, 4, 6, 8, or 10 can be created by introducing one or more nucleotide substitutions, additions or deletions into the nucleotide sequence of SEQ ID NO: 1, 3, 5, 7, or 9 or a homologous nucleotide sequence such that one or more amino acid substitutions, additions or deletions are introduced into the encoded protein. Mutations can be introduced into SEQ ID NO: 1, 3, 5, 7, or 9 or the homologous nucleotide sequence by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in Prdm16 and/or C/EBPβ is preferably replaced with another amino acid residue from the same side chain family. Alternatively, in another embodiment, mutations can be introduced randomly along all or part of a Prdm16 and/or C/EBPβ coding sequence, such as by saturation mutagenesis, and the resultant mutants can be screened for a Prdm16 and/or C/EBPβ activity described herein to identify mutants that retain Prdm16 and/or C/EBPβ activity. Following mutagenesis of SEQ ID NO: 1, 3, 5, 7, or 9, the encoded protein can be expressed recombinantly (as described herein) and the activity of the protein can be determined using, for example, assays described herein.

Prdm16 and/or C/EBPβ levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, Prdm16 and/or C/EBPβ levels are ascertained by measuring gene transcript (e.g. mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the Prdm16 and/or C/EBPβ mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding Prdm16 and/or C/EBPβ. Other suitable probes for use in the diagnostic assays of the invention are described herein. Hybridization of an mRNA with the probe indicates that Prdm16 and/or C/EBPβ is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the Prdm16 and/or C/EBPβ mRNA expression levels.

An alternative method for determining the Prdm16 and/or C/EBPβ mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA,* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the Prdm16 and/or C/EBPβ mRNA.

As an alternative to making determinations based on the absolute Prdm16 and/or C/EBPβ expression level, determinations may be based on the normalized Prdm16 and/or C/EBPβ expression level. Expression levels are normalized by correcting the absolute Prdm16 and/or C/EBPβ expression level by comparing its expression to the expression of a non-Prdm16 and/or C/EBPβ gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a Prdm16 and/or C/EBPβ protein can also be detected and/or quantified by detecting or quantifying the expressed polypeptide. The Prdm16 and/or C/EBPβ polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express Prdm16 and/or C/EBPβ.

In addition to the nucleic acid molecules encoding Prdm16 and/or C/EBPβ proteins described above, another aspect of the invention pertains to isolated nucleic acid molecules which are antisense thereto. An "antisense" nucleic acid comprises a nucleotide sequence which is complementary to a "sense" nucleic acid encoding a protein, i.e., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Prdm16 and/or C/EBPβ coding strand, or to only a portion thereof. In one embodiment, an antisense nucleic acid molecule is antisense to a "coding region" of the coding strand of a nucleotide sequence encoding Prdm16 and/or C/EBPβ. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding Prdm16 and/or C/EBPβ. The term "noncoding region" refers to 5' and 3' sequences which flank the coding region that are not translated into amino acids (i.e., also referred to as 5' and 3' untranslated regions).

II. Recombinant Expression Vectors and Host Cells

Another aspect of the invention pertains to the use of vectors, preferably expression vectors, containing a nucleic acid encoding Prdm16 and/or C/EBPβ (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a Prdm16 and/or C/EBPβ nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of Prdm16 and/or C/EBPβ in prokaryotic or eukaryotic cells. For example, Prdm16 and/or C/EBPβ can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the Prdm16 and/or C/EBPβ is cloned into a pGEX expression vector to create a vector encoding a fusion protein comprising, from the N-terminus to the C-terminus, GST-thrombin cleavage site-Prdm16 and/or similar constructs for C/EBPβ. The fusion protein can be purified by affinity chromatography using glutathione-agarose resin. Recombinant Prdm16 and/or C/EBPβ unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the Prdm16 and/or C/EBPβ expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, Prdm16 and/or C/EBPβ can be expressed in insect cells using baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to Prdm16 mRNA and/or C/EBPβ mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Prdm16 and/or C/EBPβ protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A cell culture includes host cells, media and other byproducts. Suitable media for cell culture are well known in the art. A PRDM16-C/EBPβ complex, a PRDM16 polypeptide or fragment thereof, and/or a C/EBPβ polypeptide or fragment thereof, may be secreted and isolated from a mixture of cells and medium containing the polypeptide. Alternatively, PRDM16-C/EBPβ complex, a PRDM16 polypeptide or fragment thereof, and/or a C/EBPβ polypeptide or fragment thereof, may be retained cytoplasmically and the cells harvested, lysed and the protein or protein complex isolated. A PRDM16-C/EBPβ complex, a PRDM16 polypeptide or fragment thereof, and/or a C/EBPβ polypeptide or fragment thereof, may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of PRDM16, C/EBPβ or a complex thereof. In one embodiment, the components of a PRDM16-C/EBPβ complex may be purified separately and then mixed together to form a complex. In another embodiment, the PRDM16-C/EBPβ complex may be purified from a source (e.g., a host cell, composition, cell lysate, etc.) comprising both PRDM16 and C/EBPβ polypeptide or fragments thereof.

Thus, a nucleotide sequence encoding all or a selected portion of a PRDM16 polypeptide and/or a C/EBPβ polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant PRDM16-C/EBPβ complex polypeptides by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the PRDM16-C/EBPβ complex, or PRDM16-C/EBPβ complex polypeptide, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Prdm16 and/or C/EBPβ or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Prdm16 and/or C/EBPβ protein. Accordingly, the invention further provides methods for producing Prdm16 and/or C/EBPβ protein using the host cells of the invention. In one embodiment, the method comprises culturing the host cell of invention (into which a recombinant expression vector encoding Prdm16 and/or C/EBPβ has been introduced) in a suitable medium until Prdm16 and/or C/EBPβ is produced. In another embodiment, the method further comprises isolating Prdm16 and/or C/EBPβ from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which Prdm16-coding and/or C/EBPβ-coding sequences have been introduced. Such host cells can then be used to create non-human transgenic animals in which exogenous Prdm16 and/or C/EBPβ sequences have been introduced into their genome or homologous recombinant animals in which endogenous Prdm16 and/or C/EBPβ sequences have been altered. Such animals are useful for studying the function and/or activity of Prdm16 and/or C/EBPβ and for identifying and/or evaluating modulators of Prdm16 and/or C/EBPβ activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous Prdm16 and/or C/EBPβ gene has been altered by homologous recombination between the endogenous gene and an exogenous DNA molecule introduced into a cell of the animal, e.g., an embryonic cell of the animal, prior to development of the animal.

A transgenic animal of the invention can be created by introducing Prdm16-encoding and/or C/EBPβ-encoding nucleic acid into the male pronuclei of a fertilized oocyte, e.g., by microinjection, retroviral infection, and allowing the oocyte to develop in a pseudopregnant female foster animal. The human Prdm16 and/or C/EBPβ cDNA sequence can be introduced as a transgene into the genome of a nonhuman animal. Alternatively, a nonhuman homologue of the human Prdm16 and/or C/EBPβ gene can be used as a transgene. Intronic sequences and polyadenylation signals can also be included in the transgene to increase the efficiency of expression of the transgene. A tissue-specific regulatory sequence(s) can be operably linked to the Prdm16 and/or C/EBPβ transgene to direct expression of Prdm16 and/or C/EBPβ protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the Prdm16 and/or C/EBPβ transgene in its genome and/or expression of Prdm16 and/or C/EBPβ mRNA in tissues or cells of the animals. A transgenic founder animal can then be used to breed additional animals carrying the transgene. Moreover, transgenic animals carrying a transgene encoding Prdm16 and/or C/EBPβ can further be bred to other transgenic animals carrying other transgenes.

To create a homologous recombinant animal, a vector is prepared which contains at least a portion of a Prdm16 and/or C/EBPβ gene into which a deletion, addition or substitution has been introduced to thereby alter, e.g., functionally disrupt, the Prdm16 and/or C/EBPβ gene. The Prdm16 and/or C/EBPβ gene can be a human gene (e.g., from a human genomic clone isolated from a human genomic library screened with the cDNA of SEQ ID NO: 1 or 3), but more preferably, is a nonhuman homologue of a human Prdm16 and/or C/EBPβ gene. For example, a mouse Prdm16 and/or C/EBPβ gene can be used to construct a homologous recombination vector suitable for altering an endogenous Prdm16 and/or C/EBPβ gene, respectively, in the mouse genome. In a preferred embodiment, the vector is designed such that, upon homologous recombination, the endogenous Prdm16 and/or C/EBPβ gene is functionally disrupted (i.e., no longer encodes a functional protein; also referred to as a "knock out" vector). Alternatively, the vector can be designed such that, upon homologous recombination, the endogenous Prdm16 and/or C/EBPβ gene is mutated or otherwise altered but still encodes functional protein (e.g., the upstream regulatory region can be altered to thereby alter the expression of the endogenous Prdm16 and/or C/EBPβ protein). In the homologous recombination vector, the altered portion of the Prdm16 and/or C/EBPβ gene is flanked at its 5' and 3' ends by additional nucleic acid of the Prdm16 and/or C/EBPβ gene to allow for homologous recombination to occur between the exogenous Prdm16 and/or C/EBPβ gene carried by the vector and an endogenous Prdm16 and/or C/EBPβ gene in an embryonic stem cell. The additional flanking Prdm16 and/or C/EBPβ nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Prdm16 and/or C/EBPβ gene has homologously recombined with the endogenous Prdm16 and/or C/EBPβ gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated PRDM16-C/EBPβ Complexes, PRDM16-C/EBPβ Complex Polypeptides, and Antibodies Thereto The present invention contemplates polypeptide complexes. For example, PRDM16-C/EBPβ complexes comprising (a) a full length PRDM16 polypeptide and a full length C/EBPβ polypeptide, (b) a fragment of PRDM16 and a full length C/EBPβ, (c) a full length PRDM16 and a fragment of C/EBPβ, or (d) a fragment of PRDM16 and a fragment of C/EBPβ.

The present invention makes available in a variety of embodiments soluble, purified and/or isolated forms of the PRDM16-C/EBPβ complexes or the PRDM16-C/EBPβ complex polypeptides.

In one aspect, a PRDM16-C/EBPβ complex polypeptide may comprise (a) a full-length PRDM16-C/EBPβ complex polypeptide amino acid sequence, (b) a full-length PRDM16-C/EBPβ complex polypeptide amino acid sequence with 1 to about 20 conservative amino acid substitutions, (c) a polypeptide amino acid sequence that is at least 50, 55, 60, 65, 70, 75, 80, 85, 90, 91, 92, 93, 94, 95, 96, 97, 98, 99, or 99.5% identical to an PRDM16-C/EBPβ complex polypeptide sequence of interest or (d) a fragment of the PRDM16-C/EBPβ complex polypeptide of interest (e.g., a polypeptide having less than the full-length sequence). In another aspect, the present invention contemplates a composition comprising an isolated PRDM16-C/EBPβ complex or PRDM16-C/EBPβ complex polypeptide and less than about 25%, or alternatively 15%, or alternatively 5%, contaminating biological macromolecules or polypeptides. In an exemplary embodiment, the PRDM16 fragment comprises from about amino acids 224-454, 680-880, or 881-1038 of PRDM16.

The present invention further provides compositions related to producing, detecting, or characterizing a PRDM16-C/EBPβ complex, a PRDM16 polypeptide or fragment thereof, or a C/EBPβ polypeptide or fragment thereof, such as nucleic acids, vectors, host cells, and the like. Such compositions may serve as compounds that modulate a PRDM16-C/EBPβ complex, an PRDM16 polypeptide or fragment thereof, or C/EBPβ polypeptide or fragment thereof, such as antisense nucleic acids.

In certain embodiments, a PRDM16-C/EBPβ complex polypeptide of the invention may be a fusion protein containing a domain which increases its solubility and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a PRDM16-C/EBPβ complex polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In another embodiment, provided are fusions between PRDM16 and C/EBPβ polypeptides, and nucleotide sequences encoding the fusion polypeptides. The fusion polypeptides may comprise all or a part of a PRDM16 polypeptide and all or a part of a C/EBPβ polypeptide. In one embodiment, the fusion proteins may optionally contain a linker sequence between the PRDM16 and C/EBPβ sequences. In another embodiment, the fusion proteins may contain a protease cleavage site between the PRDM16 and C/EBPβ sequences (as described further above). In an exemplary embodiment, the fusion proteins will be capable of carrying out at least one biological activity of a PRDM16-C/EBPβ complex and may be useful for identifying a modulator of the activity and/or formation of a PRDM16-C/EBPβ complex. The fusion proteins may optionally contain other heterologous sequences such as polypeptide tags or labels. In certain embodiments, the fusion proteins may be formed by chemically or enzymatically linking two separate sequences together or may be formed by expressing or synthesizing a single polypeptide sequence comprising both PRDM16 and C/EBPβ sequences.

In still another embodiment, a PRDM16-C/EBPβ complex polypeptide of the invention may be labeled with a fluorescent label to facilitate their detection, purification, or structural characterization. In an exemplary embodiment, a PRDM16-C/EBPβ complex polypeptide of the invention may be fused to a heterologous polypeptide sequence which produces a detectable fluorescent signal, including, for example, green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated Prdm16 and/or C/EBPβ proteins, and biologically active portions thereof, as well as peptide fragments suitable for use as immunogens to raise anti-Prdm16 and/or anti-C/EBPβ antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of Prdm16 and/or C/EBPβ protein in which the protein is separated from cellular components of the cells in which it is naturally or recombinantly produced. In one embodiment, the language "substantially free of cellular material" includes preparations of Prdm16 and/or C/EBPβ protein having less than about 30% (by dry weight) of non-Prdm16 and/or non-C/EBPβ protein (also referred to herein as a "contaminating protein"), more preferably less than about 20% of non-Prdm16 and/or non-C/EBPβ protein, still more preferably less than about 10% of non-Prdm16 and/or non-C/EBPβ protein, and most preferably less than about 5% non-Prdm16 and/or non-C/EBPβ protein. When the Prdm16 and/or C/EBPβ protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of Prdm16 and/or C/EBPβ protein in which the protein is separated from chemical precursors or other chemicals which are involved in the synthesis of the protein. In one embodiment, the language "substantially free of chemical precursors or other chemicals" includes preparations of Prdm16 and/or C/EBPβ protein having less than about 30% (by dry weight) of chemical precursors of non-Prdm16 and/or non-C/EBPβ chemicals, more preferably less than about 20% chemical precursors of non-Prdm16 and/or non-C/EBPβ chemicals, still more preferably less than about 10% chemical precursors of non-Prdm16 and/or non-C/EBPβ chemicals, and most preferably less than about 5% chemical precursors of non-Prdm16 and/or non-C/EBPβ chemicals. In preferred embodiments, isolated proteins or biologically active portions thereof lack contaminating proteins from the same animal from which the Prdm16 and/or C/EBPβ protein is derived. Typically, such proteins are produced by recombinant expression of, for example, a human Prdm16 and/or C/EBPβ protein in a nonhuman cell.

An isolated Prdm16 and/or C/EBPβ protein or a portion thereof of the invention has one or more of the following biological activities or, in complex, modulates (e.g., enhance) one or more of the following biological activities: 1) it can modulate the expression of cidea, adiponectin, adipsin, type II deiodinase, cig30, pgc-1α, elov3, and ucp1; 2) it can modulate the expression of mitochondrial genes including, cytochrome c, cox 4i1, cox III, cox 5b, cox8b atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

In preferred embodiments, the protein or portion thereof comprises an amino acid sequence which is sufficiently homologous to an amino acid sequence of SEQ ID NO: 2, 4, 6, 8, or 10 such that the protein or portion thereof maintains one or more of the following biological activities or, in complex, modulates (e.g., enhance) one or more of the following biological activities: 1) it can modulate the expression of cidea, adiponectin, adipsin, type II deiodinase, cig30, pgc-1α, elov3, and ucp1; 2) it can modulate the expression of mitochondrial genes including, cytochrome c, cox 4i1, cox III, cox 5b, cox8b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity. The portion of the protein is preferably a biologically active portion as described herein. In another preferred embodiment, the Prdm16 and/or C/EBPβ protein has an amino acid sequence shown in SEQ ID NO: 2, 4, 6, 8, or 10, respectively, or an amino acid sequence which is at least about 50%, preferably at least about 60%, more preferably at least about 70%, yet more preferably at least about 80%, still more preferably at least about 90%, and most preferably at least about 95% or more homologous to the amino acid sequence shown in SEQ ID NO: 2, 4, 6, 8, or 10. In yet another preferred embodiment, the Prdm16 and/or C/EBPβ protein has an amino acid sequence which is encoded by a nucleotide sequence which hybridizes, e.g., hybridizes under stringent conditions, to the nucleotide sequence of SEQ ID NO:1, 3, 5, 7, or 9 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO: 1, 3, 5, 7, or 9. The preferred Prdm16 and/or C/EBPβ proteins of the present invention also preferably possess at least one of the Prdm16 and/or C/EBPβ biological activities, or activities associated with the complex, described herein. For example, a preferred Prdm16 and/or C/EBPβ protein of the present invention includes an amino acid sequence encoded by a nucleotide sequence which hybridizes, e.g., hybridizes under stringent conditions, to the nucleotide sequence of SEQ ID NO:1, 3, 5, 7, or 9 and which can maintain one or more of the following biological activities or, in complex, modulates (e.g., enhance) one or more of the following biological activities: 1) it can modulate the expression of cidea, adiponectin, adipsin, type II deiodinase, cig30, pgc-1α, elov3, and ucp1; 2) it can modulate the expression of mitochondrial genes including, cytochrome c, cox 4i1, cox III, cox 5b, cox8b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

In other embodiments, the Prdm16 and/or C/EBPβ protein is substantially homologous to the amino acid sequence of SEQ ID NO: 2, 4 or 6 and retains the functional activity of the protein of SEQ ID NO: 2, 4, 6, 8, or 10 yet differs in amino acid sequence due to natural allelic variation or mutagenesis, as described in detail in subsection I above. Accordingly, in another embodiment, the Prdm16 and/or C/EBPβ protein is a protein which comprises an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO: 2, 4, 6, 8, or 10.

Biologically active portions of the Prdm16 and/or C/EBPβ protein include peptides comprising amino acid sequences derived from the amino acid sequence of the Prdm16 and/or C/EBPβ protein, e.g., the amino acid sequence shown in SEQ ID NO: 2, 4, 6, 8, or 10 or the amino acid sequence of a protein homologous to the Prdm16 and/or C/EBPβ protein, which include fewer amino acids than the full length Prdm16 and/or C/EBPβ protein or the full length protein which is homologous to the Prdm16 and/or C/EBPβ protein, and exhibit at least one activity of the Prdm16 and/or C/EBPβ protein, or complex thereof. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., PR domain (PRDI-BF1-RIZ homology region). In a preferred embodiment, the biologically active portion of the protein which includes one or more the domains/motifs described herein can modulate differentiation of adipocytes and/or thermogenesis in brown adipocytes. Moreover, other biologically active portions, in which other regions of the protein are deleted, can be prepared by recombinant techniques and evaluated for one or more of the activities described herein. Preferably, the biologically active portions of the Prdm16 and/or C/EBPβ protein include one or more selected domains/motifs or portions thereof having biological activity.

Prdm16 and/or C/EBPβ proteins are preferably produced by recombinant DNA techniques. For example, a nucleic acid molecule encoding the protein is cloned into an expression vector (as described above), the expression vector is introduced into a host cell (as described above) and the Prdm16 and/or C/EBPβ protein is expressed in the host cell. The Prdm16 and/or C/EBPβ protein can then be isolated from the cells by an appropriate purification scheme using standard protein purification techniques. Alternative to recombinant expression, a Prdm16 and/or C/EBPβ protein, polypeptide, or peptide can be synthesized chemically using standard peptide synthesis techniques. Moreover, native Prdm16 and/or C/EBPβ protein can be isolated from cells (e.g., brown adipocytes), for example using an anti-Prdm16 antibody and/or anti-C/EBPβ antibody (described further below).

The invention also provides Prdm16 and/or C/EBPβ chimeric or fusion proteins. As used herein, a Prdm16 and/or C/EBPβ "chimeric protein" or "fusion protein" comprises a Prdm16 and/or C/EBPβ polypeptide operatively linked to a non-Prdm16 and/or non-C/EBPβ polypeptide, respectively. A "Prdm16 and/or C/EBPβ polypeptide" refers to a polypeptide having an amino acid sequence corresponding to Prdm16 and/or C/EBPβ, whereas a "non-Prdm16 and/or non-C/EBPβ polypeptide" refers to a polypeptide having an amino acid sequence corresponding to a protein which is not substantially homologous to the Prdm16 and/or C/EBPβ protein, respectively, e.g., a protein which is different from the Prdm16 and/or C/EBPβ protein and which is derived from the same or a different organism. Within the fusion protein, the term "operatively linked" is intended to indicate that the Prdm16 and/or C/EBPβ polypeptide and the non-Prdm16 and/or non-C/EBPβ polypeptide are fused in-frame to each other. The non-Prdm16 and/or non-C/EBPβ polypeptide can be fused to the N-terminus or C-terminus of the Prdm16 and/or C/EBPβ polypeptide, respectively. For example, in one embodiment the fusion protein is a GST-Prdm16 and/or GST-C/EBPβ fusion protein in which the Prdm16 and/or C/EBPβ sequences, respectively, are fused to the C-terminus of the GST sequences. Such fusion proteins can facilitate the purification of recombinant Prdm16 and/or C/EBPβ. In another embodiment, the fusion protein is a Prdm16 and/or C/EBPβ protein containing a heterologous signal sequence at its N-terminus. In certain host cells (e.g., mammalian host cells), expression and/or secretion of Prdm16 and/or C/EBPβ can be increased through use of a heterologous signal sequence.

Preferably, a Prdm16 and/or C/EBPβ chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A Prdm16-encoding and/or C/EBPβ-encoding nucleic acid can be cloned into such an expression vector such that the fusion moiety is linked in-frame to the Prdm16 and/or C/EBPβ protein.

The present invention also pertains to homologues of the Prdm16 and/or C/EBPβ proteins which function as either a Prdm16 and/or C/EBPβ agonist (mimetic) or a Prdm16 and/or C/EBPβ antagonist. In a preferred embodiment, the Prdm16 and/or C/EBPβ agonists and antagonists stimulate or inhibit, respectively, a subset of the biological activities of the naturally occurring form of the Prdm16 and/or C/EBPβ protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the Prdm16 and/or C/EBPβ protein.

Homologues of the Prdm16 and/or C/EBPβ protein can be generated by mutagenesis, e.g., discrete point mutation or truncation of the Prdm16 and/or C/EBPβ protein. As used herein, the term "homologue" refers to a variant form of the Prdm16 and/or C/EBPβ protein which acts as an agonist or antagonist of the activity of the Prdm16 and/or C/EBPβ protein. An agonist of the Prdm16 and/or C/EBPβ protein can retain substantially the same, or a subset, of the biological activities of the Prdm16 and/or C/EBPβ protein. An antagonist of the Prdm16 and/or C/EBPβ protein can inhibit one or more of the activities of the naturally occurring form of the Prdm16 and/or C/EBPβ protein, by, for example, competitively binding to a downstream or upstream member of the Prdm16 and/or C/EBPβ cascade which includes the Prdm16 and/or C/EBPβ protein. Thus, the mammalian Prdm16 and/or C/EBPβ protein and homologues thereof of the present invention can be, for example, either positive or negative regulators of adipocyte differentiation and/or thermogenesis in brown adipocytes.

In an alternative embodiment, homologues of the Prdm16 and/or C/EBPβ protein can be identified by screening combinatorial libraries of mutants, e.g., truncation mutants, of the Prdm16 and/or C/EBPβ protein for Prdm16 and/or C/EBPβ protein agonist or antagonist activity. In one embodiment, a variegated library of Prdm16 and/or C/EBPβ variants is generated by combinatorial mutagenesis at the nucleic acid level and is encoded by a variegated gene library. A variegated library of Prdm16 and/or C/EBPβ variants can be produced by, for example, enzymatically ligating a mixture of synthetic oligonucleotides into gene sequences such that a degenerate set of potential Prdm16 and/or C/EBPβ sequences is expressible as individual polypeptides, or alternatively, as a set of larger fusion proteins (e.g., for phage display) containing the set of Prdm16 and/or C/EBPβ sequences therein. There are a variety of methods which can be used to produce libraries of potential Prdm16 and/or C/EBPβ homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Prdm16 and/or C/EBPβ sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the Prdm16 and/or C/EBPβ protein coding can be used to generate a variegated population of Prdm16 and/or C/EBPβ fragments for screening and subsequent selection of homologues of a Prdm16 and/or C/EBPβ protein. In one embodiment, a library of coding sequence fragments can be generated by treating a double stranded PCR fragment of a Prdm16 and/or C/EBPβ coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Prdm16 and/or C/EBPβ protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Prdm16 and/or C/EBPβ homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Prdm16 and/or C/EBPβ homologues (Arkin and Youvan (1992) *Proc. Natl. Acad. Sci. USA* 89:7811-7815; Delagrave et al. (1993) *Protein Engineering* 6(3):327-331).

A variety of antibodies directed to PRDM16-C/EBPβ complexes, PRDM16 polypeptides or fragments thereof, or C/EBPβ polypeptides or fragment thereof, are also provided. In one embodiment, the present invention provides an isolated antibody that has a higher binding affinity for a PRDM16-C/EBPβ complex than for the any of the components of the complex alone, including a PRDM16 polypeptide or fragment thereof, or a C/EBPβ polypeptide or fragment thereof. In an exemplary embodiment, an antibody, or antibody fragment may be capable of binding to a PRDM16-C/EBPβ complex with less than 80%, 70%, 60%, 50%, 40%, 30%, 25%, 20%, 15%, 10%, 5%, 3%, 2%, 1%, or less cross-reactivity with a component of the complex when not in the complex. In another embodiment, the invention provides an isolated antibody that binds to an interaction site on a PRDM16-C/EBPβ complex polypeptide (for example, a site on a PRDM16 polypeptide or fragment thereof that is capable of interacting with a C/EBPβ polypeptide or fragment thereof, or a site on a C/EBPβ polypeptide or fragment thereof that is capable of interacting with a PRDM16 polypeptide or fragment thereof). In still other embodiments, the isolated antibodies of the invention may disrupt or stabilize a PRDM16-C/EBPβ complex.

In one embodiment, an isolated Prdm16 and/or C/EBPβ protein, or a portion or fragment thereof, can be used as an immunogen to generate antibodies that bind Prdm16 and/or C/EBP, respectively, or a complex thereof, using standard techniques for polyclonal and monoclonal antibody preparation. The full-length Prdm16 and/or C/EBPβ protein can be used or, alternatively, antigenic peptide fragments of Prdm16 and/or C/EBPβ, or peptides in complex, can be used as immunogens. A Prdm16 and/or C/EBPβ immunogen typically is used to prepare antibodies by immunizing a suitable subject, (e.g., rabbit, goat, mouse or other mammal) with the immunogen. An appropriate immunogenic preparation can contain, for example, recombinantly expressed Prdm16 and/or C/EBPβ protein or a chemically synthesized Prdm16 and/or C/EBPβ peptide. The preparation can further include an adjuvant, such as Freund's complete or incomplete adjuvant, or similar immunostimulatory agent. Immunization of a suitable subject with an immunogenic Prdm16 and/or C/EBPβ preparation induces a polyclonal anti-Prdm16 and/or anti-C/EBPβ antibody response.

Accordingly, another aspect of the invention pertains to the use of anti-Prdm16 and/or anti-C/EBPβ antibodies. The term "antibody" as used herein refers to immunoglobulin molecules and immunologically active portions of immunoglobulin molecules, i.e., molecules that contain an antigen binding site which specifically binds (immunoreacts with) an antigen, such as prdm16 and/or C/EBPβ. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Prdm16 and/or C/EBPβ. The term "monoclonal antibody" or "monoclonal antibody composition", as used herein, refers to a population of antibody molecules that contain only one species of an antigen binding site capable of immunoreacting with a particular epitope of Prdm16 and/or C/EBPβ. A monoclonal antibody composition thus typically displays a single binding affinity for a particular Prdm16 and/or C/EBPβ protein with which it immunoreacts.

Polyclonal anti-Prdm16 and/or C/EBPβ antibodies can be prepared as described above by immunizing a suitable subject with a Prdm16 and/or C/EBPβ, or complex thereof, immunogen. The anti-Prdm16 and/or anti-C/EBPβ antibody titer in the immunized subject can be monitored over time by standard techniques, such as with an enzyme linked immunosorbent assay (ELISA) using immobilized Prdm16 and/or C/EBPβ. If desired, the antibody molecules directed against Prdm16 and/or C/EBPβ can be isolated from the mammal (e.g., from the blood) and further purified by well known techniques, such as protein A chromatography to obtain the IgG fraction. At an appropriate time after immunization, i.e., when the anti-Prdm16 and/or anti-C/EBPβ antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a Prdm16 and/or C/EBPβ immunogen as described above, and the culture supernatants of the resulting hybridoma cells are screened to identify a hybridoma producing a monoclonal antibody that binds Prdm16 and/or C/EBPβ.

Any of the many well-known protocols used for fusing lymphocytes and immortalized cell lines can be applied for the purpose of generating an anti-Prdm16 and/or anti-C/EBPβ monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag-4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Prdm16 and/or C/EBPβ, i.e., using a standard ELISA assay.

Alternative to preparing monoclonal antibody-secreting hybridomas, a monoclonal anti-prdm16 and/or anti-C/EBPβ antibody can be identified and isolated by screening a recombinant combinatorial immunoglobulin library (e.g., an antibody phage display library) with Prdm16 and/or C/EBPβ to thereby isolate immunoglobulin library members that bind Prdm16 and/or C/EBPβ. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246: 1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-Prdm16 and/or anti-C/EBPβ antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225, 539; Jones et al. (1986) *Nature* 321:552-525; Verhoeyan et al. (1988) *Science* 239:1534; and Beidler et al. (1988) *J. Immunol.* 141:4053-4060.

An anti-Prdm16 and/or anti-C/EBPβ antibody (e.g., monoclonal antibody) can be used to isolate Prdm16 and/or C/EBPβ by standard techniques, such as affinity chromatography or immunoprecipitation. An anti-Prdm16 and/or anti-C/EBPβ antibody can facilitate the purification of natural Prdm16 and/or C/EBPβ from cells and of recombinantly produced Prdm16 and/or C/EBPβ expressed in host cells. Moreover, an anti-Prdm16 and/or anti-C/EBPβ antibody can be used to detect Prdm16 and/or C/EBPβ protein (e.g., in a cellular lysate or cell supernatant) in order to evaluate the abundance and pattern of expression of the Prdm16 and/or C/EBPβ protein. Anti-Prdm16 and/or anti-C/EBPβ antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In vivo techniques for detection of Prdm16 and/or C/EBPβ protein include introducing into a subject a labeled antibody directed against the protein. For example, the antibody can be labeled with a radioactive marker whose presence and location in a subject can be detected by standard imaging techniques.

IV. Identification of Compounds that Modulate a PRDM16-C/EBPβ Complex

The PRDM16-C/EBPβ complexes and/or PRDM16-C/EBPβ complex polypeptides described herein may be used to design modulators of one or more of biological activities of the complex or complex polypeptides. In particular, information useful for the design of therapeutic and diagnostic molecules, including, for example, the protein domain, structural information, and the like for polypeptides of the invention is now available or attainable as a result of the ability to prepare, purify and characterize the complexes and complex polypeptides, and domains, fragments, variants and derivatives thereof.

In another aspect, modulators, inhibitors, or antagonists against the polypeptides of the invention, biological complexes containing them, or orthologues thereto, may be used to treat any disease or other treatable condition of a patient (including humans and animals), including, for example, obesity or obesity-related disorders.

Modulators of PRDM16-C/EBPβ complexes, other structurally related molecules, and PRDM16-C/EBPβ complex polypeptides, may be identified and developed as set forth below and otherwise using techniques and methods known to those of skill in the art. The modulators of the invention may be employed, for instance, to inhibit and treat PRDM16-C/EBPβ-mediated diseases or disorders. The modulators of the invention may elicit a change in one or more of the following activities: (a) a change in the level and/or rate of formation of a PRDM16-C/EBPβ complex, (b) a change in the activity of a PRDM16-C/EBPβ complex, (c) a change in the stability of a PRDM16-C/EBPβ complex, (d) a change in the conformation of a PRDM16-C/EBPβ complex, or (e) a change in the activity of at least one polypeptide contained in a PRDM16-C/EBPβ complex. A number of methods for identifying a molecule which modulates a PRDM16-C/EBPβ complex, or a PRDM16-C/EBPβ complex polypeptide, are known in the art. For example, in one such method, a PRDM16-C/EBPβ complex, or a PRDM16-C/EBPβ complex polypeptide, is contacted with a test compound, and the activity of the PRDM16-C/EBPβ complex, or a PRDM16-C/EBPβ complex polypeptide, in the presence of the test compound is determined, wherein a change in the activity of the PRDM16-C/EBPβ complex, or a PRDM16-C/EBPβ complex polypeptide, in the presence of the compound as compared to the activity in the absence of the compound (or in the presence of a control compound) is indicative that the test compound modulates the activity of the PRDM16-C/EBPβ complex, or a PRDM16-C/EBPβ complex polypeptide.

Compounds to be tested for their ability to act as modulators of PRDM16-C/EBPβ complexes, or PRDM16-C/EBPβ complex polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises PRDM16-C/EBPβ complex polypeptide.

A variety of assay formats will suffice and, in light of the present disclosure, those not expressly described herein may nevertheless be comprehended by one of ordinary skill in the art based on the teachings herein. Assay formats for analyzing PRDM16-C/EBPβ complex formation, PRDM16-C/EBPβ complex activity, and/or activity of a PRDM16-C/EBPβ complex polypeptide, may be generated in many different forms, and include assays based on cell-free systems, e.g. purified proteins or cell lysates, as well as cell-based assays which utilize intact cells. Simple binding assays can also be used to detect agents which modulate a PRDM16-C/EBPβ complex, for example, by enhancing the formation of a PRDM16-C/EBPβ complex, by enhancing the binding of a PRDM16-C/EBPβ complex to a substrate, and/or by enhancing the binding of a PRDM16-C/EBPβ complex polypeptide to a substrate. Another example of an assay useful for identifying a modulator of a PRDM16-C/EBPβ complex is a competitive assay that combines one or more PRDM16-C/EBPβ complex polypeptides with a potential modulator, such as, for example, polypeptides, nucleic acids, natural substrates or ligands, or substrate or ligand mimetics, under appropriate conditions for a competitive inhibition assay. PRDM16-C/EBPβ complex polypeptides can be labeled, such as by radioactivity or a colorimetric compound, such that PRDM16-C/EBPβ complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting PRDM16-C/EBPβ complexes, or complex polypeptides, as described above.

Complex formation between a PRDM16 polypeptide or a C/EBPβ polypeptide and a binding partner may be detected by a variety of methods. Modulation of the formation of PRDM16-C/EBPβ complexes may be quantified using, for example, detectably labeled proteins such as radiolabeled, fluorescently labeled, or enzymatically labeled polypeptides or binding partners, by immunoassay, or by chromatographic detection. Methods of isolating and identifying PRDM16-C/EBPβ complexes described above may be incorporated into the detection methods.

In certain embodiments, it may be desirable to immobilize a PRDM16 polypeptide and/or C/EBPβ polypeptide to facilitate separation of PRDM16 and/or C/EBPβ complexes from uncomplexed forms of one or both of the proteins, as well as to accommodate automation of the assay. Binding of a PRDM16 and/or C/EBPβ polypeptide to a binding partner may be accomplished in any vessel suitable for containing the reactants. Examples include microtitre plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of PRDM16 and/or C/EBPβ polypeptides found in the bead fraction quantified from the gel using standard electrophoretic techniques such as described in the appended examples.

Other techniques for immobilizing proteins on matrices are also available for use in the subject assay. For instance, either a PRDM16 and/or C/EBPβ polypeptide may be immobilized utilizing conjugation of biotin and streptavidin. For instance, biotinylated polypeptide molecules may be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the PRDM16 and/or C/EBPβ polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of PRDM16 and/or C/EBPβ polypeptide trapped in the PRDM16-C/EBPβ complex may be assessed with a chromogenic substrate of the enzyme, e.g. 3,3'-diamino-benzadine terahydrochloride or 4-chloro-1-napthol. Likewise, a fusion protein comprising the PRDM16 and/or C/EBPβ polypeptide and glutathione-S-transferase may be provided, and PRDM16 and/or C/EBPβ complex formation quantified by detecting the GST activity using 1-chloro-2,4-dinitrobenzene (Habig et al (1974) J Biol Chem 249:7130).

For processes that rely on immunodetection for quantitating one of the PRDM16-C/EBPβ complex polypeptides trapped in the PRDM16-C/EBPβ complex, antibodies against the PRDM16-C/EBPβ complex polypeptide, such as anti-polypeptide antibodies, may be used. Alternatively, the PRDM16 and/or C/EBPβ polypeptide to be detected in the PRDM16-C/EBPβ complex may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtitre plates, test tubes, and micro-centrifuge tubes.

In yet another embodiment, a PRDM16-C/EBPβ complex polypeptide may be used to generate an two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another.

In particular, the method makes use of chimeric genes which express hybrid proteins. To illustrate, a first hybrid gene comprises the coding sequence for a DNA-binding domain of a transcriptional activator may be fused in frame to the coding sequence for a "bait" protein, e.g., a PRDM16 and/or C/EBPβ polypeptide of sufficient length to bind to a potential interacting protein. The second hybrid protein encodes a transcriptional activation domain fused in frame to a gene encoding a "fish" protein, e.g., a potential interacting protein of sufficient length to interact with the protein-protein interaction component polypeptide portion of the bait fusion protein. If the bait and fish proteins are able to interact, e.g., form a protein-protein interaction component complex, they bring into close proximity the two domains of the transcriptional activator. This proximity causes transcription of a reporter gene which is operably linked to a transcriptional regulatory site responsive to the transcriptional activator, and expression of the reporter gene may be detected and used to score for the interaction of the bait and fish proteins. The host cell also contains a first chimeric gene which is capable of being expressed in the host cell. The gene encodes a chimeric protein, which comprises (a) a DNA-binding domain that recognizes the responsive element on the reporter gene in the host cell, and (b) a bait protein (e.g., a PRDM16 and/or C/EBPβ polypeptide). A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The DNA-binding domain of the first hybrid protein and the transcriptional activation domain of the second hybrid protein may be derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DNA-binding domains may be used in the subject constructs; such as domains of ACE1, λcI, lac repressor, jun or fos. In another embodiment, the DNA-binding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, the Brent et al. PCT publication WO94/10300).

In certain embodiments, any enzymatic activity associated with the bait or fish proteins is inactivated, e.g., dominant negative or other mutants of a protein-protein interaction component can be used.

Continuing with the illustrative example, formation of a complex between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a complex results in a detectable signal produced by the expression of the reporter gene.

In still further embodiments, the PRDM16-C/EBPβ complex, or complex polypeptide, of interest may be generated in whole cells, taking advantage of cell culture techniques to support the subject assay. For example, the PRDM16-C/EBPβ complex, or complex polypeptide, may be constituted in a prokaryotic or eukaryotic cell culture system. Advantages to generating the PRDM16-C/EBPβ complex, or complex polypeptide, in an intact cell includes the ability to screen for modulators of the level and/or activity of the PRDM16-C/EBPβ complex, or complex polypeptide, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The PRDM16-C/EBPβ complexes and PRDM16-C/EBPβ complex polypeptides can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of PRDM16-C/EBPβ complexes may be detected in a cell-free assay generated by constitution of a functional PRDM16-C/EBPβ complex in a cell lysate. In an alternate format, the assay can be derived as a reconstituted protein mixture which, as described below, offers a number of benefits over lysate-based assays.

The activity of a PRDM16-C/EBPβ complex or a PRDM16-C/EBPβ complex polypeptide may be identified and/or assayed using a variety of methods well known to the skilled artisan. For example, the activity of a PRDM16-C/EBPβ complex or a PRDM16-C/EBPβ complex polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of a PRDM16-C/EBPβ complex, or PRDM16-C/EBPβ complex polypeptide, may be assessed by monitoring changes in the phenotype of a targeted cell. For example, the detection means can include a reporter gene construct which includes a transcriptional regulatory element that is dependent in some form on the level and/or activity of a PRDM16-C/EBPβ complex, or PRDM16-C/EBPβ complex polypeptide. The PRDM16-C/EBPβ complex, or PRDM16-C/EBPβ complex polypeptide, may be provided as a fusion protein with a domain that binds to a DNA element of a reporter gene construct. The added domain of the fusion protein can be one which, through its DNA-binding ability, increases or decreases transcription of the reporter gene. Which ever the case may be, its presence in the fusion protein renders it responsive to a PRDM16-C/EBPβ complex, or PRDM16-C/EBPβ complex polypeptide. Accordingly, the level of expression of the reporter gene will vary with the level of expression of a PRDM16-C/EBPβ complex, or PRDM16-C/EBPβ complex polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of a PRDM16-C/EBPβ complex, or PRDM16-C/EBPβ complex polypeptide, present in the cell. Such embodiments of the subject assay are particularly amenable to high through-put analysis in that proliferation of the cell can provide a simple measure of inhibition of the PRDM16-C/EBPβ complex, or PRDM16-C/EBPβ complex polypeptide.

V. Methods of the Invention

The methods of the invention relate to the expression and/or activity of both Prdm16 and C/EBPβ sufficient to activate brown fat cell differentiation, wherein the differentiated brown fat cells increase energy expenditure to thereby treat obesity or an obesity related disorder, e.g., Type II diabetes.

The invention also relates to methods for increasing energy expenditure in a mammal comprising inducing expression and/or activity of both Prdm16 and C/EBPβ sufficient to activate brown fat cell differentiation in the mammal, wherein the differentiated brown fat cells promote energy expenditure thereby increasing energy expenditure in the mammal.

The term "sufficient to activate" is intended to encompass any increase in expression and/or activity of both Prdm16 and C/EBPβ that promotes, activates, stimulates, enhances, or results in brown fat differentiation.

In another aspect, the invention relates to methods for treating obesity or an obesity-related disorder, e.g., Type II diabetes, in a subject comprising administering to the subject an agent that induces expression and/or activity of both Prdm16 and C/EBPβ, wherein expression and/or activity of both Prdm16 and C/EBPβ increases respiration and energy expenditure to thereby treat obesity or an obesity-related disorder. In one embodiment, total respiration is increased following the expression and/or activity of both Prdm16 and C/EBPβ. In another embodiment, uncoupled respiration is increased following the expression and/or activity of both Prdm16 and C/EBPβ. Uncoupled respiration dissipates heat and thereby increases energy expenditure in the subject.

As used herein, the term "agent" and "therapeutic agent" is defined broadly as anything that cells from a subject with obesity or an obesity-related disorder may be exposed to in a therapeutic protocol.

The term "administering" is intended to include routes of administration which allow the agent to perform its intended function of increasing expression and/or activity of both Prdm16 and C/EBPβ. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo.

The term "effective amount" of an agent that induces expression and/or activity of both Prdm16 and C/EBPβ is that amount necessary or sufficient to promote expression and/or activity of both Prdm16 and C/EBPβ in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular respiration uncoupling agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances. U.S. Pat. No. 5,427,916, for example, describes a method for predicting the effectiveness of antineoplastic therapy in individual subjects, and illustrates certain methods which can be used in conjunction with the treatment protocols of the instant invention.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular respiration uncoupling agent to treat obesity or obesity-related disorders can be monitored by comparing two or more samples obtained from a subject undergoing anti-obesity or obesity-related disorder treatment. In general, it is preferable to obtain a first sample from the subject prior to beginning therapy and one or more samples during treatment. In such a use, a baseline of expression of cells from subjects with obesity or obesity-related disorders prior to therapy is determined and then changes in the baseline state of expression of cells from subjects with obesity or obesity-related disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with obesity or obesity-related disorders is increasing or decreasing.

Another aspect of the invention relates to a method for inducing brown fat cell differentiation in a mammal comprising expressing both Prdm16 and C/EBPβ in cells; delivering the cells expressing both Prdm16 and C/EBPβ into the mammal; and monitoring the differentiation of brown fat cells in the mammal. The cells can be delivered by well-known methods in the art (e.g., grafting, subcutaneous or intravenous injection). Increased brown adipose tissue in the mammal will warm up the body and blood of the mammal resulting in an increased energy expenditure from the cells. The increased energy expenditure will increase the metabolic rate of the subject and may be used for the treatment and/or prevention of obesity and obesity related disorders. The induction of brown fat cells may be monitored by 1) an increase or stimulation of the expression of cidea, adiponectin, adipsin, type II deiodinase, cig30, pgc-1α, elov3, and ucp1; 2) an increase or stimulation of the expression of mitochondrial genes including, cytochrome c, cox 4i1, cox III, cox 5b, cox8b, atpase b2, cox II, atp5o and ndufb5; 3) an increase or stimulation of total respiration of a cell; 4) an increase or stimulation of uncoupled respiration of a cell; 5) an increase or stimulation of heat dissipation; 6) an increase or stimulation of thermogenesis; and/or 7) an increase or stimulation of energy expenditure. The cells that can be used are described in more detail below. However, the method is suitable for obtaining cells from the mammal itself (i.e., autologous cells).

Mammalian cells (e.g., human) cells may be obtained by well known methods. Representative examples of mammalian cells useful in the present invention include, without limitation, fibroblasts (skin fibroblasts, dermal fibroblasts, primary embryonic fibroblasts, immortalized embryonic fibroblasts, and human foreskin fibroblasts), myoblasts, preadipocytes, white adipocytes, epithelial, neural cells, epidermal cells, keratinocytes, hematopoietic cells, melanocytes, chondrocytes, lymphocytes (B and T lymphocytes), macrophages, monocytes, mononuclear cells, cardiac muscle cells, skeletal muscle cells, hepatocytes and other muscle cells, etc. Moreover, the mammalian cells may be obtained from different organs, e.g., skin, lung, pancreas, liver, stomach, intestine, heart, reproductive organs, bladder, kidney, urethra and other urinary organs, etc.

Clinical use of autologous subject-derived sources of cells (e.g., skin fibroblasts) is advantageous to avoid potential adverse allogeneic immune reactivity. In other embodiments, the cells may be allogeneic, syngeneic, xenogeneic, or HLA compatible with the subject. When a combination of cell types is administered, some or all of the cell types may be autologous, allogeneic, syngeneic, xenogeneic or HLA compatible with the subject, whereas in other embodiments one or some cell types may be autologous and the other cell type(s) allogeneic, syngeneic, xenogeneic, or HLA compatible with the subject.

Methods of isolating and culturing cells for use in the methods of the present invention are well-known in the art (see, for example, Culture of Animal Cells; A manual of Basic Technique (2nd edition), Freshney, copyright 1987, Alan R. Liss, Inc., New York). In one embodiment, fibroblast or fibroblast-like cells are used. Fibroblast cells are a useful cell type because they can be obtained from developing fetuses and adult animals in large quantities. Importantly, these cells can be easily propagated in vitro with a rapid doubling time and can be clonally propagated for use in genetic engineering procedures. Confirmation of cell type can be conducted by numerous methods well-known in the art. For example, immunocytochemical staining with antibodies directed against cell type-specific markers (e.g., cytoskeletal filaments vimentin for fibroblasts or cytokeratin for epithelial cells) can be performed.

VI. Gene Therapy

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos.

4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis. Methods for generating transgenic cells typically include the steps of (1) assembling a suitable DNA construct useful for inserting a specific DNA sequence into the nuclear genome of a cell (e.g., PRDM16 and C/EBPβ); (2) transfecting the DNA construct into the cells; (3) allowing random insertion and/or homologous recombination to occur. The modification resulting from this process may be the insertion of a suitable DNA construct(s) into the target genome; deletion of DNA from the target genome; and/or mutation of the target genome. DNA constructs can comprise a gene of interest as well as a variety of elements including regulatory promoters, insulators, enhancers, and repressors as well as elements for ribosomal binding to the RNA transcribed from the DNA construct. Due to the effective recombinant DNA techniques available in conjunction with DNA sequences for regulatory elements and genes readily available in data bases and the commercial sector, a person of ordinary skill in the art can readily generate a DNA construct appropriate for establishing transgenic cells using the materials and methods known in the art.

VII. Pharmaceutical Compositions

In another aspect, the present invention provides pharmaceutically acceptable compositions which comprise a therapeutically-effective amount of an agent that modulates (e.g., enhances) Prdm16 and/or C/EBPβ expression and/or activity, or expression and/or activity of the complex, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., enhances) Prdm16 and/or C/EBPβ expression and/or activity, or expression and/or activity of the complex, or composition comprising an agent that modulates (e.g., enhances) Prdm16 and/or C/EBPβ expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) Prdm16 and/or C/EBPβ expression and/or activity, or expression and/or activity of the complex encompassed by the invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) Prdm16 and/or C/EBPβ expression and/or activity, or expression and/or activity of the complex. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., enhances) Prdm16 and/or C/EBPβ expression and/or activity, or expression and/or activity of the complex with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes.

The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., enhances) Prdm16 and/or C/EBPβ expression and/or activity, or expression and/or activity of the complex include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., enhances) Prdm16 and/or C/EBPβ expression and/or activity, or expression and/or activity of the complex, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., enhances) Prdm16 and/or C/EBPβ expression and/or activity, or expression and/or activity of the complex can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., enhances)

Prdm16 and/or C/EBPβ expression and/or activity, or expression and/or activity of the complex in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1

Materials and Methods for Examples

A. Cell Culture

Immortalized brown fat cells have been described in Uldry, M. et al. (2006) Cell Metab. 3, 333-341. Mouse embryonic fibroblasts were isolated from E13.5 C57/B16 embryos (Jackson Laboratory), and immortalized according to the methods described in Todaro, G. J. and Green, H. (1963) J. Cell Biol. 17, 299-313. Mouse dermal fibroblasts were obtained from Millipore. R2F primary skin fibroblasts isolated from human newborn foreskin from J. G. Rheinwald were cultured as per methods described in Rheinwald, J. G. et al. (2002) Mol. Cell. Biol. 22, 5157-5172. HEK293 cells and C2C12 cells were obtained from ATCC. Adipocyte differentiation in C2C12 cells was induced by treating confluent cells in DMEM containing 10% FBS, 0.5 mM isobutylmethylxanthine, 125 nM indomethacin, 5 µM dexamethasone, 850 nM insulin, 1 nM T3 and 1 µM rosiglitazone. Two days after induction, cells were switched to the maintenance medium containing 10% FBS, 850 nM insulin, 1 nM T3 and 1 µM rosiglitazone. Adipocyte differentiation in fibroblasts was induced with medium containing 5 µM dexamethosone, 850 nM insulin, 1 nM T3 and 1 µM rosiglitazone. For cAMP treatment, cells were incubated with 10 µM forskolin or 0.5 mM dibutyryl-cAMP. All chemicals for cell culture were obtained from Sigma unless otherwise indicated.

B. DNA Constructs and Viruses Production

Deletion mutants of Flag-tagged PRDM16 were amplified by PCR using full-length PRDM16 as a template, and subcloned into pMSCV-puro retroviral vector (Stratagene). Various fragments of GST-fused PRDM16 fragments (1-223, 224-454, 455-680, 680-880, 881-1038 and 1039-1176) were described in Kajimura, S. et al. (2008) Genes Dev. 22, 1397-1409. Myc-tagged C/EBP-β constructs (Bezy, O. et al. (2007) Mol. Cell. Biol. 27, 6818-6831) were from S. R. Farmer. The sequences used for retroviral shRNA expression vectors targeting C/EBP-β were 5'-GCCCTGAGTAATCACTTAAAG-3' (shβ-1) and 5'-CCGGGCCCTGAGTAATCAC-3' (shβ-2). The corresponding double-stranded DNA sequences were ligated into pSUPER-Retro (Oligoengine) for retroviral expression. For retrovirus production, Phoenix packaging cells (Kinsella, T. M. and Nolan, G. P. (1996) Hum. Gene Ther. 7, 1405-1413) were transfected at 70% confluence by calcium phosphate method with 10 µg retroviral vectors. After 48 h, the viral supernatant was collected and filtered. Cells were incubated overnight with the viral supernatant, supplemented with 8 µg ml$^{-1}$ polybrene. Subsequently, puromycin (PRDM16), hygromycin (C/EBP-β) or G418 (shRNAs) were used for selection. Fibroblasts expressing both PRDM16 and C/EBP-β were selected by puromycin and hygromycin to ensure expression of both constructs.

C. Affinity Purification of PRDM16 Transcriptional Complex

Immortalized brown fat cells stably expressing Flag-tagged wild-type, PRΔ mutant, and ZF-1Δ mutant of PRDM16 or an empty vector were grown to confluence. The cells were homogenized to prepare nuclear extracts (Kajimura, S. et al. (2008) Genes Dev. 22, 1397-1409). The nuclear extracts were incubated overnight with Flag M2 agarose (Sigma), washed in a binding buffer (180 mM KCl), and then eluted by incubating with 1× Flag peptide (0.2 mg ml$^{-1}$). The eluted materials were TCA precipitated, separated in a 4-20% acrylamide gradient gel, and visualized by silver staining, as described in Kajimura, S. et al. (2008) Genes Dev. 22, 1397-1409.

D. Mass Spectrometry

The immunoprecipitated proteins were precipitated with methanol and chloroform, and precipitates were dissolved in 50 mM Tris-HCl, pH 7.5, containing 8 M urea, 50 mM EDTA and 0.005% n-dodecyl β-d-maltoside (DDM). Proteins were reduced with dithiothreitol (DTT) and alkylated with iodoacetamide. After diluting urea concentration to 1 M with 50 mM Tris-HCl, pH 7.5, containing 0.005% DDM, trypsin was added and proteins were digested in solution at 37° C. for 12 h. The reaction was stopped with formic acid, and the resultant peptides were desalted with StageTips (Rappsilber, J. et al. (2007) Nat. Protocols 2, 1896-1906). Desalted peptides were subjected to reverse-phase LC-MS/MS using a high-resolution hybrid mass spectrometer (LTQ-Orbitrap, Thermo Scientific) with TOP10 method as described in Haas, W. et al. (2006) Mol. Cell. Proteomics 5, 1326-1337. The obtained data were searched against the International Protein Index (IPI) mouse database (Kersey, P. J. et al. (2004) Proteomics 4, 1985-1988). Proteins were identified with at least two unique valid peptides, and the false discovery rate was estimated to be 0% using target-decoy approach (Elias, J. E. and Gygi, S. P. (2007) Nat. Methods 4, 207-214).

E. Protein Interaction Analysis

HEK293 cells expressing PRDM16 or C/EBPs were collected 24 h after transfection. Total cell lysates were incubated overnight at 4° C. with Flag M2 agarose, washed and eluted with Flag peptide. The eluted materials were analysed by western blot using antibodies against C/EBP-α, C/EBP-β and C/EBP-δ (Santa Cruz). For in vitro binding assays, various fragments of the GST-fusion PRDM16 fragments were purified as described in Kajimura, S. et al. (2008) *Genes Dev.* 22, 1397-1409. [$^{35}$S]-labelled proteins were made with a TNT reticulocyte lysate kit (Promega). Equal amounts of GST-fusion proteins (2 μg) were incubated overnight at 4° C. with in vitro translated proteins in a binding buffer containing 20 mM HEPES, pH 7.7, 300 mM KCl, 2.5 mM MgCl$_2$, 0.05% NP40, 1 mM DTT and 10% glycerol. The sepharose beads were then washed five times with the binding buffer. Bound proteins were separated by SDS-PAGE and analysed by autoradiography.

F. Gene Expression Analysis

Total RNA was isolated from cells or tissues using Trizol (Invitrogen). Reverse transcriptase reactions were performed using a cDNA reverse transcription kit (Applied Biosystems). The primer sequences are listed in Table 2. Quantitative real-time PCR was performed with SYBR green fluorescent dye using an ABI9300 PCR machine. TATA-binding protein acted as an internal control.

G. Microarray Analysis

Total RNA was isolated from undifferentiated C2C12 cells transduced with scr or shβ together with PRDM16 or vector control. Array hybridization and scanning were performed by the Dana-Farber Cancer Institute Core Facility using Affymetrix GeneChip Mouse Genome 430 2.0 arrays according to established methods (Lockhart, D. J. et al. (1996) *Nat. Biotechnol.* 14, 1675-1680). The array data were analysed using the DNA-Chip Analyser software (Li, C. and Wong, W. H. (2001) *Proc. Natl. Acad. Sci. USA* 98, 31-36). The statistical significance of differences in gene expression was assessed using an unpaired t-test (P<0.05).

H. Reporter Gene Assay

The PGC1A (−2 kb) promoter linked to a luciferase reporter was transiently co-transfected with PRDM16 and/or C/EBP-β expression plasmids in brown preadipocytes using Lipofectamine 2000 (Invitrogen). Forty-eight hours after the transfection, cells were collected and reporter gene assays were carried out using the Dual Luciferase Kit (Promega). Transfection efficiency was normalized by measuring expression of *Renilla* luciferase.

I. Cellular Respiration Assay

Immortalized brown fat cells or MEFs transduced with retroviral PRDM16 and C/EBP-β or an empty vector were grown to confluence and induced to differentiate. At day 6 or 7 of differentiation, oxygen consumption was measured as described in Kajimura, S. et al. (2008) *Genes Dev.* 22, 1397-1409 and Seale, P. et al. (2007) *Cell Metab.* 6, 38-54. For cAMP-induced respiration assays, fully differentiated fat cells were incubated with 0.5 mM dibutyryl-cAMP for 12 h before measuring oxygen consumption.

J. Animals

All animal experiments were performed according to procedures approved by Beth Israel Deaconess Medical Center Institutional Animal Care and Use Committee. C/EBP-β-null mice (Cebpbtm1Vpo/J) were obtained from the Jackson Laboratory. For transplantation studies, male NCR-nude mice (NCr-Foxn1$^{nu}$) were obtained from Taconic.

K. Cell Transplantations

Immortalized MEFs (3×10$^7$) were transduced with retroviral PRDM16, C/EBP-β, vector control, or a combination of PRDM16 and C/EBP-β, and implanted subcutaneously into 7-9-week-old male nude mice (n=6 mice per group), according to methods described in Seale, P. et al. (2007) *Cell Metab.* 6, 38-54 and Green, H. and Kehinde, O. (1979) *J. Cell. Physiol.* 101, 169-171. For PET scanning studies, MEFs expressing retroviral PPARγ alone were implanted as a control. After 4-6 weeks, fat pads were carefully dissected and fixed in 4% paraformaldehyde for histological analysis. For immunohistochemistry, paraffin-embedded sections were incubated with anti-UCP1 antibody (Chemicon), followed by detection using the ABC Vectastain-Elite kit (Vector Labs) according to the manufacturer's instructions.

L. PET/CT Imaging $^{18}$FDG (100 μCi) was injected intravenously to animals acclimated for at least 48 h to room temperature. Animals were imaged or euthanized at 1 h after injection in the Longwood small animal imaging facility of Harvard Medical School. PET/CT imaging was performed using a Minerve anaesthesia bed moved between a Philips Mosaic HP small animal scanner and a Bioscan CT scanner, and co-registered using custom fiducial markers. The acquired data was reconstructed by InVivoScope software (Bioscan).

Example 2

Figure 5:
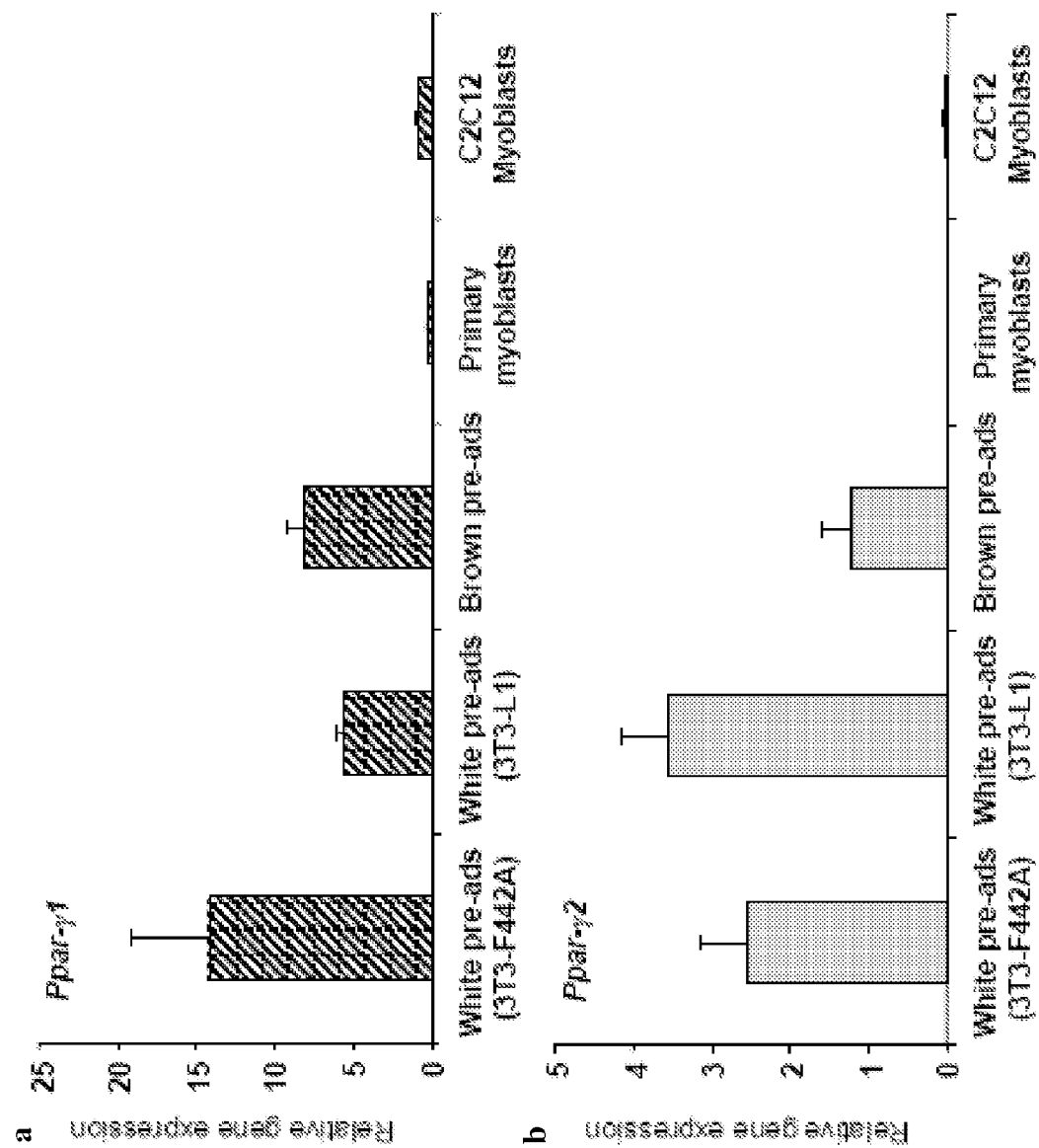
FIGS. 5A-5B show that myoblasts express low levels of PPAR-γ. mRNA levels of two PPAR-γ isoform Ppar-γ1 (A) and PPAR-γ isoform Ppar-γ2 (B) were measured in white pre-adipocyte cell lines (3T3-F442A and 3T3-L1), immortalized brown preadipocytes, primary myoblasts and C2C12 myoblast cell line. n=3-4. Data are presented as mean and s.e.m.

PRDM16 Forms a Transcriptional Complex with Active Forms of C/EBP-β by Direct Interaction and Regulates their Transcriptional Activity Because of the importance of brown adipose tissue (BAT) as a natural defence against hypothermia and obesity (Cannon, B. and Nedergaard, J. (2004) *Physiol. Rev.* 84, 277-359), and its demonstrated presence in adult humans (Nedergaard, J. et al. (2007) *Am. J. Physiol. Endocrinol. Metab.* 293, E444-E452; Cypess, A. M. et al. (2009) *N. Engl. J. Med.* 360, 1509-1517; van Marken Lichtenbelt, W. D. et al. (2009) *N. Engl. J. Med.* 360, 1500-1508; Virtanen, K. A. et al. (2009) *N. Engl. J. Med.* 360, 1518-1525), understanding its formation in mechanistic detail is critical for developing new therapeutics for metabolic diseases such as obesity and type-2 diabetes. PRDM16, a 140-kDa zinc finger protein, functions as a bidirectional switch in brown fat cell fate by stimulating the development of brown fat cells from white preadipocytes (Kajimura, S. et al. (2008) *Genes Dev.* 22, 1397-1409; Seale, P. et al. (2007) *Cell Metab.* 6, 38-54) and from Myf5-positive myoblastic precursors (Seale, P. et al. (2008) *Nature* 454, 961-967) in vitro and in vivo. At a molecular level, PRDM16 works as a transcriptional co-regulatory protein by co-activating PPARγ (peroxisome proliferator-activated receptor γ), which is considered the 'master' gene of fat cell differentiation (Tontonoz, P. et al. (1994) *Cell* 79, 1147-1156; Tontonoz, P. and Spiegelman, B. M. (2008) *Annu. Rev. Biochem.* 77, 289-312). However, both isoforms of PPARγ are expressed at very low levels in primary and immortalized myoblasts, whereas they are abundantly expressed in white and brown preadipocytes (FIGS. 5A and 5B). Hence, PRDM16 initiates the process of myoblast to brown fat conversion by complexing with other DNA-binding factors, well before the co-activation of PPARγ.

FIG. 1A illustrates the strategy described herein to identify such DNA-binding factors. Briefly, proteomic analyses of transcriptional complexes formed with wild-type PRDM16 or different mutant alleles that were differentiation-competent or -incompetent were performed. Transcription factors that co-purified preferentially with differentiation-competent PRDM16 proteins were identified; their expression in white and brown fat was then analysed and compared to that of PRDM16. Subsequently, their function was examined in the process of myoblast to brown fat conversion through PRDM16.

Figure 6:
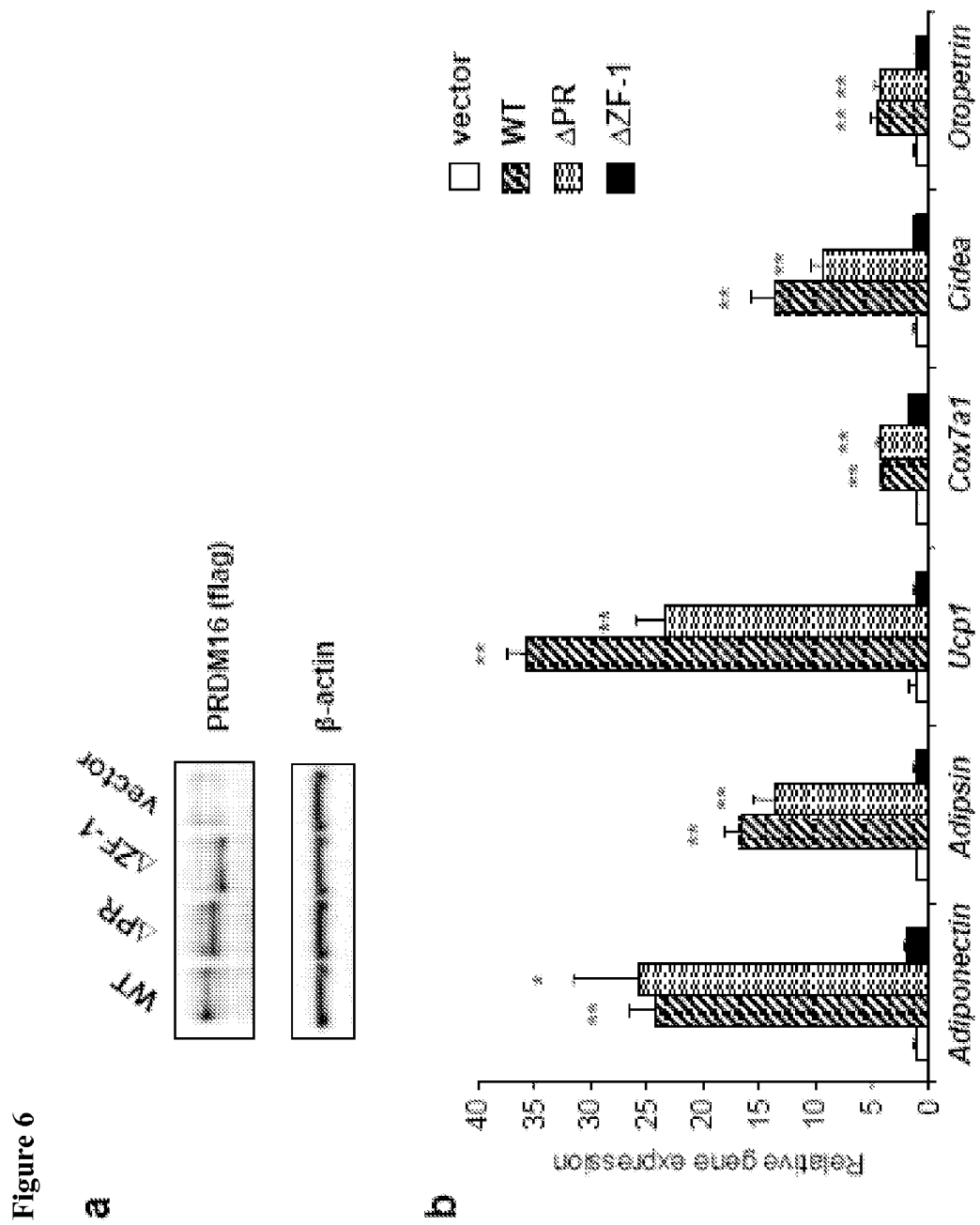
FIG. 6A-6B show that the ZF-1 region of PRDM16 is required for the induction of a brown fat gene program from C2C12 myoblasts. (A) shows wild type (WT), PR-domain deletion mutant (ΔPR), ZF-1 deletion mutant (ΔZF-1) of PRDM16 were expressed in C2C12 myoblasts at similar levels. PRDM16 (upper panel) and β-actin (lower panel) were detected by Western blotting. (B) shows that these cells were differentiated and mRNA expression of adipocyte markers (Adiponectin and Adipsin) and BAT-selective genes (Ucp1, Cox7a1, Cidea and Otopetrin) were analyzed by real-time PCR. n=4. Data are mean and s.e.m. * P<0.05, ** P<0.01.

As shown in FIG. 1B, wild type PRDM16 and a mutant protein lacking the PR (PRD1-BF1-RIZ1 homologous)

domain (ΔPR; amino acids 91-223) that shares homology to the SET chromatin remodelling domain (Mochizuki, N. et al. (2000) *Blood* 96, 3209-3214; Shing, D. C. et al. (2007) *J. Clin. Invest.* 117, 3696-3707), induced brown fat cell differentiation from myoblasts. In contrast, a mutant allele lacking zinc finger domain-1 (ΔZF-1; amino acids 224-447) completely lost its adipogenic function. The brown fat gene program was also induced by both wild-type and ΔPR, but not by ΔZF-1 (FIGS. 6A and 6B). To avoid comparing proteomic analyses of complexes from cells of very different phenotypes, all three PRDM16 forms were expressed in bona fide brown fat cells. PRDM16 complexes were then immunopurified to apparent homogeneity (FIG. 1C), and subjected to high-resolution 'shotgun' sequencing by liquid chromatography with tandem mass spectrometry (LC-MS/MS; Haas, W. et al. (2006) *Mol. Cell. Proteomics* 5, 1326-1337). In total, 49 proteins were identified in differentiation-competent PRDM16 complexes, but only eight of these (Bclaf1, Zfp655, p53 (also known as Trp53), Cebpb, Zcchc8, Zkscan3, Zfp143 and Vezf1) are known or predicted transcription factors (Table 1).

Figure 7:
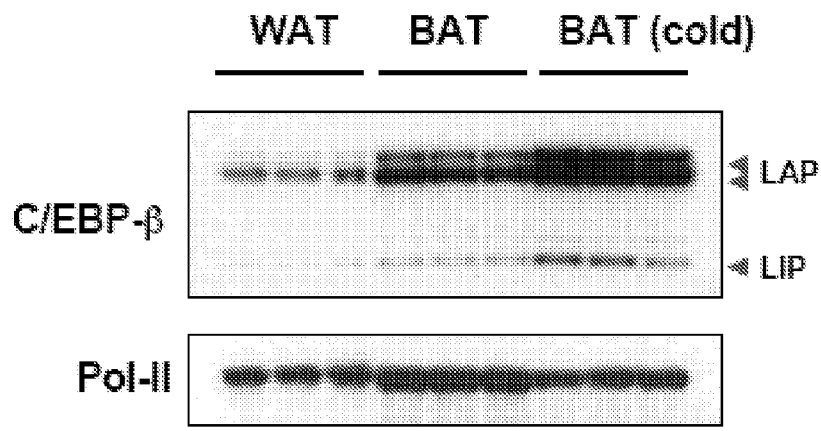
FIG. 7 shows that C/EBP-β protein is enriched in BAT. C/EBP-β protein was detected in the WAT and BAT from mice at ambient temperature, and BAT from mice kept at 4° C. for 5 hours by Western blotting. RNA polymerase II (Pol II) protein is shown as a loading control (lower panel).
Figure 8:
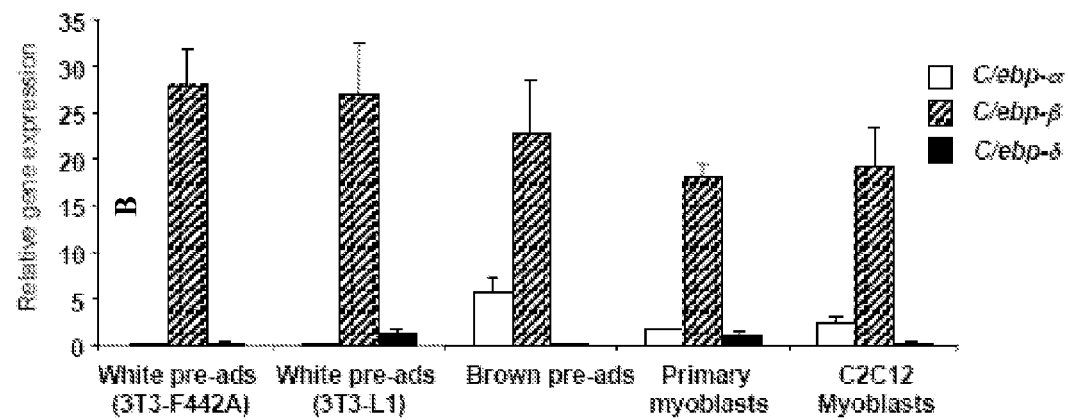
FIG. 8 shows that C/EBP-β is abundantly expressed in myoblasts. mRNA levels of three members of the C/EBP family (C/EBP-α, C/EBP-β, and C/EBP-δ) were measured in white pre-adipocyte lines (3T3-F442A and 3T3-L1), immortalized brown pre-adipocyte, primary myoblasts and C2C12 myoblast cell line. n=3-4. Data are presented as mean and s.e.m.

Because the expression of a key initiating transcription factor was presumed not to be extinguished during the brown fat cell adipogenesis, and as PRDM16 is highly enriched in BAT relative to white adipose tissue (WAT; Seale, P. et al. (2007) *Cell Metab.* 6, 38-54), it was determined whether any of these factors were similarly enriched in BAT. As shown in FIG. 1D, the expression of only Cebpb (C/EBP-β) was co-enriched with PRDM16 in BAT versus WAT. In addition, C/EBP-β protein was enriched in BAT, and further induced by cold exposure (FIG. 7). Notably, both primary and immortalized myoblasts express C/EBP-β at similar levels to those seen in preadipocytes (FIG. 8), where this factor is thought to have a very important role in adipogenesis (Wu, Z. et al. (1995) *Genes Dev.* 9, 2350-2363; Farmer, S. R. et al. (2006) *Cell Metab.* 4, 263-273).

Figure 9:
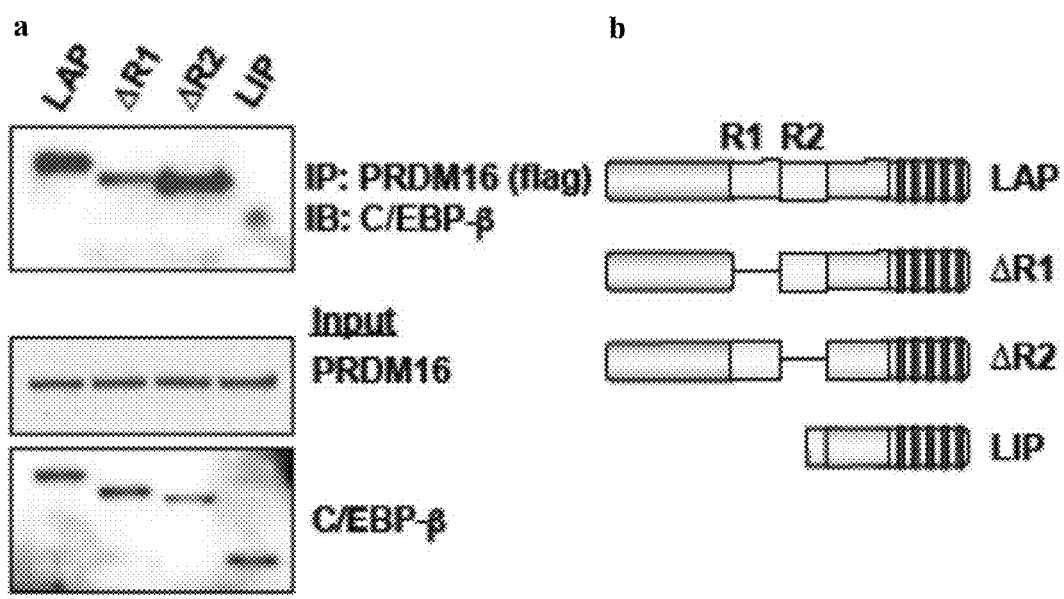
FIGS. 9A-9B show that PRDM16 does not interact with LIP. Flag-tagged full length PRDM16 was transiently expressed with several deletion mutants of C/EBP-β in HEK293 cells. (A) shows that PRDM16 was immunoprecipitated using flag M2 agarose, separated by SDS-PAGE, and C/EBP-β was detected by Western blotting. The inputs are also shown. (B) shows schematic illustrations of C/EBP-β deletion mutants. The far left box represents the activation domain of C/EBP-β. R1 and R2 domains represent repression domain-1 and -2, respectively.
Figure 10:
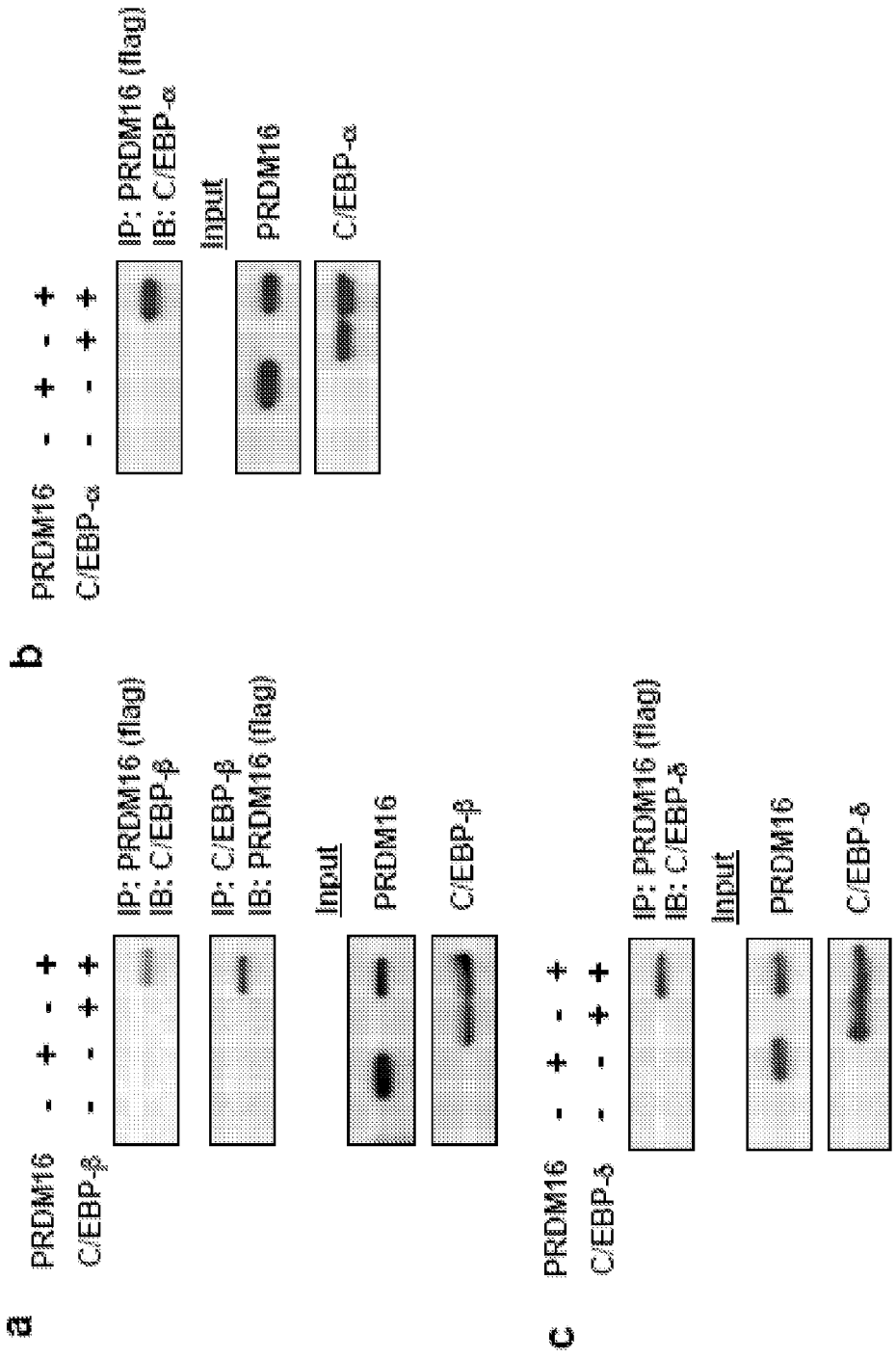
FIGS. 10A-10C show that PRDM16 physically interacts with three members of the C/EBP family. (A) shows that Flag-tagged full length PRDM16 was transiently expressed with C/EBP-β in HEK293 cells. PRDM16 or C/EBP-β was immunoprecipitated using flag M2 agarose or C/EBP-β antibody, respectively. The immunoprecipitants were separated by SDS-PAGE, and C/EBP-β or PRDM16 was detected by Western blotting. The inputs are also shown. (B) and (C) show that Flag-tagged PRDM16 was transiently expressed with C/EBP-α (B) or C/EBP-δ (C) in HEK293 cells. Interaction of PRDM16 with C/EBP-α or C/EBP-δ was analyzed as described in Example 1.
Figure 11:
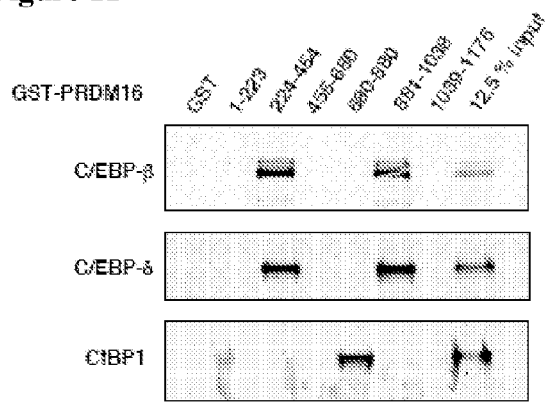
FIG. 11 shows that PRDM16 directly interacts with C/EBP-β through the two zinc finger domains. Full length C/EBP-β (top), C/EBP-δ (middle) or CtBP1 (bottom) were $^{35}$S-labeled by in vitro translation and incubated with various GST-fusion fragments of PRDM16. GST-beads were washed, separated by 4-20% gradient SDS-PAGE, and analyzed by autoradiography.

Brown fat cells express three forms of C/EBP-β, two active forms, named LAP (liver-enriched transcriptional activator protein) and a dominant-negative form, LIP (liver-enriched transcriptional inhibitory protein) (FIG. 1E; Descombes, P. and Schibler, U. (1991) *Cell* 67, 569-579). Notably, PRDM16 preferentially bound to LAP, but not to LIP (FIGS. 1E, 9A, and 9B). Independent co-expression assays in HEK293 cells confirmed the physical binding of PRDM16 and C/EBP-β. Furthermore, PRDM16 interacts with other C/EBP family members, C/EBP-α and -δ (FIGS. 10A, 10B, and 10C). This interaction is believed to be direct through the two zinc finger domains, because the zinc finger domains of the purified glutathione S-transferase (GST)-fused PRDM16 bound to in vitro translated C/EBP-β (FIG. 11).

In addition, PRDM16's effects on C/EBP-β transcriptional activity were assessed. A luciferase reporter assay was performed using the −2 kilobase (kb) Pgc1a (also known as Ppargc1a) promoter where the C/EBP-binding sites have been characterized, since C/EBP-β is known to induce Pgc1a (Wang, H. et al. (2008) *Mol. Endocrinol.* 22, 1596-1605). FIG. 1F shows that PRDM16 and C/EBP-β synergistically stimulated Pgc1a promoter activity. Taken together, these data indicate that PRDM16 forms a transcriptional complex with active forms of C/EBP-β by direct interaction, and regulates their transcriptional activity.

Example 3

Figure 2:
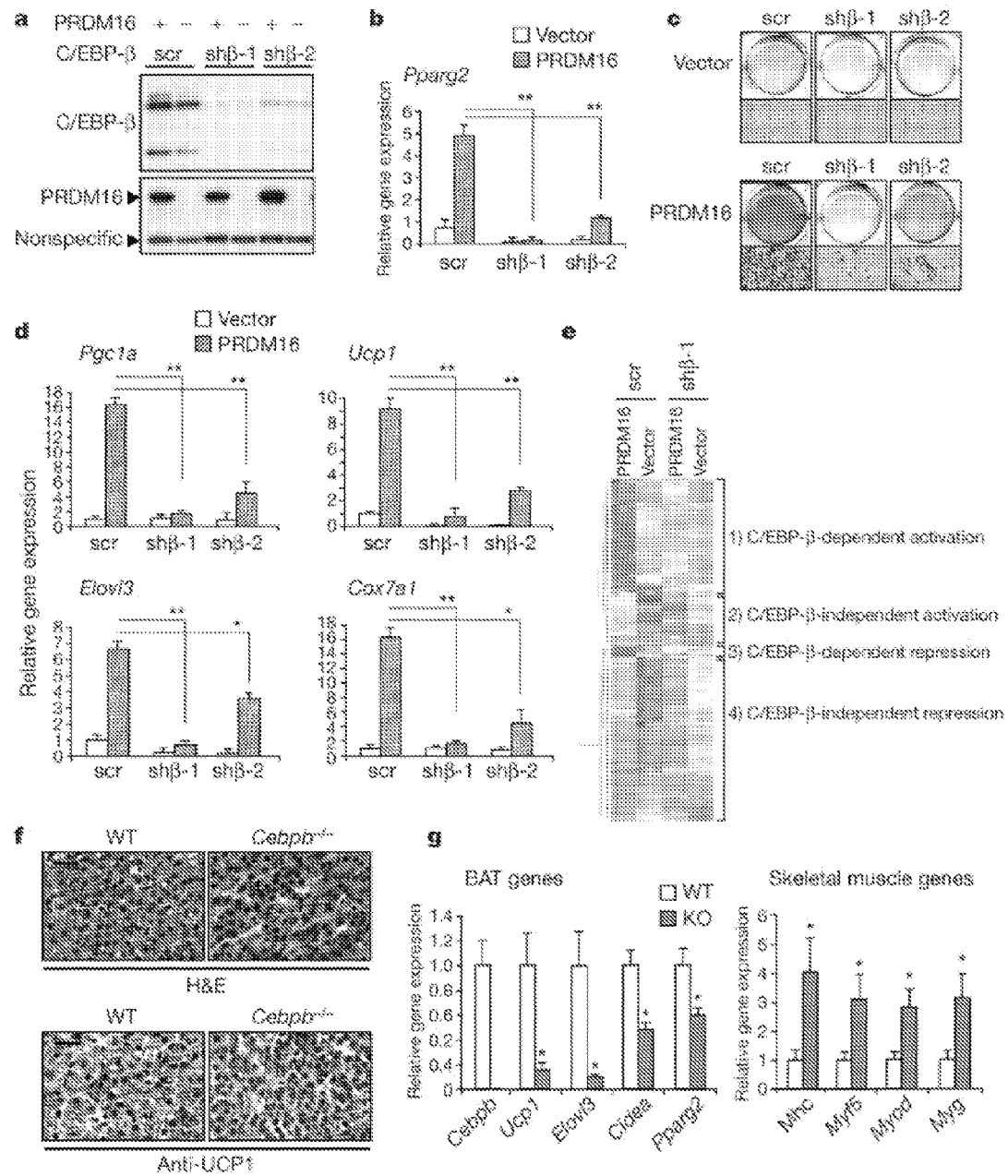
FIGS. 2A-2G show that C/EBP-β is required for initiation of the myoblast to brown fat conversion by PRDM16. (A) shows Western blot analysis for C/EBP-β and PRDM16 in C2C12 myoblasts expressing scr, shβ-1 or shβ-2, with PRDM16 or vector. (B) shows Pparg2 gene expression. n=3. (C) shows cells stained with Oil Red O 6 days after inducing adipocyte differentiation. (D) shows BAT-selective gene expression. n=4. (E) shows microarray analysis of undifferentiated C2C12 myoblasts expressing scr or shβ-1 with PRDM16 or vector. n=3. (F) shows haematoxylin and eosin (H&E) staining of BAT from wild-type (WT) and C/EBP-β knockout (KO) mice, as well as immunohistochemistry to detect UCP1 expression. Scale bars, 20 μm. (G) shows mRNA expression of BAT and skeletal-muscle-selective genes in BAT from E17.5 embryos. n=5-8; all error bars are s.e.m.; * P<0.05, ** P<0.01.
Figure 12:
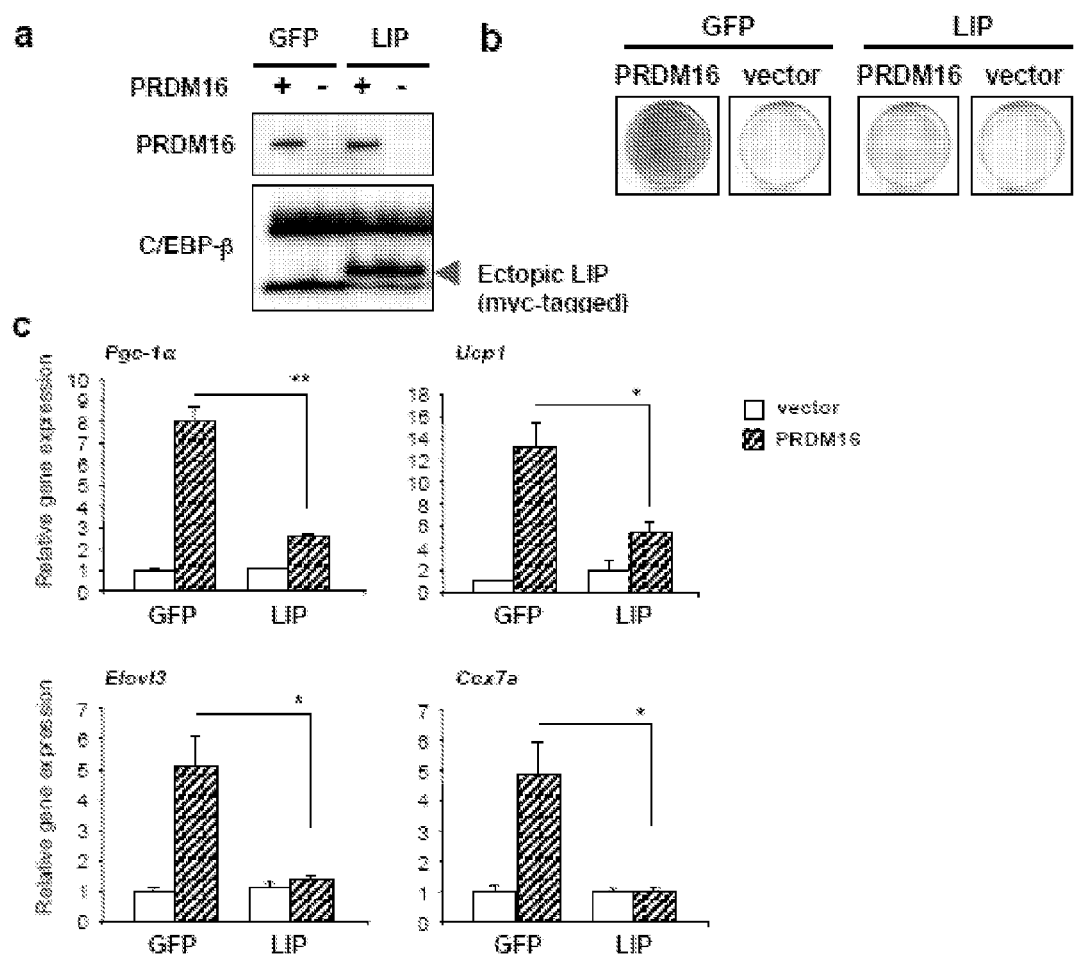
FIGS. 12A-12C show that expression of a dominant-negative form of C/EBP-β (LIP) blunts the PRDM16-induced brown fat gene program. (A) shows that GFP or a dominant-negative form of C/EBP-β (LIP) was co-expressed with PRDM16 or vector control in C2C12 myoblasts. Protein expressions of PRDM16 (top) and LIP (bottom) were detected by Western blotting. (B) shows that these cells were stained with Oil-Red-O 6 days after inducing adipocyte differentiation. (C) shows that mRNA expression of BAT-selective genes were analyzed by real-time PCR. n=3. Data are mean and s.e.m. * P<0.05, ** P<0.01.

The PRDM16-C/EBP-β Transcriptional Complex Specifically Initiates Myoblast to Brown Fat Switch To examine the functional role of the interaction between PRDM16 and C/EBP-β in the myoblast to brown fat conversion, retroviruses expressing a short hairpin (sh) scrambled control RNA (scr), or shRNAs targeting C/EBP-β (shβ-1 and shβ-2) were transduced together with PRDM16 or an empty vector into C2C12 myoblasts (FIG. 2A). Knockdown of C/EBP-β significantly blunted the induction of Pparg2 expression by PRDM16 in undifferentiated C2C12 myoblasts (FIG. 2B). Consistent with this result, Oil Red O staining showed that depletion of C/EBP-β blunted the adipogenesis induced by PRDM16 (FIG. 2C). Furthermore, induction of brown-fat-selective genes including Pgc1a, Ucp1, Elovl3 and Cox7a1 were completely or partially blocked by knockdown of C/EBP-β, correlating with the knockdown efficacy (FIG. 2D). In addition, ectopic expression of LIP, a dominant-negative form of C/EBP-β, also significantly blunted PRDM16-induced adipogenesis and brown-fat-selective gene expression (FIGS. 12A, 12B, and 12C).

Figure 13:
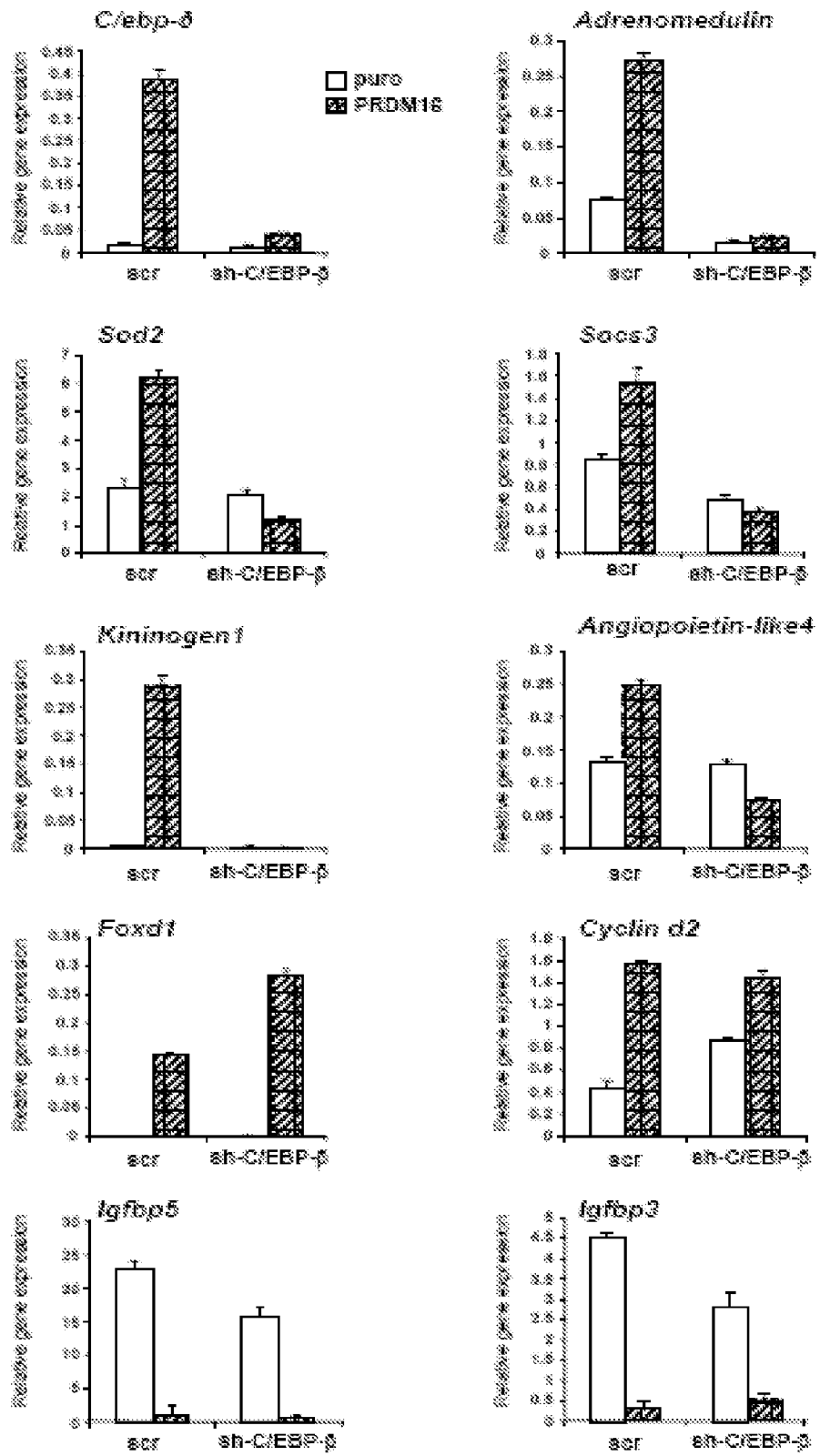
FIG. 13 shows validation of microarray analysis by real-time PCR. Undifferentiated C2C12 myoblasts were transduced with a scrambled control shRNA (scr) or shRNA targeting C/EBP-β (sh-CEBP-β) together with PRDM16 or vector control. Genes identified by the microarray analysis were individually measured by real-time PCR. n=3. Data are mean and s.e.m.

Next, a systematic approach was taken to determine what fraction of the PRDM16-regulated genes requires C/EBP-β at the initiating step of the myoblast to brown fat conversion. RNAs from undifferentiated C2C12 myoblasts expressing PRDM16 or control together with scr or shβ-1, maintained under conditions non-permissive for differentiation, were subjected to Affymetrix microarray analysis. As shown in FIG. 2E, 316 genes were significantly increased or reduced by PRDM16 (>two-fold, $P<0.05$), which were clustered into four groups: (1) genes increased by PRDM16 in a C/EBP-β-dependent manner, (2) genes increased by PRDM16 in a C/EBP-β-independent manner, (3) genes repressed by PRDM16 in a C/EBP-β-dependent manner, and (4) genes repressed by PRDM16 in a C/EBP-β-independent manner. The expression of a subset of genes identified by microarray analyses was validated by PCR with reverse transcription (RT-PCR; FIG. 13). Notably, most genes activated by PRDM16 before differentiation (62 out of 95, 65.3%) indeed required C/EBP-β, whereas most of the repressed genes (210 out of 221, 95.0%) were not grossly altered by C/EBP-β depletion.

The genetic requirement for C/EBP-β in brown fat development was further investigated by analysing C/EBP-β-deficient embryos. Defects in BAT of C/EBP-β-null newborn or adult mice have been described, although the reported phenotype was inconsistent (Tanaka, T. et al. (1997) *EMBO J.* 16, 7432-7443; Carmona, M. C. et al. (2005) *Biochem. J.* 389, 47-56). Because a large number of these embryos died within the first 24 h after birth (Tanaka, T. et al. (1997) *EMBO J.* 16, 7432-7443; Screpanti, I. et al. (1995) *EMBO J.* 14, 1932-1941), analyses were performed at late gestation (stage embryonic day (E18.5) so as to permit a clear separation of developmental changes in the BAT, as opposed to those that might occur secondarily to abnormalities in other tissues after birth. Haematoxylin and eosin staining showed that brown fat cells in knockout embryos contained significantly less lipid droplets than those in wild-type embryos, indicating defects in brown fat development per se (FIG. 2F). Moreover, UCP1 expression was severely reduced in knockout embryos (FIG. 2F), consistent with the results of Tanaka, T. et al. (1997) *EMBO J.* 16, 7432-7443. A definitive molecular characterization of the BAT from wild-type and knockout embryos was also conducted. Notably, BAT from C/EBP-β-knockout mice nearly phenocopied that from PRDM16-knockout mice at the gene expression level; that is, a broad reduction of BAT-selective gene expression, and a broad induction of the skeletal muscle gene expression (FIG. 2G). Together, these data indicate that the PRDM16-C/EBP-β transcriptional complex specifically has a critical role in the initiation of myoblast to brown fat switch. This further indicates that PRDM16 acts in Myf5-positive myoblastic precursors, at least in part, by coactivation of C/EBP-β to induce the expression of Pparg and Pgc1a. Subsequently, PRDM16 co-activates PPARγ and PGC-1α by direct binding events, which drives a complete brown fat differentiation program (FIG. 14).

Example 4

Figure 3:
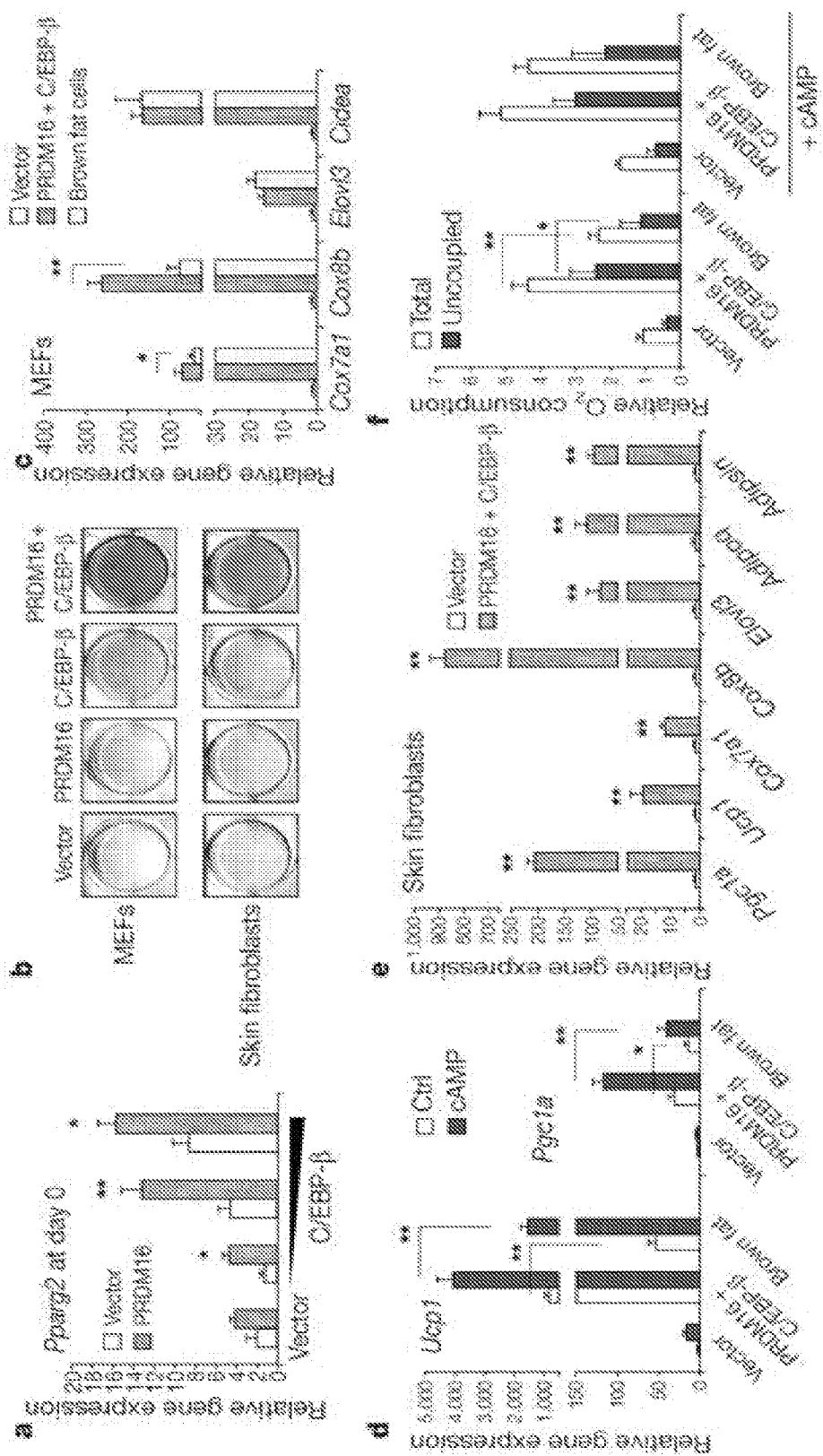
FIG. 3A-3F show that PRDM16 and C/EBP-β can reconstitute the brown fat gene program in fibroblasts. (A) shows Pparg2 expression in undifferentiated MEFs expressing indicated viral vectors. n=3. (B) shows immortalized MEFs or skin fibroblasts expressing indicated viral vectors stained with Oil Red 0 6-8 days after inducing adipocyte differentiation. (C) shows BAT-selective gene expression. (D) shows thermogenic gene expression. The cells were treated with cAMP for 4 h. n=4; ctrl, control. (E) shows BAT-selective gene expression in primary skin fibroblasts expressing vector or PRDM16 and C/EBP-β. n=3. Adipsin is also known as Cfd. (F) shows total and uncoupled cellular respiration in differentiated brown fat cells and the MEFs expressing vector or PRDM16 and C/EBP-β. The cells were treated with dibutyryl-cAMP for 12 h. n=3; all error bars are s.e.m.; * P<0.05, ** P<0.01.
Figure 14:
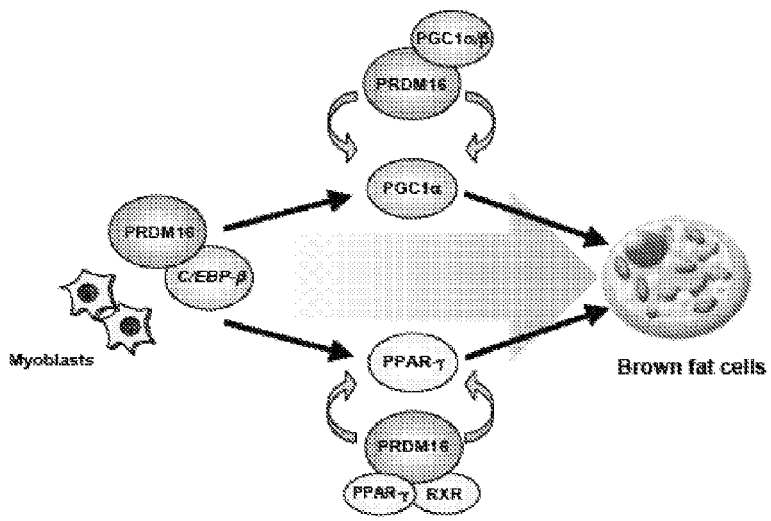
FIG. 14 shows a schematic model of the myoblast-brown fat conversion through PRDM16 and C/EBP-β. PRDM16 acts in myf5-positive myoblastic precursors, at least in part, by coactivation of C/EBP-β to induce the expression of PPAR-γ and PGC-1a. PRDM16 coactivates PPAR-γ and PGC-1α by direct binding, which drives a complete brown fat differentiation program.
Figure 15:
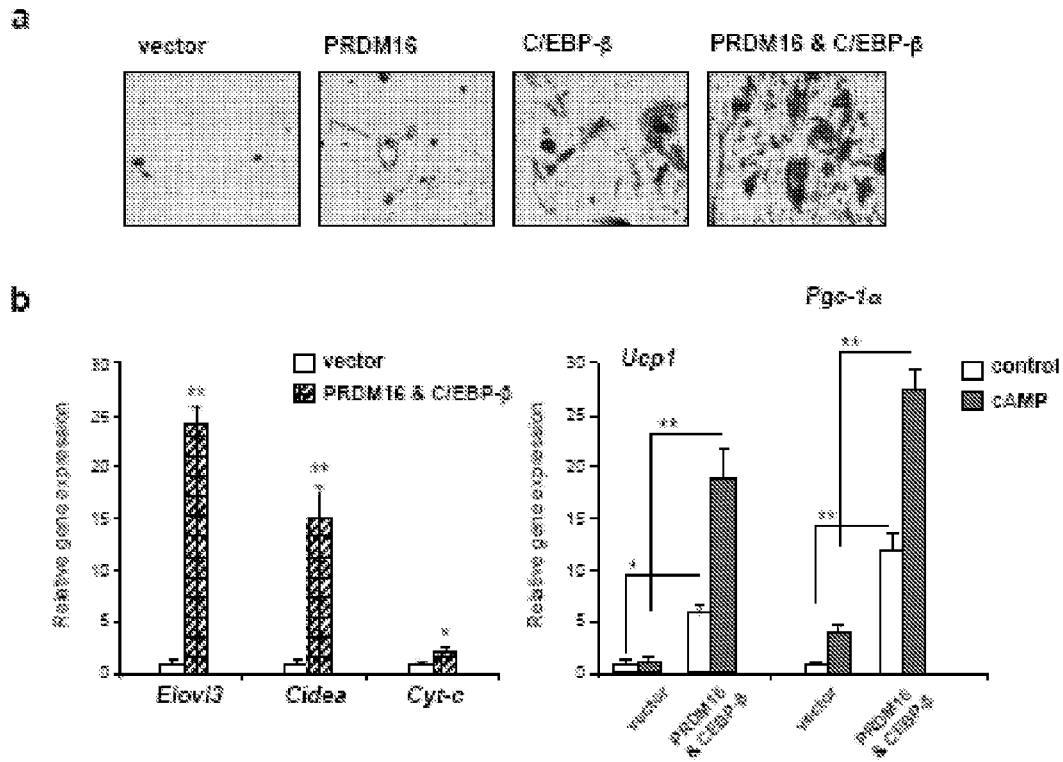
FIGS. 15A-15B show that PRDM16 and C/EBP-β induces brown fat gene program in human skin fibroblasts through PRDM16 and C/EBP-β. (A) shows that primary skin fibroblasts from human newborn foreskin were transduced with vector control, PRDM16, C/EBP-β, or combination of PRDM16 and C/EBP-β. These cells were differentiated using a standard adipocyte differentiation protocol, and stained with Oil-Red-O. (B) shows that mRNA expression of BAT-enriched genes (Elovl3, Cidea, and Cyt-c) and thermogenic genes (Ucp1 and Pgc-1α) were analyzed by realtime PCR. The cells were treated with or without cAMP (forskolin, 10 μM) for 4 hours prior to RNA isolation. n=3. Data are mean and s.e.m. * P<0.05. ** P<0.01.

The PRDM16-C/EBP-β Transcriptional Complex is Sufficient to Reconstitute a Near Complete Brown Fat Program The mechanistic model presented in FIG. 14 raises the critical question of whether the two factors are sufficient to reconstitute a brown fat program in naive cells. To this end, PRDM16 and C/EBP-β were ectopically expressed in mouse embryonic fibroblasts (MEFs) or primary skin fibroblasts with no inherent adipose or brown fat character. As shown in FIG. 3A, Pparg2 messenger RNA expression was synergistically induced by PRDM16 and C/EBP-β in a dose-dependent manner in undifferentiated fibroblasts. After 6-8 days under adipogenic conditions, both MEFs and skin fibroblasts expressing these two factors uniformly differentiated into lipid-filled adipocytes, as shown by Oil Red O staining (FIG. 3B). The single factors alone were not sufficient to robustly stimulate the differentiated state. Gene expression studies showed that PRDM16 and C/EBP-β powerfully induced mRNA levels of brown fat genes including Cox7a1 (70-fold), Cox8b (260-fold), Elovl3 (16-fold) and Cidea (170-fold) to levels comparable with or even higher than those seen in bona fide immortalized brown fat cells (FIG. 3C). Notably, as in authentic brown fat cells, mRNA level of thermogenic genes such as Pgc1a and Ucp1 were further enhanced by cyclic AMP treatment (FIG. 3D). The mechanism underlying the augmentation of cAMP effects in the engineered brown fat cells remains unknown. The mRNA levels of those genes at the basal state were activated to levels seen in cAMP-stimulated brown fat cells. Furthermore, the two factors were able to induce the brown fat gene program from primary mouse skin fibroblasts (FIG. 3D) and human skin fibroblasts isolated from newborn foreskin (FIGS. 15A and 15B).

An important characteristic of brown fat cells is their extraordinarily high rates of respiration, particularly uncoupled respiration in response to cAMP. As shown in FIG. 3F, engineered brown fat cells induced by these two factors have significantly higher levels of total and uncoupled respiration than control cells, by 4.4- and 6.5-fold, respectively, at the basal state. Notably, the engineered cells have greater basal respiration, both total and uncoupled, than bona fide brown fat cells. However, whereas the bona fide brown fat cells can increase both total and uncoupled respiration further (by 85% and 90%, respectively) in response to cAMP, engineered brown fat cells were already at their maximal respiration. That these cells are responsive to cAMP is shown by the fact that expression of thermogenic genes, such as such as Pgc1a and Ucp1, are induced by cAMP treatment (FIG. 3D).

Example 5

Figure 4:
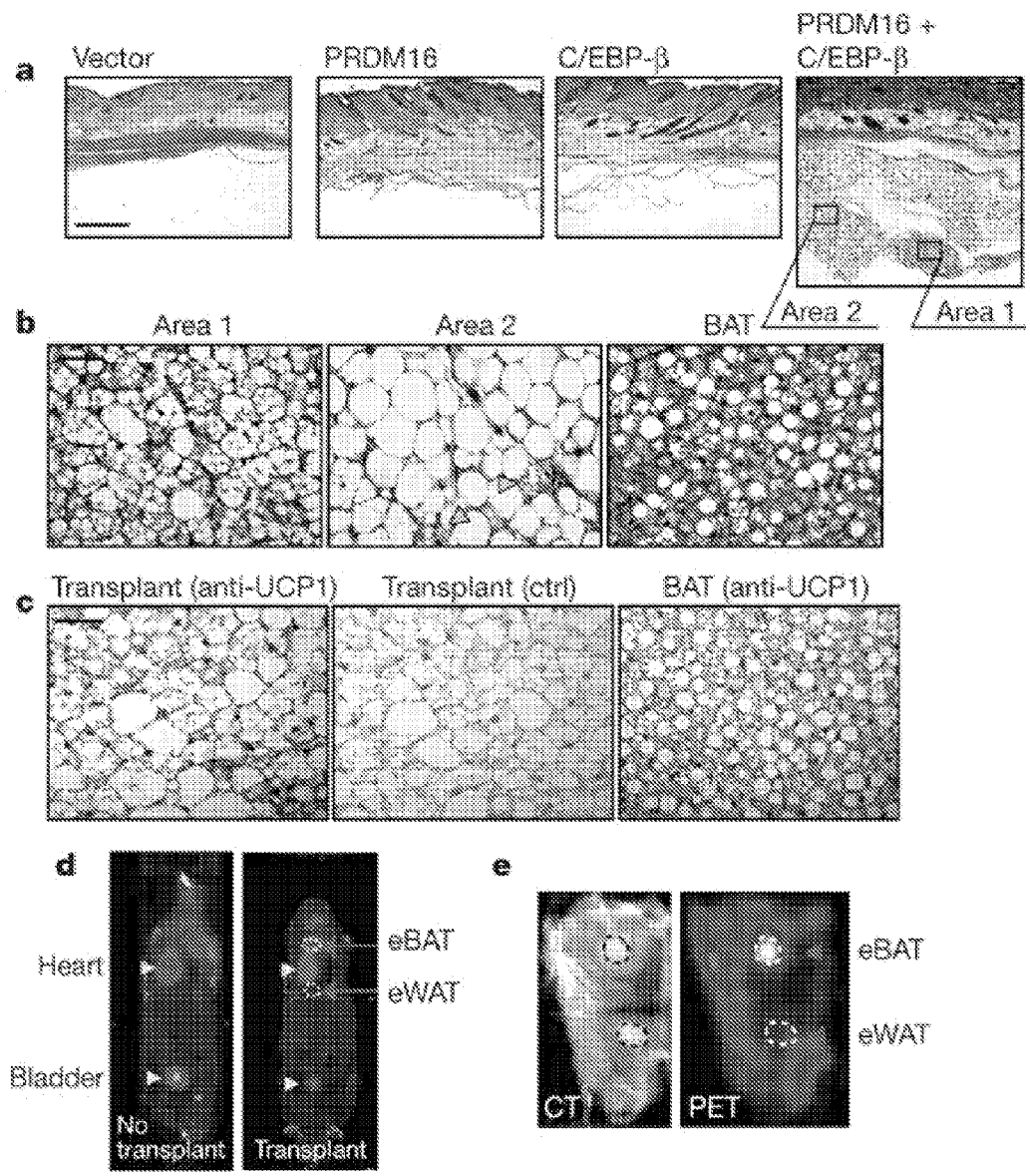
FIG. 4A-4E show generation of functional brown adipose tissue in vivo by expression of PRDM16 and C/EBP-β. (A) shows fat pads from transplanted MEFs expressing indicated viral vectors were stained by H&E. Scale bar, 500 μm. (B) shows high magnification images of H&E staining in the transplants expressing PRDM16 and C/EBP-β and endogenous BAT. Arrowheads show multilocular fat cells. Scale bar, 50 μm. (C) shows immunohistochemistry to detect UCP1 expression in the transplant (left, anti-UCP1; middle, negative control) and BAT (right). Scale bar, 50 μm. (D) shows PET/computed tomography image of mice with engineered BAT (eBAT) and engineered WAT (eWAT). (E) shows computed tomography (CT) image (left) and PET image (right) of mouse skin with the eBAT and eWAT.

The PRDM16-C/EBP-β Transcriptional Complex can Generate Functional Brown Adipose Tissue In Vivo The finding that the combination of PRDM16 and C/EBP-β is sufficient to reconstitute a near complete brown fat program offers an opportunity for controlling brown fat levels and function in vivo. Accordingly, transplantation studies were conducted (Green, H. and Kehinde, O. (1979) *J. Cell. Physiol.* 101, 169-171) using undifferentiated MEFs expressing vector, PRDM16, C/EBP-β, or a combination of the two factors. As shown by haematoxylin and eosin staining (FIG. 4A), the cells expressing vector or PRDM16 or C/EBP-β alone did not form visible fat tissues. In contrast, the cells expressing both PRDM16 and C/EBP-β formed very distinct fat pads in vivo. At high magnification, the engineered fat tissue induced by the two factors contained 'multilocular' fat cells, a morphological characteristic of brown fat in vivo (FIG. 4B). The population of multilocular fat cells (area 1) is mixed with regions of 'unilocular' fat cells (area 2). Notably, immunohistochemical analyses showed that the engineered adipose tissue was UCP1-positive in both the multilocular and unilocular fat cells (FIG. 4C).

Figure 16:
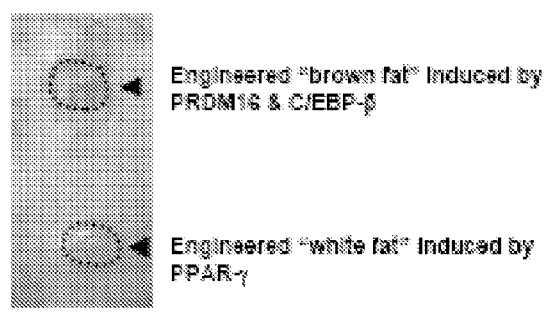
FIGS. 16A-16B show induction of brown fat gene program by PRDM16 and C/EBP-β in MEFs used for transplantation. (A) shows that immortalized MEFs were transduced with combination of PRDM16 and C/EBP-β or PPAR-γ —alone. These cells were implanted subcutaneously into 7-9 week-old male nude mice (n=6). After 4-6 weeks, the fat pads with similar sizes were carefully dissected. (B) shows that mRNA expression of BAT-selective genes (Ucp1, Pgc-1a, Cox7a1, Cox8b, Cidea, Elovl3, and Glut4) and general adipose marker genes (Adiponectin and Adipsin) were analyzed by real-time PCR. n=6. Data are mean and s.e.m. ** P<0.01.
Figure 16:
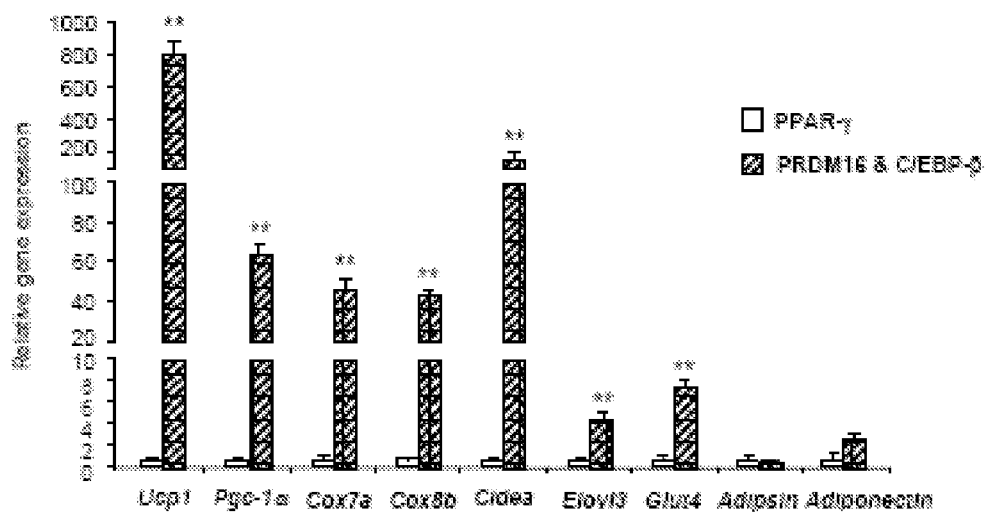

To characterize the activity of engineered brown fat tissue in vivo further, positron emission tomography (PET) with fluorodeoxyglucose ($^{18}$FDG) recently used to detect active BAT in adult humans (Nedergaard, J. et al. (2007) *Am. J. Physiol. Endocrinol. Metab.* 293, E444-E452; Cypess, A. M. et al. (2009)*N. Engl. J. Med.* 360, 1509-1517; van Marken Lichtenbelt, W. D. et al. (2009) *N. Engl. J. Med.* 360, 1500-1508; Virtanen, K. A. et al. (2009) *N. Engl. J. Med.* 360, 1518-1525), was used. This technique measures glucose uptake, with brown fat functioning in vivo as an active 'sink' for glucose. To this end, two adipose tissues with similar sizes were engineered in the same nude mice: a 'brown' fat tissue induced by PRDM16 and C/EBP-β, and a 'white' fat tissue induced by PPARγ alone as a control (FIG. 16A). The induction of BAT-selective genes by PRDM16 and C/EBP-β was confirmed in the cultured cells by RT-PCR (FIG. 16B). As shown in FIG. 4D, PET scanning detected a signal in mice from the engineered BAT. To enhance the sensitivity and specificity of the PET signal from the engineered fat tissues, the skin with these fat tissues attached was removed and scanned. The combination of computed tomography image and PET image (FIG. 4E) clearly showed that the PET signal was detected from the engineered BAT, but not from the engineered WAT.

These results indicate that the engineered brown fat cells function as a sink for active glucose disposal. Given the incredible capacity of BAT to dissipate stored chemical energy and thus counteract obesity, the PRDM16 pathway can be used to drive brown fat development in vivo in a therapeutic setting. Natural or synthetic compounds that can induce PRDM16 in white fat precursors or in myoblastic cells now have great value in human metabolic disease. Alternatively, as demonstrated herein, engineered brown fat induced by PRDM16 and C/EBP-β in amounts that are both clinically acceptable and therapeutically useful can be autologously transplanted.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for inducing differentiation of autologous fibroblast, autologous myoblast, or autologous fibroblast and myoblast cells into brown fat cells at a subcutaneous transplantation site in a mammal comprising:
   a) expressing both Prdm16 and C/EBPβ in vitro using genetically engineered autologous fibroblast, autologous myoblast, or autologous fibroblast and myoblast cells, comprising recombinant DNA encoding Prdm16 and C/EBPβ; and
   b) transplanting the genetically engineered autologous cells expressing both Prdm16 and C/EBPβ into a transplantation site in the mammal by subcutaneous transplantation.

2. The method of claim 1, wherein the autologous fibroblast cells are selected from the group consisting of skin fibroblasts, dermal fibroblasts, primary embryonic fibroblasts, immortalized embryonic fibroblasts, and human foreskin fibroblasts.

3. A method for inducing differentiation of autologous fibroblast, autologous myoblast, or autologous fibroblast and myoblast cells into brown fat cells at a subcutaneous transplantation site in a mammal comprising:
   a) obtaining autologous fibroblast, autologous myoblast, or autologous fibroblast and myoblast cells from the mammal;
   b) genetically engineering the autologous fibroblast, autologous myoblast, or autologous fibroblast and myoblast cells with recombinant DNA encoding Prdm16 and C/EBPβ and expressing both Prdm16 and C/EBPβ in the genetically engineered autologous cells; and
   c) transplanting the genetically engineered autologous cells expressing both Prdm16 and C/EBPβ into a transplantation site in the mammal by subcutaneous transplantation.

4. The method of claim 3, wherein the autologous fibroblast cells are selected from the group consisting of skin fibroblasts, dermal fibroblasts, embryonic fibroblasts, and human foreskin fibroblasts.

5. The method of claim 1 or 3, wherein the mammal is a human.

* * * * *